US010905736B2

(12) United States Patent
Fogelman et al.

(10) Patent No.: US 10,905,736 B2
(45) Date of Patent: Feb. 2, 2021

(54) EZETIMIBE-ASSOCIATED APOA-I MIMETIC PEPTIDES SHOWING ENHANCED SYNERGISM

(71) Applicant: The Regents of the University of California, Oakland, CA (US)

(72) Inventors: Alan M. Fogelman, Los Angeles, CA (US); Srinivasa T. Reddy, Cerritos, CA (US); Mohamad Navab, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 282 days.

(21) Appl. No.: 15/702,435

(22) Filed: Sep. 12, 2017

(65) Prior Publication Data

US 2018/0085420 A1    Mar. 29, 2018

Related U.S. Application Data

(60) Provisional application No. 62/401,102, filed on Sep. 28, 2016.

(51) Int. Cl.
| *A61K 38/04* | (2006.01) |
| *A61K 9/14* | (2006.01) |
| *A61K 9/16* | (2006.01) |
| *C12N 15/82* | (2006.01) |
| *A61K 9/00* | (2006.01) |
| *A61K 38/17* | (2006.01) |
| *C07K 14/775* | (2006.01) |

(52) U.S. Cl.
CPC ............ *A61K 38/04* (2013.01); *A61K 9/0053* (2013.01); *A61K 9/141* (2013.01); *A61K 9/1635* (2013.01); *A61K 38/1709* (2013.01); *C07K 14/775* (2013.01); *C12N 15/8241* (2013.01); *C12N 15/8257* (2013.01); *A61K 9/1617* (2013.01)

(58) Field of Classification Search
CPC .. A61K 31/397; A61K 38/04; A61K 38/1709; A61K 9/0053; A61K 9/141; A61K 9/1617; A61K 9/1635; C07K 14/775; C12N 15/8241; C12N 15/8257
See application file for complete search history.

(56) References Cited

U.S. PATENT DOCUMENTS

| 6,596,544 | B1 | 7/2003 | Fogelman et al. |
| 6,664,230 | B1 | 12/2003 | Fogelman et al. |
| 6,869,568 | B2 | 3/2005 | Fogelman et al. |
| 6,930,085 | B2 | 8/2005 | Fogelman et al. |
| 6,933,279 | B2 | 8/2005 | Fogelman et al. |
| 7,144,862 | B2 | 12/2006 | Fogelman et al. |
| 7,148,197 | B2 | 12/2006 | Fogelman et al. |
| 7,166,578 | B2 | 1/2007 | Fogelman et al. |
| 7,199,102 | B2 | 4/2007 | Fogelman et al. |
| 7,250,304 | B2 | 7/2007 | Fogelman et al. |
| 7,531,514 | B2 | 5/2009 | Fogelman et al. |
| 7,579,319 | B2 | 8/2009 | Fogelman et al. |
| 7,638,494 | B2 | 12/2009 | Fogelman et al. |
| 7,723,045 | B2 | 5/2010 | Fogelman et al. |
| 7,723,303 | B2 | 5/2010 | Fogelman et al. |
| 7,807,640 | B2 | 10/2010 | Fogelman et al. |
| 7,820,784 | B2 | 10/2010 | Fogelman et al. |
| 7,994,132 | B2 | 8/2011 | Fogelman et al. |
| 8,048,851 | B2 | 11/2011 | Fogelman et al. |
| 8,148,328 | B2 | 4/2012 | Fogelman et al. |
| 8,236,754 | B2 | 8/2012 | Fogelman et al. |
| 8,404,635 | B2 | 3/2013 | Fogelman et al. |
| 9,539,300 | B2 | 1/2017 | Fogelman et al. |
| 2003/0040505 | A1 | 2/2003 | Fogelman et al. |
| 2004/0254120 | A1* | 12/2004 | Fogelman ............ A61K 31/366 514/1.1 |
| 2005/0164950 | A1 | 7/2005 | Fogelman et al. |
| 2005/0187141 | A1 | 8/2005 | Fogelman et al. |
| 2006/0173067 | A1 | 8/2006 | Fogelman et al. |
| 2006/0205669 | A1 | 9/2006 | Fogelman et al. |
| 2007/0060527 | A1 | 3/2007 | Fogelman et al. |

(Continued)

FOREIGN PATENT DOCUMENTS

| WO | WO 2001/075168 A1 | 10/2001 |
| WO | WO 2001/075170 A1 | 10/2001 |

(Continued)

OTHER PUBLICATIONS

Carla S. M. Pereira, Ethyl lactate as a solvent: Properties, applications and production processes—a review, : Green Chem., 2011, 13, 2658.*
Jacqueline(Bennet, BLONDES(2009,2010(Green(Chennistry(Projects, published 2010.*
PCT International Search Report and Written Opinion dated Dec. 26, 2017 issued in PCT/US2017/051206.
PCT International Preliminary Report on Patentability dated Apr. 2, 2019 issued in PCT/US2017/051206.
Chattopadhyay et al., (2015) "Efficacy of tomato concentrates in mouse models of dyslipidemia and cancer", *Pharmacology Research & Perspectives*, 3(4): e00154 (13 pages).

(Continued)

*Primary Examiner* — James H Alstrum-Acevedo
*Assistant Examiner* — Erinne R Dabkowski
(74) *Attorney, Agent, or Firm* — Tom Hunter; Weaver .Austin Villeneuve & Sampson LLP

(57) ABSTRACT

In various embodiments, ezetimibe-associated apoA-I mimetic peptide are provided that show improved synergistic activity between ezetimibe and the apoA-I peptide in vivo. In certain embodiments the peptide component is a transgenic 6F and the ezetimibe-associated apoA-I mimetic peptide is an Ez-T6F peptide. Methods of making the Ez-apoA-I peptides are also provided. In certain embodiments the methods involve incubating ezetimibe and an apoAI mimetic peptide (e.g., T6F) in a solution comprising ethyl acetate and acetic acid or in a solution comprising ethyl lactate and lactic acid; and drying the solution to provide a dry ezetimibe-associated apoA-I mimetic peptide.

26 Claims, 62 Drawing Sheets

Specification includes a Sequence Listing.

(56) References Cited

U.S. PATENT DOCUMENTS

| | | |
|---|---|---|
| 2008/0096814 A1 | 4/2008 | Fogelman et al. |
| 2008/0293639 A1 | 11/2008 | Fogelman et al. |
| 2010/0227825 A1 | 9/2010 | Fogelman et al. |
| 2010/0240598 A1 | 9/2010 | Fogelman et al. |
| 2011/0183889 A1 | 7/2011 | Fogelman et al. |
| 2012/0004720 A1 | 1/2012 | Fogelman et al. |
| 2014/0213502 A1 | 7/2014 | Remaley et al. |
| 2016/0074473 A1 | 3/2016 | Turney et al. |
| 2017/0158751 A1 | 6/2017 | Fogelman et al. |
| 2017/0280761 A1 | 10/2017 | Fogelman et al. |

FOREIGN PATENT DOCUMENTS

| | | | |
|---|---|---|---|
| WO | WO 2002/015923 A1 | 2/2002 | |
| WO | WO 2003/086326 A2 | 10/2003 | |
| WO | WO 2004/034977 A3 | 4/2004 | |
| WO | WO 2005/016280 A2 | 2/2005 | |
| WO | WO-2005009955 A1 * | 2/2005 | ........... C07D 205/08 |
| WO | WO 2006/020652 A2 | 2/2006 | |
| WO | WO 2006/034056 A2 | 3/2006 | |
| WO | WO 2006/063132 A2 | 6/2006 | |
| WO | WO 2006/118805 A2 | 11/2006 | |
| WO | WO 2007/095126 A2 | 8/2007 | |
| WO | WO 2008/021088 A2 | 2/2008 | |
| WO | WO 2009/032749 A2 | 3/2009 | |
| WO | WO 2009/073725 A2 | 6/2009 | |
| WO | WO 2013/148214 A1 | 10/2013 | |
| WO | WO 2015/175968 A1 | 11/2015 | |
| WO | WO 2018/063796 A1 | 4/2018 | |

OTHER PUBLICATIONS

Chattopadhyay et al., (2016) "Tg6F ameliorates the increase in oxidized phospholipids in the jejunum of mice fed unsaturated LysoPC or WD." *J Lipid Res.* 57:832-847.

Maugeais et al., (2013) "rHDL administration increases reverse cholesterol transport in mice, but is not additive on top of ezetimibe or cholestyramine treatment", *Atherosclerosis*, 229: 94-101.

Mukherjee et al., (2017) "Transgenic Tomatoes Expressing the 6F Peptide and Ezetimibe Prevent Diet-induced Increases of Interferon-b and Cholesterol 25-hydroxylase in Jejunum", *Journal of Lipid Research*, 58: 1636-1647.

* cited by examiner

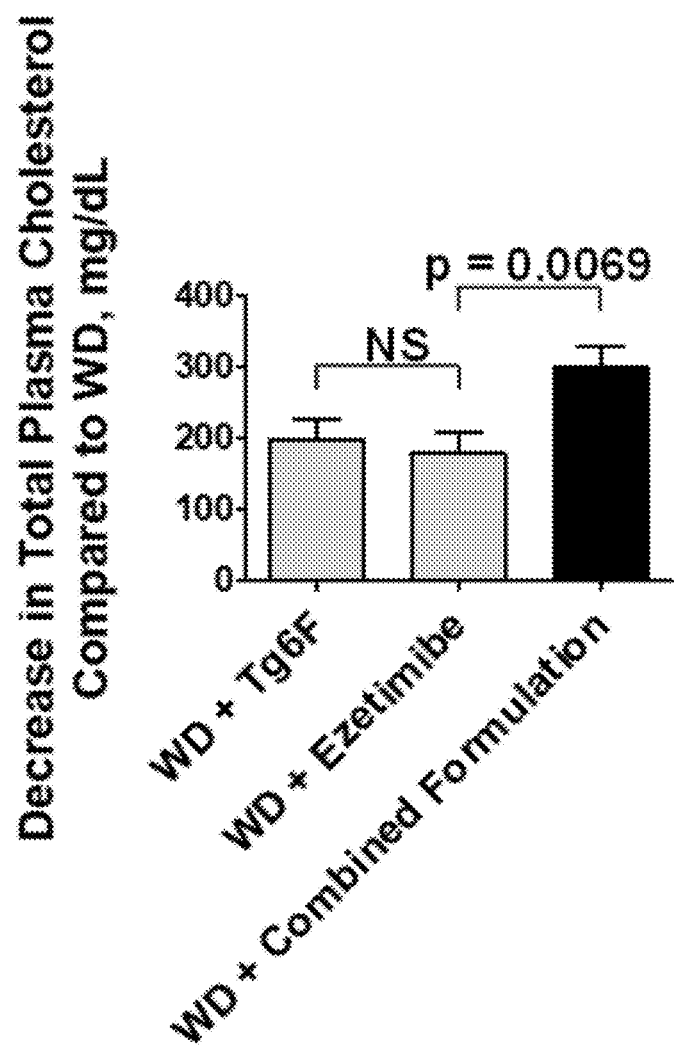
Fig. 15, cont'd.

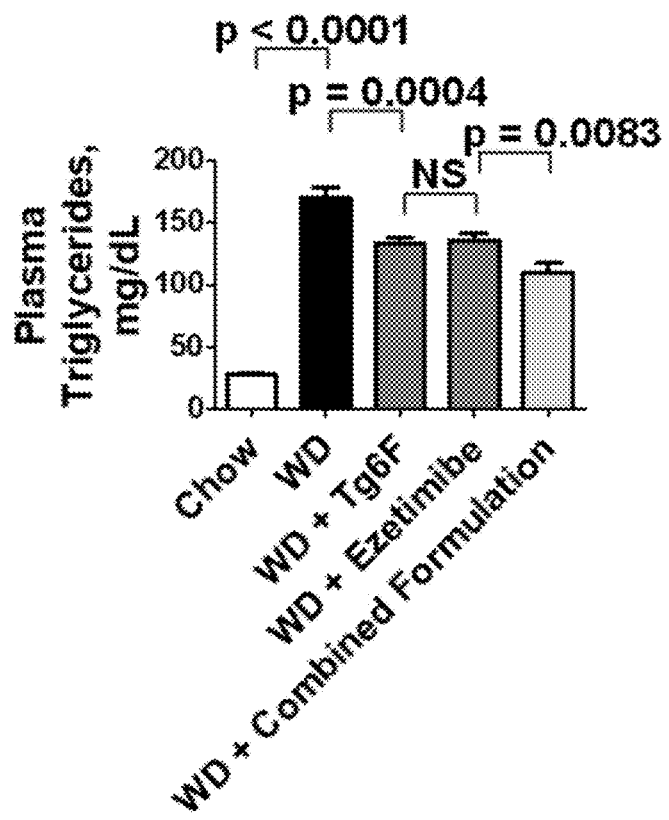
Fig. 15, cont'd.

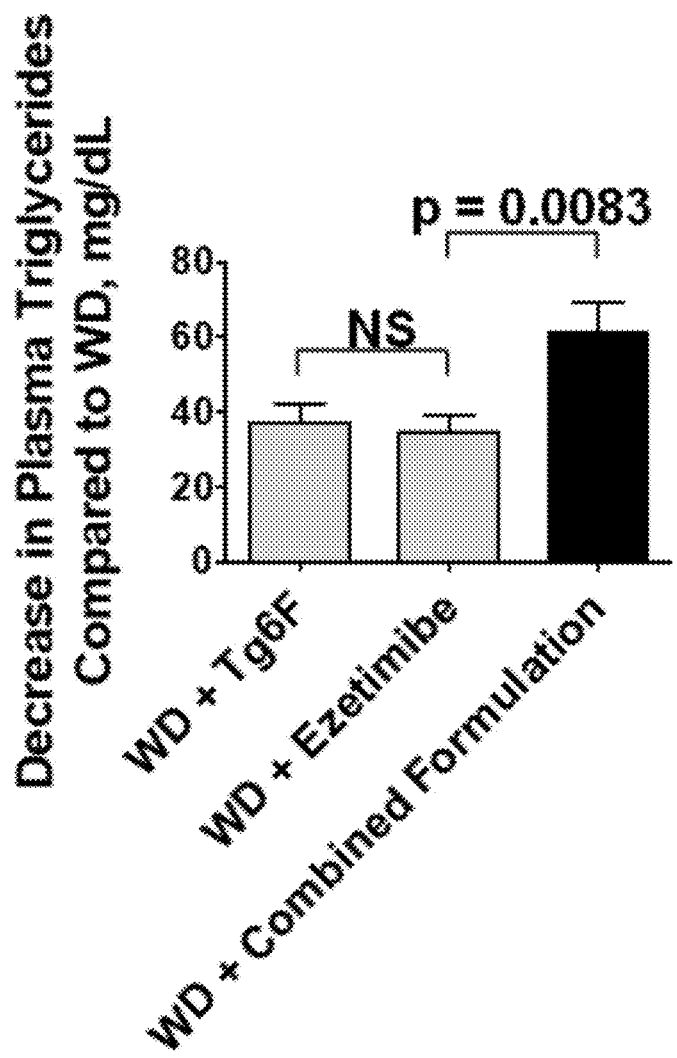
*Fig. 15, cont'd.*

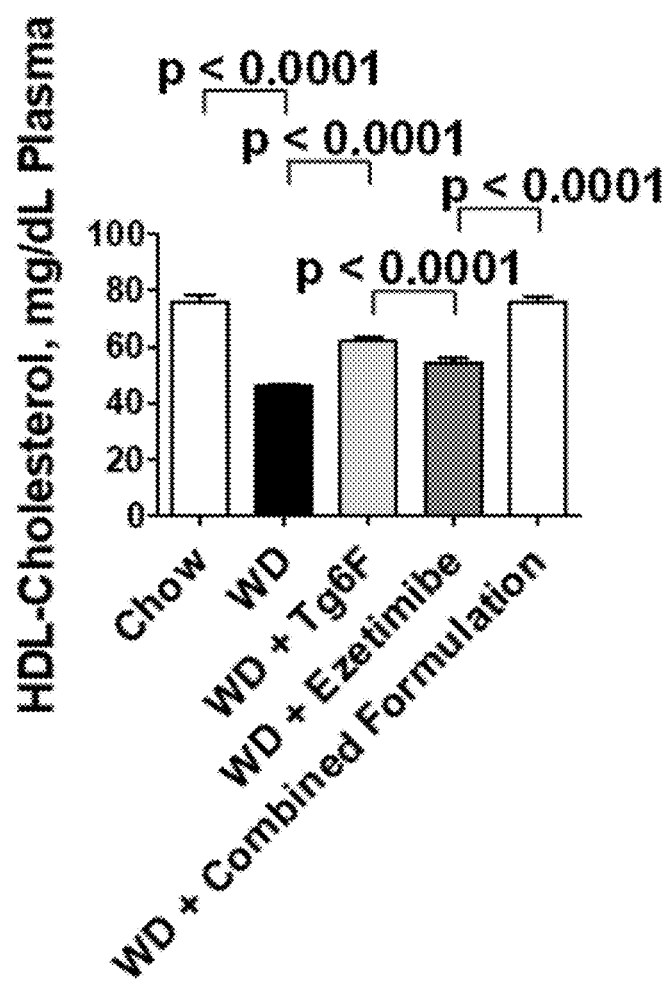
Fig. 15, cont'd.

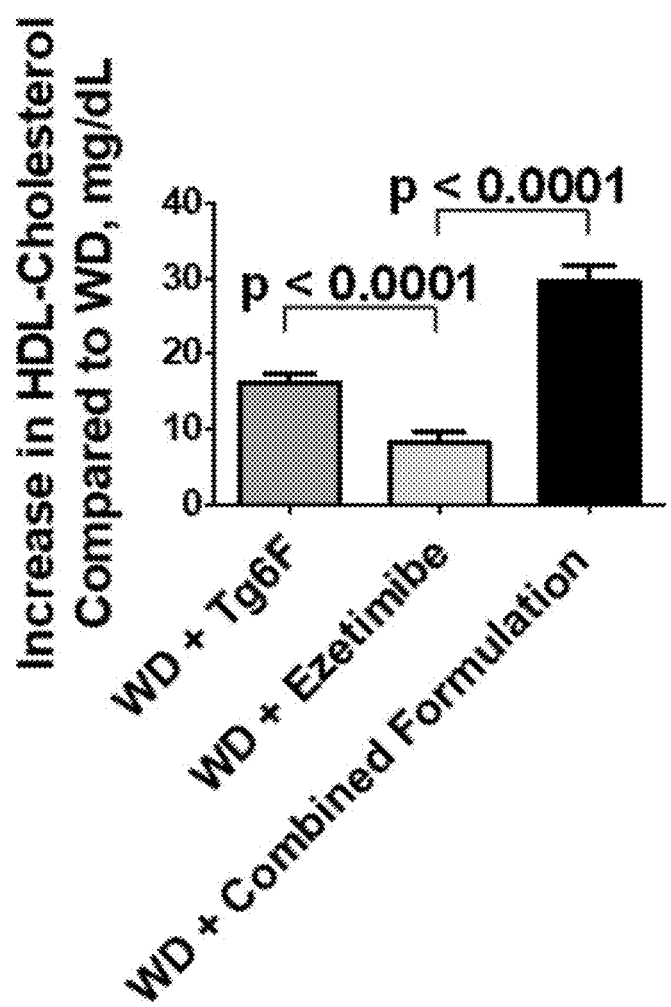
Fig. 15, cont'd.

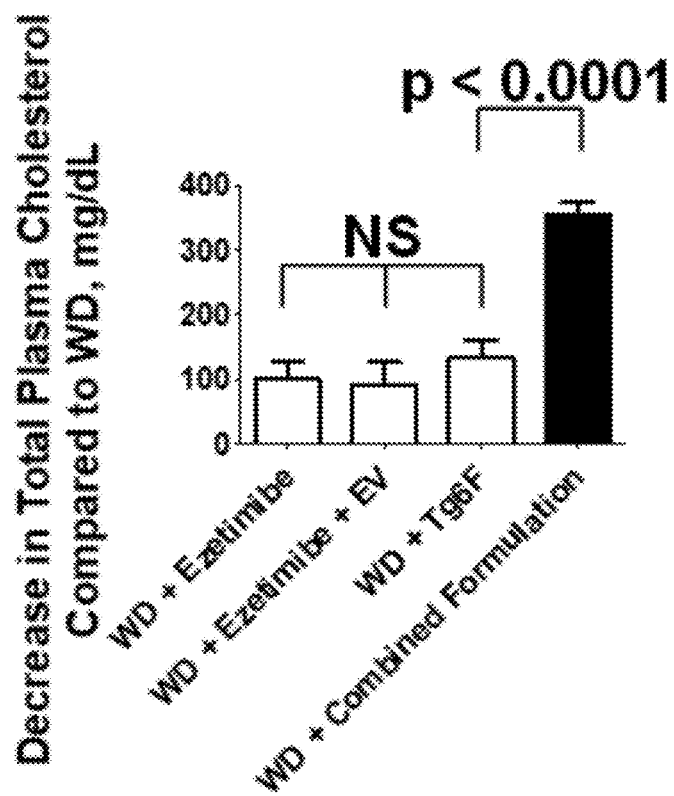
*Fig. 16, cont'd.*

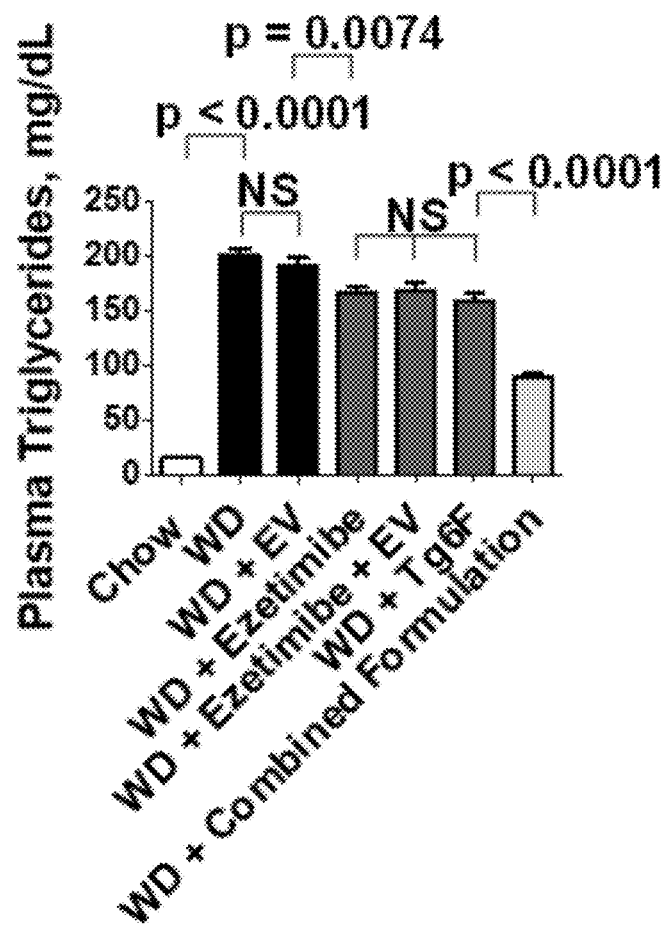
*Fig. 16, cont'd.*

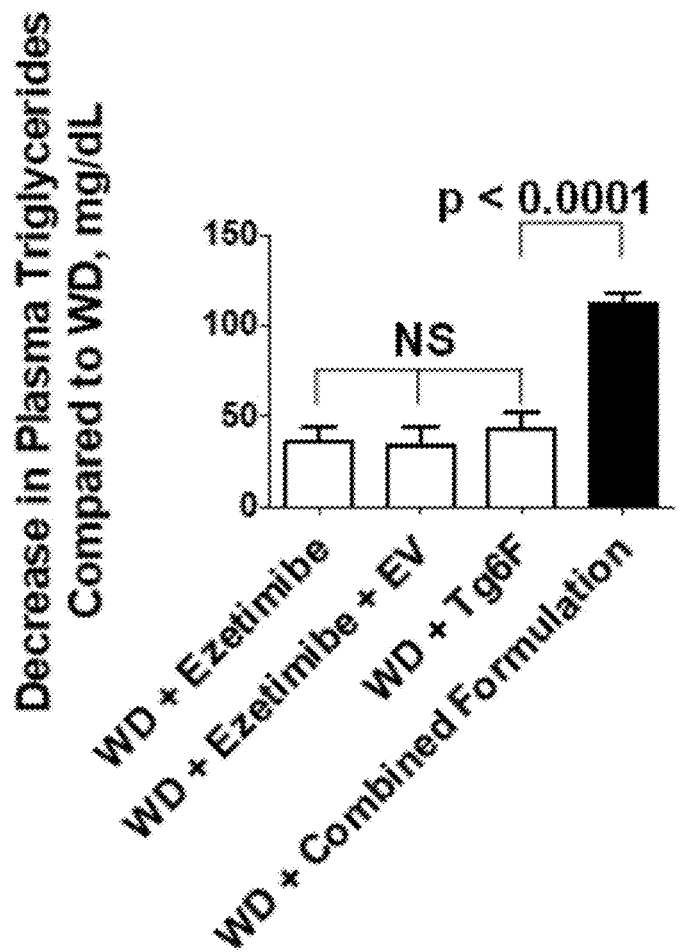
Fig. 16, cont'd.

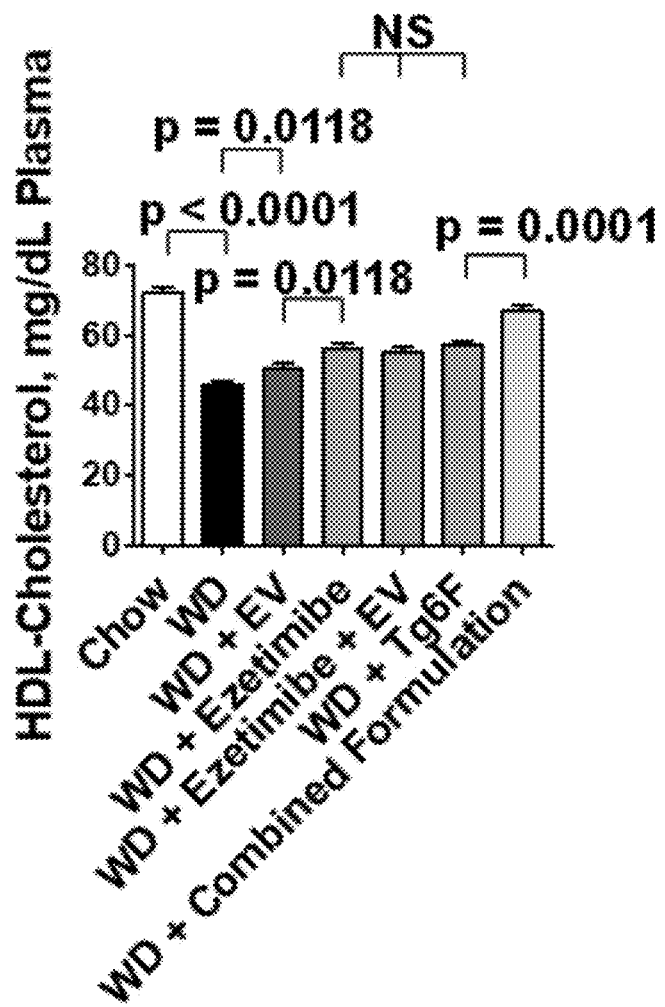
Fig. 16, cont'd.

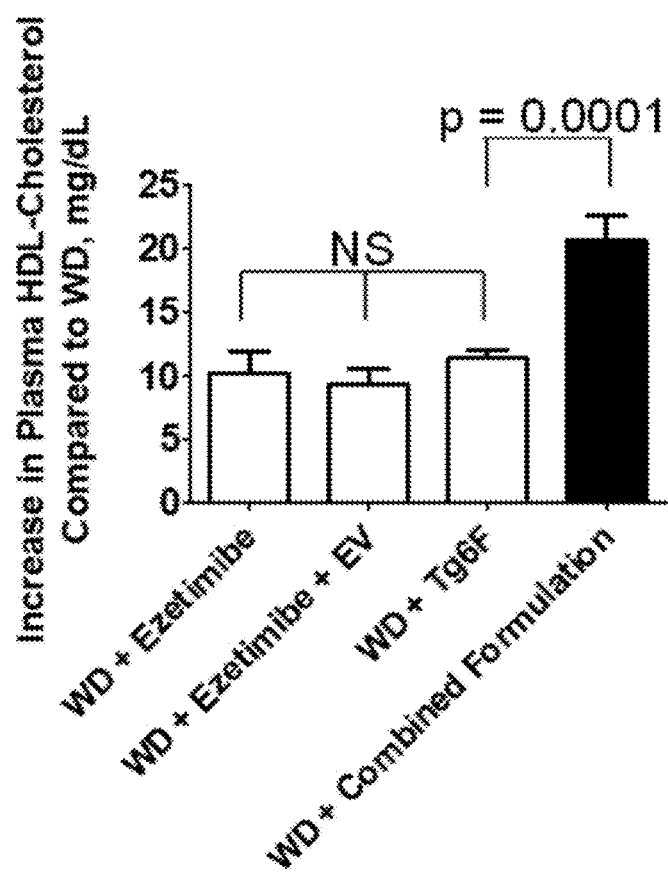
*Fig. 16, cont'd.*

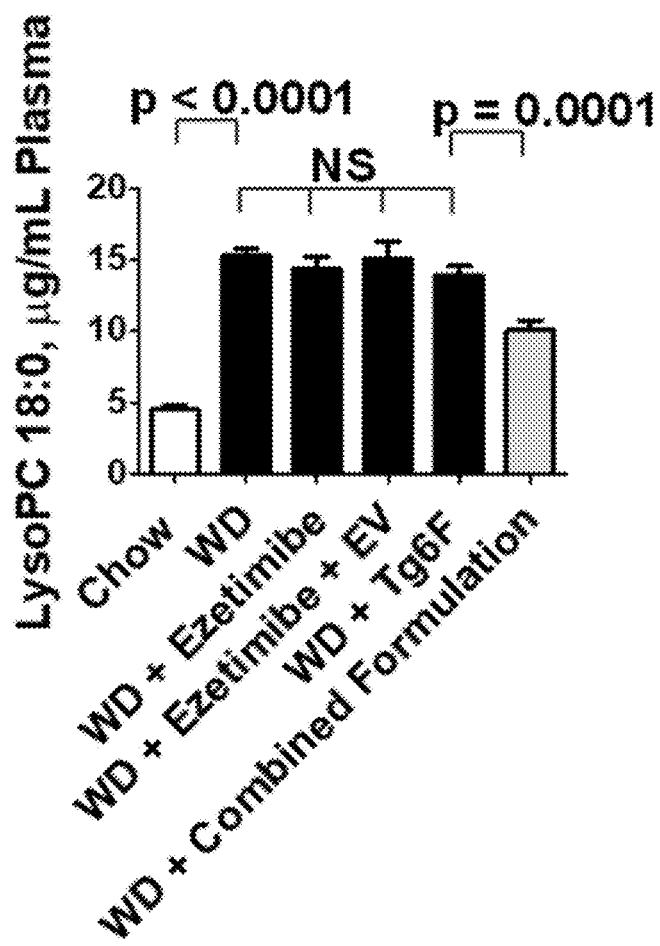
Fig. 16, cont'd.

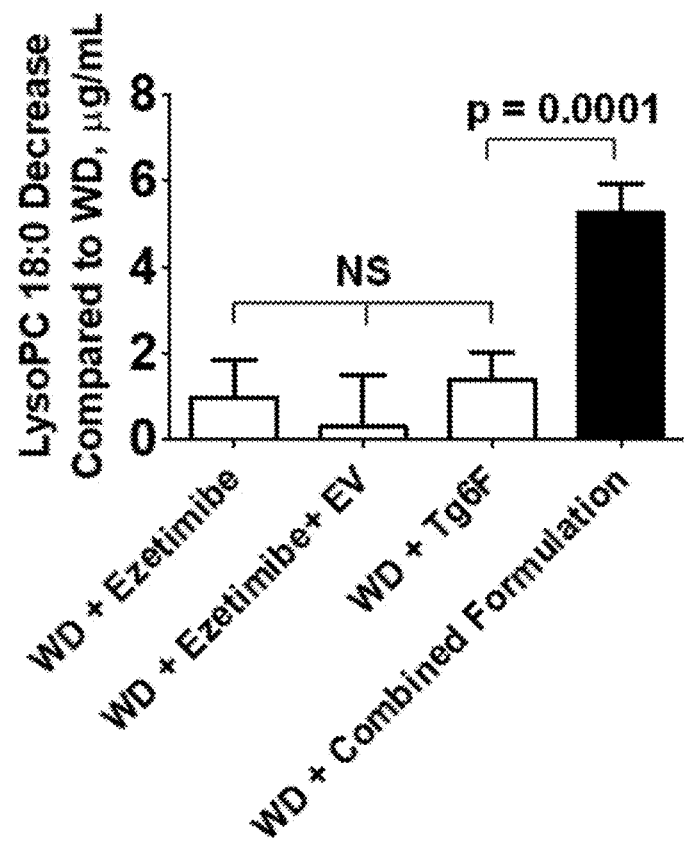
*Fig. 16, cont'd.*

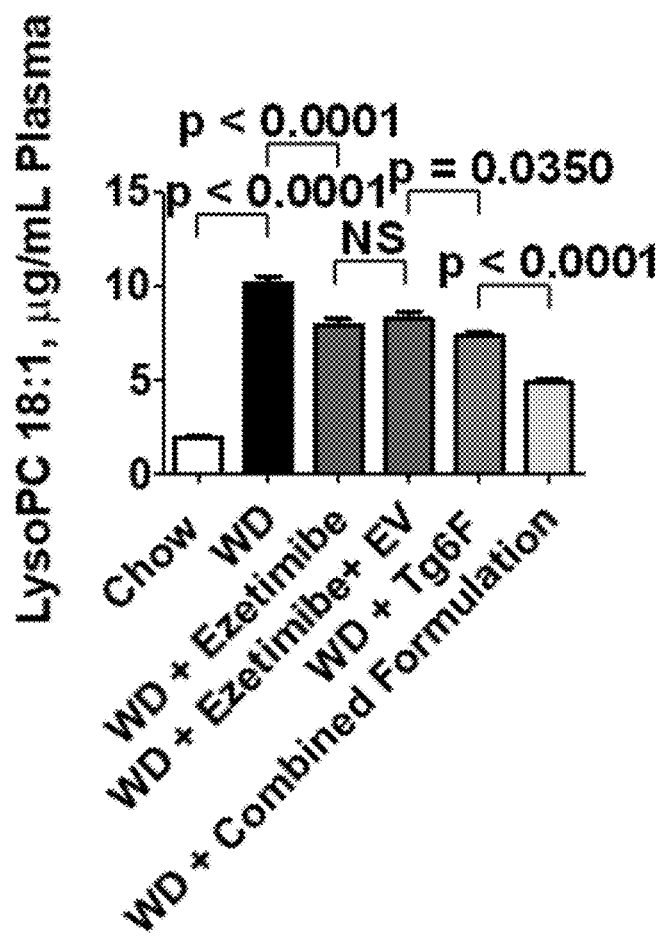
*Fig. 16, cont'd.*

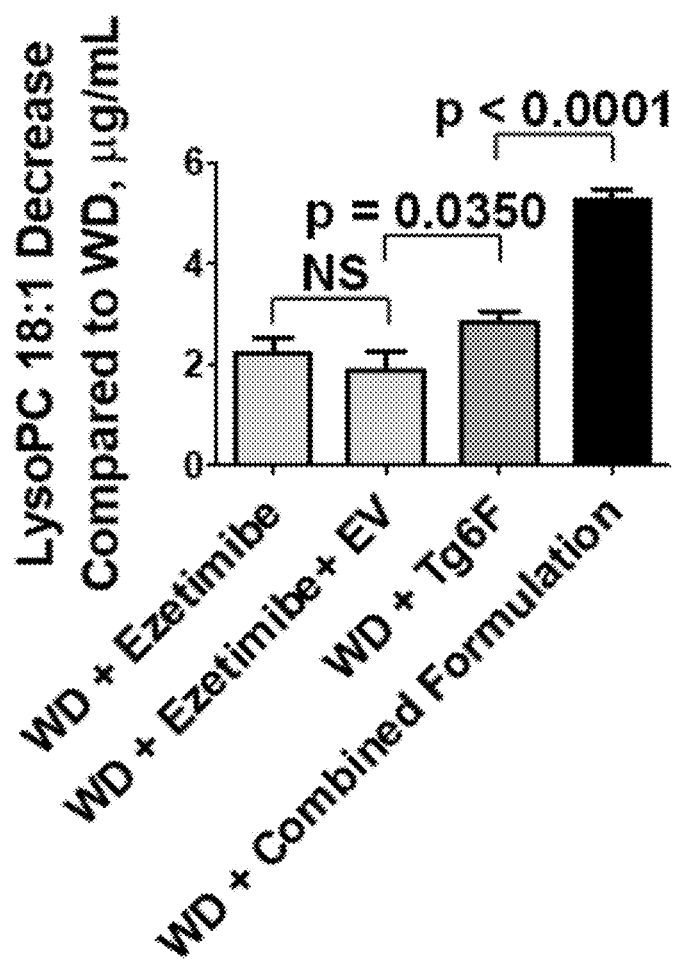
*Fig. 16, cont'd.*

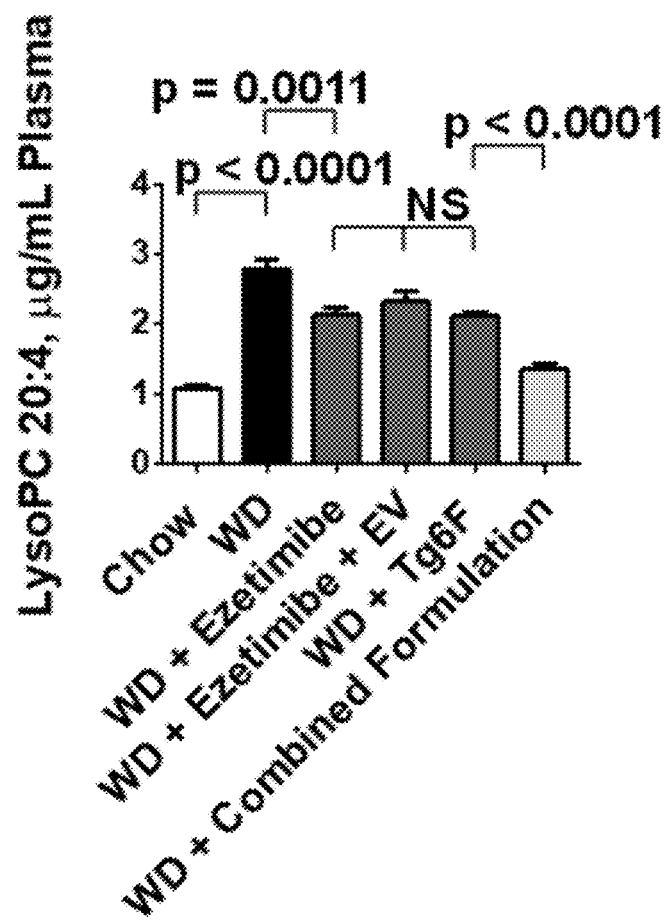
Fig. 16, cont'd.

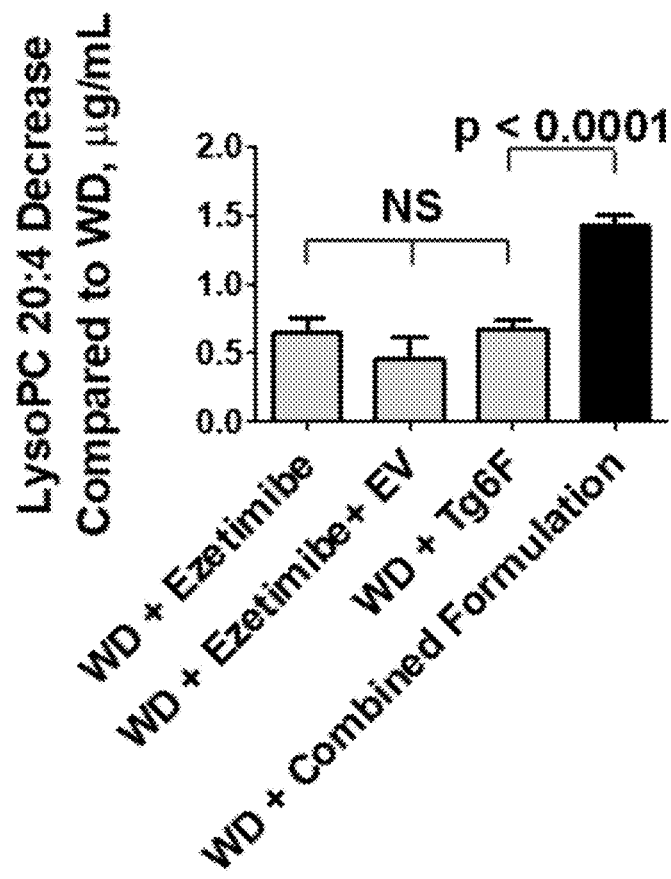
*Fig. 16, cont'd.*

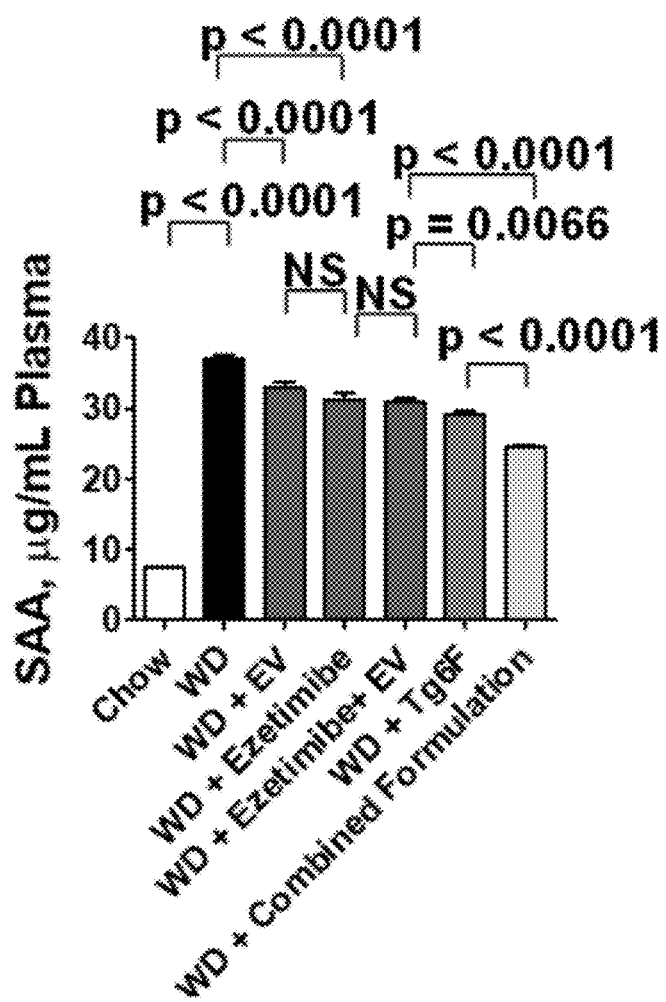
*Fig. 16, cont'd.*

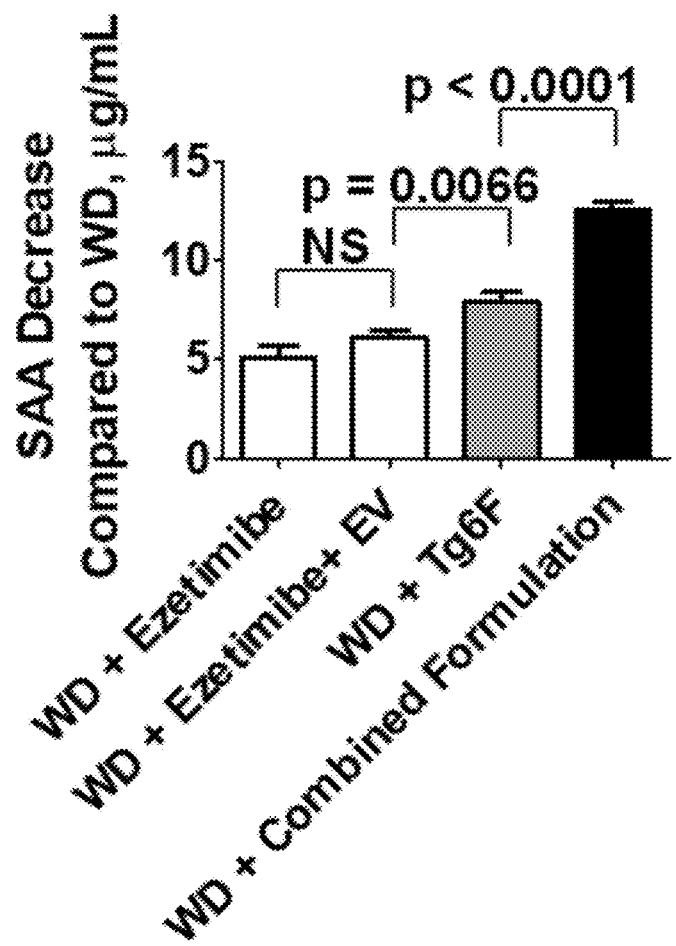
*Fig. 16, cont'd.*

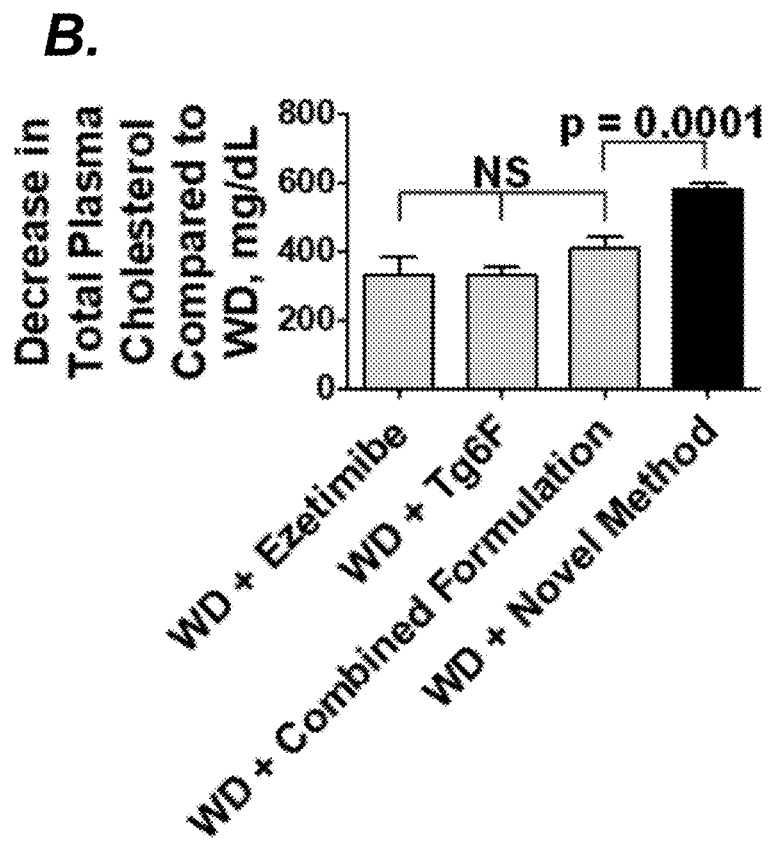
*Fig. 17, cont'd.*

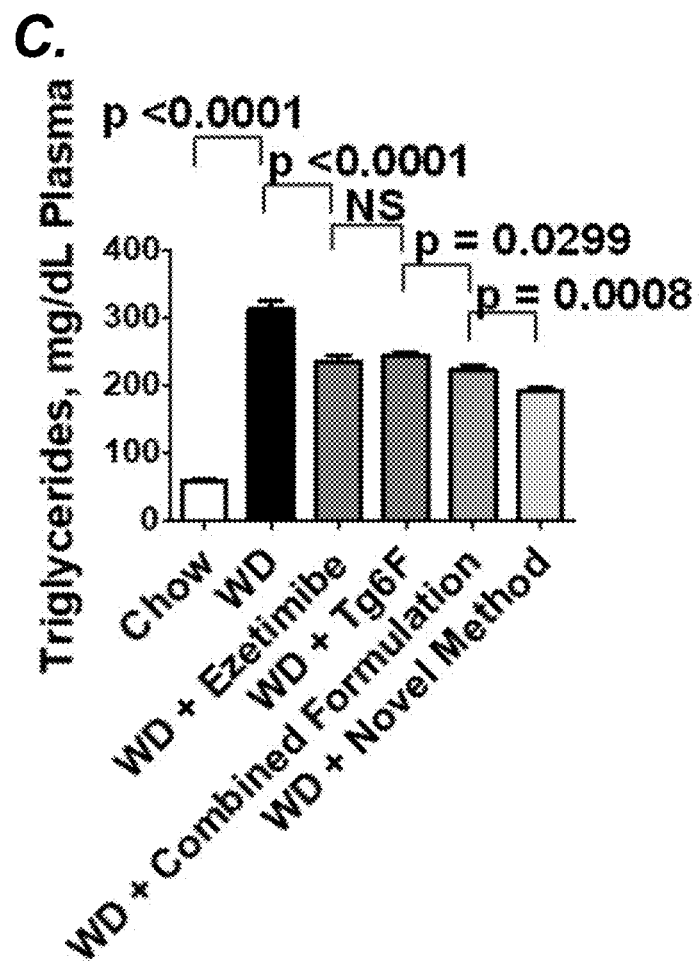
*Fig. 17, cont'd.*

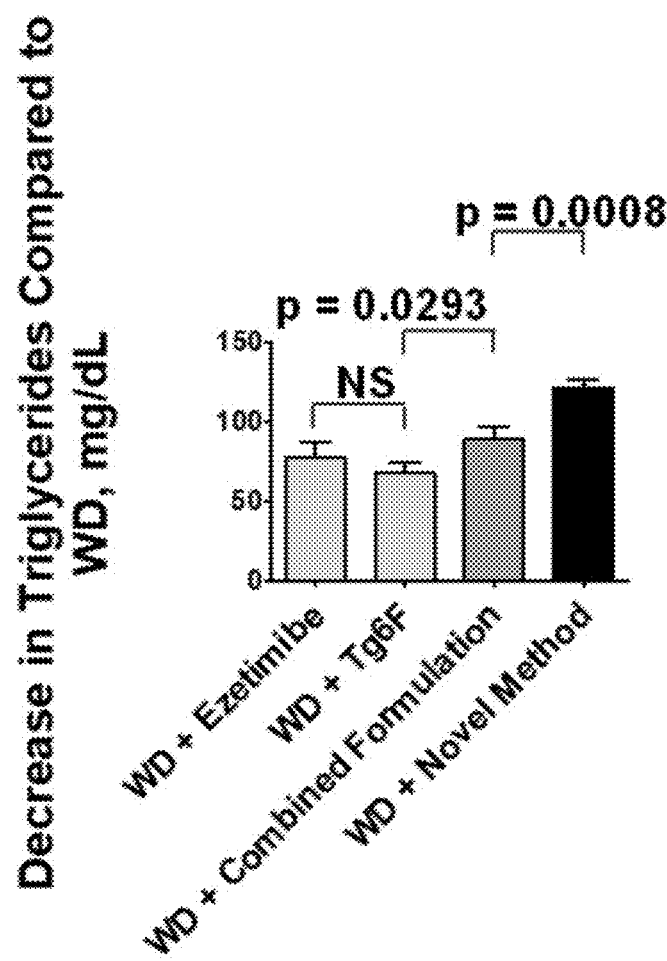
Fig. 17, cont'd.

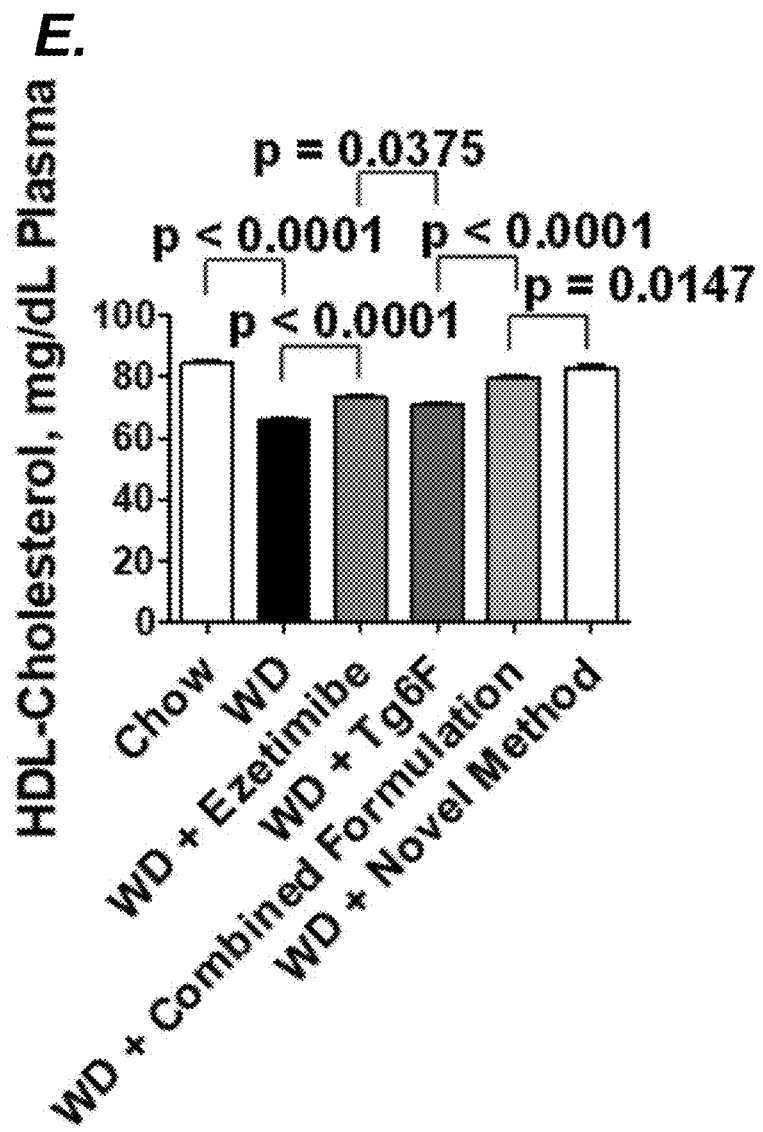
*Fig. 17, cont'd.*

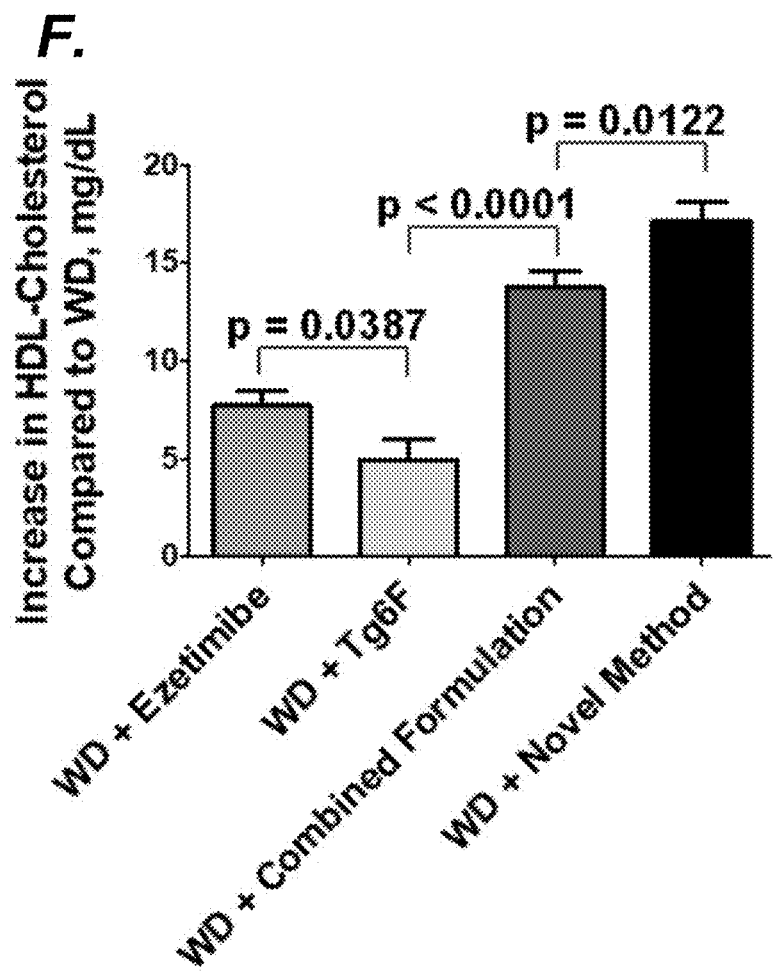
*Fig. 17, cont'd.*

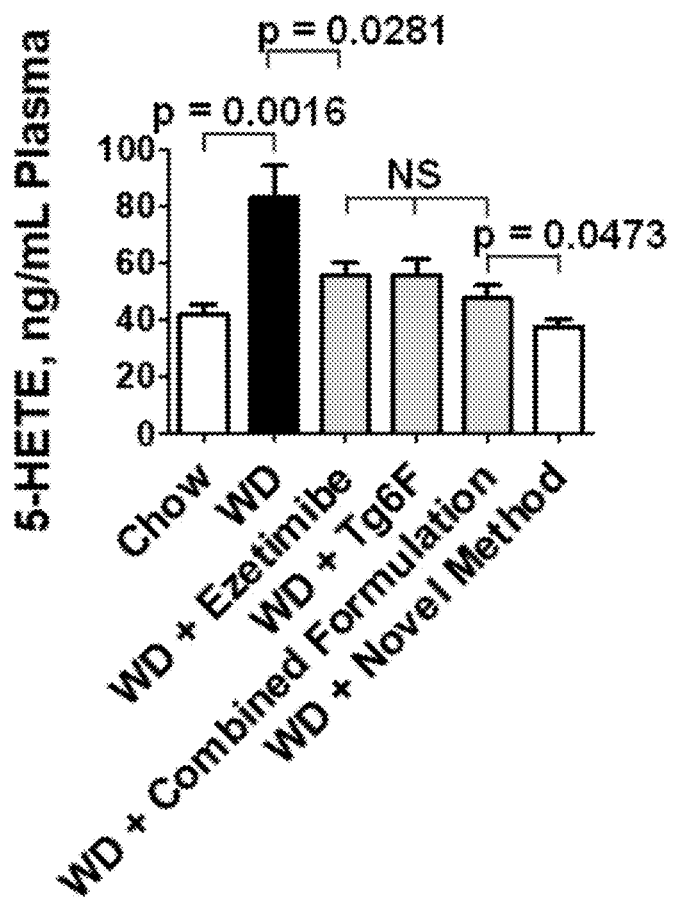
Fig. 17, cont'd.

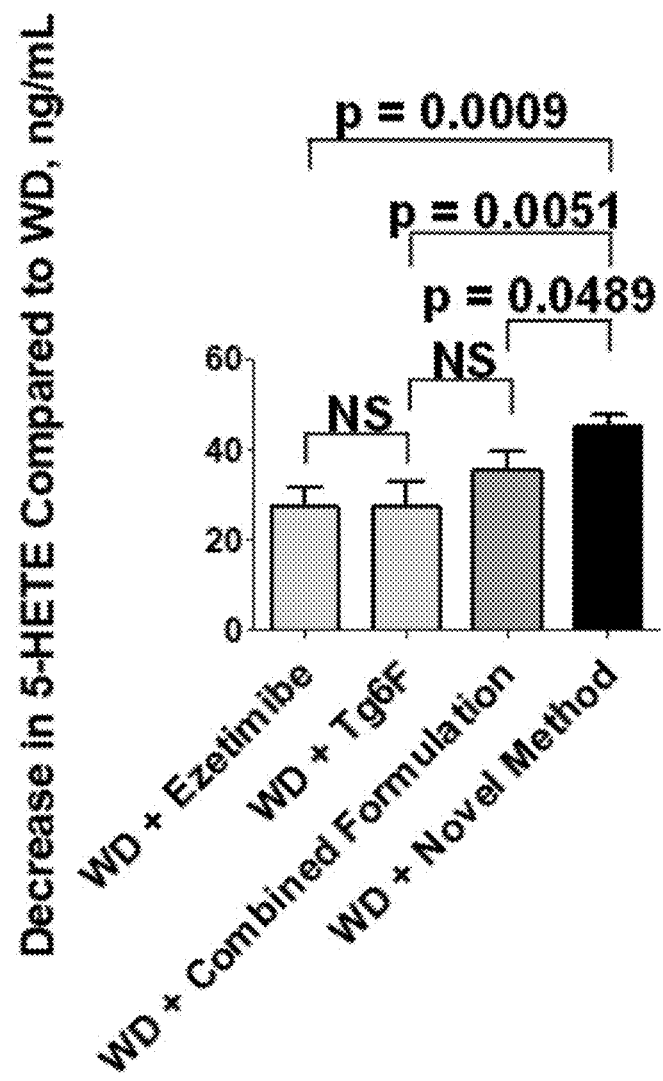
Fig. 17, cont'd.

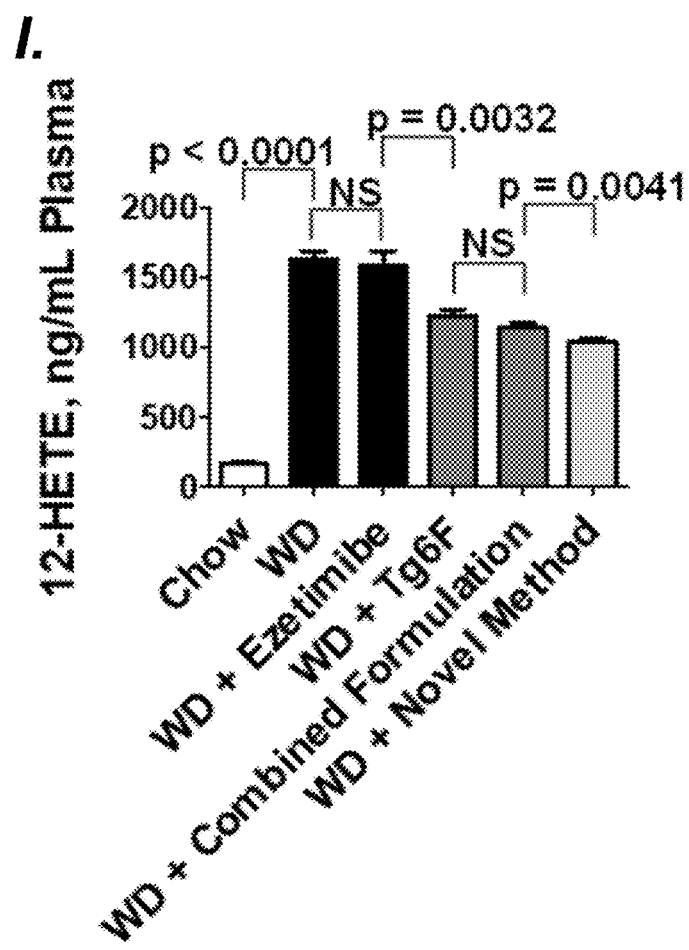
*Fig. 17, cont'd.*

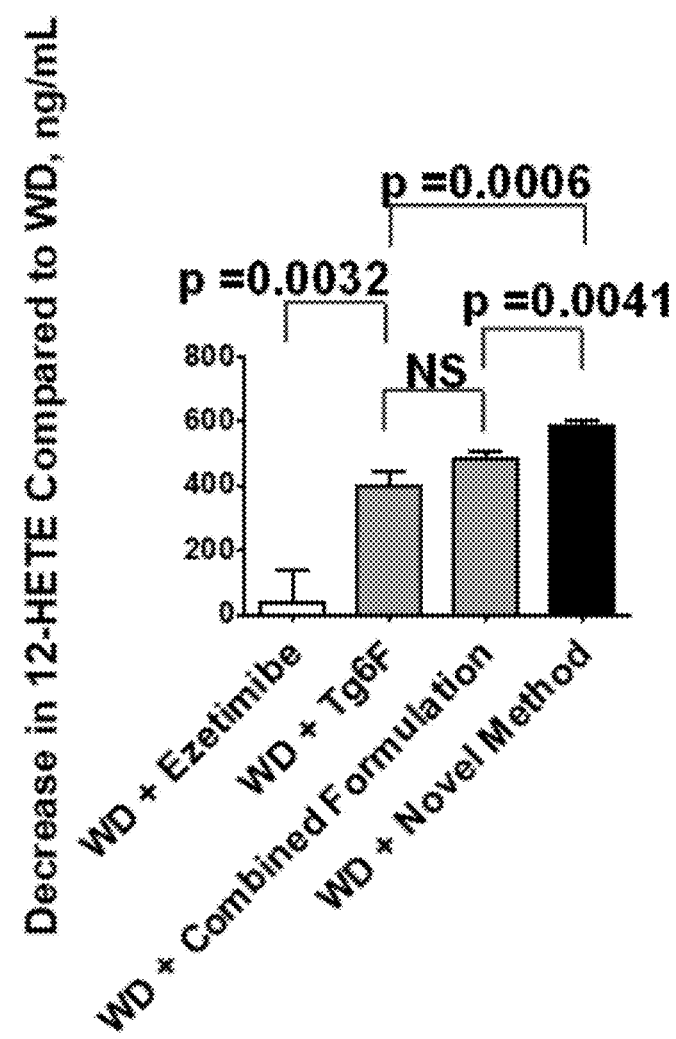
Fig. 17, cont'd.

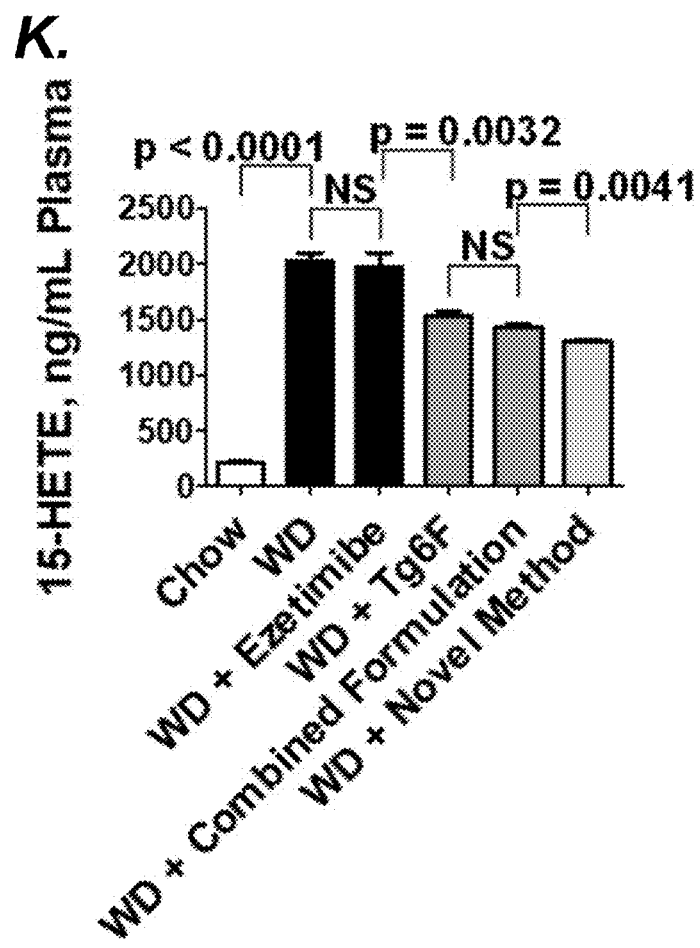
*Fig. 17, cont'd.*

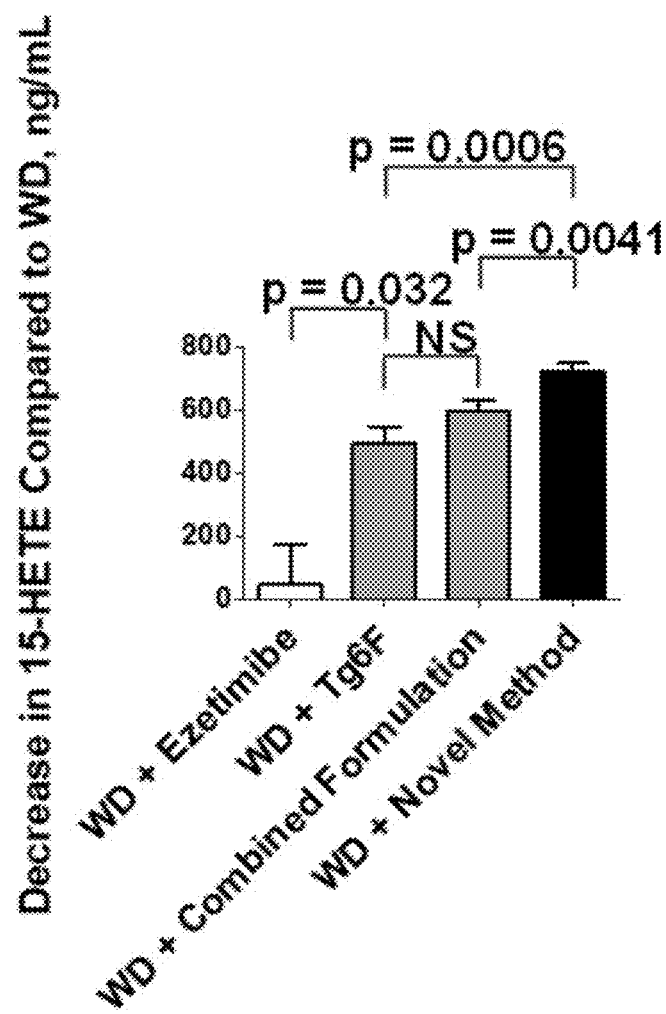
Fig. 17, cont'd.

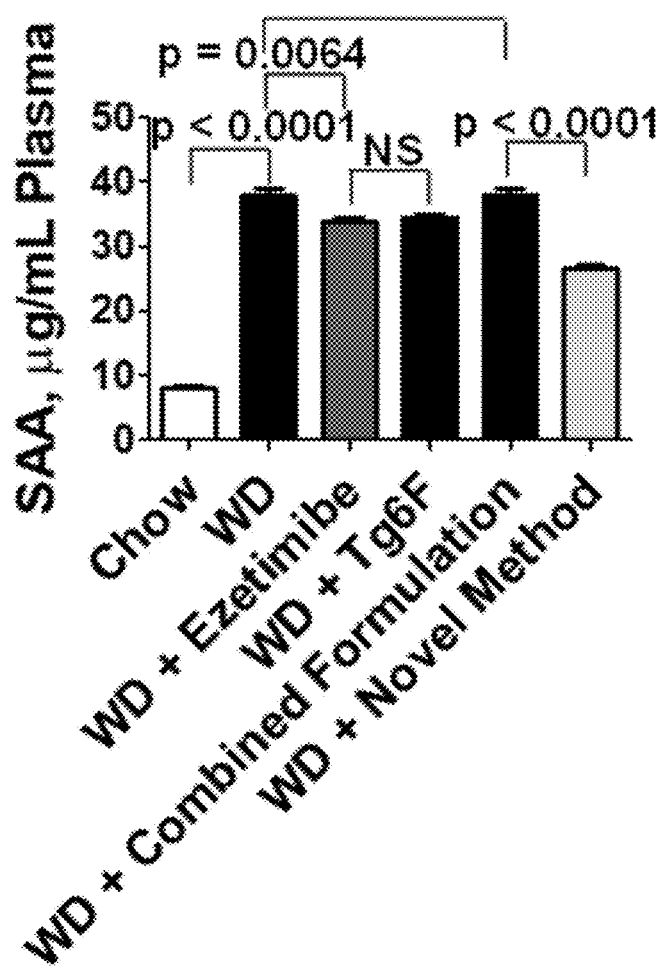
Fig. 17, cont'd.

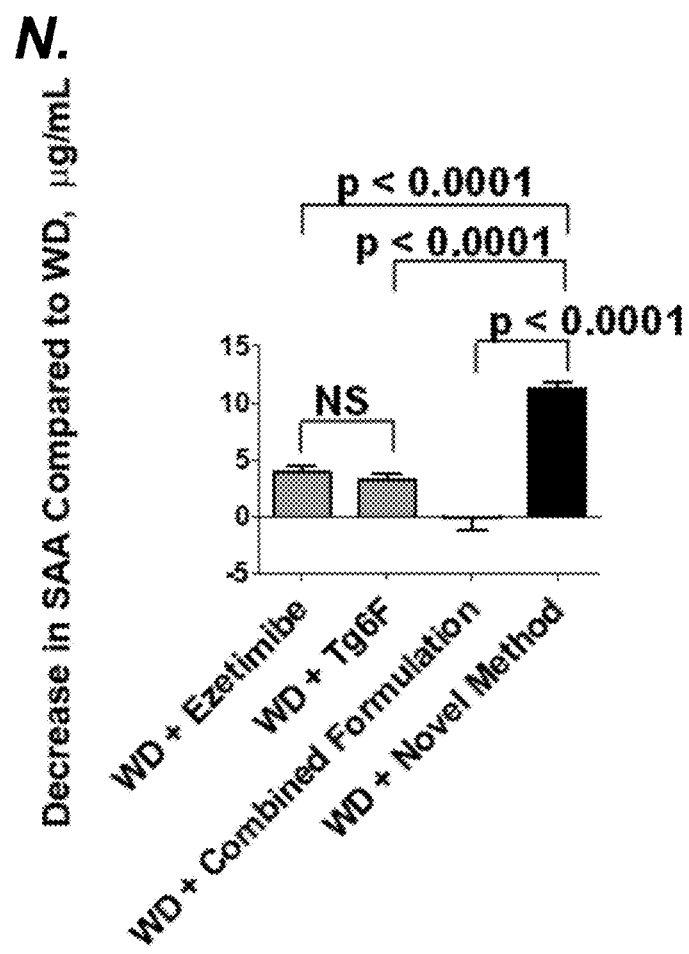
Fig. 17, cont'd.

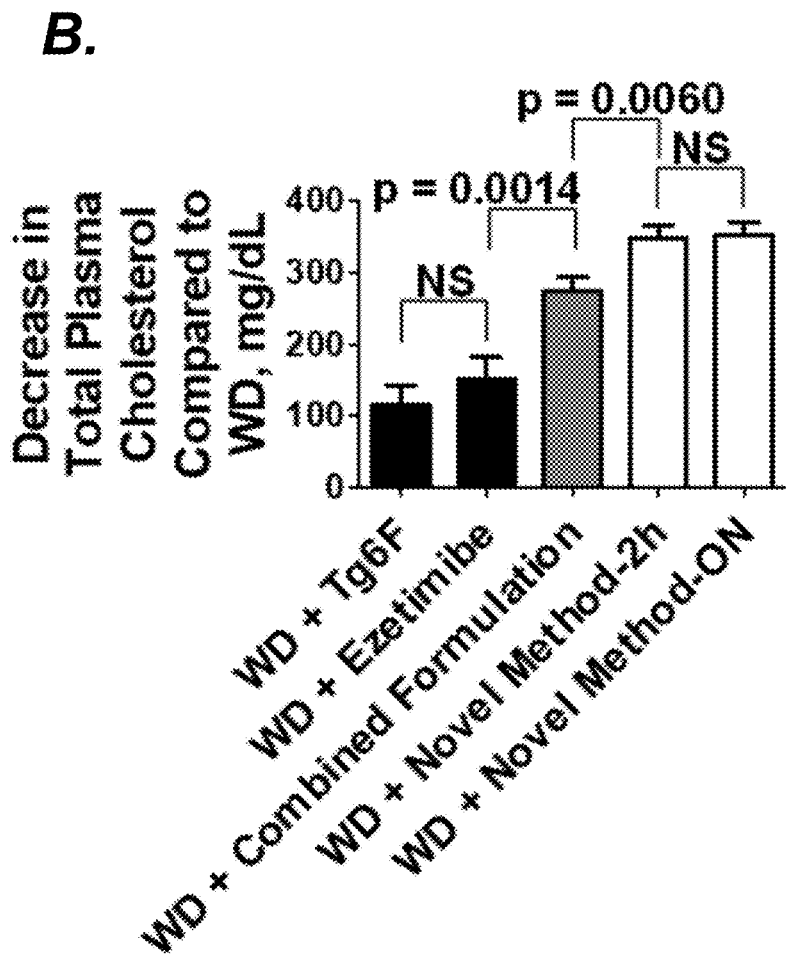
*Fig. 18, cont'd.*

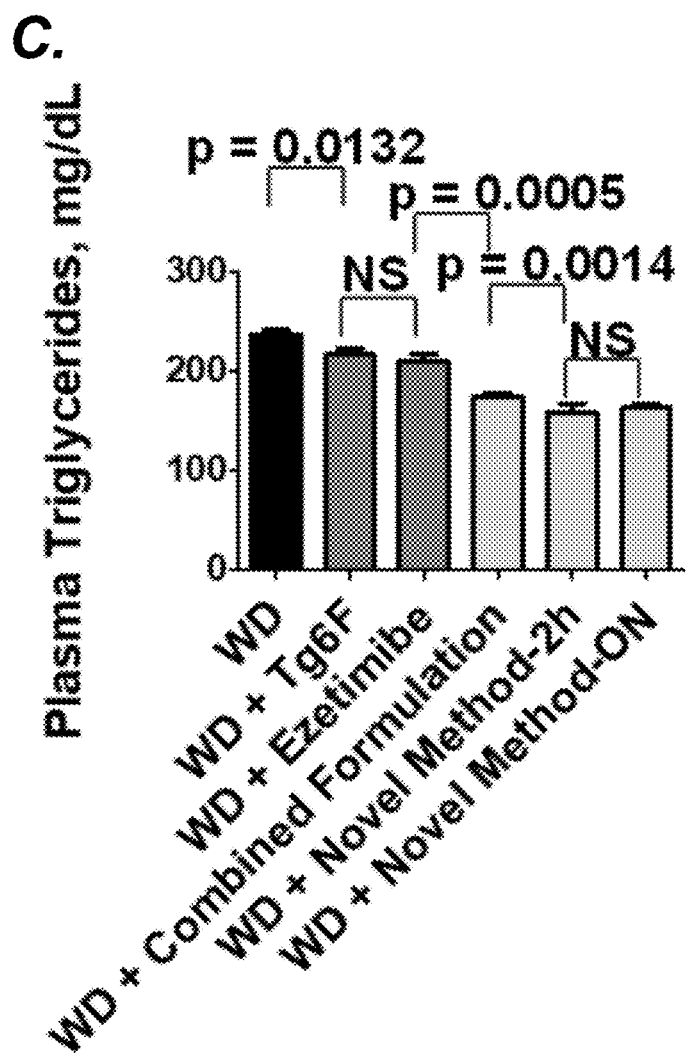
Fig. 18, cont'd.

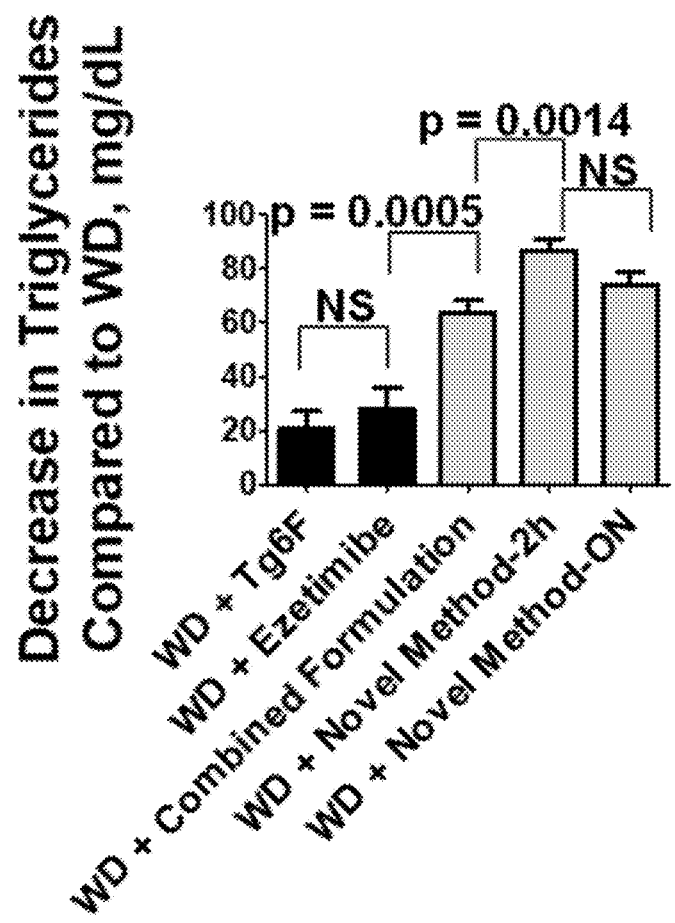
*Fig. 18, cont'd.*

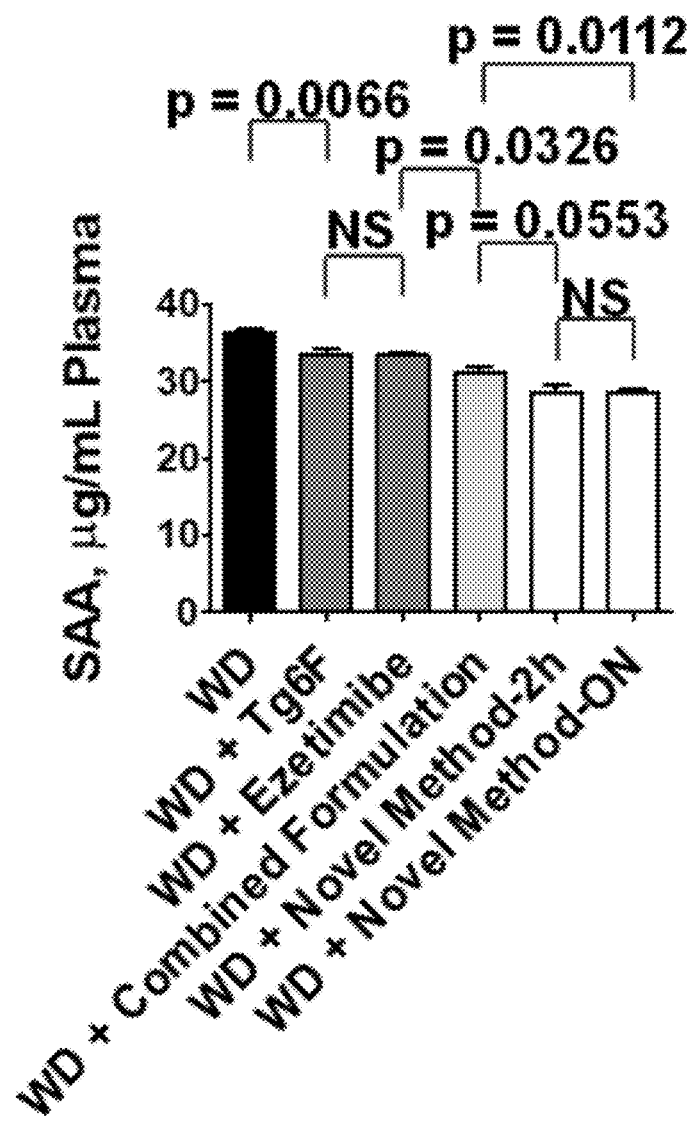
Fig. 18, cont'd.

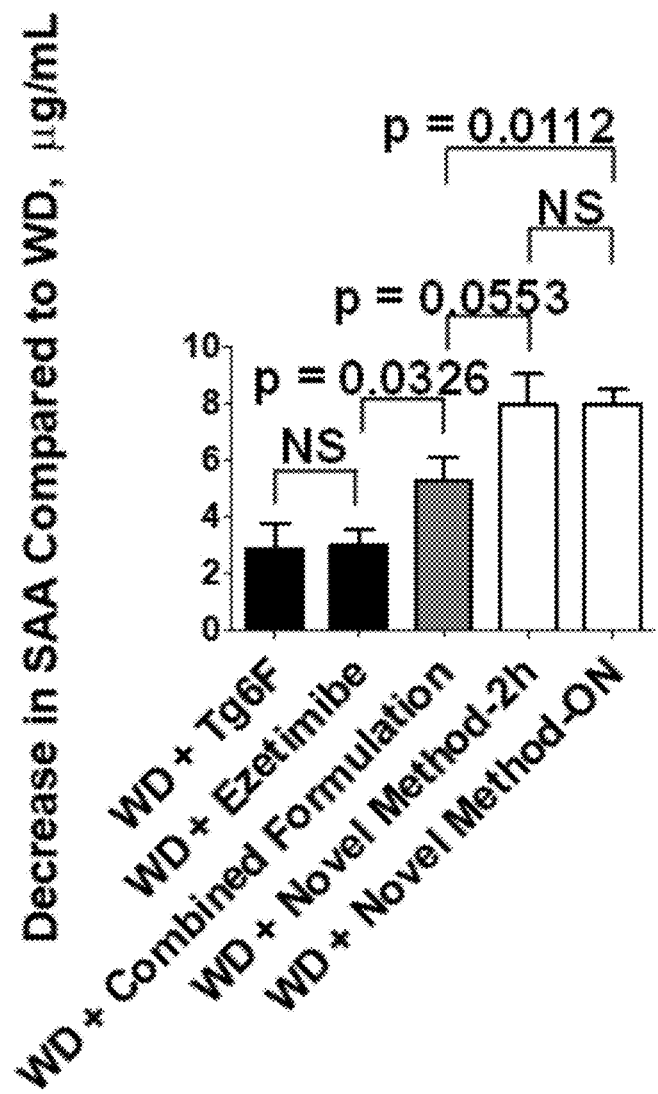
*Fig. 18, cont'd.*

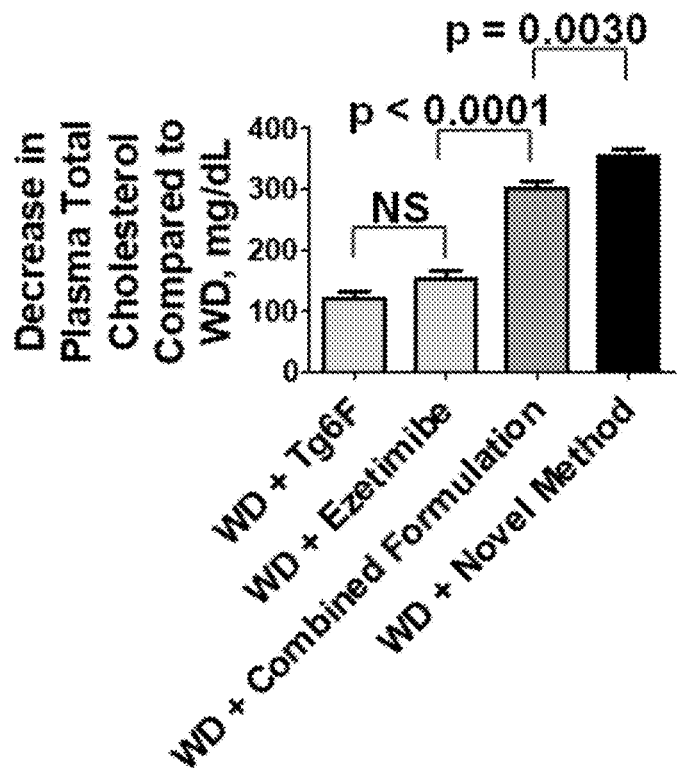
*Fig. 19, cont'd.*

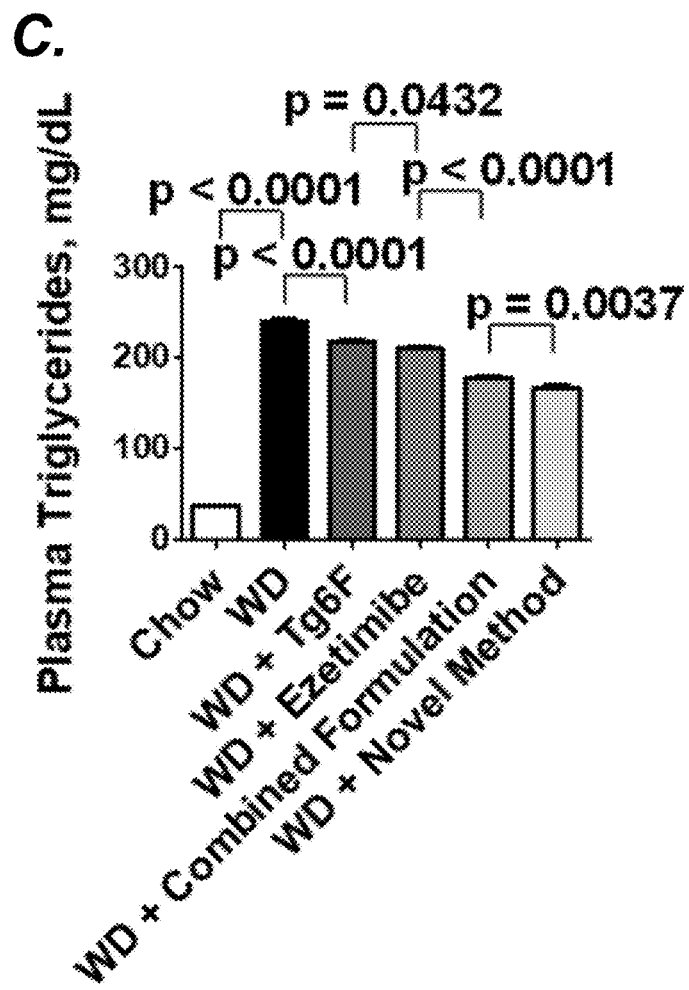
Fig. 19, cont'd.

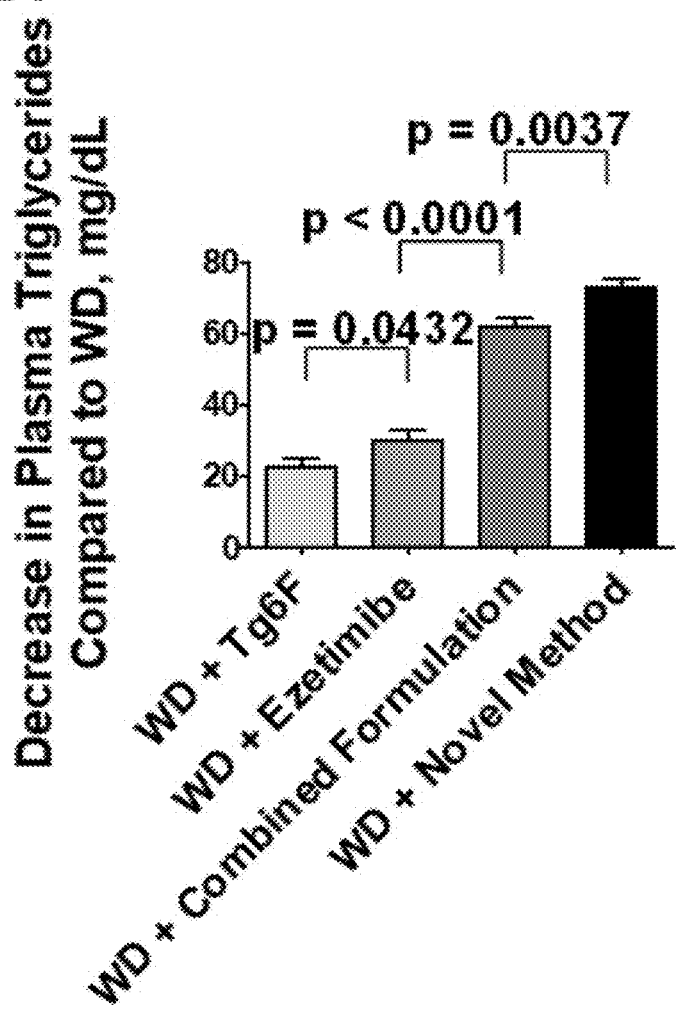
Fig. 19, cont'd.

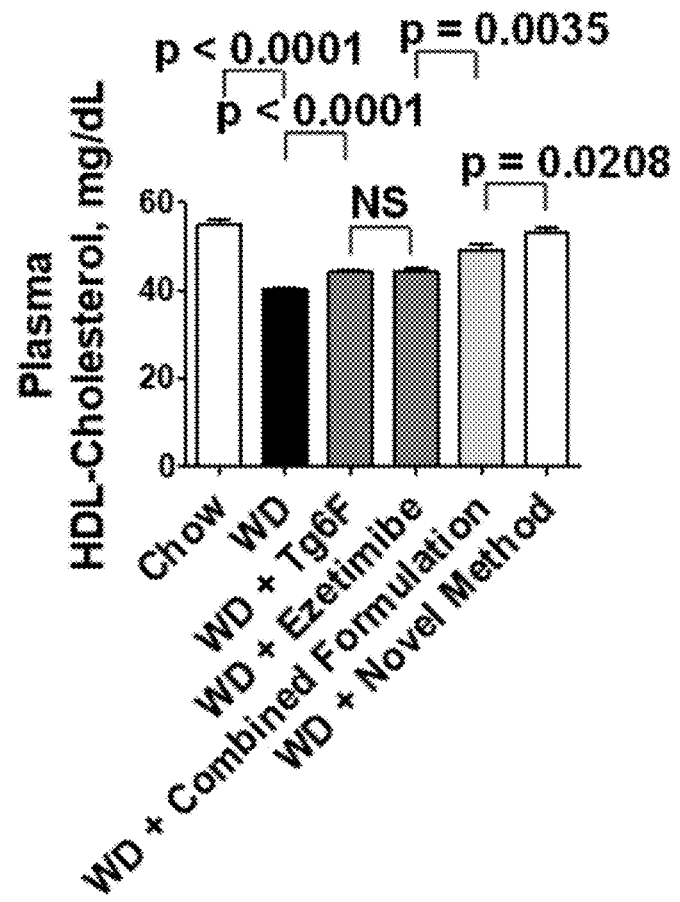
Fig. 19, cont'd.

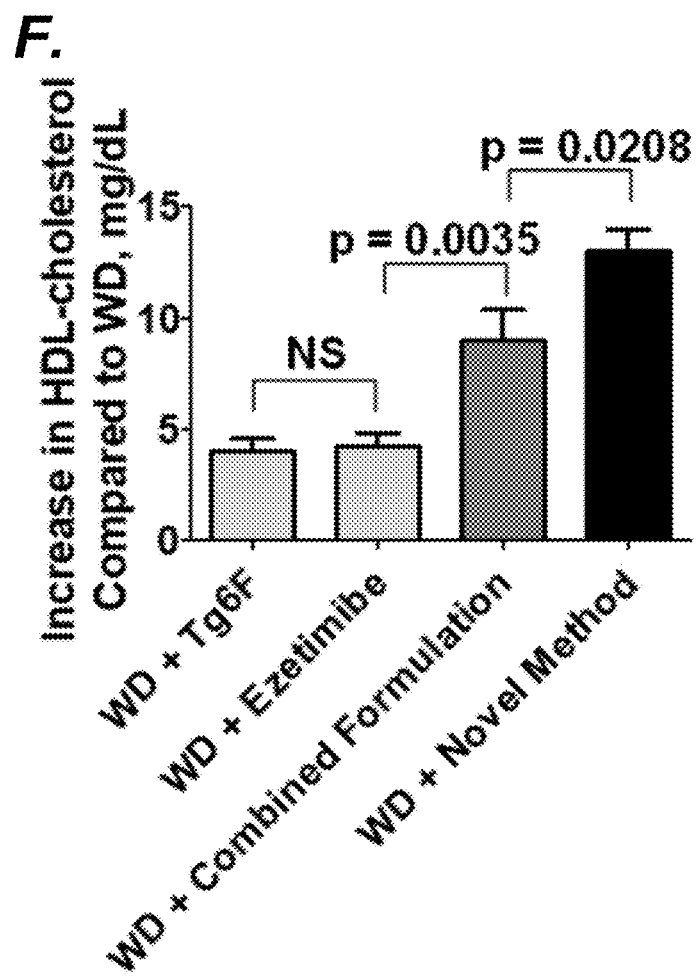
Fig. 19, cont'd.

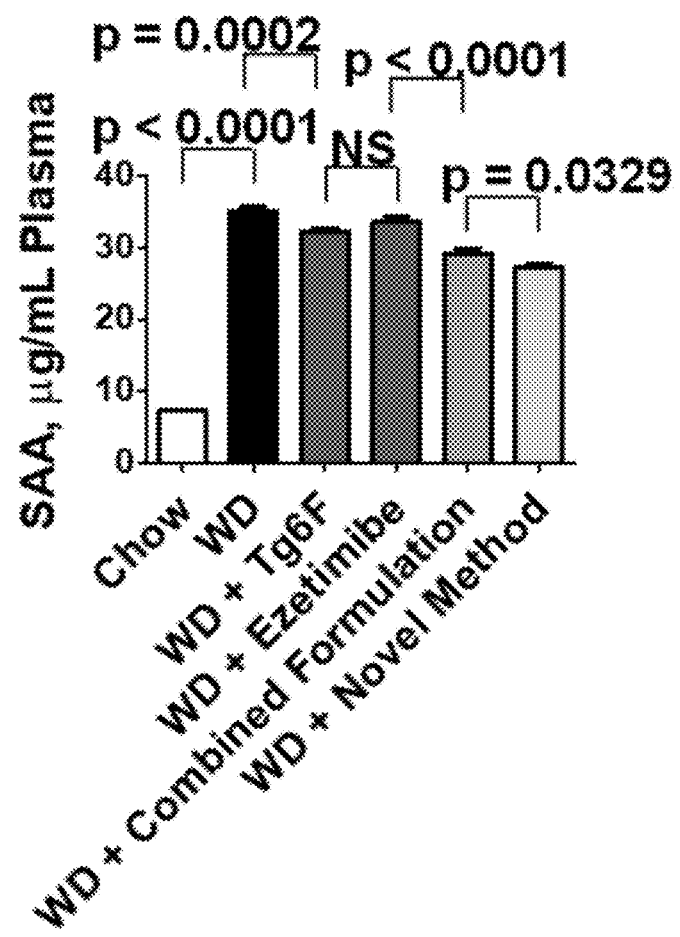
Fig. 19, cont'd.

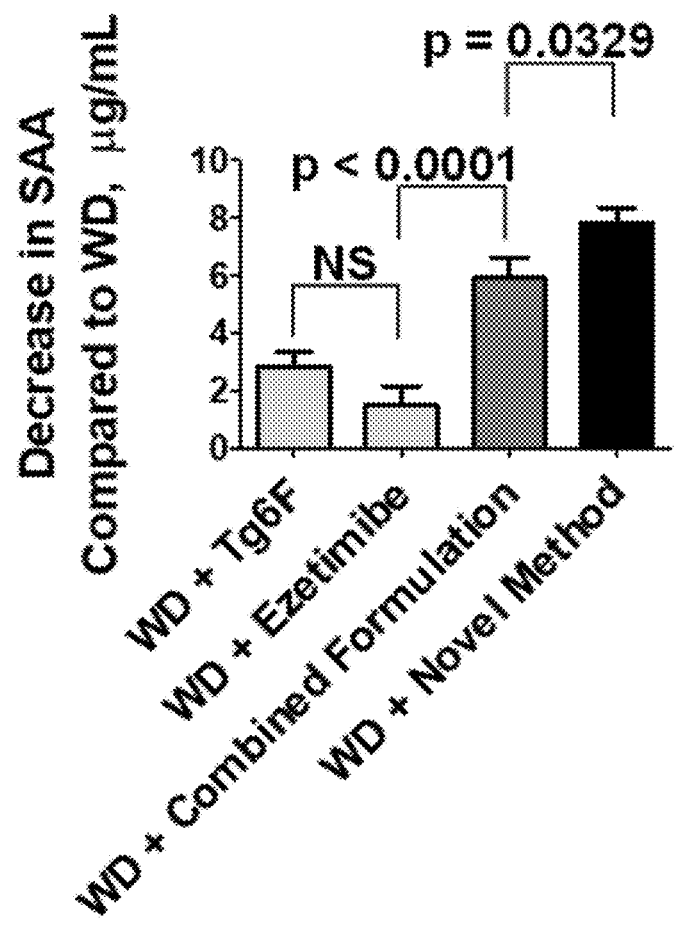
Fig. 19, cont'd.

EZETIMIBE-ASSOCIATED APOA-I MIMETIC PEPTIDES SHOWING ENHANCED SYNERGISM

CROSS-REFERENCE TO RELATED APPLICATIONS

This application claims benefit of and priority to U.S. Ser. No. 62/401,102, filed on Sep. 28, 2016, which is incorporated herein by reference in its entirety for all purposes.

STATEMENT OF GOVERNMENTAL SUPPORT

This invention was made with Government support under HL030568, awarded by the National Institutes of Health. The Government has certain rights in the invention.

INCORPORATION OF SEQUENCE LISTING

Incorporated herein by reference in its entirety is the Sequence Listing for the application. The Sequence Listing is disclosed on a computer-readable ASCII text file titled, "UCLA-P174US_ST25.txt", created on Dec. 4, 2017. The sequence listing text file is 169 kb in size.

BACKGROUND

Mimetics of apolipoprotein A-I (apoA-I) containing only 18 amino acids showed promise in animal models of disease (Getz and Reardon (2011) *J Inflamm. Res.* 4: 83-92; Navab et al. (2012) *Arterioscler. Thromb. Vasc. Biol.* 32: 2553-2560), and improved HDL function in humans when given orally at high doses despite achieving low plasma peptide levels (Bloedon (2008) *J. Lipid Res.* 49: 1344-1352). However, when high plasma levels were achieved with low doses of peptide given intravenously or by subcutaneous (SQ) injection, no improvement in HDL function was seen (Watson et al. (2011) *J. Lipid Res.* 52: 361-373). Studies in mice indicated that the major site of action for these peptides is in the intestine and that a high dose of peptide is required for efficacy (Navab et al. (2011) *J. Lipid Res.* 52: 1200-1210; Navab et al. (2012) *J. Lipid Res.* 53: 437-445).

The high dose requirement provides a barrier to use in humans because of the cost of chemically synthesizing these peptides. To overcome this barrier an 18 amino acid peptide (6F peptide, DWLKAFYDKFFEKFKEFF (SEQ ID NO:1) was transgenically expressed in tomatoes (Chattopadhyay et al. (2013) *J. Lipid Res.* 54: 995-1010). Feeding LDL receptor-null (LDLR$^{-/-}$) mice a Western diet (WD) for 13 weeks containing 2.2% by weight of freeze dried tomato powder made from transgenic tomatoes expressing the apoA-I mimetic peptide 6F (Tg6F) reduced plasma serum amyloid A (SAA) levels, reduced plasma total cholesterol levels, reduced plasma triglyceride levels, reduced plasma unsaturated (but not saturated) lysophosphatidic acid (LPA) levels, increased plasma paraoxonase-1 activity, increased plasma HDL-cholesterol levels, and decreased the extent of aortic atherosclerosis by about 50% (Chattopadhyay et al. (2013) *J. Lipid Res.* 54: 995-1010; Getz and Reardon (2013) *J. Lipid Res.* 54: 878-880).

Two hours after LDLR$^{-/-}$ mice finished eating WD containing Tg6F, intact 6F peptide was found in the small intestine but not in the plasma (Chattopadhyay et al. (2013) *J. Lipid Res.* 54: 995-1010). Plasma levels of unsaturated (but not saturated) LPA correlated with the extent of aortic atherosclerosis. The content of LPA in the tissue of the small intestine was found to decrease after feeding Tg6F and the level of LPA (but not cholesterol) in the tissue of the small intestine correlated with the extent of aortic atherosclerosis (Id.).

Without any purification steps, when the transgenic tomatoes expressing 6F peptide were freeze-dried, ground into powder and fed to a mouse model of dyslipidemia and atherosclerosis at only 2.2% of a high-fat high-cholesterol diet by weight, the transgenic tomatoes significantly reduced dyslipidemia, inflammation and atherosclerosis in the mice. This provided a daily dose of approximately 40 mg/kg/day.

SUMMARY

In various embodiments, novel ezetimibe-associated apoA-I mimetic peptides are provided as well as uses thereof. It was surprising discovery that an ezetimibe-associated ApoA-I mimetic peptide (Ez-ApoA-I pepide) could be produced by incubating ezeimibe and Tg6F peptide together in a solution comprising ethyl acetate with 5% acetic acid followed by removal of the ethyl acetate. Suprisingly, this resulted in a significantly more effective preparation. In particular the ezetimibe-associated ApoA-I mimetic peptide showed greater biological activity than equivalent amounts of ezetimibe and ApoA-I peptide when administered in a combined formulation.

Various embodiments contemplated herein may include, but need not be limited to, one or more of the following:

Embodiment 1

A method of preparing an ezetimibe-associated apoA-I mimetic peptide, said method comprising:
  incubating ezetimibe and said apoAI mimetic peptide in a solution comprising ethyl acetate and acetic acid or in a solution comprising ethyl lactate and lactic acid; and
  drying said solution to provide a dry ezetimibe-associated apoA-I mimetic peptide.

Embodiment 2

The method of embodiment 1, wherein said incubating comprising incubating 0.1:10 or 0.5:10 or 1:10, or 2:10 or 4:10 or 5:10, or 6:10, or 7:10, or 8:10, or 9:10, or 1:1 ezetimibe:Tg6F by weight.

Embodiment 3

The method of embodiment 1, wherein said incubating comprising incubating 1:10 ezetimibe:Tg6F by weight.

Embodiment 4

The method according to any one of embodiments 1-3, wherein said drying comprises:
  drying said solution to produce a dry residue; resuspending said residue in water to provide a resuspended mixture; and
  drying the resuspended mixture to provide a dry powder extract comprising ezetimibe-associated apoA-I mimetic peptide.

Embodiment 5

The method of embodiment 4, wherein said resuspending comprises re-suspending said residue in distilled water.

Embodiment 6

The method of embodiment 4, wherein said resuspending comprises re-suspending said residue in de-ionized water.

Embodiment 7

The method of embodiment 4, wherein said resuspending comprises re-suspending said residue in food-grade water.

Embodiment 8

The method according to any one of embodiments 4-7, wherein said drying the resuspended mixture comprises lyophilizing said mixture to provide said dry powder extract.

Embodiment 9

The method according to any one of embodiments 1-8, wherein the incubating peptide with ezetimibe is for at least about 10 minutes, or at least about 15 minutes, or at least about 30 minutes, or at least about 45 minutes, or at least about 1 hr, or at least about 1.5 hour, or at least about 2 hrs, or at least about 3 hrs, or at least about 4 hrs, or at least about 5 hours, or at least about 6 hrs, or at least about 12 hours, or at least about 1 day.

Embodiment 10

The method according to any one of embodiments 1-8, wherein said incubating is for about 2 hrs.

Embodiment 11

The method according to any one of embodiments 1-10, wherein said incubating is at room temperature.

Embodiment 12

The method according to any one of embodiments 1-11, wherein said incubating comprises incubating said ezetimibe and said apoAI mimetic peptide in a solution comprising ethyl acetate and acetic acid.

Embodiment 13

The method of embodiment 12, wherein said solution comprises about 1% to about 25% acetic acid, or about 2% to about 20% acetic acid, or about 3% to about 15% acetic acid, or about 4% to about 10% acetic acid, or about 4% to about 8% acetic acid, or from about 4% to about 6% acetic acid.

Embodiment 14

The method of embodiment 13, wherein said solution comprises about 5% acetic acid.

Embodiment 15

The method according to any one of embodiments 1-11, wherein said incubating comprises incubating said ezetimibe and said apoAI mimetic peptide in a solution comprising ethyl lactate and lactic acid.

Embodiment 16

The method of embodiment 15, wherein said solution comprises about 1% to about 25% lactic acid, or about 2% to about 20% lactic acid, or about 3% to about 15% lactic acid, or about 4% to about 10% lactic acid, or about 4% to about 8% lactic acid, or from about 4% to about 6% lactic acid.

Embodiment 17

The method of embodiment 15, wherein said solution comprises about 5% lactic acid.

Embodiment 18

The method according to any one of embodiments 1-17, wherein said apoA-I mimetic peptide is a chemically synthesized peptide.

Embodiment 19

The method according to any one of embodiments 1-17, wherein said apoA-I mimetic peptide is a peptide recombinantly expressed in a plant cell.

Embodiment 20

The method of embodiment 19, wherein said apoA-I mimetic peptide is provided as a tissue of a transgenic plant wherein said tissue contains a heterologous ApoA-I mimetic peptide expressed by said plant.

Embodiment 21

The method of embodiment 20, wherein:
said tissue is provided as a substantially dry powder;
said powder is mixed with said solution comprising ethyl acetate and acetic acid or with said solution comprising ethyl lactate and lactic acid, to form an extraction mixture; and
said extraction mixture is incubated before addition of said ezetimibe.

Embodiment 22

The method of embodiment 21, wherein said extraction mixture is incubated for at least about 15 minutes, or at least about ½ hour, or at least about 1 hour, or at least about 2 hours, or at least about 3 hours, or at least about 4 hours, or at least about 5 hours, or at least about 6 hours, or at least about 7 hours, or at least about 12 hours, or at least about 18 hours, or at least about 24 hours, or at least about 48 hours, or at least about 72 hours, or at least about 96 hours.

Embodiment 23

The method of embodiment 21, wherein said extraction mixture is incubated overnight.

Embodiment 24

The method according to any one of embodiments 20-23, wherein, wherein said providing tissue comprises providing said tissue as a freeze-dried powder.

Embodiment 25

The method according to any one of embodiments 20-24, wherein said tissue of a transgenic plant comprises tissue of a tomato plant.

Embodiment 26

The method of embodiment 25, wherein said tissue of transgenic plant comprises a tomato fruit.

Embodiment 27

The method according to any one of embodiments 20-24, wherein said tissue of a transgenic plant comprises tissue of a plant selected from the group consisting of tomatoes, carrots, potatoes, apples, pears, plums, peaches, oranges, kiwis, papayas, pineapples, guava, lilikoi, starfruit, lychee, mango, grape, pomegranate, mustard greens, kale, chard, lettuce, soybean, rice, corn and other grains (e.g., wheat, rice, barley, bulgur, faro, kamut, kaniwa, millet, oats, quinoa, rice, rye, sorghum, spelt, teff, triticale, and the like), berries such as strawberries, blueberries, blackberries, goji berries, and raspberries, banana, rice, turnip, maize, grape, fig, plum, potato, safflower seeds, nuts (e.g., almond, walnut, pecan, peanut, cashew, macadamia, hazelnut, etc.), legumes (e.g., alfalfa, clover, peas, beans (including black beans), lentils, lupins, mesquite, carob, soybeans, and the like).

Embodiment 28

The method according to any one of embodiments 20-27, wherein said peptide is expressed under the control of a CaMV promoter, or under the control of an E8 promoter, or under the control of an E4/E8 hybrid promoter.

Embodiment 29

The method according to any one of embodiments 20-28, wherein said ApoA-I mimetic peptide comprises the amino acid sequence

```
(6F)                      (SEQ ID NO: 1)
    DWLKAFYDKFFEKFKEFF.
```

Embodiment 30

The method according to any one of embodiments 20-28, wherein said ApoA-I mimetic peptide comprises the amino acid sequence

```
(rev6F)                   (SEQ ID NO: 15)
    FFEKFKEFFKDYFAKLWD.
```

Embodiment 31

The method according to any one of embodiments 20-28, wherein said ApoA-I mimetic peptide comprises the amino acid sequence

```
(4F)                      (SEQ ID NO: 6)
    DWFKAFYDKVAEKFKEAF.
```

Embodiment 32

The method according to any one of embodiments 20-28, wherein said ApoA-I mimetic peptide comprises the amino acid sequence

```
(rev4F)                   (SEQ ID NO: 13)
    FAEKFKEAVKDYFAKFWD.
```

Embodiment 33

The method according to any one of embodiments 20-28, wherein said heterologous ApoA-I mimetic peptide comprises the amino acid sequence,

```
    LLEQLNEQFNWVSRLANL.
```

Embodiment 34

The method according to any one of embodiments 20-28, wherein said heterologous ApoA-I mimetic peptide comprises the amino acid sequence

```
    LVGRQLEEFL.
```

Embodiment 35

The method according to any one of embodiments 20-28, wherein said ApoA-I mimetic peptide comprises an amino acid sequence selected from the group consisting of

```
                              (SEQ ID NO: 1)
DWLKAFYDKFFEKFKEFF, (SEQ ID NO: 2)
DWLKAFYDKVAEKLKEAF, (SEQ ID NO: 3)
DWLKAFYDKVAEKLKEAF, (SEQ ID NO: 4)
DWFKAFYDKVAEKLKEAF, (SEQ ID NO: 5)
DWLKAFYDKVAEKFKEAF, (SEQ ID NO: 6)
DWFKAFYDKVAEKFKEAF, (SEQ ID NO: 7)
DWLKAFYDKVFEKFKEFF, (SEQ ID NO: 1)
DWLKAFYDKFFEKFKEFF, (SEQ ID NO: 8)
DWFKAFYDKFFEKFKEFF, (SEQ ID NO: 9)
DWLKAFYDKVAEKLKEFF, (SEQ ID NO: 10)
FAEKLKEAVKDYFAKLWD, (SEQ ID NO: 11)
FAEKLKEAVKDYFAKLWD, (SEQ ID NO: 12)
FAEKLKEAVKDYFAKFWD, (SEQ ID NO: 13)
FAEKFKEAVKDYFAKFWD, (SEQ ID NO: 14)
FFEKFKEFVKDYFAKLWD,
```

```
FFEKFKEFFKDYFAKLWD,                           (SEQ ID NO: 15)
FFEKFKEFFKDYFAKFWD,                           (SEQ ID NO: 16)
DWLKAFYDKVFEKFKEAF,                           (SEQ ID NO: 17)
DWLKAFYDKVFEKLKEFF,                           (SEQ ID NO: 18)
DWLKAFYDKVAEKFKEFF,                           (SEQ ID NO: 19)
DWLKAFYDKVFEKFKEFF,                           (SEQ ID NO: 20)
EWLKLFYEKVLEKFKEAF,                           (SEQ ID NO: 21)
EWLKAFYDKVAEKFKEAF,                           (SEQ ID NO: 22)
EWLKAFYDKVAEKLKEFF,                           (SEQ ID NO: 23)
EWLKAFYDKVFEKFKEAF,                           (SEQ ID NO: 24)
EWLKAFYDKVFEKLKEFF,                           (SEQ ID NO: 25)
EWLKAFYDKVAEKFKEFF,                           (SEQ ID NO: 26)
EWLKAFYDKVFEKFKEFF,                           (SEQ ID NO: 27)
AFYDKVAEKLKEAF,                               (SEQ ID NO: 28)
AFYDKVAEKFKEAF,                               (SEQ ID NO: 29)
AFYDKVAEKFKEAF,                               (SEQ ID NO: 30)
AFYDKFFEKFKEFF,                               (SEQ ID NO: 31)
AFYDKFFEKFKEFF,                               (SEQ ID NO: 32)
AFYDKVAEKFKEAF,                               (SEQ ID NO: 33)
AFYDKVAEKLKEFF,                               (SEQ ID NO: 34)
AFYDKVFEKFKEAF,                               (SEQ ID NO: 35)
AFYDKVFEKLKEFF,                               (SEQ ID NO: 36)
AFYDKVAEKFKEFF,                               (SEQ ID NO: 37)
KAFYDKVFEKFKEF,                               (SEQ ID NO: 38)
LFYEKVLEKFKEAF,                               (SEQ ID NO: 39)
AFYDKVAEKFKEAF,                               (SEQ ID NO: 40)
AFYDKVAEKLKEFF,                               (SEQ ID NO: 41)
AFYDKVFEKFKEAF,                               (SEQ ID NO: 42)
AFYDKVFEKLKEFF,                               (SEQ ID NO: 43)
AFYDKVAEKFKEFF,                               (SEQ ID NO: 44)
AFYDKVFEKFKEFF,                               (SEQ ID NO: 45)
DWLKALYDKVAEKLKEAL,                           (SEQ ID NO: 46)
DWFKAFYEKVAEKLKEFF,                           (SEQ ID NO: 47)
DWFKAFYEKFFEKFKEFF,                           (SEQ ID NO: 48)
EWLKALYEKVAEKLKEAL,                           (SEQ ID NO: 49)
EWLKAFYEKVAEKLKEAF,                           (SEQ ID NO: 50)
EWFKAFYEKVAEKLKEFF,                           (SEQ ID NO: 51)
EWLKAFYEKVFEKFKEFF,                           (SEQ ID NO: 52)
EWLKAFYEKFFEKFKEFF,                           (SEQ ID NO: 53)
EWFKAFYEKFFEKFKEFF,                           (SEQ ID NO: 54)
DFLKAWYDKVAEKLKEAW,                           (SEQ ID NO: 55)
EFLKAWYEKVAEKLKEAW,                           (SEQ ID NO: 56)
DFWKAWYDKVAEKLKEWW,                           (SEQ ID NO: 57)
EFWKAWYEKVAEKLKEWW,                           (SEQ ID NO: 58)
DKLKAFYDKVFEWAKEAF,                           (SEQ ID NO: 59)
DKWKAVYDKFAEAFKEFL,                           (SEQ ID NO: 60)
EKLKAFYEKVFEWAKEAF,                           (SEQ ID NO: 61)
EKWKAVYEKFAEAFKEFL,                           (SEQ ID NO: 62)
DWLKAFVDKFAEKFKEAY,                           (SEQ ID NO: 63)
EKWKAVYEKFAEAFKEFL,                           (SEQ ID NO: 64)
DWLKAFVYDKVFKLKEFF,                           (SEQ ID NO: 65)
EWLKAFVYEKVFKLKEFF,                           (SEQ ID NO: 66)
DWLRAFYDKVAEKLKEAF,                           (SEQ ID NO: 67)
EWLRAFYEKVAEKLKEAF,                           (SEQ ID NO: 68)
```

DWLKAFYDRVAEKLKEAF, (SEQ ID NO: 69)

EWLKAFYERVAEKLKEAF, (SEQ ID NO: 70)

DWLKAFYDKVAERLKEAF, (SEQ ID NO: 71)

EWLKAFYEKVAERLKEAF, (SEQ ID NO: 72)

DWLKAFYDKVAEKLREAF, (SEQ ID NO: 73)

EWLKAFYEKVAEKLREAF, (SEQ ID NO: 74)

DWLKAFYDRVAERLKEAF, (SEQ ID NO: 75)

EWLKAFYERVAERLKEAF, (SEQ ID NO: 76)

DWLRAFYDKVAEKLREAF, (SEQ ID NO: 77)

EWLRAFYEKVAEKLREAF, (SEQ ID NO: 78)

DWLRAFYDRVAEKLKEAF, (SEQ ID NO: 79)

EWLRAFYERVAEKLKEAF, (SEQ ID NO: 80)

DWLKAFYDKVAERLREAF, (SEQ ID NO: 81)

EWLKAFYEKVAERLREAF, (SEQ ID NO: 82)

DWLRAFYDKVAERLKEAF, (SEQ ID NO: 83)

EWLRAFYEKVAERLKEAF, (SEQ ID NO: 84)

DWLKAFYDKVAEKLKEAFPDWLKAFYDKVAEKLKEAF, (SEQ ID NO: 85)

DWLKAFYDKVAEKLKEFFPDWLKAFYDKVAEKLKEFF, (SEQ ID NO: 86)

DWFKAFYDKVAEKLKEAFPDWFKAFYDKVAEKLKEAF, (SEQ ID NO: 87)

DKLKAFYDKVFEWAKEAFPDKLKAFYDKVFEWLKEAF, (SEQ ID NO: 88)

DKWKAVYDKFAEAFKEFLPDKWKAVYDKFAEAFKEFL, (SEQ ID NO: 89)

DWFKAFYDKVAEKFKEAFPDWFKAFYDKVAEKFKEAF, (SEQ ID NO: 90)

DWLKAFVYDKVFKLKEFFPDWLKAFVYDKVFKLKEFF, (SEQ ID NO: 91)

DWLKAFYDKFAEKFKEFFPDWLKAFYDKFAEKFKEFF, (SEQ ID NO: 92)

EWFKAFYEKVAEKFKEAF, (SEQ ID NO: 93)

DWFKAFYDKVAEKF, (SEQ ID NO: 94)

FKAFYDKVAEKFKE, (SEQ ID NO: 95)

FKAFYEKVAEKFKE, (SEQ ID NO: 96)

FKAFYDKVAEKFKE, (SEQ ID NO: 97)

FKAFYEKVAEKFKE, (SEQ ID NO: 98)

DWFKAFYDKVAEKFKEAF, (SEQ ID NO: 99)

EWFKAFYEKVAEKFKEAF, (SEQ ID NO: 100)

AFYDKVAEKFKEAF, (SEQ ID NO: 101)

DWFKAFYDKVAEKF, (SEQ ID NO: 102)

DWLKAFYDKVFEKFKEFF, (SEQ ID NO: 103)

EWLKAFYEKVFEKFKEFF, (SEQ ID NO: 104)

AFYDKVFEKFKEFF, (SEQ ID NO: 105)

AFYEKVFEKFKEFF, (SEQ ID NO: 106)

DWLKAFYDKVFEKF, (SEQ ID NO: 107)

EWLKAFYEKVFEKF, (SEQ ID NO: 108)

LKAFYDKVFEKFKE, (SEQ ID NO: 109)

LKAFYEKVFEKFKE, (SEQ ID NO: 110)

EWFKAFYEKVADKFKDAF, (SEQ ID NO: 111)

EWFKAFYDKVADKFKEAF, (SEQ ID NO: 112)

DWFKAFYEKVADKFKEAF, (SEQ ID NO: 113)

DWFKAFYEKVAEKFKDAF, (SEQ ID NO: 114)

DFWKAFYDKVAEKFKEAF, (SEQ ID NO: 115)

EFWKAFYEKVADKFKDAF, (SEQ ID NO: 116)

EFWKAFYDKVADKFKEAF, (SEQ ID NO: 117)

DFWKAFYEKVADKFKEAF, (SEQ ID NO: 118)

DFWKAFYEKVAEKFKDAF, (SEQ ID NO: 119)

DWFKAYFDKVAEKFKEAF, (SEQ ID NO: 120)

EWFKAYFEKVADKFKDAF, (SEQ ID NO: 121)

EWFKAYFDKVADKFKEAF, (SEQ ID NO: 122)

-continued

DWFKAYFEKVADKFKEAF, (SEQ ID NO: 123)

DWFKAYFEKVAEKFKDAF, (SEQ ID NO: 124)

DWFKAFVDKYAEKFKEAF, (SEQ ID NO: 125)

EWFKAFVEKYADKFKDAF, (SEQ ID NO: 126)

EWFKAFVDKYADKFKEAF, (SEQ ID NO: 127)

DWFKAFVEKYADKFKEAF, (SEQ ID NO: 128)

DWFKAFVEKYAEKFKDAF, (SEQ ID NO: 129)

DWFKAFYDKAVEKFKEAF, (SEQ ID NO: 130)

EWFKAFYEKAVDKFKDAF, (SEQ ID NO: 131)

EWFKAFYDKAVDKFKEAF, (SEQ ID NO: 132)

DWFKAFYEKAVDKFKEAF, (SEQ ID NO: 133)

DWFKAFYEKAVEKFKDAF, (SEQ ID NO: 134)

DWFKAFYDKVFEKAKEAF, (SEQ ID NO: 135)

EWFKAFYEKVFDKAKDAF, (SEQ ID NO: 136)

EWFKAFYDKVFDKAKEAF, (SEQ ID NO: 137)

DWFKAFYEKVFDKAKEAF, (SEQ ID NO: 138)

DWFKAFYEKVFEKAKDAF, (SEQ ID NO: 139)

DWFKAFYDKVAEKAKEFF, (SEQ ID NO: 140)

EWFKAFYEKVADKAKDFF, (SEQ ID NO: 141)

EWFKAFYDKVADKAKEFF, (SEQ ID NO: 142)

DWFKAFYEKVADKAKEFF, (SEQ ID NO: 143)

DWFKAFYEKVAEKAKDFF, (SEQ ID NO: 144)

DWFKAFYDKVAEKFKEFA, (SEQ ID NO: 145)

EWFKAFYEKVADKFKDFA, (SEQ ID NO: 146)

EWFKAFYDKVADKFKEFA, (SEQ ID NO: 147)

DWFKAFYEKVADKFKEFA, (SEQ ID NO: 148)

DWFKAFYEKVAEKFKDFA, (SEQ ID NO: 149)

DAFKAFYDKVAEKFKEWF, (SEQ ID NO: 150)

EAFKAFYEKVADKFKDWF, (SEQ ID NO: 151)

EAFKAFYDKVADKFKEWF, (SEQ ID NO: 152)

DAFKAFYEKVADKFKEWF, (SEQ ID NO: 153)

DAFKAFYEKVAEKFKDWF, (SEQ ID NO: 154)

DAFKAFYDKVWEKFKEAF, (SEQ ID NO: 155)

EAFKAFYEKVWDKFKDAF, (SEQ ID NO: 156)

EAFKAFYDKVWDKFKEAF, (SEQ ID NO: 157)

DAFKAFYEKVWDKFKEAF, (SEQ ID NO: 158)

DAFKAFYEKVWEKFKDAF, (SEQ ID NO: 159)

DYFKAFWDKVAEKFKEAF, (SEQ ID NO: 160)

EYFKAFWEKVADKFKDAF, (SEQ ID NO: 161)

EYFKAFWDKVADKFKEAF, (SEQ ID NO: 162)

DYFKAFWEKVADKFKEAF, (SEQ ID NO: 163)

DYFKAFWEKVAEKFKDAF, (SEQ ID NO: 164)

DWAKAFYDKVAEKFKEFF, (SEQ ID NO: 165)

EWAKAFYEKVADKFKDFF, (SEQ ID NO: 166)

EWAKAFYDKVADKFKEFF, (SEQ ID NO: 167)

DWAKAFYEKVADKFKEFF, (SEQ ID NO: 168)

DWAKAFYEKVAEKFKDFF, (SEQ ID NO: 169)

DWFKAAYDKVAEKFKEFF, (SEQ ID NO: 170)

EWFKAAYEKVADKFKDFF, (SEQ ID NO: 171)

EWFKAAYDKVADKFKEFF, (SEQ ID NO: 172)

DWFKAAYEKVADKFKEFF, (SEQ ID NO: 173)

DWFKAAYEKVAEKFKDFF, (SEQ ID NO: 174)

DWFKAFADKVAEKFKEYF, (SEQ ID NO: 175)

EWFKAFAEKVADKFKDYF, (SEQ ID NO: 176)

EWFKAFADKVADKFKEYF, (SEQ ID NO: 177)

DWFKAFAEKVADKFKEYF, (SEQ ID NO: 178)

DWFKAFAEKVAEKFKDYF, (SEQ ID NO: 179)

DWFKAFYDKAAEKFKEVF, (SEQ ID NO: 180)

EWFKAFYEKAADKFKDVF, (SEQ ID NO: 181)

EWFKAFYDKAADKFKEVF, (SEQ ID NO: 182)

DWFKAFYEKAADKFKEVF, (SEQ ID NO: 183)

DWFKAFYEKAAEKFKDVF, (SEQ ID NO: 184)

DWYKAFFDKVAEKFKEAF, (SEQ ID NO: 185)

EWYKAFFEKVADKFKDAF, (SEQ ID NO: 186)

EWYKAFFDKVADKFKEAF, (SEQ ID NO: 187)

DWYKAFFEKVADKFKEAF, (SEQ ID NO: 188)

DWYKAFFEKVAEKFKDAF, (SEQ ID NO: 189)

DWVKAFYDKFAEKFKEAF, (SEQ ID NO: 190)

EWVKAFYEKFADKFKDAF, (SEQ ID NO: 191)

EWVKAFYDKFADKFKEAF, (SEQ ID NO: 192)

DWVKAFYEKFADKFKEAF, (SEQ ID NO: 193)

DWVKAFYEKFAEKFKDAF, (SEQ ID NO: 194)

DWFKAFFDKVAEKYKEAF, (SEQ ID NO: 195)

EWFKAFFEKVADKYKDAF, (SEQ ID NO: 196)

EWFKAFFDKVADKYKEAF, (SEQ ID NO: 197)

DWFKAFFEKVADKYKEAF, (SEQ ID NO: 198)

DWFKAFFEKVADKYKEAF, (SEQ ID NO: 199)

DWFKAFFDKVAEKFKEAY, (SEQ ID NO: 200)

EWFKAFFEKVADKFKDAY, (SEQ ID NO: 201)

EWFKAFFDKVADKFKEAY, (SEQ ID NO: 202)

DWFKAFFEKVADKFKEAY, (SEQ ID NO: 203)

DWFKAFFEKVAEKFKDAY, (SEQ ID NO: 204)

DWFKAFYDKFAEKFKEAV, (SEQ ID NO: 205)

EWFKAFYEKFADKFKDAV, (SEQ ID NO: 206)

EWFKAFYDKFADKFKEAV, (SEQ ID NO: 207)

DWFKAFYEKFADKFKEAV, (SEQ ID NO: 208)

DWFKAFYEKFAEKFKDAV, (SEQ ID NO: 209)

DKFKAFYDKVAEKFWEAF, (SEQ ID NO: 210)

EKFKAFYEKVADKFWDAF, (SEQ ID NO: 211)

EKFKAFYDKVADKFWEAF, (SEQ ID NO: 212)

DKFKAFYEKVADKFWEAF, (SEQ ID NO: 213)

DKFKAFYEKVAEKFWDAF, (SEQ ID NO: 214)

DKWKAFYDKVAEKFFEAF, (SEQ ID NO: 215)

EKWKAFYEKVADKFFDAF, (SEQ ID NO: 216)

EKWKAFYDKVADKFFEAF, (SEQ ID NO: 217)

DKWKAFYEKVADKFFEAF, (SEQ ID NO: 218)

DKWKAFYEKVAEKFFDAF, (SEQ ID NO: 219)

DKFKAFYDKWAEVFKEAF, (SEQ ID NO: 220)

EKFKAFYEKWADVFKDAF, (SEQ ID NO: 221)

EKFKAFYDKWADVFKEAF, (SEQ ID NO: 222)

DKFKAFYEKWADVFKEAF, (SEQ ID NO: 223)

DKFKAFYEKWAEVFKDAF, (SEQ ID NO: 224)

DKFKAFYDKVAEFWKEAF, (SEQ ID NO: 225)

EKFKAFYEKVADFWKDAF, (SEQ ID NO: 226)

EKFKAFYDKVADFWKEAF, (SEQ ID NO: 227)

DKFKAFYEKVADFWKEAF, (SEQ ID NO: 228)

DKFKAFYEKVAEFWKDAF, (SEQ ID NO: 229)

FAEKFKEAVKDYFAKFWD, (SEQ ID NO: 230)

FADKFKDAVKEYFAKFWE, (SEQ ID NO: 231)

FADKFKEAVKDYFAKFWE, (SEQ ID NO: 232)

FAEKFKDAVKEYFAKFWD, (SEQ ID NO: 233)

FAEKFKDAVKDYFAKFWE, (SEQ ID NO: 234)

FWEKFKEAVKDYFAKFAD, (SEQ ID NO: 235)

FWDKFKDAVKEYFAKFAE, (SEQ ID NO: 236)

FADKFKEAVKDYFAKFWE, (SEQ ID NO: 237)

FAEKFKDAVKEYFAKFWD, (SEQ ID NO: 238)

FAEKFKDAVKDYFAKFWE, (SEQ ID NO: 239)

FFEKFKEAVKDYFAKAWD, (SEQ ID NO: 240)

FFDKFKDAVKEYFAKAWE, (SEQ ID NO: 241)

FFDKFKEAVKDYFAKAWE, (SEQ ID NO: 242)

FFEKFKDAVKEYFAKAWD, (SEQ ID NO: 243)

FFEKFKDAVKDYFAKAWE, (SEQ ID NO: 244)

FAEKAKEFVKDYFAKFWD, (SEQ ID NO: 245)

FADKAKDFVKEYFAKFWE, (SEQ ID NO: 246)

FADKAKEFVKDYFAKFWE, (SEQ ID NO: 247)

FAEKAKDFVKEYFAKFWD, (SEQ ID NO: 248)

FAEKAKDFVKDYFAKFWE, (SEQ ID NO: 249)

FAEKFKEVAKDYFAKFWD, (SEQ ID NO: 250)

FADKFKDVAKEYFAKFWE, (SEQ ID NO: 251)

FADKFKEVAKDYFAKFWE, (SEQ ID NO: 252)

FAEKFKDVAKEYFAKFWD, (SEQ ID NO: 253)

FAEKFKDVAKDYFAKFWE, (SEQ ID NO: 254)

FAEKFKEAYKDVFAKFWD, (SEQ ID NO: 255)

FADKFKDAYKEVFAKFWE, (SEQ ID NO: 256)

FADKFKEAYKDVFAKFWE, (SEQ ID NO: 257)

FAEKFKDAYKEVFAKFWD, (SEQ ID NO: 258)

FAEKFKDAYKDVFAKFWE, (SEQ ID NO: 259)

FAEKFKEAVKDFYAKFWD, (SEQ ID NO: 260)

FADKFKDAVKEFYAKFWE, (SEQ ID NO: 261)

FADKFKEAVKDFYAKFWE, (SEQ ID NO: 262)

FAEKFKDAVKEFYAKFWD, (SEQ ID NO: 263)

FAEKFKDAVKDFYAKFWE, (SEQ ID NO: 264)

FAEKFWEAVKDYFAKFKD, (SEQ ID NO: 265)

FADKFWDAVKEYFAKFKE, (SEQ ID NO: 266)

FADKFWEAVKDYFAKFKE, (SEQ ID NO: 267)

FAEKFWDAVKEYFAKFKD, (SEQ ID NO: 268)

FAEKFWDAVKDYFAKFKE, (SEQ ID NO: 269)

AFEKFKEAVKDYFAKFWD, (SEQ ID NO: 270)

AFDKFKDAVKEYFAKFWE, (SEQ ID NO: 271)

AFDKFKEAVKDYFAKFWE, (SEQ ID NO: 272)

AFEKFKDAVKEYFAKFWD, (SEQ ID NO: 273)

AFEKFKDAVKDYFAKFWE, (SEQ ID NO: 274)

VAEKFKEAFKDYFAKFWD, (SEQ ID NO: 275)

VADKFKDAFKEYFAKFWE, (SEQ ID NO: 276)

VADKFKEAFKDYFAKFWE, (SEQ ID NO: 277)

VAEKFKDAFKEYFAKFWD, (SEQ ID NO: 278)

VAEKFKDAFKDYFAKFWE, (SEQ ID NO: 279)

YAEKFKEAVKDFFAKFWD, (SEQ ID NO: 280)

YADKFKDAVKEFFAKFWE, (SEQ ID NO: 281)

YADKFKEAVKDFFAKFWE, (SEQ ID NO: 282)

YAEKFKDAVKEFFAKFWD, (SEQ ID NO: 283)

YAEKFKDAVKDFFAKFWE, (SEQ ID NO: 284)

AAEKFKEFVKDYFAKFWD, (SEQ ID NO: 285)

AADKFKDFVKEYFAKFWE, (SEQ ID NO: 286)

AADKFKEFVKDYFAKFWE, (SEQ ID NO: 287)

AAEKFKDFVKEYFAKFWD, (SEQ ID NO: 288)

AAEKFKDFVKDYFAKFWE, (SEQ ID NO: 289)

FFEKAKEAVKDYFAKFWD, (SEQ ID NO: 290)

FFDKAKDAVKEYFAKFWE, (SEQ ID NO: 291)

FFDKAKEAVKDYFAKFWE, (SEQ ID NO: 292)

FFEKAKDAVKEYFAKFWD, (SEQ ID NO: 293)

FFEKAKDAVKDYFAKFWE, (SEQ ID NO: 294)

FYEKFKEAVKDAFAKFWD, (SEQ ID NO: 295)

FYDKFKDAVKEAFAKFWE, (SEQ ID NO: 296)

FYDKFKEAVKDAFAKFWE, (SEQ ID NO: 297)

FYEKFKDAVKEAFAKFWD, (SEQ ID NO: 298)

FYEKFKDAVKDAFAKFWE, (SEQ ID NO: 299)

FVEKFKEAAKDYFAKFWD, (SEQ ID NO: 300)

FVDKFKDAAKEYFAKFWE, (SEQ ID NO: 301)

FVDKFKEAAKDYFAKFWE, (SEQ ID NO: 302)

FVEKFKDAAKEYFAKFWD, (SEQ ID NO: 303)

FVEKFKDAAKDYFAKFWE, (SEQ ID NO: 304)

FAEKYKEAVKDFFAKFWD, (SEQ ID NO: 305)

FADKYKDAVKEFFAKFWE, (SEQ ID NO: 306)

FADKYKEAVKDFFAKFWE, (SEQ ID NO: 307)

FAEKYKDAVKEFFAKFWD, (SEQ ID NO: 308)

FAEKYKDAVKDFFAKFWE, (SEQ ID NO: 309)

FAEKVKEAFKDYFAKFWD, (SEQ ID NO: 310)

FADKVKDAFKEYFAKFWE, (SEQ ID NO: 311)

FADKVKEAFKDYFAKFWE, (SEQ ID NO: 312)

FAEKVKDAFKEYFAKFWD, (SEQ ID NO: 313)

FAEKVKDAFKDYFAKFWE, (SEQ ID NO: 314)

FAEKFKEYVKDAFAKFWD, (SEQ ID NO: 315)

FADKFKDYVKEAFAKFWE, (SEQ ID NO: 316)

FADKFKEYVKDAFAKFWE, (SEQ ID NO: 317)

FAEKFKDYVKEAFAKFWD, (SEQ ID NO: 318)

FAEKFKDYVKDAFAKFWE, (SEQ ID NO: 319)

FAEKFKEAFKDYVAKFWD, (SEQ ID NO: 320)

FADKFKDAFKEYVAKFWE, (SEQ ID NO: 321)

FADKFKEAFKDYVAKFWE, (SEQ ID NO: 322)

FAEKFKDAFKEYVAKFWD, (SEQ ID NO: 323)

FAEKFKDAFKDYVAKFWE, (SEQ ID NO: 324)

FAEKFKEAFKDYFAKVWD, (SEQ ID NO: 325)

FADKFKDAFKEYFAKVWE, (SEQ ID NO: 326)

FADKFKEAFKDYFAKVWE, (SEQ ID NO: 327)

FAEKFKDAFKEYFAKVWD, (SEQ ID NO: 328)

FAEKFKDAFKDYFAKVWE, (SEQ ID NO: 329)

FAEKFKEAVKDFFAKYWD, (SEQ ID NO: 330)

FADKFKDAVKEFFAKYWE, (SEQ ID NO: 331)

FADKFKEAVKDFFAKYWE, (SEQ ID NO: 332)

FAEKFKDAVKEFFAKYWD, (SEQ ID NO: 333)

FAEKFKDAVKDFFAKYWE, (SEQ ID NO: 334)

WAEKFFEAVKDYFAKFKD, (SEQ ID NO: 335)

WADKFFDAVKEYFAKFKE, (SEQ ID NO: 336)

WADKFFEAVKDYFAKFKE, (SEQ ID NO: 337)

WAEKFFDAVKEYFAKFKD, (SEQ ID NO: 338)

WAEKFFDAVKDYFAKFKE, (SEQ ID NO: 339)

FAEKWFEAVKDYFAKFKD, (SEQ ID NO: 340)

FADKWFDAVKEYFAKFKE, (SEQ ID NO: 341)

FADKWFEAVKDYFAKFKE, (SEQ ID NO: 342)

FAEKWFDAVKEYFAKFKD, (SEQ ID NO: 343)

FAEKWFDAVKDYFAKFKE, (SEQ ID NO: 344)

FAEKFVEAWKDYFAKFKD, (SEQ ID NO: 345)

FADKFVDAWKEYFAKFKE, (SEQ ID NO: 346)

FADKFVEAWKDYFAKFKE, (SEQ ID NO: 347)

FAEKFVDAWKEYFAKFKD, (SEQ ID NO: 348)

FAEKFVDAWKDYFAKFKE, (SEQ ID NO: 349)

FYEKFAEAVKDWFAKFKD, (SEQ ID NO: 350)

FYDKFADAVKEWFAKFKE, (SEQ ID NO: 351)

FYDKFAEAVKDWFAKFKE, (SEQ ID NO: 352)

FYEKFADAVKEWFAKFKD, (SEQ ID NO: 353)

FYEKFADAVKDWFAKFKE, (SEQ ID NO: 354)

DWFKHFYDKVAEKFKEAF, (SEQ ID NO: 355)

EWFKHFYEKVADKFKDAF, (SEQ ID NO: 356)

EWFKHFYDKVAEKFKEAF, (SEQ ID NO: 357)

DWFKHFYEKVAEKFKEAF, (SEQ ID NO: 358)

DWFKHFYDKVADKFKEAF, (SEQ ID NO: 359)

DWFKHFYDKVAEKFKDAF, (SEQ ID NO: 360)

DWHKFFYDKVAEKFKEAF, (SEQ ID NO: 361)

EWHKFFYEKVADKFKDAF, (SEQ ID NO: 362)

EWHKFFYDKVAEKFKEAF, (SEQ ID NO: 363)

DWHKFFYEKVAEKFKEAF, (SEQ ID NO: 364)

DWHKFFYDKVADKFKEAF, (SEQ ID NO: 365)

DWHKFFYDKVAEKFKDAF, (SEQ ID NO: 366)

DWFKFHYDKVAEKFKEAF, (SEQ ID NO: 367)

EWFKFHYEKVADKFKDAF, (SEQ ID NO: 368)

EWFKFHYDKVAEKFKEAF, (SEQ ID NO: 369)

DWFKFHYEKVAEKFKEAF, (SEQ ID NO: 370)

DWFKFHYDKVADKFKEAF, (SEQ ID NO: 371)

DWFKFHYDKVAEKFKDAF, (SEQ ID NO: 372)

DWFKVFYDKHAEKFKEAF, (SEQ ID NO: 373)

EWFKVFYEKHADKFKDAF, (SEQ ID NO: 374)

EWFKVFYDKHAEKFKEAF, (SEQ ID NO: 375)

DWFKVFYEKHAEKFKEAF, (SEQ ID NO: 376)

DWFKVFYDKHADKFKEAF, (SEQ ID NO: 377)

DWFKVFYDKHAEKFKDAF, (SEQ ID NO: 378)

DWFKAFYDKVAEKFKEHF, (SEQ ID NO: 379)

EWFKAFYEKVADKFKDHF, (SEQ ID NO: 380)

EWFKAFYDKVAEKFKEHF, (SEQ ID NO: 381)

DWFKAFYEKVAEKFKEHF, (SEQ ID NO: 382)

DWFKAFYDKVADKFKEHF, (SEQ ID NO: 383)

DWFKAFYDKVAEKFKDHF, (SEQ ID NO: 384)

DWFKAFYDKVAEKFKEFH, (SEQ ID NO: 385)

EWFKAFYEKVADKFKDFH, (SEQ ID NO: 386)

EWFKAFYDKVAEKFKEFH, (SEQ ID NO: 387)

DWFKAFYDKVAEKFKEFH, (SEQ ID NO: 388)

DWFKAFYEKVAEKFKEFH, (SEQ ID NO: 389)

DWFKAFYDKVAEKFKEFH, (SEQ ID NO: 390)

DWFKAFYDKVAEKFKDFH, (SEQ ID NO: 391)

FAEKFKEAVKDYFAKFWD, (SEQ ID NO: 392)

FHEKFKEAVKDYFAKFWD, (SEQ ID NO: 393)

FHEKFKEAVKEYFAKFWE, (SEQ ID NO: 394)

FHDKFKDAVKDYFAKFWD, (SEQ ID NO: 395)

FHDKFKDAVKEYFAKFWE, (SEQ ID NO: 396)

FHDKFKEAVKDYFAKFWD, (SEQ ID NO: 397)

FHEKFKDAVKDYFAKFWD, (SEQ ID NO: 398)

FHEKFKEAVKEYFAKFWD, (SEQ ID NO: 399)

FHEKFKEAVKDYFAKFWE, (SEQ ID NO: 400)

HFEKFKEAVKDYFAKFWD, (SEQ ID NO: 401)

HFDKFKDAVKEYFAKFWE, (SEQ ID NO: 402)

HFEKFKEAVKEYFAKFWE, (SEQ ID NO: 403)

HFDKFKEAVKDYFAKFWD, (SEQ ID NO: 404)

HFEKFKDAVKDYFAKFWD, (SEQ ID NO: 405)

HFEKFKEAVKEYFAKFWD, (SEQ ID NO: 406)

HFEKFKEAVKDYFAKFWE, (SEQ ID NO: 407)

FFEKHKEAVKDYFAKFWD, (SEQ ID NO: 408)

FFDKHKDAVKEYFAKFWE, (SEQ ID NO: 409)

FFEKHKEAVKEYFAKFWE, (SEQ ID NO: 410)

FFDKHKDAVKDYFAKFWD, (SEQ ID NO: 411)

FFDKHKEAVKDYFAKFWD, (SEQ ID NO: 412)

FFEKHKEAVKEYFAKFWD, (SEQ ID NO: 413)

FFEKHKEAVKDYFAKFWE, (SEQ ID NO: 414)

FVEKFKEAHKDYFAKFWD, (SEQ ID NO: 415)

FVDKFKDAHKEYFAKFWE, (SEQ ID NO: 416)

FVEKFKEAHKEYFAKFWE, (SEQ ID NO: 417)

FVDKFKDAHKDYFAKFWD, (SEQ ID NO: 418)

FVDKFKEAHKDYFAKFWD, (SEQ ID NO: 419)

FVEKFKDAHKDYFAKFWD, (SEQ ID NO: 420)

FVEKFKEAHKEYFAKFWD, (SEQ ID NO: 421)

FVEKFKEAHKDYFAKFWE, (SEQ ID NO: 422)

FAEKFKEHVKDYFAKFWD, (SEQ ID NO: 423)

FADKFKDHVKEYFAKFWE, (SEQ ID NO: 424)

FAEKFKEHVKEYFAKFWE, (SEQ ID NO: 425)

FADKFKDHVKDYFAKFWD, (SEQ ID NO: 426)

FADKFKEHVKDYFAKFWD, (SEQ ID NO: 427)

FAEKFKDHVKDYFAKFWD, (SEQ ID NO: 428)

FAEKFKEHVKEYFAKFWD, (SEQ ID NO: 429)

FAEKFKEHVKDYFAKFWE, (SEQ ID NO: 430)

FAEKFKEFVKDYHAKFWD, (SEQ ID NO: 431)

FADKFKDFVKEYHAKFWE, (SEQ ID NO: 432)

FADKFKEFVKDYHAKFWD, (SEQ ID NO: 433)

FAEKFKDFVKDYHAKFWD, (SEQ ID NO: 434)

FADKFKDFVKDYHAKFWD, (SEQ ID NO: 435)

FAEKFKEFVKEYHAKFWE, (SEQ ID NO: 436)

FAEKFKEFVKEYHAKFWD, (SEQ ID NO: 437)

FAEKFKEFVKDYHAKFWE, (SEQ ID NO: 438)

FAEKFKEFVKDYFAKHWD, (SEQ ID NO: 439)

FADKFKDFVKEYFAKHWE, (SEQ ID NO: 440)

FAEKFKEFVKEYFAKHWE, (SEQ ID NO: 441)

FADKFKDFVKDYFAKHWD, (SEQ ID NO: 442)

FADKFKEFVKDYFAKHWD, (SEQ ID NO: 443)

FAEKFKDFVKDYFAKHWD, (SEQ ID NO: 444)

FAEKFKEFVKEYFAKHWD, (SEQ ID NO: 445)

FAEKFKEFVKDYFAKHWE, (SEQ ID NO: 446)

FAEKFKEAVKEYFAKFWE, (SEQ ID NO: 447)

FADKFKDAVKDYFAKFWD, (SEQ ID NO: 448)

FAERFREAVKDYFAKFWD, (SEQ ID NO: 449)

FAEKFREAVKDYFAKFWD, (SEQ ID NO: 450)

FAEKFKEAVRDYFAKFWD, (SEQ ID NO: 451)

FAEKFKEAVKDYFARFWD, (SEQ ID NO: 452)

FAEKFKEAVKEYFAKFWE, (SEQ ID NO: 453)

FADKFKDAVKDYFAKFWD, (SEQ ID NO: 454)

FAERFREAVKDYFAKFWD, (SEQ ID NO: 455)

FAEKFREAVKDYFAKFWD, (SEQ ID NO: 456)

FAEKFKEAVRDYFAKFWD, (SEQ ID NO: 457)

FAEKFKEAVKDYFARFWD, (SEQ ID NO: 458)

FAEKFKEAVKEYFAKFWE, (SEQ ID NO: 459)

FADKFKDAVKDYFAKFWD, (SEQ ID NO: 460)

FAERFREAVKDYFAKFWD, (SEQ ID NO: 461)

FAEKFREAVKDYFAKFWD, (SEQ ID NO: 462)

FAEKFKEAVRDYFAKFWD, (SEQ ID NO: 463)

FAEKFKEAVKDYFARFWD, (SEQ ID NO: 464)

FAERFREAVKDYFAKFWD, (SEQ ID NO: 465)

FAEKFREAVKDYFAKFWD, (SEQ ID NO: 466)

FAEKFKEAVRDYFAKFWD, (SEQ ID NO: 467)

FAEKFKEAVKDYFARFWD, (SEQ ID NO: 468)

FAEKFKEAVKEYFAKFWE, (SEQ ID NO: 469)

FADKFKDAVKDYFAKFWD, (SEQ ID NO: 470)

FAERFREAVKDYFAKFWD, (SEQ ID NO: 471)

FAEKFREAVKDYFAKFWD, (SEQ ID NO: 472)

FAEKFKEAVRDYFAKFWD, (SEQ ID NO: 473)

FAEKFKEAVKDYFARFWD, (SEQ ID NO: 474)

LFEKFAEAFKDYVAKWKD, (SEQ ID NO: 475)

LFERFAEAFKDYVAKWKD, (SEQ ID NO: 476)

LFEKFAEAFRDYVAKWKD, (SEQ ID NO: 477)

LFEKFAEAFKDYVARWKD, (SEQ ID NO: 478)

LFEKFAEAFKDYVAKWRD, (SEQ ID NO: 479)

LFEKFAEAFKEYVAKWKE, (SEQ ID NO: 480)

LFDKFADAFKDYVAKWKD, (SEQ ID NO: 481)

LFDKFAEAFKDYVAKWKD, (SEQ ID NO: 482)

LFEKFADAFKDYVAKWKD, (SEQ ID NO: 483)

LFEKFAEAFKEYVAKWKD, (SEQ ID NO: 484)

LFEKFAEAFKDYVAKWKE, (SEQ ID NO: 485)

FAEKAWEFVKDYFAKLKD, (SEQ ID NO: 486)

FAERAWEFVKDYFAKLKD, (SEQ ID NO: 487)

FAEKAWEFVKDYFAKLKD, (SEQ ID NO: 488)

FAEKAWEFVKDYFAKLKD, (SEQ ID NO: 489)

FAEKAWEFVKDYFAKLRD, (SEQ ID NO: 490)

FAEKAWEFVKEYFAKLKE, (SEQ ID NO: 491)

FADKAWDFVKDYFAKLKD, (SEQ ID NO: 492)

FADKAWEFVKDYFAKLKD, (SEQ ID NO: 493)

FAEKAWDFVKDYFAKLKD, (SEQ ID NO: 494)

FAEKAWEFVKEYFAKLKD, (SEQ ID NO: 495)

FAEKAWEFVKDYFAKLKE, (SEQ ID NO: 496)

FFEKFKEFVKDYFAKLWD, (SEQ ID NO: 497)

FFEKFKEFVKEYFAKLWE, (SEQ ID NO: 498)

FFDKFKDFVKDYFAKLWD, (SEQ ID NO: 499)

FFERFKEFVKDYFAKLWD, (SEQ ID NO: 500)

FFEKFREFVKDYFAKLWD, (SEQ ID NO: 501)

FFEKFKEFVRDYFAKLWD, (SEQ ID NO: 502)

FFEKFKEFVKDYFARLWD, (SEQ ID NO: 503)

FFDKFKEFVKDYFAKLWD, (SEQ ID NO: 504)

FFEKFKDFVKDYFAKLWD, (SEQ ID NO: 505)

FFEKFKEFVKEYFAKLWD, (SEQ ID NO: 506)

FFEKFKEFVKDYFAKLWE, (SEQ ID NO: 507)

FLEKFKEFVKDYFAKFWD, (SEQ ID NO: 508)

FLEKFKEFVKEYFAKFWE, (SEQ ID NO: 509)

FLDKFKEFVKDYFAKFWD, (SEQ ID NO: 510)

FLDKFKEFVKDYFAKFWD, (SEQ ID NO: 511)

FLEKFKDFVKDYFAKFWD, (SEQ ID NO: 512)

FLEKFKEFVKEYFAKFWD, (SEQ ID NO: 513)

FLEKFKEFVKDYFAKFWE, (SEQ ID NO: 514)

FLERFKEFVKDYFAKFWD, (SEQ ID NO: 515)

FLEKFREFVKDYFAKFWD, (SEQ ID NO: 516)

FLEKFKEFVRDYFAKFWD, (SEQ ID NO: 517)

FLEKFKEFVKDYFARFWD, (SEQ ID NO: 518)

FFEKFKEFFKDYFAKLWD, (SEQ ID NO: 519)

FFEKFKEFFKEYFAKLWE, (SEQ ID NO: 520)

FFDKFKDFFKDYFAKLWD, (SEQ ID NO: 521)

FFERFKEFFKDYFAKLWD, (SEQ ID NO: 522)

FFEKFREFFKDYFAKLWD, (SEQ ID NO: 523)

FFEKFKEFFRDYFAKLWD, (SEQ ID NO: 524)

FFERFKEFFKDYFARLWD, (SEQ ID NO: 525)

FFDKFKEFFKDYFAKLWD, (SEQ ID NO: 526)

FFEKFKDFFKDYFAKLWD, (SEQ ID NO: 527)

FFEKFKEFFKEYFAKLWD, (SEQ ID NO: 528)

FFEKFKEFFKDYFAKLWE, (SEQ ID NO: 529)

FAEKFKEAVKDYFAKFWD, (SEQ ID NO: 530)

FAEKFKEAVKEYFAKFWE, (SEQ ID NO: 531)

FADKFKDAVKDYFAKFWD, (SEQ ID NO: 532)

FAERFREAVKDYFAKFWD, (SEQ ID NO: 533)

FAEKFREAVKDYFAKFWD, (SEQ ID NO: 534)

FAEKFKEAVRDYFAKFWD, (SEQ ID NO: 535)

FAEKFKEAVKDYFARFWD, (SEQ ID NO: 536)

DKWKAVYDKFAEAFKEFF, (SEQ ID NO: 537)

EKWKAVYEKFAEAFKEFF, (SEQ ID NO: 538)

DKWKAVYDKFADAFKDFF, (SEQ ID NO: 539)

DRWKAVYDKFAEAFKEFF, (SEQ ID NO: 540)

DKWRAVYDKFAEAFKEFF, (SEQ ID NO: 541)

DKWKAVYDRFAEAFKEFF, (SEQ ID NO: 542)

DKWKAVYDKFAEAFREFF, (SEQ ID NO: 543)

FFEKFAEAFKDYVAKWKD, (SEQ ID NO: 544)

FFEKFAEAFKEYVAKWKE, (SEQ ID NO: 545)

FFDKFADAFKDYVAKWKD, (SEQ ID NO: 546)

FFERFAEAFKDYVAKWKD, (SEQ ID NO: 547)

FFERFAEAFRDYVAKWKD, (SEQ ID NO: 548)

FFEKFAEAFKDYVARWKD, (SEQ ID NO: 549)

FFERFAEAFKDYVAKWRD, (SEQ ID NO: 550)

FFDKFAEAFKDYVAKWKD, (SEQ ID NO: 551)

FFEKFADAFKDYVAKWKD, (SEQ ID NO: 552)

FFERFAEAFKEYVAKWKD, (SEQ ID NO: 553)

FFERFAEAFKDYVAKWKE, (SEQ ID NO: 554)

FFEKFKEFFKDYFAKFWD, (SEQ ID NO: 555)

FFDKFKDFFKDYFAKFWD, (SEQ ID NO: 556)

FFEKFKEFFKEYFAKFWE, (SEQ ID NO: 557)

FFERFKEFFKDYFAKFWD, (SEQ ID NO: 558)

FFEKFREFFKDYFAKFWD, (SEQ ID NO: 559)

FFEKFKEFFRDYFAKFWD, (SEQ ID NO: 560)

FFEKFKEFFKDYFARFWD, (SEQ ID NO: 561)

FFDKFKEFFKDYFAKFWD, (SEQ ID NO: 562)

FFEKFKDFFKDYFAKFWD, (SEQ ID NO: 563)

FFEKFKEFFKEYFAKFWD, (SEQ ID NO: 564)

FFEKFKEFFKDYFAKFWE, (SEQ ID NO: 565)

EVRAKLEEQAQQIRLQAEAFQARLKSWFEPLVE, (SEQ ID NO: 566)

EVRAKLEEQAQQIRLQAEAFQARLKSWFE, (SEQ ID NO: 567)

EVRSKLEEWFAAFREFAEEFLARLKS, (SEQ ID NO: 568)

PVLDLFRELLNELLEALKQKLK, (SEQ ID NO: 569)

DWLKAFYDKVAEKLKEAFPDWAKAAYDKAAEKAKEAA, (SEQ ID NO: 570)

EELKEKLEELKEKLEEKLPEELKEKLEELKEKLEEKL, (SEQ ID NO: 571)

EELKAKLEELKAKLEEKLPEELKAKLEELKAKLEEKL, (SEQ ID NO: 572)

EKLKALLEKLLAKLKELLPEKLKALLEKLLAKLKELL, (SEQ ID NO: 573)

EWLKELLEKLLEKLKELLPEWLKELLEKLLEKLKELL, (SEQ ID NO: 574)

EKFKELLEKFLEKFKELLPEKFKELLEKFLEKFKELL, (SEQ ID NO: 575)

EKLKELLEKLLELLKKLLPEKLKELLEKLLELLKKLL, (SEQ ID NO: 576)

EKLKELLEKLKAKLEELLPEKLKELLEKLKAKLEELL, (SEQ ID NO: 577)

EKLKELLEKLLAKLKELLPEKLKELLEKLLAKLKELL, (SEQ ID NO: 578)

EKFKELLEKLLEKLKELLPEKFKELLEKLLEKLKELL, (SEQ ID NO: 579)

EKLKAKLEELKAKLEELLPEKLKAKLEELKAKLEELL, (SEQ ID NO: 580)

EELKELLKELLKKLEKLLPELKELLKELLKKLEKLL, (SEQ ID NO: 581)

EELKKLLEELLKKLKELLPEELKKLLEELLKKLKELL, (SEQ ID NO: 582)

EKLKELLEKLLEKLKELLAEKLKELLEKLLEKLKELL, (SEQ ID NO: 583)

EKLKELLEKLLEKLKELLAAEKLKELLEKLLEKLKELL, (SEQ ID NO: 584)

EKLKAKLEELKAKLEELLPEKAKAALEEAKAKAEELA, (SEQ ID NO: 585)

EKLKAKLEELKAKLEELLPEHAKAALEEAKCKAEELA, (SEQ ID NO: 586)

DHLKAFYDKVACKLKEAFPDWAKAAYDKAAEKAKEAA, (SEQ ID NO: 587)

DWLKAFYDKVAEKLKEAFPDHAKAAYDKAACKAKEAA, (SEQ ID NO: 588)

DWLKAFYDKVACKLKEAFPDWAKAAYNKAAEKAKEAA, (SEQ ID NO: 589)

DHLKAFYDKVAEKLKEAFPDWAKAAYDKAAEKAKEAA, (SEQ ID NO: 590)

VLESFKVSFLSALEEYTKKLNTQ, (SEQ ID NO: 591)

DKWKAVYDKFAEAFKEFL, (SEQ ID NO: 592)

DKLKAFYDKVFEWAKEAF, (SEQ ID NO: 593)

DQYYLRVTTVA, (SEQ ID NO: 595)

ECKPCLKQTCMKFYARVCR, (SEQ ID NO: 596)

FSRASSIIDELFQD, (SEQ ID NO: 597)

IQNAVNGVKQIKTLIEKTNEE, (SEQ ID NO: 598)

LLEQLNEQFNWVSRLANL, (SEQ ID NO: 599)

LLEQLNEQFNWVSRLANLTEGE, (SEQ ID NO: 600)

LLEQLNEQFNWVSRLANLTQGE, (SEQ ID NO: 601)

LVGRQLEEFL, (SEQ ID NO: 602)

MNGDRIDSLLEN, (SEQ ID NO: 603)

NELQEMSNQGSKYVNKEIQNAVNGV, (SEQ ID NO: 604)

PCLKQTCMKFYARVCR, (SEQ ID NO: 605)

PFLEMIHEAQQAMDI, (SEQ ID NO: 606)

PGVCNETMMALWEECK, (SEQ ID NO: 607)

PKFMETVAEKALQEYRKKHRE, (SEQ ID NO: 608)

PSGVTEVVVKLFDS, (SEQ ID NO: 609)

PSQAKLRRELDESLQVAERLTRKYNELLKSYQ, (SEQ ID NO: 610)

PTEFIREGDDD, (SEQ ID NO: 611)

QQTHMLDVMQD, (SEQ ID NO: 612)

RKTLLSNLEEAKKKKEDALNETRESETKLKEL, (SEQ ID NO: 613)

RMKDQCDKCREILSV, (SEQ ID NO: 614)

GVFAKIFKWISGLFKKIG, (SEQ ID NO: 615)

GIKKFLGSIWKFIKAFVG, (SEQ ID NO: 616)

GFKKFLGSWAKIYKAFVG, (SEQ ID NO: 617)

GFRRFLGSWARIYRAFVG, (SEQ ID NO: 618)

TEELRVRLASHLRKLRKRLL, (SEQ ID NO: 619)

TEELRVRLASHLRKLRK, (SEQ ID NO: 620)

LRVRLASHLRKLRKRLL, (SEQ ID NO: 621)

RLASHLRKLRKRLL, (SEQ ID NO: 622)

SHLRKLRKRLL, (SEQ ID NO: 623)

LRKLRKRLL, (SEQ ID NO: 624)

LRKLRKRLLLRKLRKRLL, (SEQ ID NO: 625)

LRKLRKRLLLRKLRKRLLLRKLRKRLL, (SEQ ID NO: 626)

RQIKIWFQNRRMKWKKCLRVRLASHLRKLRKRLL, (SEQ ID NO: 627)

LRVRLASHLRKLRKRLL, (SEQ ID NO: 628)

EELRVRLASHLRKLRKRLLRDADDLQKRLAVYEEQAQQIRLQAEAFQA
RLKSWFEPLVEDM, (SEQ ID NO: 629)

CEELRVRLASHLRKLRKRLLRDADDLQKRLAVY, (SEQ ID NO: 630)

LRKLRKRLLRDADDLLRKLRKRLLRDADDL, (SEQ ID NO: 631)

TEELRVRLASHLRKLRKRLL, (SEQ ID NO: 632)

TEELRVRLASHLEKLRKRLL, (SEQ ID NO: 633)

TEELRVRLASHLRELRKRLL, (SEQ ID NO: 634)

LREKKLRVSALRTHRLELRL, (SEQ ID NO: 635)

LRKLRKRLLRDWLKAFYDKVAEKLKEAF, (SEQ ID NO: 636)

LRRLRRRLLRDWLKAFYDKVAEKLKEAF, (SEQ ID NO: 637)

and

RRRRRRRRRDWLKAFYDKVAEKLKEAF. (SEQ ID NO: 638)

Embodiment 36

The method according to any one of embodiments 1-35, wherein said ezetimibe-associated apoA-I mimetic pepide is effective to decrease plasma total cholesterol in said mammal, and/or to decrease plasma plasma triglyceride in said mammal, and/or to decrease plasma 5-HETE in said mammal, and/or to decrease plasma 12-HETE in said mammal, and/or to decrease plasma 15-HETE in said mammal, and/or to decrease SAA levels in said mammal, and/or to increase plasma paraoxonase activity in said mammal, and/or to decrease plasma levels of lyophosphatidic acid (LPA) in a mammal when fed to said mammal alone or as a component of a food or diet.

Embodiment 37

The method according to any one of embodiments 1-36, wherein said ezetimibe-associated apoA-I mimetic pepide, when fed to a mammal, lowers plasma total cholesterol to a greater amount than a mixed ezetimibe apoA-I peptide formulation containing the same amounts of ezetimibe and apoA-I peptide.

Embodiment 38

The method according to any one of embodiments 1-37, wherein said ezetimibe-associated apoA-I mimetic pepide, when fed to a mammal, lowers plasma triglyceride, and/or raises plasma HDL cholesterol to a greater amount than a mixed ezetimibe apoA-I peptide formulation containing the same amounts of ezetimibe and apoA-I peptide.

Embodiment 39

The method according to any one of embodiments 1-38, wherein said ezetimibe-associated apoA-I mimetic pepide, when fed to a mammal, lowers plasma 5-HETE to a greater amount than a mixed ezetimibe apoA-I peptide formulation containing the same amounts of ezetimibe and apoA-I peptide.

Embodiment 40

The method according to any one of embodiments 1-39, wherein said ezetimibe-associated apoA-I mimetic pepide, when fed to a mammal, lowers plasma 12-HETE to a greater amount than a mixed ezetimibe apoA-I peptide formulation containing the same amounts of ezetimibe and apoA-I peptide.

Embodiment 41

The method according to any one of embodiments 1-40, wherein said ezetimibe-associated apoA-I mimetic pepide, when fed to a mammal, lowers plasma 15-HETE to a greater amount than a mixed ezetimibe apoA-I peptide formulation containing the same amounts of ezetimibe and apoA-I peptide.

Embodiment 42

The method according to any one of embodiments 1-41, wherein said ezetimibe-associated apoA-I mimetic pepide, when fed to a mammal, lowers plasma SAA to a greater amount than a mixed ezetimibe apoA-I peptide formulation containing the same amounts of ezetimibe and apoA-I peptide.

Embodiment 43

An ezetimibe-associated apoA-I mimetic peptide, wherein said ezetimibe associated apoA-I mimetic has greater biological activity than a mixed ezetimibe apoA-I peptide formulation containing the same amounts of ezetimibe and apoA-I peptide.

Embodiment 44

The ezetimibe-associated apoA-I mimetic peptide of embodiment 43, wherein said ezetimibe-associated apoA-I mimetic pepide, when fed to a mammal, lowers plasma total cholesterol to a greater amount than a mixed ezetimibe apoA-I peptide formulation containing the same amounts of ezetimibe and apoA-I peptide.

Embodiment 45

The ezetimibe-associated apoA-I mimetic peptide according to any one of embodiments 43-44, wherein said ezetimibe-associated apoA-I mimetic pepide, when fed to a mammal, lowers plasma triglyceride, and/or raises plasma HDL cholesterol to a greater amount than a mixed ezetimibe apoA-I peptide formulation containing the same amounts of ezetimibe and apoA-I peptide.

Embodiment 46

The ezetimibe-associated apoA-I mimetic peptide according to any one of embodiments 43-45, wherein said ezetimibe-associated apoA-I mimetic pepide, when fed to a mammal, lowers plasma 5-HETE to a greater amount than a mixed ezetimibe apoA-I peptide formulation containing the same amounts of ezetimibe and apoA-I peptide.

Embodiment 47

The ezetimibe-associated apoA-I mimetic peptide according to any one of embodiments 43-46, wherein said ezetimibe-associated apoA-I mimetic pepide, when fed to a mammal, lowers plasma 12-HETE to a greater amount than a mixed ezetimibe apoA-I peptide formulation containing the same amounts of ezetimibe and apoA-I peptide.

Embodiment 48

The ezetimibe-associated apoA-I mimetic peptide according to any one of embodiments 43-47, wherein said ezetimibe-associated apoA-I mimetic pepide, when fed to a mammal, lowers plasma 15-HETE to a greater amount than a mixed ezetimibe apoA-I peptide formulation containing the same amounts of ezetimibe and apoA-I peptide.

Embodiment 49

The ezetimibe-associated apoA-I mimetic peptide according to any one of embodiments 43-48, wherein said ezetimibe-associated apoA-I mimetic pepide, when fed to a mammal, lowers plasma SAA to a greater amount than a mixed ezetimibe apoA-I peptide formulation containing the same amounts of ezetimibe and apoA-I peptide.

Embodiment 50

The ezetimibe-associated apoA-I mimetic peptide according to any one of embodiments 43-49, wherein said apoA-I mimetic peptide is a chemically synthesized peptide.

Embodiment 51

The ezetimibe-associated apoA-I mimetic peptide according to any one of embodiments 43-49 is a peptide recombinantly expressed in a plant cell.

Embodiment 52

The ezetimibe-associated apoA-I mimetic peptide of embodiment 51, wherein said apoA-I mimetic peptide is derived from a tissue of a transgenic plant wherein said tissue contains a heterologous ApoA-I mimetic peptide expressed by said plant.

Embodiment 53

The ezetimibe-associated apoA-I mimetic peptide according to any one of embodiments 43-52, wherein said ApoA-I mimetic peptide comprises the amino acid sequence DWLKAFYDKFFEKFKEFF (6F) (SEQ ID NO:1).

Embodiment 54

The ezetimibe-associated apoA-I mimetic peptide according to any one of embodiments 43-52, wherein said ApoA-I mimetic peptide comprises the amino acid sequence FFEKFKEFFKDYFAKLWD (rev6F) (SEQ ID NO:15).

Embodiment 55

The ezetimibe-associated apoA-I mimetic peptide according to any one of embodiments 43-52, wherein said ApoA-I mimetic peptide comprises the amino acid sequence DWFKAFYDKVAEKFKEAF (4F) (SEQ ID NO:6).

Embodiment 56

The ezetimibe-associated apoA-I mimetic peptide according to any one of embodiments 43-52, wherein said ApoA-I mimetic peptide comprises the amino acid sequence FAEKFKEAVKDYFAKFWD (rev4F) (SEQ ID NO:13).

Embodiment 57

The ezetimibe-associated apoA-I mimetic peptide according to any one of embodiments 43-52, wherein said ApoA-I mimetic peptide comprises the amino acid sequence, LLEQLNEQFNWVSRLANL.

Embodiment 58

The ezetimibe-associated apoA-I mimetic peptide according to any one of embodiments 43-52, wherein said ApoA-I mimetic peptide comprises the amino acid sequence LVGRQLEEFL.

Embodiment 59

The ezetimibe-associated apoA-I mimetic peptide according to any one of embodiments 43-52, wherein said ApoA-I mimetic peptide comprises an amino acid sequence selected from the group consisting of

DWLKAFYDKFFEKFKEFF, (SEQ ID NO: 1)

DWLKAFYDKVAEKLKEAF, (SEQ ID NO: 2)

DWLKAFYDKVAEKLKEAF, (SEQ ID NO: 3)

DWFKAFYDKVAEKLKEAF, (SEQ ID NO: 4)

DWLKAFYDKVAEKFKEAF, (SEQ ID NO: 5)

DWFKAFYDKVAEKFKEAF, (SEQ ID NO: 6)

DWLKAFYDKVFEKFKEFF, (SEQ ID NO: 7)

DWLKAFYDKFFEKFKEFF, (SEQ ID NO: 1)

DWFKAFYDKFFEKFKEFF, (SEQ ID NO: 8)

DWLKAFYDKVAEKLKEFF, (SEQ ID NO: 9)

FAEKLKEAVKDYFAKLWD, (SEQ ID NO: 10)

FAEKLKEAVKDYFAKLWD, (SEQ ID NO: 11)

FAEKLKEAVKDYFAKFWD, (SEQ ID NO: 12)

FAEKFKEAVKDYFAKFWD, (SEQ ID NO: 13)

FFEKFKEFVKDYFAKLWD, (SEQ ID NO: 14)

FFEKFKEFFKDYFAKLWD, (SEQ ID NO: 15)

FFEKFKEFFKDYFAKFWD, (SEQ ID NO: 16)

DWLKAFYDKVFEKFKEAF, (SEQ ID NO: 17)

DWLKAFYDKVFEKLKEFF, (SEQ ID NO: 18)

DWLKAFYDKVAEKFKEFF, (SEQ ID NO: 19)

DWLKAFYDKVFEKFKEFF, (SEQ ID NO: 20)

EWLKLFYEKVLEKFKEAF, (SEQ ID NO: 21)

EWLKAFYDKVAEKFKEAF, (SEQ ID NO: 22)

EWLKAFYDKVAEKLKEFF, (SEQ ID NO: 23)

EWLKAFYDKVFEKFKEAF, (SEQ ID NO: 24)

EWLKAFYDKVFEKLKEFF, (SEQ ID NO: 25)

EWLKAFYDKVAEKFKEFF, (SEQ ID NO: 26)

EWLKAFYDKVFEKFKEFF, (SEQ ID NO: 27)

AFYDKVAEKLKEAF, (SEQ ID NO: 28)

AFYDKVAEKFKEAF, (SEQ ID NO: 29)

AFYDKVAEKFKEAF, (SEQ ID NO: 30)

AFYDKFFEKFKEFF, (SEQ ID NO: 31)

AFYDKFFEKFKEFF, (SEQ ID NO: 32)

AFYDKVAEKFKEAF, (SEQ ID NO: 33)

AFYDKVAEKLKEFF, (SEQ ID NO: 34)

AFYDKVFEKFKEAF, (SEQ ID NO: 35)

AFYDKVFEKLKEFF, (SEQ ID NO: 36)

AFYDKVAEKFKEFF, (SEQ ID NO: 37)

KAFYDKVFEKFKEF, (SEQ ID NO: 38)

LFYEKVLEKFKEAF, (SEQ ID NO: 39)

AFYDKVAEKFKEAF, (SEQ ID NO: 40)

AFYDKVAEKLKEFF, (SEQ ID NO: 41)

AFYDKVFEKFKEAF, (SEQ ID NO: 42)

AFYDKVFEKLKEFF, (SEQ ID NO: 43)

AFYDKVAEKFKEFF, (SEQ ID NO: 44)

AFYDKVFEKFKEFF, (SEQ ID NO: 45)

DWLKALYDKVAEKLKEAL, (SEQ ID NO: 46)

```
                                              (SEQ ID NO: 47)
DWFKAFYEKVAEKLKEFF, (SEQ ID NO: 48)
DWFKAFYEKFFEKFKEFF, (SEQ ID NO: 49)
EWLKALYEKVAEKLKEAL, (SEQ ID NO: 50)
EWLKAFYEKVAEKLKEAF, (SEQ ID NO: 51)
EWFKAFYEKVAEKLKEFF, (SEQ ID NO: 52)
EWLKAFYEKVFEKFKEFF, (SEQ ID NO: 53)
EWLKAFYEKFFEKFKEFF, (SEQ ID NO: 54)
EWFKAFYEKFFEKFKEFF, (SEQ ID NO: 55)
DFLKAWYDKVAEKLKEAW, (SEQ ID NO: 56)
EFLKAWYEKVAEKLKEAW, (SEQ ID NO: 57)
DFWKAWYDKVAEKLKEWW, (SEQ ID NO: 58)
EFWKAWYEKVAEKLKEWW, (SEQ ID NO: 59)
DKLKAFYDKVFEWAKEAF, (SEQ ID NO: 60)
DKWKAVYDKFAEAFKEFL, (SEQ ID NO: 61)
EKLKAFYEKVFEWAKEAF, (SEQ ID NO: 62)
EKWKAVYEKFAEAFKEFL, (SEQ ID NO: 63)
DWLKAFVDKFAEKFKEAY, (SEQ ID NO: 64)
EKWKAVYEKFAEAFKEFL, (SEQ ID NO: 65)
DWLKAFVYDKVFKLKEFF, (SEQ ID NO: 66)
EWLKAFVYEKVFKLKEFF, (SEQ ID NO: 67)
DWLRAFYDKVAEKLKEAF, (SEQ ID NO: 68)
EWLRAFYEKVAEKLKEAF, (SEQ ID NO: 69)
DWLKAFYDRVAEKLKEAF, (SEQ ID NO: 70)
EWLKAFYERVAEKLKEAF, (SEQ ID NO: 71)
DWLKAFYDKVAERLKEAF, (SEQ ID NO: 72)
EWLKAFYEKVAERLKEAF, (SEQ ID NO: 73)
DWLKAFYDKVAEKLREAF, (SEQ ID NO: 74)
EWLKAFYEKVAEKLREAF, (SEQ ID NO: 75)
DWLKAFYDRVAERLKEAF, (SEQ ID NO: 76)
EWLKAFYERVAERLKEAF, (SEQ ID NO: 77)
DWLRAFYDKVAEKLREAF, (SEQ ID NO: 78)
EWLRAFYEKVAEKLREAF, (SEQ ID NO: 79)
DWLRAFYDRVAEKLKEAF, (SEQ ID NO: 80)
EWLRAFYERVAEKLKEAF, (SEQ ID NO: 81)
DWLKAFYDKVAERLREAF, (SEQ ID NO: 82)
EWLKAFYEKVAERLREAF, (SEQ ID NO: 83)
DWLRAFYDKVAERLKEAF, (SEQ ID NO: 84)
EWLRAFYEKVAERLKEAF, (SEQ ID NO: 85)
DWLKAFYDKVAEKLKEAFPDWLKAFYDKVAEKLKEAF, (SEQ ID NO: 86)
DWLKAFYDKVAEKLKEFFPDWLKAFYDKVAEKLKEFF, (SEQ ID NO: 87)
DWFKAFYDKVAEKLKEAFPDWFKAFYDKVAEKLKEAF, (SEQ ID NO: 88)
DKLKAFYDKVFEWAKEAFPDKLKAFYDKVFEWLKEAF, (SEQ ID NO: 89)
DKWKAVYDKFAEAFKEFLPDKWKAVYDKFAEAFKEFL, (SEQ ID NO: 90)
DWFKAFYDKVAEKFKEAFPDWFKAFYDKVAEKFKEAF, (SEQ ID NO: 91)
DWLKAFVYDKVFKLKEFFPDWLKAFVYDKVFKLKEFF, (SEQ ID NO: 92)
DWLKAFYDKFAEKFKEFFPDWLKAFYDKFAEKFKEFF, (SEQ ID NO: 93)
EWFKAFYEKVAEKFKEAF, (SEQ ID NO: 94)
DWFKAFYDKVAEKF, (SEQ ID NO: 95)
FKAFYDKVAEKFKE, (SEQ ID NO: 96)
FKAFYEKVAEKFKE, (SEQ ID NO: 97)
FKAFYDKVAEKFKE, (SEQ ID NO: 98)
FKAFYEKVAEKFKE, (SEQ ID NO: 99)
DWFKAFYDKVAEKFKEAF, (SEQ ID NO: 100)
EWFKAFYEKVAEKFKEAF,
```

AFYDKVAEKFKEAF, (SEQ ID NO: 101)

DWFKAFYDKVAEKF, (SEQ ID NO: 102)

DWLKAFYDKVFEKFKEFF, (SEQ ID NO: 103)

EWLKAFYEKVFEKFKEFF, (SEQ ID NO: 104)

AFYDKVFEKFKEFF, (SEQ ID NO: 105)

AFYEKVFEKFKEFF, (SEQ ID NO: 106)

DWLKAFYDKVFEKF, (SEQ ID NO: 107)

EWLKAFYEKVFEKF, (SEQ ID NO: 108)

LKAFYDKVFEKFKE, (SEQ ID NO: 109)

LKAFYEKVFEKFKE, (SEQ ID NO: 110)

EWFKAFYEKVADKFKDAF, (SEQ ID NO: 111)

EWFKAFYDKVADKFKEAF, (SEQ ID NO: 112)

DWFKAFYEKVADKFKEAF, (SEQ ID NO: 113)

DWFKAFYEKVAEKFKDAF, (SEQ ID NO: 114)

DFWKAFYDKVAEKFKEAF, (SEQ ID NO: 115)

EFWKAFYEKVADKFKDAF, (SEQ ID NO: 116)

EFWKAFYDKVADKFKEAF, (SEQ ID NO: 117)

DFWKAFYEKVADKFKEAF, (SEQ ID NO: 118)

DFWKAFYEKVAEKFKDAF, (SEQ ID NO: 119)

DWFKAYFDKVAEKFKEAF, (SEQ ID NO: 120)

EWFKAYFEKVADKFKDAF, (SEQ ID NO: 121)

EWFKAYFDKVADKFKEAF, (SEQ ID NO: 122)

DWFKAYFEKVADKFKEAF, (SEQ ID NO: 123)

DWFKAYFEKVAEKFKDAF, (SEQ ID NO: 124)

DWFKAFVDKYAEKFKEAF, (SEQ ID NO: 125)

EWFKAFVEKYADKFKDAF, (SEQ ID NO: 126)

EWFKAFVDKYADKFKEAF, (SEQ ID NO: 127)

DWFKAFVEKYADKFKEAF, (SEQ ID NO: 128)

DWFKAFVEKYAEKFKDAF, (SEQ ID NO: 129)

DWFKAFYDKAVEKFKEAF, (SEQ ID NO: 130)

EWFKAFYEKAVDKFKDAF, (SEQ ID NO: 131)

EWFKAFYDKAVDKFKEAF, (SEQ ID NO: 132)

DWFKAFYEKAVDKFKEAF, (SEQ ID NO: 133)

DWFKAFYEKAVEKFKDAF, (SEQ ID NO: 134)

DWFKAFYDKVFEKAKEAF, (SEQ ID NO: 135)

EWFKAFYEKVFDKAKDAF, (SEQ ID NO: 136)

EWFKAFYDKVFDKAKEAF, (SEQ ID NO: 137)

DWFKAFYEKVFDKAKEAF, (SEQ ID NO: 138)

DWFKAFYEKVFEKAKDAF, (SEQ ID NO: 139)

DWFKAFYDKVAEKAKEFF, (SEQ ID NO: 140)

EWFKAFYEKVADKAKDFF, (SEQ ID NO: 141)

EWFKAFYDKVADKAKEFF, (SEQ ID NO: 142)

DWFKAFYEKVADKAKEFF, (SEQ ID NO: 143)

DWFKAFYEKVAEKAKDFF, (SEQ ID NO: 144)

DWFKAFYDKVAEKFKEFA, (SEQ ID NO: 145)

EWFKAFYEKVADKFKDFA, (SEQ ID NO: 146)

EWFKAFYDKVADKFKEFA, (SEQ ID NO: 147)

DWFKAFYEKVADKFKEFA, (SEQ ID NO: 148)

DWFKAFYEKVAEKFKDFA, (SEQ ID NO: 149)

DAFKAFYDKVAEKFKEWF, (SEQ ID NO: 150)

EAFKAFYEKVADKFKDWF, (SEQ ID NO: 151)

EAFKAFYDKVADKFKEWF, (SEQ ID NO: 152)

DAFKAFYEKVADKFKEWF, (SEQ ID NO: 153)

DAFKAFYEKVAEKFKDWF, (SEQ ID NO: 154)

-continued

DAFKAFYDKVWEKFKEAF, (SEQ ID NO: 155)

EAFKAFYEKVWDKFKDAF, (SEQ ID NO: 156)

EAFKAFYDKVWDKFKEAF, (SEQ ID NO: 157)

DAFKAFYEKVWDKFKEAF, (SEQ ID NO: 158)

DAFKAFYEKVWEKFKDAF, (SEQ ID NO: 159)

DYFKAFWDKVAEKFKEAF, (SEQ ID NO: 160)

EYFKAFWEKVADKFKDAF, (SEQ ID NO: 161)

EYFKAFWDKVADKFKEAF, (SEQ ID NO: 162)

DYFKAFWEKVADKFKEAF, (SEQ ID NO: 163)

DYFKAFWEKVAEKFKDAF, (SEQ ID NO: 164)

DWAKAFYDKVAEKFKEFF, (SEQ ID NO: 165)

EWAKAFYEKVADKFKDFF, (SEQ ID NO: 166)

EWAKAFYDKVADKFKEFF, (SEQ ID NO: 167)

DWAKAFYEKVADKFKEFF, (SEQ ID NO: 168)

DWAKAFYEKVAEKFKDFF, (SEQ ID NO: 169)

DWFKAAYDKVAEKFKEFF, (SEQ ID NO: 170)

EWFKAAYEKVADKFKDFF, (SEQ ID NO: 171)

EWFKAAYDKVADKFKEFF, (SEQ ID NO: 172)

DWFKAAYEKVADKFKEFF, (SEQ ID NO: 173)

DWFKAAYEKVAEKFKDFF, (SEQ ID NO: 174)

DWFKAFADKVAEKFKEYF, (SEQ ID NO: 175)

EWFKAFAEKVADKFKDYF, (SEQ ID NO: 176)

EWFKAFADKVADKFKEYF, (SEQ ID NO: 177)

DWFKAFAEKVADKFKEYF, (SEQ ID NO: 178)

DWFKAFAEKVAEKFKDYF, (SEQ ID NO: 179)

DWFKAFYDKAAEKFKEVF, (SEQ ID NO: 180)

EWFKAFYEKAADKFKDVF, (SEQ ID NO: 181)

-continued

EWFKAFYDKAADKFKEVF, (SEQ ID NO: 182)

DWFKAFYEKAADKFKEVF, (SEQ ID NO: 183)

DWFKAFYEKAAEKFKDVF, (SEQ ID NO: 184)

DWYKAFFDKVAEKFKEAF, (SEQ ID NO: 185)

EWYKAFFEKVADKFKDAF, (SEQ ID NO: 186)

EWYKAFFDKVADKFKEAF, (SEQ ID NO: 187)

DWYKAFFEKVADKFKEAF, (SEQ ID NO: 188)

DWYKAFFEKVAEKFKDAF, (SEQ ID NO: 189)

DWVKAFYDKFAEKFKEAF, (SEQ ID NO: 190)

EWVKAFYEKFADKFKDAF, (SEQ ID NO: 191)

EWVKAFYDKFADKFKEAF, (SEQ ID NO: 192)

DWVKAFYEKFADKFKEAF, (SEQ ID NO: 193)

DWVKAFYEKFAEKFKDAF, (SEQ ID NO: 194)

DWFKAFFDKVAEKYKEAF, (SEQ ID NO: 195)

EWFKAFFEKVADKYKDAF, (SEQ ID NO: 196)

EWFKAFFDKVADKYKEAF, (SEQ ID NO: 197)

DWFKAFFEKVADKYKEAF, (SEQ ID NO: 198)

DWFKAFFEKVADKYKEAF, (SEQ ID NO: 199)

DWFKAFFDKVAEKFKEAY, (SEQ ID NO: 200)

EWFKAFFEKVADKFKDAY, (SEQ ID NO: 201)

EWFKAFFDKVADKFKEAY, (SEQ ID NO: 202)

DWFKAFFEKVADKFKEAY, (SEQ ID NO: 203)

DWFKAFFEKVAEKFKDAY, (SEQ ID NO: 204)

DWFKAFYDKFAEKFKEAV, (SEQ ID NO: 205)

EWFKAFYEKFADKFKDAV, (SEQ ID NO: 206)

EWFKAFYDKFADKFKEAV, (SEQ ID NO: 207)

DWFKAFYEKFADKFKEAV, (SEQ ID NO: 208)

DWFKAFYEKFAEKFKDAV, (SEQ ID NO: 209)

DKFKAFYDKVAEKFWEAF, (SEQ ID NO: 210)

EKFKAFYEKVADKFWDAF, (SEQ ID NO: 211)

EKFKAFYDKVADKFWEAF, (SEQ ID NO: 212)

DKFKAFYEKVADKFWEAF, (SEQ ID NO: 213)

DKFKAFYEKVAEKFWDAF, (SEQ ID NO: 214)

DKWKAFYDKVAEKFFEAF, (SEQ ID NO: 215)

EKWKAFYEKVADKFFDAF, (SEQ ID NO: 216)

EKWKAFYDKVADKFFEAF, (SEQ ID NO: 217)

DKWKAFYEKVADKFFEAF, (SEQ ID NO: 218)

DKWKAFYEKVAEKFFDAF, (SEQ ID NO: 219)

DKFKAFYDKWAEVFKEAF, (SEQ ID NO: 220)

EKFKAFYEKWADVFKDAF, (SEQ ID NO: 221)

EKFKAFYDKWADVFKEAF, (SEQ ID NO: 222)

DKFKAFYEKWADVFKEAF, (SEQ ID NO: 223)

DKFKAFYEKWAEVFKDAF, (SEQ ID NO: 224)

DKFKAFYDKVAEFWKEAF, (SEQ ID NO: 225)

EKFKAFYEKVADFWKDAF, (SEQ ID NO: 226)

EKFKAFYDKVADFWKEAF, (SEQ ID NO: 227)

DKFKAFYEKVADFWKEAF, (SEQ ID NO: 228)

DKFKAFYEKVAEFWKDAF, (SEQ ID NO: 229)

FAEKFKEAVKDYFAKFWD, (SEQ ID NO: 230)

FADKFKDAVKEYFAKFWE, (SEQ ID NO: 231)

FADKFKEAVKDYFAKFWE, (SEQ ID NO: 232)

FAEKFKDAVKEYFAKFWD, (SEQ ID NO: 233)

FAEKFKDAVKDYFAKFWE, (SEQ ID NO: 234)

FWEKFKEAVKDYFAKFAD, (SEQ ID NO: 235)

FWDKFKDAVKEYFAKFAE, (SEQ ID NO: 236)

FADKFKEAVKDYFAKFWE, (SEQ ID NO: 237)

FAEKFKDAVKEYFAKFWD, (SEQ ID NO: 238)

FAEKFKDAVKDYFAKFWE, (SEQ ID NO: 239)

FFEKFKEAVKDYFAKAWD, (SEQ ID NO: 240)

FFDKFKDAVKEYFAKAWE, (SEQ ID NO: 241)

FFDKFKEAVKDYFAKAWE, (SEQ ID NO: 242)

FFEKFKDAVKEYFAKAWD, (SEQ ID NO: 243)

FFEKFKDAVKDYFAKAWE, (SEQ ID NO: 244)

FAEKAKEFVKDYFAKFWD, (SEQ ID NO: 245)

FADKAKDFVKEYFAKFWE, (SEQ ID NO: 246)

FADKAKEFVKDYFAKFWE, (SEQ ID NO: 247)

FAEKAKDFVKEYFAKFWD, (SEQ ID NO: 248)

FAEKAKDFVKDYFAKFWE, (SEQ ID NO: 249)

FAEKFKEVAKDYFAKFWD, (SEQ ID NO: 250)

FADKFKDVAKEYFAKFWE, (SEQ ID NO: 251)

FADKFKEVAKDYFAKFWE, (SEQ ID NO: 252)

FAEKFKDVAKEYFAKFWD, (SEQ ID NO: 253)

FAEKFKDVAKDYFAKFWE, (SEQ ID NO: 254)

FAEKFKEAYKDVFAKFWD, (SEQ ID NO: 255)

FADKFKDAYKEVFAKFWE, (SEQ ID NO: 256)

FADKFKEAYKDVFAKFWE, (SEQ ID NO: 257)

FAEKFKDAYKEVFAKFWD, (SEQ ID NO: 258)

FAEKFKDAYKDVFAKFWE, (SEQ ID NO: 259)

FAEKFKEAVKDFYAKFWD, (SEQ ID NO: 260)

FADKFKDAVKEFYAKFWE, (SEQ ID NO: 261)

FADKFKEAVKDFYAKFWE, (SEQ ID NO: 262)

FAEKFKDAVKEFYAKFWD, (SEQ ID NO: 263)

FAEKFKDAVKDFYAKFWE, (SEQ ID NO: 264)

FAEKFWEAVKDYFAKFKD, (SEQ ID NO: 265)

FADKFWDAVKEYFAKFKE, (SEQ ID NO: 266)

FADKFWEAVKDYFAKFKE, (SEQ ID NO: 267)

FAEKFWDAVKEYFAKFKD, (SEQ ID NO: 268)

FAEKFWDAVKDYFAKFKE, (SEQ ID NO: 269)

AFEKFKEAVKDYFAKFWD, (SEQ ID NO: 270)

AFDKFKDAVKEYFAKFWE, (SEQ ID NO: 271)

AFDKFKEAVKDYFAKFWE, (SEQ ID NO: 272)

AFEKFKDAVKEYFAKFWD, (SEQ ID NO: 273)

AFEKFKDAVKDYFAKFWE, (SEQ ID NO: 274)

VAEKFKEAFKDYFAKFWD, (SEQ ID NO: 275)

VADKFKDAFKEYFAKFWE, (SEQ ID NO: 276)

VADKFKEAFKDYFAKFWE, (SEQ ID NO: 277)

VAEKFKDAFKEYFAKFWD, (SEQ ID NO: 278)

VAEKFKDAFKDYFAKFWE, (SEQ ID NO: 279)

YAEKFKEAVKDFFAKFWD, (SEQ ID NO: 280)

YADKFKDAVKEFFAKFWE, (SEQ ID NO: 281)

YADKFKEAVKDFFAKFWE, (SEQ ID NO: 282)

YAEKFKDAVKEFFAKFWD, (SEQ ID NO: 283)

YAEKFKDAVKDFFAKFWE, (SEQ ID NO: 284)

AAEKFKEFVKDYFAKFWD, (SEQ ID NO: 285)

AADKFKDFVKEYFAKFWE, (SEQ ID NO: 286)

AADKFKEFVKDYFAKFWE, (SEQ ID NO: 287)

AAEKFKDFVKEYFAKFWD, (SEQ ID NO: 288)

AAEKFKDFVKDYFAKFWE, (SEQ ID NO: 289)

FFEKAKEAVKDYFAKFWD, (SEQ ID NO: 290)

FFDKAKDAVKEYFAKFWE, (SEQ ID NO: 291)

FFDKAKEAVKDYFAKFWE, (SEQ ID NO: 292)

FFEKAKDAVKEYFAKFWD, (SEQ ID NO: 293)

FFEKAKDAVKDYFAKFWE, (SEQ ID NO: 294)

FYEKFKEAVKDAFAKFWD, (SEQ ID NO: 295)

FYDKFKDAVKEAFAKFWE, (SEQ ID NO: 296)

FYDKFKEAVKDAFAKFWE, (SEQ ID NO: 297)

FYEKFKDAVKEAFAKFWD, (SEQ ID NO: 298)

FYEKFKDAVKDAFAKFWE, (SEQ ID NO: 299)

FVEKFKEAAKDYFAKFWD, (SEQ ID NO: 300)

FVDKFKDAAKEYFAKFWE, (SEQ ID NO: 301)

FVDKFKEAAKDYFAKFWE, (SEQ ID NO: 302)

FVEKFKDAAKEYFAKFWD, (SEQ ID NO: 303)

FVEKFKDAAKDYFAKFWE, (SEQ ID NO: 304)

FAEKYKEAVKDFFAKFWD, (SEQ ID NO: 305)

FADKYKDAVKEFFAKFWE, (SEQ ID NO: 306)

FADKYKEAVKDFFAKFWE, (SEQ ID NO: 307)

FAEKYKDAVKEFFAKFWD, (SEQ ID NO: 308)

FAEKYKDAVKDFFAKFWE, (SEQ ID NO: 309)

FAEKVKEAFKDYFAKFWD, (SEQ ID NO: 310)

FADKVKDAFKEYFAKFWE, (SEQ ID NO: 311)

FADKVKEAFKDYFAKFWE, (SEQ ID NO: 312)

FAEKVKDAFKEYFAKFWD, (SEQ ID NO: 313)

FAEKVKDAFKDYFAKFWE, (SEQ ID NO: 314)

FAEKFKEYVKDAFAKFWD, (SEQ ID NO: 315)

FADKFKDYVKEAFAKFWE, (SEQ ID NO: 316)

FADKFKEYVKDAFAKFWE, (SEQ ID NO: 317)

FAEKFKDYVKEAFAKFWD, (SEQ ID NO: 318)

FAEKFKDYVKDAFAKFWE, (SEQ ID NO: 319)

FAEKFKEAFKDYVAKFWD, (SEQ ID NO: 320)

FADKFKDAFKEYVAKFWE, (SEQ ID NO: 321)

FADKFKEAFKDYVAKFWE, (SEQ ID NO: 322)

FAEKFKDAFKEYVAKFWD, (SEQ ID NO: 323)

FAEKFKDAFKDYVAKFWE, (SEQ ID NO: 324)

FAEKFKEAFKDYFAKVWD, (SEQ ID NO: 325)

FADKFKDAFKEYFAKVWE, (SEQ ID NO: 326)

FADKFKEAFKDYFAKVWE, (SEQ ID NO: 327)

FAEKFKDAFKEYFAKVWD, (SEQ ID NO: 328)

FAEKFKDAFKDYFAKVWE, (SEQ ID NO: 329)

FAEKFKEAVKDFFAKYWD, (SEQ ID NO: 330)

FADKFKDAVKEFFAKYWE, (SEQ ID NO: 331)

FADKFKEAVKDFFAKYWE, (SEQ ID NO: 332)

FAEKFKDAVKEFFAKYWD, (SEQ ID NO: 333)

FAEKFKDAVKDFFAKYWE, (SEQ ID NO: 334)

WAEKFFEAVKDYFAKFKD, (SEQ ID NO: 335)

WADKFFDAVKEYFAKFKE, (SEQ ID NO: 336)

WADKFFEAVKDYFAKFKE, (SEQ ID NO: 337)

WAEKFFDAVKEYFAKFKD, (SEQ ID NO: 338)

WAEKFFDAVKDYFAKFKE, (SEQ ID NO: 339)

FAEKWFEAVKDYFAKFKD, (SEQ ID NO: 340)

FADKWFDAVKEYFAKFKE, (SEQ ID NO: 341)

FADKWFEAVKDYFAKFKE, (SEQ ID NO: 342)

FAEKWFDAVKEYFAKFKD, (SEQ ID NO: 343)

FAEKWFDAVKDYFAKFKE, (SEQ ID NO: 344)

FAEKFVEAWKDYFAKFKD, (SEQ ID NO: 345)

FADKFVDAWKEYFAKFKE, (SEQ ID NO: 346)

FADKFVEAWKDYFAKFKE, (SEQ ID NO: 347)

FAEKFVDAWKEYFAKFKD, (SEQ ID NO: 348)

FAEKFVDAWKDYFAKFKE, (SEQ ID NO: 349)

FYEKFAEAVKDWFAKFKD, (SEQ ID NO: 350)

FYDKFADAVKEWFAKFKE, (SEQ ID NO: 351)

FYDKFAEAVKDWFAKFKE, (SEQ ID NO: 352)

FYEKFADAVKEWFAKFKD, (SEQ ID NO: 353)

FYEKFADAVKDWFAKFKE, (SEQ ID NO: 354)

DWFKHFYDKVAEKFKEAF, (SEQ ID NO: 355)

EWFKHFYEKVADKFKDAF, (SEQ ID NO: 356)

EWFKHFYDKVAEKFKEAF, (SEQ ID NO: 357)

DWFKHFYEKVAEKFKEAF, (SEQ ID NO: 358)

DWFKHFYDKVADKFKEAF, (SEQ ID NO: 359)

DWFKHFYDKVAEKFKDAF, (SEQ ID NO: 360)

DWHKFFYDKVAEKFKEAF, (SEQ ID NO: 361)

EWHKFFYEKVADKFKDAF, (SEQ ID NO: 362)

EWHKFFYDKVAEKFKEAF, (SEQ ID NO: 363)

DWHKFFYEKVAEKFKEAF, (SEQ ID NO: 364)

DWHKFFYDKVADKFKEAF, (SEQ ID NO: 365)

DWHKFFYDKVAEKFKDAF, (SEQ ID NO: 366)

DWFKFHYDKVAEKFKEAF, (SEQ ID NO: 367)

EWFKFHYEKVADKFKDAF, (SEQ ID NO: 368)

EWFKFHYDKVAEKFKEAF, (SEQ ID NO: 369)

DWFKFHYEKVAEKFKEAF, (SEQ ID NO: 370)

DWFKFHYDKVADKFKEAF, (SEQ ID NO: 371)

DWFKFHYDKVAEKFKDAF, (SEQ ID NO: 372)

DWFKVFYDKHAEKFKEAF, (SEQ ID NO: 373)

EWFKVFYEKHADKFKDAF, (SEQ ID NO: 374)

EWFKVFYDKHAEKFKEAF, (SEQ ID NO: 375)

DWFKVFYEKHAEKFKEAF, (SEQ ID NO: 376)

DWFKVFYDKHADKFKEAF, (SEQ ID NO: 377)

DWFKVFYDKHAEKFKDAF, (SEQ ID NO: 378)

DWFKAFYDKVAEKFKEHF, (SEQ ID NO: 379)

EWFKAFYEKVADKFKDHF, (SEQ ID NO: 380)

EWFKAFYDKVAEKFKEHF, (SEQ ID NO: 381)

DWFKAFYEKVAEKFKEHF, (SEQ ID NO: 382)

DWFKAFYDKVADKFKEHF, (SEQ ID NO: 383)

DWFKAFYDKVAEKFKDHF, (SEQ ID NO: 384)

DWFKAFYDKVAEKFKEFH, (SEQ ID NO: 385)

EWFKAFYEKVADKFKDFH, (SEQ ID NO: 386)

EWFKAFYDKVAEKFKEFH, (SEQ ID NO: 387)

DWFKAFYDKVAEKFKEFH, (SEQ ID NO: 388)

DWFKAFYEKVAEKFKEFH, (SEQ ID NO: 389)

DWFKAFYDKVAEKFKEFH, (SEQ ID NO: 390)

DWFKAFYDKVAEKFKDFH, (SEQ ID NO: 391)

FAEKFKEAVKDYFAKFWD, (SEQ ID NO: 392)

FHEKFKEAVKDYFAKFWD, (SEQ ID NO: 393)

FHEKFKEAVKEYFAKFWE, (SEQ ID NO: 394)

FHDKFKDAVKDYFAKFWD, (SEQ ID NO: 395)

FHDKFKDAVKEYFAKFWE, (SEQ ID NO: 396)

FHDKFKEAVKDYFAKFWD, (SEQ ID NO: 397)

FHEKFKDAVKDYFAKFWD, (SEQ ID NO: 398)

FHEKFKEAVKEYFAKFWD, (SEQ ID NO: 399)

FHEKFKEAVKDYFAKFWE, (SEQ ID NO: 400)

HFEKFKEAVKDYFAKFWD, (SEQ ID NO: 401)

HFDKFKDAVKEYFAKFWE, (SEQ ID NO: 402)

HFEKFKEAVKEYFAKFWE, (SEQ ID NO: 403)

HFDKFKEAVKDYFAKFWD, (SEQ ID NO: 404)

HFEKFKDAVKDYFAKFWD, (SEQ ID NO: 405)

HFEKFKEAVKEYFAKFWD, (SEQ ID NO: 406)

HFEKFKEAVKDYFAKFWE, (SEQ ID NO: 407)

FFEKHKEAVKDYFAKFWD, (SEQ ID NO: 408)

FFDKHKDAVKEYFAKFWE, (SEQ ID NO: 409)

FFEKHKEAVKEYFAKFWE, (SEQ ID NO: 410)

FFDKHKDAVKDYFAKFWD, (SEQ ID NO: 411)

FFDKHKEAVKDYFAKFWD, (SEQ ID NO: 412)

FFEKHKEAVKEYFAKFWD, (SEQ ID NO: 413)

FFEKHKEAVKDYFAKFWE, (SEQ ID NO: 414)

FVEKFKEAHKDYFAKFWD, (SEQ ID NO: 415)

FVDKFKDAHKEYFAKFWE, (SEQ ID NO: 416)

FVEKFKEAHKEYFAKFWE, (SEQ ID NO: 417)

FVDKFKDAHKDYFAKFWD, (SEQ ID NO: 418)

FVDKFKEAHKDYFAKFWD, (SEQ ID NO: 419)

FVEKFKDAHKDYFAKFWD, (SEQ ID NO: 420)

FVEKFKEAHKEYFAKFWD, (SEQ ID NO: 421)

FVEKFKEAHKDYFAKFWE, (SEQ ID NO: 422)

FAEKFKEHVKDYFAKFWD, (SEQ ID NO: 423)

FADKFKDHVKEYFAKFWE, (SEQ ID NO: 424)

FAEKFKEHVKEYFAKFWE, (SEQ ID NO: 425)

FADKFKDHVKDYFAKFWD, (SEQ ID NO: 426)

FADKFKEHVKDYFAKFWD, (SEQ ID NO: 427)

FAEKFKDHVKDYFAKFWD, (SEQ ID NO: 428)

FAEKFKEHVKEYFAKFWD, (SEQ ID NO: 429)

FAEKFKEHVKDYFAKFWE, (SEQ ID NO: 430)

FAEKFKEFVKDYHAKFWD, (SEQ ID NO: 431)

FADKFKDFVKEYHAKFWE, (SEQ ID NO: 432)

FADKFKEFVKDYHAKFWD, (SEQ ID NO: 433)

FAEKFKDFVKDYHAKFWD, (SEQ ID NO: 434)

FADKFKDFVKDYHAKFWD, (SEQ ID NO: 435)

FAEKFKEFVKEYHAKFWE, (SEQ ID NO: 436)

FAEKFKEFVKEYHAKFWD, (SEQ ID NO: 437)

FAEKFKEFVKDYHAKFWE, (SEQ ID NO: 438)

FAEKFKEFVKDYFAKHWD, (SEQ ID NO: 439)

FAEKFKEFVKDYFAKHWD, (SEQ ID NO: 440)

FADKFKDFVKEYFAKHWE, (SEQ ID NO: 441)

FAEKFKEFVKEYFAKHWE, (SEQ ID NO: 442)

FADKFKDFVKDYFAKHWD, (SEQ ID NO: 443)

FADKFKEFVKDYFAKHWD, (SEQ ID NO: 444)

FAEKFKDFVKDYFAKHWD, (SEQ ID NO: 445)

FAEKFKEFVKEYFAKHWD, (SEQ ID NO: 446)

FAEKFKEFVKDYFAKHWE, (SEQ ID NO: 447)

FAEKFKEAVKEYFAKFWE, (SEQ ID NO: 448)

FADKFKDAVKDYFAKFWD, (SEQ ID NO: 449)

FAERFREAVKDYFAKFWD, (SEQ ID NO: 450)

FAEKFREAVKDYFAKFWD, (SEQ ID NO: 451)

FAEKFKEAVRDYFAKFWD, (SEQ ID NO: 452)

FAEKFKEAVKDYFARFWD, (SEQ ID NO: 453)

FAEKFKEAVKEYFAKFWE, (SEQ ID NO: 454)

FADKFKDAVKDYFAKFWD, (SEQ ID NO: 455)

FAERFREAVKDYFAKFWD, (SEQ ID NO: 456)

FAEKFREAVKDYFAKFWD, (SEQ ID NO: 457)

FAEKFKEAVRDYFAKFWD, (SEQ ID NO: 458)

FAEKFKEAVKDYFARFWD, (SEQ ID NO: 459)

FAEKFKEAVKEYFAKFWE, (SEQ ID NO: 460)

FADKFKDAVKDYFAKFWD, (SEQ ID NO: 461)

FAERFREAVKDYFAKFWD, (SEQ ID NO: 462)

FAEKFREAVKDYFAKFWD, (SEQ ID NO: 463)

FAEKFKEAVRDYFAKFWD, (SEQ ID NO: 464)

FAEKFKEAVKDYFARFWD, (SEQ ID NO: 465)

FAERFREAVKDYFAKFWD, (SEQ ID NO: 466)

FAEKFREAVKDYFAKFWD, (SEQ ID NO: 467)

FAEKFKEAVRDYFAKFWD, (SEQ ID NO: 468)

FAEKFKEAVKDYFARFWD, (SEQ ID NO: 469)

FAEKFKEAVKEYFAKFWE, (SEQ ID NO: 470)

FADKFKDAVKDYFAKFWD, (SEQ ID NO: 471)

FAERFREAVKDYFAKFWD, (SEQ ID NO: 472)

FAEKFREAVKDYFAKFWD, (SEQ ID NO: 473)

FAEKFKEAVRDYFAKFWD, (SEQ ID NO: 474)

FAEKFKEAVKDYFARFWD, (SEQ ID NO: 475)

LFEKFAEAFKDYVAKWKD, (SEQ ID NO: 476)

LFERFAEAFKDYVAKWKD, (SEQ ID NO: 477)

LFEKFAEAFRDYVAKWKD, (SEQ ID NO: 478)

LFEKFAEAFKDYVARWKD,

-continued

LFEKFAEAFKDYVAKWRD, (SEQ ID NO: 479)

LFEKFAEAFKEYVAKWKE, (SEQ ID NO: 480)

LFDKFADAFKDYVAKWKD, (SEQ ID NO: 481)

LFDKFAEAFKDYVAKWKD, (SEQ ID NO: 482)

LFEKFADAFKDYVAKWKD, (SEQ ID NO: 483)

LFEKFAEAFKEYVAKWKD, (SEQ ID NO: 484)

LFEKFAEAFKDYVAKWKE, (SEQ ID NO: 485)

FAEKAWEFVKDYFAKLKD, (SEQ ID NO: 486)

FAERAWEFVKDYFAKLKD, (SEQ ID NO: 487)

FAEKAWEFVKDYFAKLKD, (SEQ ID NO: 488)

FAEKAWEFVKDYFAKLKD, (SEQ ID NO: 489)

FAEKAWEFVKDYFAKLRD, (SEQ ID NO: 490)

FAEKAWEFVKEYFAKLKE, (SEQ ID NO: 491)

FADKAWDFVKDYFAKLKD, (SEQ ID NO: 492)

FADKAWEFVKDYFAKLKD, (SEQ ID NO: 493)

FAEKAWDFVKDYFAKLKD, (SEQ ID NO: 494)

FAEKAWEFVKEYFAKLKD, (SEQ ID NO: 495)

FAEKAWEFVKDYFAKLKE, (SEQ ID NO: 496)

FFEKFKEFVKDYFAKLWD, (SEQ ID NO: 497)

FFEKFKEFVKEYFAKLWE, (SEQ ID NO: 498)

FFDKFKDFVKDYFAKLWD, (SEQ ID NO: 499)

FFERFKEFVKDYFAKLWD, (SEQ ID NO: 500)

FFEKFREFVKDYFAKLWD, (SEQ ID NO: 501)

FFEKFKEFVRDYFAKLWD, (SEQ ID NO: 502)

FFEKFKEFVKDYFARLWD, (SEQ ID NO: 503)

FFDKFKEFVKDYFAKLWD, (SEQ ID NO: 504)

FFEKFKDFVKDYFAKLWD, (SEQ ID NO: 505)

FFEKFKEFVKEYFAKLWD, (SEQ ID NO: 506)

FFEKFKEFVKDYFAKLWE, (SEQ ID NO: 507)

FLEKFKEFVKDYFAKFWD, (SEQ ID NO: 508)

FLEKFKEFVKEYFAKFWE, (SEQ ID NO: 509)

FLDKFKEFVKDYFAKFWD, (SEQ ID NO: 510)

FLDKFKEFVKDYFAKFWD, (SEQ ID NO: 511)

FLEKFKDFVKDYFAKFWD, (SEQ ID NO: 512)

FLEKFKEFVKEYFAKFWD, (SEQ ID NO: 513)

FLEKFKEFVKDYFAKFWE, (SEQ ID NO: 514)

FLERFKEFVKDYFAKFWD, (SEQ ID NO: 515)

FLEKFREFVKDYFAKFWD, (SEQ ID NO: 516)

FLEKFKEFVRDYFAKFWD, (SEQ ID NO: 517)

FLEKFKEFVKDYFARFWD, (SEQ ID NO: 518)

FFEKFKEFFKDYFAKLWD, (SEQ ID NO: 519)

FFEKFKEFFKEYFAKLWE, (SEQ ID NO: 520)

FFDKFKDFFKDYFAKLWD, (SEQ ID NO: 521)

FFERKEFFKDYFAKLWD, (SEQ ID NO: 522)

FFEKFREFFKDYFAKLWD, (SEQ ID NO: 523)

FFEKFKEFFRDYFAKLWD, (SEQ ID NO: 524)

FFERFKEFFKDYFARLWD, (SEQ ID NO: 525)

FFDKFKEFFKDYFAKLWD, (SEQ ID NO: 526)

FFEKFKDFFKDYFAKLWD, (SEQ ID NO: 527)

FFEKFKEFFKEYFAKLWD, (SEQ ID NO: 528)

FFEKFKEFFKDYFAKLWE, (SEQ ID NO: 529)

FAEKFKEAVKDYFAKFWD, (SEQ ID NO: 530)

FAEKFKEAVKEYFAKFWE, (SEQ ID NO: 531)

FADKFKDAVKDYFAKFWD, (SEQ ID NO: 532)

-continued

FAERFREAVKDYFAKFWD, (SEQ ID NO: 533)

FAEKFREAVKDYFAKFWD, (SEQ ID NO: 534)

FAEKFKEAVRDYFAKFWD, (SEQ ID NO: 535)

FAEKFKEAVKDYFARFWD, (SEQ ID NO: 536)

DKWKAVYDKFAEAAFKEFF, (SEQ ID NO: 537)

EKWKAVYEKFAEAAFKEFF, (SEQ ID NO: 538)

DKWKAVYDKFADAFKDFF, (SEQ ID NO: 539)

DRWKAVYDKFAEAAFKEFF, (SEQ ID NO: 540)

DKWRAVYDKFAEAAFKEFF, (SEQ ID NO: 541)

DKWKAVYDRFAEAAFKEFF, (SEQ ID NO: 542)

DKWKAVYDKFAEAFREFF, (SEQ ID NO: 543)

FFEKFAEAFKDYVAKWKD, (SEQ ID NO: 544)

FFEKFAEAFKEYVAKWKE, (SEQ ID NO: 545)

FFDKFADAFKDYVAKWKD, (SEQ ID NO: 546)

FFERFAEAFKDYVAKWKD, (SEQ ID NO: 547)

FFERFAEAFRDYVAKWKD, (SEQ ID NO: 548)

FFEKFAEAFKDYVARWKD, (SEQ ID NO: 549)

FFERFAEAFKDYVAKWRD, (SEQ ID NO: 550)

FFDKFAEAFKDYVAKWKD, (SEQ ID NO: 551)

FFEKFADAFKDYVAKWKD, (SEQ ID NO: 552)

FFERFAEAFKEYVAKWKD, (SEQ ID NO: 553)

FFERFAEAFKDYVAKWKE, (SEQ ID NO: 554)

FFEKFKEFFKDYFAKFWD, (SEQ ID NO: 555)

FFDKFKDFFKDYFAKFWD, (SEQ ID NO: 556)

FFEKFKEFFKEYFAKFWE, (SEQ ID NO: 557)

FFERFKEFFKDYFAKFWD, (SEQ ID NO: 558)

FFEKFREFFKDYFAKFWD, (SEQ ID NO: 559)

FFEKFKEFFRDYFAKFWD, (SEQ ID NO: 560)

FFEKFKEFFKDYFARFWD, (SEQ ID NO: 561)

FFDKFKEFFKDYFAKFWD, (SEQ ID NO: 562)

FFEKFKDFFKDYFAKFWD, (SEQ ID NO: 563)

FFEKFKEFFKEYFAKFWD, (SEQ ID NO: 564)

FFEKFKEFFKDYFAKFWE, (SEQ ID NO: 565)

EVRAKLEEQAQQIRLQAEAFQARLKSWFEPLVE, (SEQ ID NO: 566)

EVRAKLEEQAQQIRLQAEAFQARLKSWFE, (SEQ ID NO: 567)

EVRSKLEEWFAAFREFAEEFLARLKS, (SEQ ID NO: 568)

PVLDLFRELLNELLEALKQKLK, (SEQ ID NO: 569)

DWLKAFYDKVAEKLKEAFPDWAKAAYDKAAEKAKEAA, (SEQ ID NO: 570)

EELKEKLEELKEKLEEKLPEELKEKLEELKEKLEEKL, (SEQ ID NO: 571)

EELKAKLEELKAKLEEKLPEELKAKLEELKAKLEEKL, (SEQ ID NO: 572)

EKLKALLEKLLAKLKELLPEKLKALLEKLLAKLKELL, (SEQ ID NO: 573)

EWLKELLEKLLEKLKELLPEWLKELLEKLLEKLKELL, (SEQ ID NO: 574)

EKFKELLEKFLEKFKELLPEKFKELLEKFLEKFKELL, (SEQ ID NO: 575)

EKLKELLEKLLELLKKLLPEKLKELLEKLLELLKKLL, (SEQ ID NO: 576)

EKLKELLEKLKAKLEELLPEKLKELLEKLKAKLEELL, (SEQ ID NO: 577)

EKLKELLEKLLAKLKELLPEKLKELLEKLLAKLKELL, (SEQ ID NO: 578)

EKFKELLEKLLEKLKELLPEKFKELLEKLLEKLKELL, (SEQ ID NO: 579)

EKLKAKLEELKAKLEELLPEKLKAKLEELKAKLEELL, (SEQ ID NO: 580)

EELKELLKELLKKLEKLLPELKELLKELLKKLEKLL, (SEQ ID NO: 581)

EELKKLLEELLKKLKELLPEELKKLLEELLKKLKELL, (SEQ ID NO: 582)

EKLKELLEKLLEKLKELLAEKLKELLEKLLEKLKELL, (SEQ ID NO: 583)

EKLKELLEKLLEKLKELLAAEKLKELLEKLLEKLKELL, (SEQ ID NO: 584)

EKLKAKLEELKAKLEELLPEKAKAALEEAKAKAEELA, (SEQ ID NO: 585)

EKLKAKLEELKAKLEELLPEHAKAALEEAKCKAEELA, (SEQ ID NO: 586)

-continued

DHLKAFYDKVACKLKEAFPDWAKAAYDKAAEKAKEAA, (SEQ ID NO: 587)

DWLKAFYDKVAEKLKEAFPDHAKAAYDKAACKAKEAA, (SEQ ID NO: 588)

DWLKAFYDKVACKLKEAFPDWAKAAYNKAAEKAKEAA, (SEQ ID NO: 589)

DHLKAFYDKVAEKLKEAFPDWAKAAYDKAAEKAKEAA, (SEQ ID NO: 590)

VLESFKVSFLSALEEYTKKLNTQ, (SEQ ID NO: 591)

DKWKAVYDKFAEAFKEFL, (SEQ ID NO: 592)

DKLKAFYDKVFEWAKEAF, (SEQ ID NO: 593)

DQYYLRVTTVA, (SEQ ID NO: 595)

ECKPCLKQTCMKFYARVCR, (SEQ ID NO: 596)

FSRASSIIDELFQD, (SEQ ID NO: 597)

IQNAVNGVKQIKTLIEKTNEE, (SEQ ID NO: 598)

LLEQLNEQFNWVSRLANL, (SEQ ID NO: 599)

LLEQLNEQFNWVSRLANLTEGE, (SEQ ID NO: 600)

LLEQLNEQFNWVSRLANLTQGE, (SEQ ID NO: 601)

LVGRQLEEFL, (SEQ ID NO: 602)

MNGDRIDSLLEN, (SEQ ID NO: 603)

NELQEMSNQGSKYVNKEIQNAVNGV, (SEQ ID NO: 604)

PCLKQTCMKFYARVCR, (SEQ ID NO: 605)

PFLEMIHEAQQAMDI, (SEQ ID NO: 606)

PGVCNETMMALWEECK, (SEQ ID NO: 607)

PKFMETVAEKALQEYRKKHRE, (SEQ ID NO: 608)

PSGVTEVVVKLFDS, (SEQ ID NO: 609)

PSQAKLRRELDESLQVAERLTRKYNELLKSYQ, (SEQ ID NO: 610)

PTEFIREGDDD, (SEQ ID NO: 611)

QQTHMLDVMQD, (SEQ ID NO: 612)

RKTLLSNLEEAKKKKEDALNETRESETKLKEL, (SEQ ID NO: 613)

RMKDQCDKCREILSV, (SEQ ID NO: 614)

GVFAKIFKWISGLFKKIG, (SEQ ID NO: 615)

GIKKFLGSIWKFIKAFVG, (SEQ ID NO: 616)

GFKKFLGSWAKIYKAFVG, (SEQ ID NO: 617)

GFRRFLGSWARIYRAFVG, (SEQ ID NO: 618)

TEELRVRLASHLRKLRKRLL, (SEQ ID NO: 619)

TEELRVRLASHLRKLRK, (SEQ ID NO: 620)

LRVRLASHLRKLRKRLL, (SEQ ID NO: 621)

RLASHLRKLRKRLL, (SEQ ID NO: 622)

SHLRKLRKRLL, (SEQ ID NO: 623)

LRKLRKRLL, (SEQ ID NO: 624)

LRKLRKRLLLRKLRKRLL, (SEQ ID NO: 625)

LRKLRKRLLLRKLRKRLLLRKLRKRLL, (SEQ ID NO: 626)

RQIKIWFQNRRMKWKKCLRVRLASHLRKLRKRLL, (SEQ ID NO: 627)

LRVRLASHLRKLRKRLL, (SEQ ID NO: 628)

EELRVRLASHLRKLRKRLLRDADDLQKRLAVYEEQAQQIRLQAEAFQARLKSWFEPLVEDM, (SEQ ID NO: 629)

CEELRVRLASHLRKLRKRLLRDADDLQKRLAVY, (SEQ ID NO: 630)

LRKLRKRLLRDADDLLRKLRKRLLRDADDL, (SEQ ID NO: 631)

TEELRVRLASHLRKLRKRLL, (SEQ ID NO: 632)

TEELRVRLASHLEKLRKRLL, (SEQ ID NO: 633)

TEELRVRLASHLRELRKRLL, (SEQ ID NO: 634)

LREKKLRVSALRTHRLELRL, (SEQ ID NO: 635)

LRKLRKRLLRDWLKAFYDKVAEKLKEAF, (SEQ ID NO: 636)

LRRLRRRLLRDWLKAFYDKVAEKLKEAF, (SEQ ID NO: 637)
and

RRRRRRRRRRDWLKAFYDKVAEKLKEAF. (SEQ ID NO: 638)

Embodiment 60

The ezetimibe-associated apoA-I mimetic peptide according to any one of embodiments 43-59, wherein said peptide is obtainable using a method according to any one of embodiments 1-23.

Embodiment 61

The ezetimibe-associated apoA-I mimetic peptide according to any one of embodiments 43-59, wherein said peptide is prepared using a method according to any one of embodiments 1-23.

Embodiment 62

A pharmaceutical formulation comprising:
an ezetimibe-associated apoA-I mimetic peptide according to any one of embodiments 43-61; and
a pharmaceutically acceptable carrier or diluent.

Embodiment 63

The formulation of embodiment 62, wherein said ezetimibe-associated peptide is in a pharmaceutically acceptable excipient suitable for oral administration.

Embodiment 64

The formulation according to any one of embodiments 62-63, wherein said ezetimibe-associated peptide is provided as a unit dosage formulation.

Embodiment 65

The formulation according to any one of embodiments 62-34, wherein said ezetimibe-associated peptide is formulated for administration by a route selected from the group consisting of oral administration, nasal administration, rectal administration, intraperitoneal injection, intravascular injection, subcutaneous injection, transcutaneous administration, and intramuscular injection.

Embodiment 66

A method for the treatment or prophylaxis of a pathology characterized by an inflammatory response, said method comprising administering to a mammal in need thereof an effective amount of an ezetimibe-associated peptide according to any one of embodiments 43-61 and/or a pharmaceutical formulation according to any one of embodiments 62-65.

Embodiment 67

The method of embodiment 66, wherein said pathology is atherosclerosis.

Embodiment 68

The method of embodiment 67, wherein said mammal is diagnosed with atherosclerosis and said administering comprises administering a sufficient amount of said ezetimibe-associated peptide and/or a pharmaceutical formulation to ameliorate one or more symptoms of atherosclerosis and/or to reduce one or more markers of an atherosclerotic pathology.

Embodiment 69

The method of embodiment 67, wherein said mammal is at risk for atherosclerosis and said administering comprises administering a sufficient amount of extract, and/or protein powder, and/or nutritional supplement to reduce the risk for atherosclerosis, and/or to improve a risk marker for atherosclerosis, and/or to slow the progression of atherosclerosis.

Embodiment 70

The method of embodiment 69, wherein said risk marker is HDL/LDL, CRP, triglycerides, SAA, paraoxonase activity, Lp(a), oxidized LDL or antibodies to oxidized LDL, or $sPLA_2$.

Embodiment 71

The method according to any one of embodiments 66-70, wherein said pathology is macular degeneration.

Embodiment 72

The method according to any one of embodiments 66-70, wherein said pathology is dyslipidemia.

Embodiment 73

The method according to any one of embodiments 66-70, wherein said pathology is Alzheimer's disease.

Embodiment 74

The method according to any one of embodiments 66-70, wherein said pathology is Crohn's disease.

Embodiment 75

The method according to any one of embodiments 66-70, wherein said pathology is ulcerative colitis.

Embodiment 76

The method according to any one of embodiments 66-70, wherein said pathology is cancer.

Embodiment 77

The method of embodiment 76, wherein said cancer is a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CIVIL), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CIVIL), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sézary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 78

The method of embodiment 76, wherein said cancer is a cancer selected from the group consisting of ovarian cancer, endometrial cancer, colon cancer, and familial adenomatous polyposis.

Embodiment 79

The method of embodiment 76, wherein said cancer is a cancer selected from the group consisting of ovarian cancer, breast cancer, and colon cancer.

Embodiment 80

The method according to any one of embodiments 76-79, wherein said method produces one or more effects selected from the group consisting of decreasing tumor burden, extending 1 survival, a decrease in or suppression of tumor growth and/or metastasis, a decrease in tumor angiogenesis, and a decrease in tumor invasiveness.

Embodiment 81

The method of embodiment 80, wherein said method decreases tumor burden.

Embodiment 82

The method of embodiment 80, wherein said method decreases and/or suppresses tumor growth and/or metastasis.

Embodiment 83

The method of embodiment 80, wherein said method decreases tumor angiogenesis.

Embodiment 84

The method of embodiment 80, wherein said method decreases tumor invasiveness.

Embodiment 85

The method according to any one of embodiments 66-84, wherein said ezetimibe-associated peptide and/or a pharmaceutical formulation is administered in an amount sufficient to reduce lyophosphatidic acid (LPA) levels in said mammal.

Embodiment 86

The method according to any one of embodiments 66-85, wherein said mammal is a human.

Embodiment 87

The method according to any one of embodiments 66-85, wherein said mammal is a non-human mammal.

Embodiment 88

The method of embodiment 87, wherein said non-human mammal is a non-human mammal selected from the group consisting of a canine, a feline, an equine, a porcine, a bovine, and a largomorph.

Embodiment 89

A method of preventing or reducing the uptake of one or more dietary pro-inflammatory micro-lipid components in a mammal, said method comprising administering to the mammal an effective amount of an ezetimibe-associated peptide according to any one of embodiments 43-61 and/or a pharmaceutical formulation according to any one of embodiments 62-65.

Embodiment 90

The method of embodiment 89, wherein said one or more dietary pro-inflammatory micro-lipid components comprises lysophosphatidic acid.

Embodiment 91

The method according to any one of embodiments 89-90, wherein said one or more dietary pro-inflammatory microlipid components comprises phosphatidic acid.

Embodiment 92

The method according to any one of embodiments 89-91, wherein said mammal has or is at risk for atherosclerosis.

Embodiment 93

The method of embodiment 92, wherein said mammal is diagnosed with atherosclerosis.

Embodiment 94

The method of embodiment 92, wherein said mammal is determined to be at risk for atherosclerosis.

Embodiment 95

The method of embodiment 94, wherein said mammal is determined to be at risk said risk by measurement of a marker selected from the group consisting of HDL/LDL, CRP, triglycerides, SAA, paraoxonase activity, Lp(a), oxidized LDL or antibodies to oxidized LDL, or sPLA$_2$.

Embodiment 96

The method according to any one of embodiments 89-95, wherein said ezetimibe-associated peptide and/or a pharmaceutical formulation is administered in an amount sufficient to reduce lyophosphatidic acid (LPA) levels in said mammal.

Embodiment 97

The method according to any one of embodiments 89-96, wherein said mammal is a human.

Embodiment 98

The method according to any one of embodiments 89-96, wherein said mammal is a non-human mammal.

Embodiment 99

The method of embodiment 98, wherein said non-human mammal is a non-human mammal selected from the group consisting of a canine, a feline, an equine, a porcine, a bovine, and a lagomorph.

Definitions

The HDL inflammatory index refers to the ability of HDL to inhibit LDL-induced monocyte chemotactic activity. In certain embodiments the HDL-inflammatory index is calculated by comparing the monocyte chemotactic activity generated by a standard control LDL in the absence and presence of the test HDL. In the absence of the test HDL the monocyte chemotactic activity is normalized to 1.0. If the monocyte chemotactic activity increases upon addition of the test HDL, the HDL-inflammatory index is >1.0 and the test HDL is classified as pro-inflammatory. If the monocyte chemotactic activity decreases upon addition of the test HDL, the HDL-inflammatory index is <1.0 and the HDL is classified as anti-inflammatory. A reduction in HDL inflammatory index is considered an improvement in HDL inflammatory index.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers, however a recombinantly expressed peptide typically consists of amino acids that are all found in the host organism (e.g., naturally occurring amino acids).

The term "an amphipathic helical peptide" refers to a peptide comprising at least one amphipathic helix (amphipathic helical domain). Certain amphipathic helical peptides contemplated herein can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) *Proteins: Structure, Function, and Genetics* 8: 103-117).

"Apolipoprotein J" (apo J) is known by a variety of names including clusterin, TRPM2, GP80, and SP 40 (see, e.g., Fritz (1995) Pp 112 In: *Clusterin: Role in Vertebrate Development, Function, and Adaptation* (Harmony JAK Ed.), R.G. Landes, Georgetown, Tex.,). It was first described as a heterodimeric glycoprotein and a component of the secreted proteins of cultured rat Sertoli cells (see, e.g., Kissinger et al. (1982) *Biol. Reprod.;* 27: 233240). The translated product is a single-chain precursor protein that undergoes intracellular cleavage into a disulfide-linked 34 kDa α subunit and a 47 kDa β subunit (see, e.g., Collard and Griswold (1987) *Biochem.,* 26: 3297-3303). It has been associated with cellular injury, lipid transport, apoptosis and it may be involved in clearance of cellular debris caused by cell injury or death. Clusterin has been shown to bind to a variety of molecules with high affinity including lipids, peptides, and proteins and the hydrophobic probe 1-anilino-8-naphthalenesulfonate (Bailey et al. (2001) *Biochem.,* 40: 11828-11840).

The class G amphipathic helix is found in globular proteins, and thus, the name class G. The feature of this class of amphipathic helix is that it possesses a random distribution of positively charged and negatively charged residues on the polar face with a narrow nonpolar face. Because of the narrow nonpolar face this class does not readily associate with phospholipid (see, e.g., Segrest et al. (1990) *Proteins: Structure, Function, and Genetics.* 8: 103-117; Erratum (1991) *Proteins: Structure, Function and Genetics,* 9: 79). Several exchangeable apolipoproteins possess similar but not identical characteristics to the G amphipathic helix. Similar to the class G amphipathic helix, this other class possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix (see, e.g., Segrest et al. (1992) *J. Lipid Res.,* 33: 141-166; Anantharamaiah et al. (1993) Pp. 109-142 In: *The Amphipathic Helix,* Epand, R. M. Ed CRC Press, Boca Raton, Fla.). Computer programs to identify and classify amphipathic helical domains have been described by Jones et al. (1992)

J. *Lipid Res.* 33: 287-296) and include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like.

The term "treat" when used with reference to treating, e.g. a pathology or disease refers to the mitigation and/or elimination of one or more symptoms of that pathology or disease, and/or a reduction in the rate of onset or severity of one or more symptoms of that pathology or disease, and/or the prevention of that pathology or disease.

The term "ameliorating" when used with respect to "ameliorating one or more symptoms of atherosclerosis" refers to a reduction, prevention, or elimination of one or more symptoms characteristic of atherosclerosis and/or associated pathologies. Such a reduction includes, but is not limited to a reduction or elimination of oxidized phospholipids, a reduction in atherosclerotic plaque formation and rupture, a reduction in clinical events such as heart attack, angina, or stroke, a decrease in hypertension, a decrease in inflammatory protein biosynthesis, reduction in plasma cholesterol, and the like.

A "transgenic plant" is a plant that expresses in at least some of the cells of the plant a heterologous peptide. In certain embodiments the heterologous peptide consists of, or comprises the amino acid sequence of one or more apolipoprotein(s) or apolipoprotein mimetics, e.g., an apoA-I mimetic, and/or a G* peptide, and/or an apoE peptide, e.g., as described herein. In certain embodiments the transgenic plant is a plant that at least a portion of which is edible by a human and/or by a non-human mammal.

The term "biological activity" when used with respect to an apolipoprotein peptide, an apolipoprotein peptide mimetic, a peptide/protein comprising one or more apolipoprotein and/or apolipoprotein mimetic domains indicates that the peptide, when fed to a mammal lowers plasma SAA levels, and/or increases paraoxonase activity, and/or reduces levels of lysophosphatidic acid, and/or reduces levels of metabolites of arachidonic and linoleic acids. A transgenic plant or portion thereof having biological activity indicates that the plant or portion thereof when fed to a mammal lowers plasma SAA levels, and/or increases paraoxonase activity, and/or reduces levels of lysophosphatidic acid, and/or reduces levels of metabolites of arachidonic and linoleic acids.

The term "recombinant nucleic acid" as used herein refers to nucleic acid, originally formed in vitro, in general, in a form not normally found in nature.

A "heterologous" DNA coding sequence is a structural coding sequence that is not native to the plant being transformed, or a coding sequence that has been engineered for improved characteristics of its protein product. Heterologous, with respect to the promoter, refers to a coding sequence that does not exist in nature in the same gene with the promoter to which it is currently attached.

By "promoter" or "promoter segment" (e.g., a tomato E8 promoter or E4 promoter or hybrid E4/E8 promoter) is meant a sequence of DNA that functions alone as a promoter or as a component of a promoter herein to direct transcription of a downstream gene, and can include promoter or promoter segments derived by means of ligation with operator regions, random or controlled mutagenesis, addition or duplication of enhancer sequences, addition or modification with synthetic linkers, and the like.

By an E8 or an E4 gene promoter is meant a promoter obtained from an E8 or E4 gene considered to share sequence identity with the tomato E8 or E4 gene sequences (e.g., as described in U.S. Pat. No. 6,118,049), or a particular region or regions thereof, or from a gene having at least about 70%, preferably at least about 80%, more preferably at least about 85%, even more preferably at least about 90% sequence identify, or at least about 95% sequence identity, or at least about 98% sequence identity over a length of polynucleotide sequence corresponding to the tomato E8 or tomato E4 gene sequences.

The term "conservative substitution" is used in reference to proteins or peptides to reflect amino acid substitutions that do not substantially alter the activity (e.g., ability to reduce SAA, and/or ability to increase paroxonase in a mammal. Typically conservative amino acid substitutions involve substitution one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A "macro-lipid component of the diet" refers to a lipid component of a mammal's diet that is typically present in milligram amounts per gram of diet. In a Western diet such macro-lipid components typically include, but are not limited to phospholipids such as phosphatidylcholine and sterols such as cholesterol. Even lysophosphatidylcholine is likely to be present in milligram quantities after phosphatidylcholine is acted upon in the Duodenum by $PLA_2$ and hence, in various embodiments, can be regarded as a macro-lipid component.

A "micro-lipid component of the diet" refers to a lipid component of a mammal's diet that is typically present in microgram (or lower) amounts per gram of diet. Illustrative microlipid components typically include, but are not limited to lysophosphatidic acid, phosphatidic acid, and the like.

The term "ezetimibe" refers to (3R,4S)-1-(4-fluorophenyl)-3-[(3S)-3-(4-fluorophenyl)-3-hydroxypropyl]-4-(4-hydroxyphenyl)azetidin-2-one, the pharmaceutical also known as ZETIA® or EZETROL® which is typically used as a drug to lower plasma cholesterol levels. Without being bound by a particular theory, it is believed that ezetimibe acts by decreasing cholesterol absorption in the small intestine.

The phrase "a mixed ezetimibe apoA-I peptide formulation" or "combined (ezetimibe/apoA-I) formulation") refers to a formulation in which ezetimibe and an apoA-I peptide are provided as separate components that are simply combined, e.g., by mixing the dry powders.

The phrase "ezetimibe-associated apoA-I mimetic peptide" or "Ez-peptide" (e.g., Ez-T6F) refers to an apoA-I mimetic peptide that has been reacted with ezetimibe (e.g., by incubating ezetimibe with the peptide in a solution comprising ethyl acetate and acetic acid or in a solution comprising ethyl lactate and lactic acid) as described herein. The ezetimibe-associated apoA-I mimetic peptide may be designated Ez-peptide. Thus, for example, an ezetimibe associated transgenic 6F peptice (Tg6F) may be designated Ez-Tg6F.

DETAILED DESCRIPTION

Methods of transgenically expressing apoA-I memetic peptides (e.g., the 6F peptide) in various plants including tomatoes were previously described (see, e.g., PCT Publication No: WO 2013/148214 A1). Without any purification steps, when the transgenic tomatoes were freeze-dried, ground into powder and fed to a mouse model of dyslipidemia and atherosclerosis at only 2.2% of a high-fat high-cholesterol diet by weight, the transgenic tomatoes significantly reduced dyslipidemia, inflammation and atherosclerosis in the mice.

This amount of plant matter provided a daily dose to mice of approximately 40 mg/kg/day. Delivery of an equivalent dosage to a human would require the human to eat approximately 150 grams of freeze-dried tomato powder three times daily. Accordingly, concentration methods were developed to reduces the volume of plant matter (e.g., tomato powder) required to only 3%-4% of that volume (see, e.g., PCT/US2015/031134). The methods typically involved expresses one or more peptides that have ApoA-I activity in a plant tissue. The tissue comprising heterologous ApoA-I peptide was provided as a substantially dry powder that was mixed with a solution comprising ethyl acetate and acetic acid or with a solution comprising ethyl lactate and lactic acid, to form an extraction mixture. In various embodiments, the mixture is incubated (e.g., at room temperature, or at an elevated temperature (e.g., up to about 30° C., or up to about 35° C., or up to about 37° C. or 38° C., or up to about 40° C.) to extract/concentrate the ApoA-I peptide activity. The supernatant was then dried down to provide a concentrate.

While simply coadministation of the transgenic 6F peptide in combination with ezetimibe (a cholesterol uptake inhibitor) may be contemplated, it was a surprising discovery that an ezetimibe-associated ApoA-I mimetic peptide could be produced by adding the same dose of ezetimibe to the to the supernatant of Tg6F that had been incubated overnight in ethyl acetate with 5% acetic acid followed by an additional two hour incubation at room temperature and removal of the ethyl acetate. Suprisingly, this resulted in a significantly more effective preparation.

Figure 1:
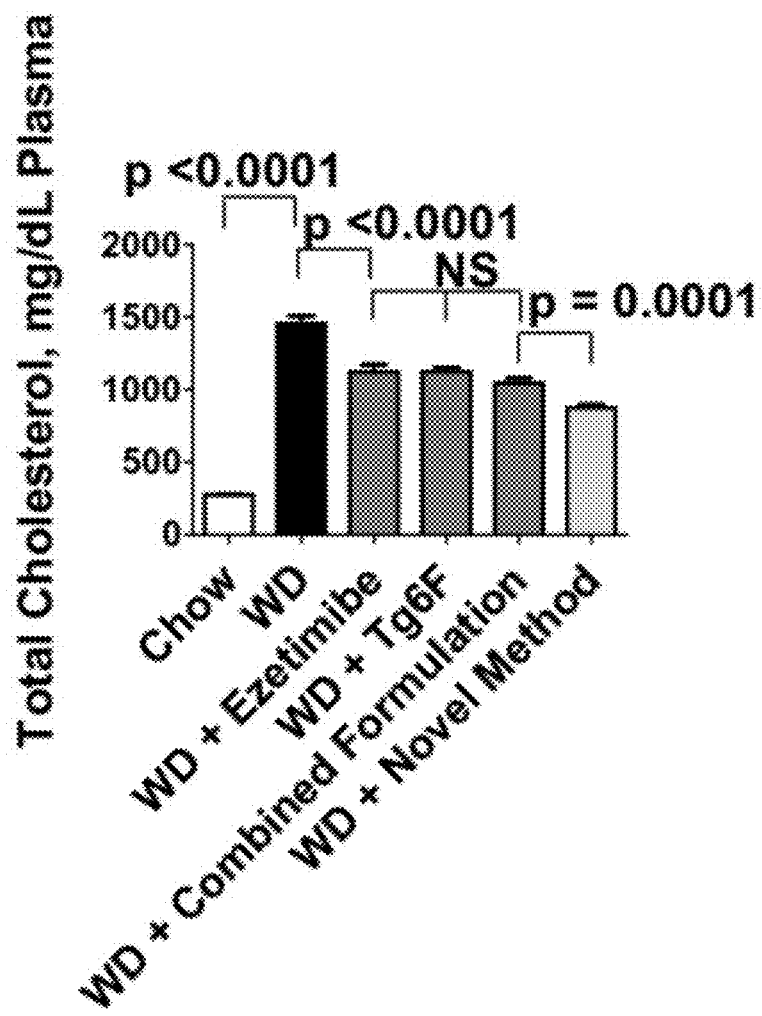
FIG. 1 shows total plasma cholesterol for female LDLR null mice age 5-8 months (n=20 per group) fed standard mouse chow (Chow) or a Western diet high in cholesterol and fat (WD) or fed WD+0.06% by weight of a freeze-dried concentrate of transgenic tomatoes expressing the apoA-I mimetic peptide 6F, or fed WD with ezetimibe added to give a daily dose of 10 mg/kg body weight/day (WD+Ezetimibe), or the mice were fed WD with Tg6F added at 0.06% by weight plus Ezetimibe (each added separately to the diet by mixing the dried powders into the diet) to give a daily dose of Ezetimibe of 10 mg/kg body weight, or the mice were fed WD to which was added 0.06% ezetimibe-associated Tg6F (Ez-Tg6F) by weight containing sufficient Ezetimibe to give a daily dose of 10 mg/kg body weight/day that was prepared as described herein. NS=Not Significant.

More specifically, it was suprirsingly observed that if instead of adding the same doses of Tg6F and Ezetimibe separately to the diet and feeding the diet as a combined formulation to a subject (e.g., mice in the Examples herein), addition of an ezetimibe-associated peptide (e.g., Ez-Tg6F) providing the same dosage of ezetimibe and peptide would produce a significantly better result. FIG. 1 shows the case for plasma Total Cholesterol. In the example shown, the separate addition of Tg6F and Ezetimibe to the diet which was fed to the mice as a combined formulation did not significantly reduce plasma Total Cholesterol beyond the addition of either agent alone, but the addition to the diet of the same doses of Tg6F and Ezetimibe as ezetimibe-associated Tg6F (Ez-Tg6F) prepared by the novel method described above, was significantly more effective in reducing plasma Total Cholesterol than either agent added alone.

In view of these discoveries and the additional data shown in the Examples herein, it is believed that ezetimibe-associated ApoA-I peptides prepared as described herein, e.g., by incubating ezetimibe and the apoAI mimetic peptide in a solution comprising ethyl acetate and acetic acid or in a solution comprising ethyl lactate and lactic acid, and drying the solution to provide a dry ezetimibe-associated apoA-I mimetic peptide can provide superior biological activity and efficacy than separate administration of ezetimibe and the apoA-I mimetic peptide or than combined formulations comprising ezetimibe and the apoA-I mimetic peptide.

In certain embodiments the apoA-I peptide is a chemically synthesized peptide. However, in other embodiments the ApoA-I peptide is a recombinant peptide expressed in a tissue (e.g., in a plant tissue). In the latter case, the association with ezetimibe can readily be incorporated into the concentration protocol to provide an ezetimibe-associated peptide.

In either case, in certain embodiments, the ezetimibe-associated apoA-I mimetic peptide is prepared by incubating ezetimibe and one or more apoAI mimetic peptide(s) in a solution comprising ethyl acetate and acetic acid or in a solution comprising ethyl lactate and lactic acid, and then drying the solution to provide a dry ezetimibe-associated apoA-I mimetic peptide. In certain embodiments the drying comprises drying said solution to produce a dry residue; resuspending said residue in water to provide a resuspended mixture; and drying (e.g., lyophilizing) the resuspended mixture to provide a dry powder extract comprising ezetimibe-associated apoA-I mimetic peptide.

In certain embodiments the incubation of ezetimibe with peptide is for at least about 10 minutes, or at least about 15 minutes, or at least about 30 minutes, or at least about 45 minutes, or at least about 1 hr, or at least about 1.5 hour, or at least about 2 hrs, or at least about 3 hrs, or at least about 4 hrs, or at least about 5 hours, or at least about 6 hrs, or at least about 12 hours, or at least about 1 day. In certain embodiments the incubating is for about 2 hrs. In certain embodiments the incubating is at room temperature.

Where the apoA-I mimetic peptide is provided as a heterologous peptide expressed in a plant, the plant tissue may be extracted in a solution comprising ethyl acetate and acetic acid or in a solution comprising ethyl lactate and lactic acid prior to combination with ezetimibe. In certain embodiments this extraction mixture is incubated for at least about 15 minutes, or at least about ½ hour, or at least about 1 hour, or at least about 2 hours, or at least about 3 hours, or at least about 4 hours, or at least about 5 hours, or at least about 6 hours, or at least about 7 hours, or at least about 12 hours, or at least about 18 hours, or at least about 24 hours, or at least about 48 hours, or at least about 72 hours, or at least about 96 hours.

In certain embodiments the extraction from plant tissue and the reaction with ezetimibe may occur simultaneously. Thus, both components (peptide and ezetimibe) can be added to a solution comprising ethyl acetate and acetic acid or in a solution comprising ethyl lactate and lactic acid and incubated (e.g. for at least about 15 minutes, or at least about ½ hour, or at least about 1 hour, or at least about 2 hours, or at least about 3 hours, or at least about 4 hours, or at least about 5 hours, or at least about 6 hours, or at least about 7 hours, or at least about 12 hours, or at least about 18 hours, or at least about 24 hours, or at least about 48 hours, or at least about 72 hours, or at least about 96 hours).

In certain embodiments any of these reactions are carried out at room temperature, or at an elevated temperature (e.g., up to about 30° C., or up to about 35° C., or up to about 37° C. or 38° C., or up to about 40° C.

In certain embodiments the solution comprising ethyl acetate and acetic acid comprises about 1% to about 25% acetic acid, or about 2% to about 20% acetic acid, or about 3% to about 15% acetic acid, or about 4% to about 10% acetic acid, or about 4% to about 8% acetic acid, or from about 4% to about 6% acetic acid. In certain embodiments the solution comprising ethyl lactate and lactic acid comprises about 1% to about 25% lactic acid, or about 2% to about 20% lactic acid, or about 3% to about 15% lactic acid, or about 4% to about 10% lactic acid, or about 4% to about 8% lactic acid, or from about 4% to about 6% lactic acid.

In certain embodiments the ratio of ezetimibe and apoA-I peptide incubated together ranges from about 1:10 (ezetimibe:Tg6F by weight) or in some cases 0.1:10 or 0.5:10 or 2:10 or 4:10 or 1:1.

In view of the foregoing, it is believed the synergistic activity of ezetimibe and apoA-I peptide is significantly improved when formulated as an ezetimibe-associated ApoA-I peptide. In certain embodiments the ezetimibe-associated apoA-I mimetic pepide, when fed to a mammal, lowers plasma total cholesterol to a greater amount than a mixed ezetimibe apoA-I peptide formulation containing the same amounts of ezetimibe and apoA-I peptide. In certain embodiments the ezetimibe-associated apoA-I mimetic pepide, when fed to a mammal, lowers plasma triglyceride to a greater amount than a mixed ezetimibe apoA-I peptide formulation containing the same amounts of ezetimibe and apoA-I peptide. In certain embodiments the ezetimibe-associated apoA-I mimetic pepide, when fed to a mammal, lowers plasma 5-HETE to a greater amount than a mixed ezetimibe apoA-I peptide formulation containing the same amounts of ezetimibe and apoA-I peptide. In certain embodiments the ezetimibe-associated apoA-I mimetic pepide, when fed to a mammal, lowers plasma 12-HETE to a greater amount than a mixed ezetimibe apoA-I peptide formulation containing the same amounts of ezetimibe and apoA-I peptide. In certain embodiments the ezetimibe-associated apoA-I mimetic pepide, when fed to a mammal, lowers plasma 15-HETE to a greater amount than a mixed ezetimibe apoA-I peptide formulation containing the same amounts of ezetimibe and apoA-I peptide. In certain embodiments the ezetimibe-associated apoA-I mimetic pepide, when fed to a mammal, lowers plasma SAA to a greater amount than a mixed ezetimibe apoA-I peptide formulation containing the same amounts of ezetimibe and apoA-I peptide.

As noted above, after incubation, the liquid phase of the mixture can be collected and dried to provide a concentrated dry powder extract that displays the biological activity of the ezetimibe-associated apoA-I mimetic peptide. In certain embodiments this collecting and drying can comprise drying the liquid phase to produce a dry residue and optionally, resuspending said residue in water (e.g. distilled water, de-ionized water, food-grade water) or a buffer to provide a resuspended mixture; and optionally drying the resuspended mixture to provide the dry powder extract.

In various embodiments the drying operations can be performed using any conventional drying procedure including, but not limited to lyophilization, drying at room temperature (e.g., under a dry gas such as argon), drying at elevated temperature, drying at low pressure, and the like.

The resulting extract can optionally be compounded with any edible components for administration to a subject.

While the concentration protocol is illustrated with respect to a transgenic tomato plant expressing a heterologous 6F peptide, it is believe the same protocols can be effectively utilized with any of a number of other plants/plant tissues expressing any one or more peptides having ApoA-I activity.

Thus, in various embodiments the transgenic plant tissue comprises a tissue from a transgenic plant such as tomatoes, carrots, potatoes, apples, pears, plums, peaches, oranges, kiwis, papayas, pineapples, guava, lilikoi, starfruit, lychee, mango, grape, pomegranate, mustard greens, kale, chard, lettuce, soybean, rice, corn and other grains (e.g., wheat, rice, barley, bulgur, faro, kamut, kaniwa, millet, oats, quinoa, rice, rye, sorghum, spelt, teff, triticale, and the like), berries such as strawberries, blueberries, blackberries, goji berries, and raspberries, banana, rice, turnip, maize, grape, fig, plum, potato, safflower seeds, nuts (e.g., almond, walnut, pecan, peanut, cashew, macadamia, hazelnut, etc.), legumes (e.g., alfalfa, clover, peas, beans (including black beans), lentils, lupins, mesquite, carob, soybeans, and the like). In certain embodiments the plant is selected from the group consisting of tomato, rice, tobacco, turnip, maize, corn, soybean, grape, fig, plum, potato, carrot, pomegranate, mustard greens, chard, kale, lettuce, broccoli, and safflower seeds.

In certain embodiments the tissue of the transgenic plant comprises a fruit (e.g. a tomato). In certain embodiments the tissue of the transgenic plant comprises a seed, a leaf, a root, a tuber, a flower, and the like.

ApoA-I Mimetics and Other Peptides for Use in Ez-Peptides.

Having demonstrated that the 6F peptide when expressed in a plant (e.g., a tomato) shows significant biological activity when the peptide is processed with ezetimibe as described herein to provide an ezetimibe-associated peptide, it is believed that similar results can be obtained with any of a number of other therapeutic peptides comprising or consisting of domains that are therapeutic peptide sequences and these results can be obtained by chemically synthesized peptides and/or by expression of the peptide(s) in tomato or other plants, e.g., as described herein and in PCT Publication No: WO 2013/148214 A1 and in Chattopadhyay et al. (2013) *J. Lipid Res.*, 54: 995-10101, and Navab et al. (2013) *J. Lipid Res.*, 54: 3403-3418.

In certain embodiments these peptides include, but are not limited to class A amphipathic helical peptides, class A amphipathic helical peptide mimetics of apoA-I having aromatic or aliphatic residues in the non-polar face, Apo-J (G* peptides), apoE peptides, and the like, and peptide mimetics, e.g., as described below.

ApoA-I Mimetic Peptides.

In certain embodiments the peptides used there to prepare ezetimibe-modified peptides comprise or consist of apoA-I mimetic peptides. In certain embodiments such peptides include, but are not limited to, class A amphipathic helical peptides, e.g. as described in U.S. Pat. No. 6,664,230, and PCT Publications WO 02/15923 and WO 2004/034977, which are incorporated herein by reference for the peptide sequences disclosed therein. It was discovered that peptides comprising a class A amphipathic helix ("class A peptides"), in addition to being capable of mitigating one or more symptoms of atherosclerosis are also useful in the treatment of one or more of the other indications described herein.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) *Meth. Enzymol*, 128: 626-668). It is noted that the fourth exon of apo A-I, when folded into 3.667 residues/turn produces a class A amphipathic helical structure.

Significant biological activity has been demonstrated for various apoA-I mimetic peptides including, but not limited to the peptides designated 4F, retro (reverse 4F), 5F, 6F, and the like. Various class A peptides inhibited lesion development in atherosclerosis-susceptible mice. In addition, the peptides show varying, but significant degrees of efficacy in mitigating one or more symptoms of the various pathologies described herein. A number of such peptides described in PCT patent application Nos: PCT/US2001/026497 (WO 2002/015923), PCT/US2003/032442 (WO 2004/034977), PCT/US2008/085409, and in Bielicki et al. (2010) *J. Lipid Res.* 51: 1496-1503, Zheng et al. (2011) *Biochemistry*, 50: 4068-4076, Di Bartolo et al. (2011) *Lipids in Health and Disease* 10: 224. In certain embodiments the peptides used for the preparation of ezetimibe associated peptides (Ez-peptides) described herein comprise one or more domains that have an amino acid sequence shown in Table 1 or the reverse sequence.

TABLE 1

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| 18A | DWLKAFYDKVAEKLKEAF | 2 |
| 2F | DWLKAFYDKVAEKLKEAF | 3 |
| 3F | DWFKAFYDKVAEKLKEAF | 4 |
| 3F14 | DWLKAFYDKVAEKFKEAF | 5 |
| 4F | DWFKAFYDKVAEKFKEAF | 6 |

TABLE 1-continued

Certain ApoA-I mimetic peptides that can be used for the preparation
of ezetimibe associated peptides (Ez-peptides), e.g., as described
herein. The table includes various class A and/or class Y peptide
analogs. For each sequence listed in this table, the retro form of the
sequence is also comtemplated. Thus, for example where the
6F peptide sequence DWLKAFYDKFFEKFKEFF (SEQ ID NO: 1) is shown, the retro
amino acid sequence FFEKFKEFFKDYFAKLWD (SEQ ID NO: 15) is also contemplated.

| Peptide Name | Amino Acid Sequence | SEQ ID NO. |
| --- | --- | --- |
| 5F | DWLKAFYDKVFEKFKEFF | 7 |
| 6F | DWLKAFYDKFFEKFKEFF | 1 |
| 7F | DWFKAFYDKFFEKFKEFF | 8 |
|  | DWLKAFYDKVAEKLKEFF | 9 |
| Rev18A | FAEKLKEAVKDYFAKLWD | 10 |
| Rev2F | FAEKLKEAVKDYFAKLWD | 11 |
| Ref3F | FAEKLKEAVKDYFAKFWD | 12 |
| Rev4F | FAEKFKEAVKDYFAKFWD | 13 |
| Rev5F | FFEKFKEFVKDYFAKLWD | 14 |
| Rev6F | FFEKFKEFFKDYFAKLWD | 15 |
| Rev7F | FFEKFKEFFKDYFAKFWD | 16 |
|  | DWLKAFYDKVFEKFKEAF | 17 |
|  | DWLKAFYDKVFEKLKEFF | 18 |
|  | DWLKAFYDKVAEKFKEFF | 19 |
|  | DWLKAFYDKVFEKFKEFF | 20 |
|  | EWLKLFYEKVLEKFKEAF | 21 |
|  | EWLKAFYDKVAEKFKEAF | 22 |
|  | EWLKAFYDKVAEKLKEFF | 23 |
|  | EWLKAFYDKVFEKFKEAF | 24 |
|  | EWLKAFYDKVFEKLKEFF | 25 |
|  | EWLKAFYDKVAEKFKEFF | 26 |
|  | EWLKAFYDKVFEKFKEFF | 27 |
|  | AFYDKVAEKLKEAF | 28 |
|  | AFYDKVAEKFKEAF | 29 |
|  | AFYDKVAEKFKEAF | 30 |
|  | AFYDKFFEKFKEFF | 31 |
|  | AFYDKFFEKFKEFF | 32 |
|  | AFYDKVAEKFKEAF | 33 |
|  | AFYDKVAEKLKEFF | 34 |
|  | AFYDKVFEKFKEAF | 35 |
|  | AFYDKVFEKLKEFF | 36 |
|  | AFYDKVAEKFKEFF | 37 |
|  | KAFYDKVFEKFKEF | 38 |
|  | LFYEKVLEKFKEAF | 39 |
|  | AFYDKVAEKFKEAF | 40 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
| --- | --- | --- |
| | AFYDKVAEKLKEFF | 41 |
| | AFYDKVFEKFKEAF | 42 |
| | AFYDKVFEKLKEFF | 43 |
| | AFYDKVAEKFKEFF | 44 |
| | AFYDKVFEKFKEFF | 45 |
| | DWLKALYDKVAEKLKEAL | 46 |
| | DWFKAFYEKVAEKLKEFF | 47 |
| | DWFKAFYEKFFEKFKEFF | 48 |
| | EWLKALYEKVAEKLKEAL | 49 |
| | EWLKAFYEKVAEKLKEAF | 50 |
| | EWFKAFYEKVAEKLKEFF | 51 |
| | EWLKAFYEKVFEKFKEFF | 52 |
| | EWLKAFYEKFFEKFKEFF | 53 |
| | EWFKAFYEKFFEKFKEFF | 54 |
| | DFLKAWYDKVAEKLKEAW | 55 |
| | EFLKAWYEKVAEKLKEAW | 56 |
| | DFWKAWYDKVAEKLKEWW | 57 |
| | EFWKAWYEKVAEKLKEWW | 58 |
| | DKLKAFYDKVFEWAKEAF | 59 |
| | DKWKAVYDKFAEAFKEFL | 60 |
| | EKLKAFYEKVFEWAKEAF | 61 |
| | EKWKAVYEKFAEAFKEFL | 62 |
| | DWLKAFVDKFAEKFKEAY | 63 |
| | EKWKAVYEKFAEAFKEFL | 64 |
| | DWLKAFVYDKVFKLKEFF | 65 |
| | EWLKAFVYEKVFKLKEFF | 66 |
| | DWLRAFYDKVAEKLKEAF | 67 |
| | EWLRAFYEKVAEKLKEAF | 68 |
| | DWLKAFYDRVAEKLKEAF | 69 |
| | EWLKAFYERVAEKLKEAF | 70 |
| | DWLKAFYDKVAERLKEAF | 71 |
| | EWLKAFYEKVAERLKEAF | 72 |
| | DWLKAFYDKVAEKLREAF | 73 |
| | EWLKAFYEKVAEKLREAF | 74 |
| | DWLKAFYDRVAERLKEAF | 75 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| | EWLKAFYERVAERLKEAF | 76 |
| | DWLRAFYDKVAEKLREAF | 77 |
| | EWLRAFYEKVAEKLREAF | 78 |
| | DWLRAFYDRVAEKLKEAF | 79 |
| | EWLRAFYERVAEKLKEAF | 80 |
| | DWLKAFYDKVAERLREAF | 81 |
| | EWLKAFYEKVAERLREAF | 82 |
| | DWLRAFYDKVAERLKEAF | 83 |
| | EWLRAFYEKVAERLKEAF | 84 |
| | DWLKAFYDKVAEKLKEAFPDWLKAFYDKVAEKLKEAF | 85 |
| | DWLKAFYDKVAEKLKEFFPDWLKAFYDKVAEKLKEFF | 86 |
| | DWFKAFYDKVAEKLKEAFPDWFKAFYDKVAEKLKEAF | 87 |
| | DKLKAFYDKVFEWAKEAFPDKLKAFYDKVFEWLKEAF | 88 |
| | DKWKAVYDKFAEAFKEFLPDKWKAVYDKFAEAFKEFL | 89 |
| | DWFKAFYDKVAEKFKEAFPDWFKAFYDKVAEKFKEAF | 90 |
| | DWLKAFVYDKVFKLKEFFPDWLKAFVYDKVFKLKEFF | 91 |
| | DWLKAFYDKFAEKFKEFFPDWLKAFYDKFAEKFKEFF | 92 |
| | EWFKAFYEKVAEKFKEAF | 93 |
| | DWFKAFYDKVAEKF | 94 |
| | FKAFYDKVAEKFKE | 95 |
| | FKAFYEKVAEKFKE | 96 |
| | FKAFYDKVAEKFKE | 97 |
| | FKAFYEKVAEKFKE | 98 |
| | DWFKAFYDKVAEKFKEAF | 99 |
| | EWFKAFYEKVAEKFKEAF | 100 |
| | AFYDKVAEKFKEAF | 101 |
| | DWFKAFYDKVAEKF | 102 |
| | DWLKAFYDKVFEKFKEFF | 103 |
| | EWLKAFYEKVFEKFKEFF | 104 |
| | AFYDKVFEKFKEFF | 105 |
| | AFYEKVFEKFKEFF | 106 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| | DWLKAFYDKVFEKF | 107 |
| | EWLKAFYEKVFEKF | 108 |
| | LKAFYDKVFEKFKE | 109 |
| | LKAFYEKVFEKFKE | 110 |
| [Switch D-E]-1-4F | EWFKAFYEKVADKFKDAF | 111 |
| [Switch D-E]-2-4F | EWFKAFYDKVADKFKEAF | 112 |
| [Switch D-E]-3-4F | DWFKAFYEKVADKFKEAF | 113 |
| [Switch D-E]-4-4F | DWFKAFYEKVAEKFKDAF | 114 |
| 4F-2 | DFWKAFYDKVAEKFKEAF | 115 |
| [Switch D-E]-1-4F-2 | EFWKAFYEKVADKFKDAF | 116 |
| [Switch D-E]-2-4F-2 | EFWKAFYDKVADKFKEAF | 117 |
| [Switch D-E]-3-4F-2 | DFWKAFYEKVADKFKEAF | 118 |
| [Switch D-E]-4-4F-2 | DFWKAFYEKVAEKFKDAF | 119 |
| 4F-3 | DWFKAYFDKVAEKFKEAF | 120 |
| [Switch D-E]-1-4F-5 | EWFKAYFEKVADKFKDAF | 121 |
| [Switch D-E]-2-4F-5 | EWFKAYFDKVADKFKEAF | 122 |
| [Switch D-E]-3-4F-5 | DWFKAYFEKVADKFKEAF | 123 |
| [Switch D-E]-4-4F-5 | DWFKAYFEKVAEKFKDAF | 124 |
| 4F-4 | DWFKAFVDKYAEKFKEAF | 125 |
| [Switch D-E]-1-4F-4 | EWFKAFVEKYADKFKDAF | 126 |
| [Switch D-E]-2-4F-4 | EWFKAFVDKYADKFKEAF | 127 |
| [Switch D-E]-3-4F-4 | DWFKAFVEKYADKFKEAF | 128 |
| [Switch D-E]-4-4F | DWFKAFVEKYAEKFKDAF | 129 |
| 4-F-5 | DWFKAFYDKAVEKFKEAF | 130 |
| [Switch D-E]-1-4F-5 | EWFKAFYEKAVDKFKDAF | 131 |
| [Switch D-E]-2-4F-5 | EWFKAFYDKAVDKFKEAF | 132 |
| [Switch D-E]-3-4F-5 | DWFKAFYEKAVDKFKEAF | 133 |
| [Switch D-E]-4-4F-5 | DWFKAFYEKAVEKFKDAF | 134 |
| 4F-6 | DWFKAFYDKVFEKAKEAF | 135 |
| [Switch D-E]-1-4F-6 | EWFKAFYEKVFDKAKDAF | 136 |
| [Switch D-E]-2-4F-6 | EWFKAFYDKVFDKAKEAF | 137 |
| [Switch D-E]-3-4F-6 | DWFKAFYEKVFDKAKEAF | 138 |
| [Switch D-E]-4-4F-6 | DWFKAFYEKVFEKAKDAF | 139 |
| 4F-7 | DWFKAFYDKVAEKAKEFF | 140 |
| [Switch D-E]-1-4F-7 | EWFKAFYEKVADKAKDFF | 141 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [Switch D-E]-2-4F-7 | EWFKAFYDKVADKAKEFF | 142 |
| [Switch D-E]-3-4F-7 | DWFKAFYEKVADKAKEFF | 143 |
| [Switch D-E]-4-4F-7 | DWFKAFYEKVAEKAKEFF | 144 |
| 4F-8 | DWFKAFYDKVAEKFKEFA | 145 |
| [Switch D-E]-1-4F-8 | EWFKAFYEKVADKFKDFA | 146 |
| [Switch D-E]-2-4F-8 | EWFKAFYDKVADKFKEFA | 147 |
| [Switch D-E]-3-4F-8 | DWFKAFYEKVADKFKEFA | 148 |
| [Switch D-E]-4-4F-8 | DWFKAFYEKVAEKFKDFA | 149 |
| 4F-9 | DAFKAFYDKVAEKFKEWF | 150 |
| [Switch D-E]-1-4F-9 | EAFKAFYEKVADKFKDWF | 151 |
| [Switch D-E]-2-4F-9 | EAFKAFYDKVADKFKEWF | 152 |
| [Switch D-E]-3-4F-9 | DAFKAFYEKVADKFKE | 153 |
| [Switch D-E]-4-4F-9 | DAFKAFYEKVAEKFKDWF | 154 |
| 4F-10 | DAFKAFYDKVWEKFKEAF | 155 |
| [Switch D-E]-1-4F-10 | EAFKAFYEKVWDKFKDAF | 156 |
| [Switch D-E]-2-4F-10 | EAFKAFYDKVWDKFKEAF | 157 |
| [Switch D-E]-3-4F-10 | DAFKAFYEKVWDKFKEAF | 158 |
| [Switch D-E]-4-4F-10 | DAFKAFYEKVWEKFKDAF | 159 |
| 4F-11 | DYFKAFWDKVAEKFKEAF | 160 |
| [Switch D-E]-1-4F-11 | EYFKAFWEKVADKFKDAF | 161 |
| [Switch D-E]-2-4F-11 | EYFKAFWDKVADKFKEAF | 162 |
| [Switch D-E]-3-4F-11 | DYFKAFWEKVADKFKEAF | 163 |
| [Switch D-E]-4-4F-11 | DYFKAFWEKVAEKFKDAF | 164 |
| 4F-12 | DWAKAFYDKVAEKFKEFF | 165 |
| [Switch D-E]-1-4F-12 | EWAKAFYEKVADKFKDFF | 166 |
| [Switch D-E]-2-4F-12 | EWAKAFYDKVADKFKEFF | 167 |
| [Switch D-E]-3-4F-12 | DWAKAFYEKVADKFKEFF | 168 |
| [Switch D-E]-4-4F-12 | DWAKAFYEKVAEKFKDFF | 169 |
| 4F-13 | DWFKAAYDKVAEKFKEFF | 170 |
| [Switch D-E]-1-4F-13 | EWFKAAYEKVADKFKDFF | 171 |
| [Switch D-E]-2-4F-13 | EWFKAAYDKVADKFKEFF | 172 |
| [Switch D-E]-3-4F-13 | DWFKAAYEKVADKFKEFF | 173 |
| [Switch D-E]-4-4F-13 | DWFKAAYEKVAEKFKDFF | 174 |
| 4F-14 | DWFKAFADKVAEKFKEYF | 175 |
| [Switch D-E]-1-4F-14 | EWFKAFAEKVADKFKDYF | 176 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
| --- | --- | --- |
| [Switch D-E]-2-4F-14 | EWFKAFADKVADKFKEYF | 177 |
| [Switch D-E]-3-4F-14 | DWFKAFAEKVADKFKEYF | 178 |
| [Switch D-E]-4-4F | DWFKAFAEKVAEKFKDYF | 179 |
| 4F-15 | DWFKAFYDKAAEKFKEVF | 180 |
| [Switch D-E]-1-4F-15 | EWFKAFYEKAADKFKDVF | 181 |
| [Switch D-E]-2-4F-15 | EWFKAFYDKAADKFKEVF | 182 |
| [Switch D-E]-3-4F-15 | DWFKAFYEKAADKFKEVF | 183 |
| [Switch D-E]-4-4F-15 | DWFKAFYEKAAEKFKDVF | 184 |
| 4F-16 | DWYKAFFDKVAEKFKEAF | 185 |
| [Switch D-E]-1-4F-16 | EWYKAFFEKVADKFKDAF | 186 |
| [Switch D-E]-2-4F-16 | EWYKAFFDKVADKFKEAF | 187 |
| [Switch D-E]-3-4F-16 | DWYKAFFEKVADKFKEAF | 188 |
| [Switch D-E]-4-4F-16 | DWYKAFFEKVAEKFKDAF | 189 |
| 4F-17 | DWVKAFYDKFAEKFKEAF | 190 |
| [Switch D-E]-1-4F-17 | EWVKAFYEKFADKFKDAF | 191 |
| [Switch D-E]-2-4F-17 | EWVKAFYDKFADKFKEAF | 192 |
| [Switch D-E]-3-4F-17 | DWVKAFYEKFADKFKEAF | 193 |
| [Switch D-E]-4-4F-17 | DWVKAFYEKFAEKFKDAF | 194 |
| 4F-18 | DWFKAFFDKVAEKYKEAF | 195 |
| [Switch D-E]-1-4F-18 | EWFKAFFEKVADKYKDAF | 196 |
| [Switch D-E]-2-4F-18 | EWFKAFFDKVADKYKEAF | 197 |
| [Switch D-E]-3-4F-18 | DWFKAFFEKVADKYKEAF | 198 |
| [Switch D-E]-3-4F-18 | DWFKAFFEKVADKYKEAF | 199 |
| 4F-19 | DWFKAFFDKVAEKFKEAY | 200 |
| [Switch D-E]-1-4F-19 | EWFKAFFEKVADKFKDAY | 201 |
| [Switch D-E]-2-4F-19 | EWFKAFFDKVADKFKEAY | 202 |
| [Switch D-E]-3-4F-19 | DWFKAFFEKVADKFKEAY | 203 |
| [Switch D-E]-4-4F-19 | DWFKAFFEKVAEKFKDAY | 204 |
| 4F-20 | DWFKAFYDKFAEKFKEAV | 205 |
| [Switch D-E]-1-4F-20 | EWFKAFYEKFADKFKDAV | 206 |
| [Switch D-E]-2-4F-20 | EWFKAFYDKFADKFKEAV | 207 |
| [Switch D-E]-3-4F-20 | DWFKAFYEKFADKFKEAV | 208 |
| [Switch D-E]-4-4F-20 | DWFKAFYEKFAEKFKDAV | 209 |
| 4F-21 | DKFKAFYDKVAEKFWEAF | 210 |
| [Switch D-E]-1-4F-21 | EKFKAFYEKVADKFWDAF | 211 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [Switch D-E]-2-4F-21 | EKFKAFYDKVADKFWEAF | 212 |
| [Switch D-E]-3-4F-21 | DKFKAFYEKVADKFWEAF | 213 |
| [Switch D-E]-4-4F-21 | DKFKAFYEKVAEKFWDAF | 214 |
| 4F-22 | DKWKAFYDKVAEKFFEAF | 215 |
| [Switch D-E]-1-4F-22 | EKWKAFYEKVADKFFDAF | 216 |
| [Switch D-E]-2-4F-22 | EKWKAFYDKVADKFFEAF | 217 |
| [Switch D-E]-3-4F-22 | DKWKAFYEKVADKFFEAF | 218 |
| [Switch D-E]-4-4F-22 | DKWKAFYEKVAEKFFDAF | 219 |
| 4F-23 | DKPKAFYDKWAEVFKEAF | 220 |
| [Switch D-E]-1-4F-23 | EKPKAFYEKWADVFKDAF | 221 |
| [Switch D-E]-2-4F-23 | EKPKAFYDKWADVFKEAF | 222 |
| [Switch D-E]-3-4F-23 | DKPKAFYEKWADVFKEAF | 223 |
| [Switch D-E]-4-4F-23 | DKPKAFYEKWAEVFKDAF | 224 |
| 4F-24 | DKFKAFYDKVAEFWKEAF | 225 |
| [Switch D-E]-1-4F-24 | EKFKAFYEKVADFWKDAF | 226 |
| [Switch D-E]-2-4F-24 | EKFKAFYDKVADFWKEAF | 227 |
| [Switch D-E]-3-4F-24 | DKFKAFYEKVADFWKEAF | 228 |
| [Switch D-E]-4-4F-24 | DKFKAFYEKVAEFWKDAF | 229 |
| Rev-4F | FAEKFKEAVKDYFAKFWD | 230 |
| [Switch D-E]-1-Rev-4F | FADKFKDAVKEYFAKFWE | 231 |
| [Switch D-E]-2-Rev-4F | FADKFKEAVKDYFAKFWE | 232 |
| [Switch D-E]-3-Rev-4F | FAEKFKDAVKEYFAKFWD | 233 |
| [Switch D-E]-4-Rev-4F | FAEKFKDAVKDYFAKFWE | 234 |
| Rev-4F-1 | FWEKFKEAVKDYFAKFAD | 235 |
| [Switch D-E]-1-Rev-4F-1 | FWDKFKDAVKEYFAKFAE | 236 |
| [Switch D-E]-2-Rev-4F-1 | FADKFKEAVKDYFAKFWE | 237 |
| [Switch D-E]-3-Rev-4F-1 | FAEKFKDAVKEYFAKFWD | 238 |
| [Switch D-E]-4-Rev-4F-1 | FAEKFKDAVKDYFAKFWE | 239 |
| Rev-4F-2 | FFEKFKEAVKDYFAKAWD | 240 |
| [Switch D-E]-1-Rev-4F-2 | FFDKFKDAVKEYFAKAWE | 241 |
| [Switch D-E]-2-Rev-4F-2 | FFDKFKEAVKDYFAKAWE | 242 |
| [Switch D-E]-3-Rev-4F-2 | FFEKFKDAVKEYFAKAWD | 243 |
| [Switch D-E]-4-Rev-4F-2 | FFEKFKDAVKDYFAKAWE | 244 |
| Rev-4F-3 | FAEKAKEFVKDYFAKFWD | 245 |
| [Switch D-E]-1-Rev-4F-3 | FADKAKDFVKEYFAKFWE | 246 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [Switch D-E]-2-Rev-4F-3 | FA<u>D</u>KAKEFVKDYFAKFW<u>E</u> | 247 |
| [Switch D-E]-3-Rev-4F-3 | FAEKAK<u>D</u>FVK<u>E</u>YFAKFWD | 248 |
| [Switch D-E]-4-Rev-4F-3 | FAEKAK<u>D</u>FVKDYFAKFW<u>E</u> | 249 |
| Rev-4F-4 | FAEKFKE<u>VA</u>KDYFAKFWD | 250 |
| [Switch D-E]-1-Rev-4F-4 | FA<u>D</u>KFK<u>D</u>VAK<u>E</u>YFAKFW<u>E</u> | 251 |
| [Switch D-E]-2-Rev-4F-4 | FA<u>D</u>KFKEVAKDYFAKFW<u>E</u> | 252 |
| [Switch D-E]-3-Rev-4F-4 | FAEKFK<u>D</u>VAK<u>E</u>YFAKFWD | 253 |
| [Switch D-E]-4-Rev-4F-4 | FAEKFK<u>D</u>VAKDYFAKFW<u>E</u> | 254 |
| Rev-4F-5 | FAEKFKEA<u>Y</u>KD<u>V</u>FAKFWD | 255 |
| [Switch D-E]-1-Rev-4F-5 | FA<u>D</u>KFK<u>D</u>AYK<u>E</u>VFAKFW<u>E</u> | 256 |
| [Switch D-E]-2-Rev-4F-5 | FA<u>D</u>KFKEAYKDVFAKFW<u>E</u> | 257 |
| [Switch D-E]-3-Rev-4F-5 | FAEKFK<u>D</u>AYK<u>E</u>VFAKFWD | 258 |
| [Switch D-E]-4-Rev-4F-5 | FAEKFK<u>D</u>AYKDVFAKFW<u>E</u> | 259 |
| Rev-4F-6 | FAEKFKEAVKD<u>FY</u>AKFWD | 260 |
| [Switch D-E]-1-Rev-4F-6 | FA<u>D</u>KFK<u>D</u>AVK<u>E</u>FYAKFW<u>E</u> | 261 |
| [Switch D-E]-2-Rev-4F-6 | FA<u>D</u>KFKEAVKDFYAKFW<u>E</u> | 262 |
| [Switch D-E]-3-Rev-4F-6 | FAEKFK<u>D</u>AVK<u>E</u>FYAKFWD | 263 |
| [Switch D-E]-4-Rev-4F-6 | FAEKFK<u>D</u>AVKDFYAKFW<u>E</u> | 264 |
| Rev-4F-7 | FAEKF<u>W</u>EAVKDYFAKF<u>K</u>D | 265 |
| [Switch D-E]-1-Rev-4F-7 | FA<u>D</u>KFW<u>D</u>AVK<u>E</u>YFAKFK<u>E</u> | 266 |
| [Switch D-E]-2-Rev-4F-7 | FA<u>D</u>KFWEAVKDYFAKFK<u>E</u> | 267 |
| [Switch D-E]-3-Rev-4F-7 | FAEKFW<u>D</u>AVK<u>E</u>YFAKFKD | 268 |
| [Switch D-E]-4-Rev-4F-7 | FAEKFW<u>D</u>AVKDYFAKFK<u>E</u> | 269 |
| Rev-4F-8 | <u>AF</u>EKFKEAVKDYFAKFWD | 270 |
| [Switch D-E]-1-Rev-4F-8 | AF<u>D</u>KFK<u>D</u>AVK<u>E</u>YFAKFW<u>E</u> | 271 |
| [Switch D-E]-2-Rev-4F-8 | AF<u>D</u>KFKEAVKDYFAKFW<u>E</u> | 272 |
| [Switch D-E]-3-Rev-4F-8 | AFEKFK<u>D</u>AVK<u>E</u>YFAKFWD | 273 |
| [Switch D-E]-4-Rev-4F-8 | AFEKFK<u>D</u>AVKDYFAKFW<u>E</u> | 274 |
| Rev-F-9 | <u>V</u>AEKFKEA<u>F</u>KDYFAKFWD | 275 |
| [Switch D-E]-1-Rev-4F-9 | VA<u>D</u>KFK<u>D</u>AFK<u>E</u>YFAKFW<u>E</u> | 276 |
| [Switch D-E]-2-Rev-4F-9 | VA<u>D</u>KFKEAFKDYFAKFW<u>E</u> | 277 |
| [Switch D-E]-3-Rev-4F-9 | VAEKFK<u>D</u>AFK<u>E</u>YFAKFWD | 278 |
| [Switch D-E]-4-Rev-4F-9 | VAEKFK<u>D</u>AFKDYFAKFW<u>E</u> | 279 |
| Rev-4F-10 | <u>Y</u>AEKFKEAVKD<u>F</u>FAKFWD | 280 |
| [Switch D-E]-1-Rev-4F-10 | YA<u>D</u>KFK<u>D</u>AVK<u>E</u>FFAKFW<u>E</u> | 281 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [Switch D-E]-2-Rev-4F-10 | YADKFKEAVKDFFAKFWE | 282 |
| [Switch D-E]-3-Rev-4F-10 | YAEKFKDAVKEFFAKFWD | 283 |
| [Switch D-E]-4-Rev-4F-10 | YAEKFKDAVKDFFAKFWE | 284 |
| Rev-4F-11 | AAEKFKEFVKDYFAKFWD | 285 |
| [Switch D-E]-1-Rev-4F-11 | AADKFDFVKEYFAKFWE | 286 |
| [Switch D-E]-2-Rev-4F-11 | AADKFKEFVKDYFAKFWE | 287 |
| [Switch D-E]-3-Rev-4F-11 | AAEKFKDFVKEYFAKFWD | 288 |
| Switch D-E]-4-Rev-4F-11 | AAEKFKDFVKDYFAKFWE | 289 |
| Rev-4F-12 | FFEKAKEAVKDYFAKFWD | 290 |
| [Switch D-E]-1-Rev-4F-12 | FFDKAKDAVKEYFAKFWE | 291 |
| [Switch D-E]-2-Rev-4F-12 | FFDKAKEAVKDYFAKFWE | 292 |
| [Switch D-E]-3-Rev-4F-12 | FFEKAKDAVKEYFAKFWD | 293 |
| [Switch D-E]-4-Rev-4F-12 | FFEKAKDAVKDYFAKFWE | 294 |
| Rev-4F-13 | FYEKFKEAVKDAFAKFWD | 295 |
| [Switch D-E]-1-Rev-4F-13 | FYDKFKDAVKEAFAKFWE | 296 |
| [Switch D-E]-2-Rev-4F-13 | FYDKFKEAVKDAFAKFWE | 297 |
| [Switch D-E]-3-Rev-4F-13 | FYEKFKDAVKEAFAKFWD | 298 |
| [Switch D-E]-4-Rev-4F-13 | FYEKFKDAVKDAFAKFWE | 299 |
| Rev-4F-14 | FVEKFKEAAKDYFAKFWD | 300 |
| [Switch D-E]-1-Rev-4F-14 | FVDKFDAAKEYFAKFWE | 301 |
| [Switch D-E]-2-Rev-4F-14 | FVDKFKEAAKDYFAKFWE | 302 |
| [Switch D-E]-3-Rev-4F-14 | FVEKFKDAAKEYFAKFWD | 303 |
| [Switch D-E]-4-Rev-4F-14 | FVEKFKDAAKDYFAKFWE | 304 |
| Rev-4F-15 | FAEKYKEAVKDFFAKFWD | 305 |
| [Switch D-E]-1-Rev-4F-15 | FADKYKDAVKEFFAKFWE | 306 |
| [Switch D-E]-2-Rev-4F-15 | FADKYKEAVKDFFAKFWE | 307 |
| [Switch D-E]-3-Rev-4F-15 | FAEKYKDAVKEFFAKFWD | 308 |
| [Switch D-E]-4-Rev-4F-15 | FAEKYKDAVKDFFAKFWE | 309 |
| Rev-4F-16 | FAEKVKEAFKDYFAKFWD | 310 |
| [Switch D-E]-1-Rev-4F-16 | FADKVKAFKEYFAKFWE | 311 |
| [Switch D-E]-2-Rev-4F-16 | FADKVKEAFKDYFAKFWE | 312 |
| [Switch D-E]-3-Rev-4F-16 | FAEKVKDAFKEYFAKFWD | 313 |
| [Switch D-E]-4-Rev-4F-16 | FAEKVKDAFKDYFAKFWE | 314 |
| Rev-4F-17 | FAEKFKEYVKDAFAKFWD | 315 |
| [Switch D-E]-1-Rev-4F-17 | FADKFKDYVKEAFAKFWE | 316 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [Switch D-E]-2-Rev-4F-17 | FADKFKEYVKDAFAKFWE | 317 |
| [Switch D-E]-3-Rev-4F-17 | FAEKFKDYVKEAFAKFWD | 318 |
| [Switch D-E]-4-Rev-4F-17 | FAEKFKDYVKDAFAKFWE | 319 |
| Rev-4F-18 | FAEKFKEAFKDYVAKFWD | 320 |
| [Switch D-E]-1-Rev-4F-18 | FADKFKDAFKEYVAKFWE | 321 |
| [Switch D-E]-2-Rev-4F-18 | FADKFKEAFKDYVAKFWE | 322 |
| [Switch D-E]-3-Rev-4F-18 | FAEKFKDAFKEYVAKFWD | 323 |
| [Switch D-E]-4-Rev-4F-18 | FAEKFKDAFKDYVAKFWE | 324 |
| Rev-4F-19 | FAEKFKEAFKDYFAKVWD | 325 |
| [Switch D-E]-1-Rev-4F-19 | FADKFKDAFKEYFAKVWE | 326 |
| [Switch D-E]-2-Rev-4F-19 | FADKFKEAFKDYFAKVWE | 327 |
| [Switch D-E]-3-Rev-4F-19 | FAEKFKDAFKEYFAKVWD | 328 |
| Switch D-E]-4-Rev-4F-19 | FAEKFKDAFKDYFAKVWE | 329 |
| Rev-4F-20 | FAEKFKEAVKDFFAKYWD | 330 |
| [Switch D-E]-1-Rev-4F-20 | FADKFKDAVKEFFAKYWE | 331 |
| [Switch D-E]-2-Rev-4F-20 | FADKFKEAVKDFFAKYWE | 332 |
| [Switch D-E]-3-Rev-4F-20 | FAEKFKDAVKEFFAKYWD | 333 |
| [Switch D-E]-4-Rev-4F-20 | FAEKFKDAVKDFFAKYWE | 334 |
| Rev-4F-21 | WAEKFFEAVKDYFAKFKD | 335 |
| [Switch D-E]-1-Rev-4F-7 | WADKFFDAVKEYFAKFKE | 336 |
| [Switch D-E]-2-Rev-4F-7 | WADKFFEAVKDYFAKFKE | 337 |
| [Switch D-E]-3-Rev-4F-7 | WAEKFFDAVKEYFAKFKD | 338 |
| Switch D-E]-4-Rev-4F-7 | WAEKFFDAVKDYFAKFKE | 339 |
| Rev-4F-22 | FAEKWFEAVKDYFAKFKD | 340 |
| [Switch D-E]-1-Rev-4F-22 | FADKWFDAVKEYFAKFKE | 341 |
| [Switch D-E]-2-Rev-4F-22 | FADKWFEAVKDYFAKFKE | 342 |
| [Switch D-E]-3-Rev-4F-22 | FAEKWFDAVKEYFAKFKD | 343 |
| [Switch D-E]-4-Rev-4F-22 | FAEKWFDAVKDYFAKFKE | 344 |
| Rev-4F-23 | FAEKFVEAWKDYFAKFKD | 345 |
| [Switch D-E]-1-Rev-4F-23 | FADKFVDAWKEYFAKFKE | 346 |
| [Switch D-E]-2-Rev-4F-23 | FADKFVEAWKDYFAKFKE | 347 |
| [Switch D-E]-3-Rev-4F-23 | FAEKFVDAWKEYFAKFKD | 348 |
| [Switch D-E]-4-Rev-4F-23 | FAEKFVDAWKDYFAKFKE | 349 |
| Rev-4F-24 | FYEKFAEAVKDWFAKFKD | 350 |
| [Switch D-E]-1-Rev-4F-24 | FYDKFADAVKEWFAKFKE | 351 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
| --- | --- | --- |
| [Switch D-E]-2-Rev-4F-24 | FYDKFAEAVKDWFAKFKE | 352 |
| [Switch D-E]-3-Rev-4F-24 | FYEKFADAVKEWFAKFKD | 353 |
| [Switch D-E]-4-Rev-4F-24 | FYEKFADAVKDWFAKFKE | 354 |
| [A-5 > H] 4F | DWFKHFYDKVAEKFKEAF | 355 |
| [A-5 > H, D-E switched]4F | EWFKHFYEKVADKFKDAF | 356 |
| [A-5 > H, D-1 > E]4F | EWFKHFYDKVAEKFKEAF | 357 |
| [A-5 > H, D-8 > E]4-F | DWFKHFYEKVAEKFKEAF | 358 |
| [A-5 > H, E-12 > D] 4F | DWFKHFYDKVADKFKEAF | 359 |
| [A-5 > H, E-16 > D] 4F | DWFKHFYDKVAEKFKDAF | 360 |
| [F-3 > H, A-5 > F]-4F | DWHKFFYDKVAEKFKEAF | 361 |
| [F-3 > H, A-5 > F, D-E switched]-4F | EWHKFFYEKVADKFKDAF | 362 |
| [F-3 > H, A-5 > F, D-1 > E]-4F | EWHKFFYDKVAEKFKEAF | 363 |
| [F-3 > H, A-5 > F, D-8 > E]-4F | DWHKFFYEKVAEKFKEAF | 364 |
| [F-3 > H, A-5 > F, E-12 > D]-4F | DWHKFFYDKVADKFKEAF | 365 |
| [F-3 > H, A-5 > F, E-16 > D]-4F | DWHKFFYDKVAEKFKDAF | 366 |
| [A-5 > F, F-6 > H]4F | DWFKFHYDKVAEKFKEAF | 367 |
| [A-5 > F, F-6 > H, D-E switched]4F | EWFKFHYEKVADKFKDAF | 368 |
| [[A-5 > F, F-6 > H, D-1 > E]4F | EWFKFHYDKVAEKFKEAF | 369 |
| [A-5 > F, F-6 > H, D-8 > E]4F | DWFKFHYEKVAEKFKEAF | 370 |
| [A-5 > F, F-6 > H, E-12 > D]4F | DWFKFHYDKVADKFKEAF | 371 |
| [A-5 > F, F-6 > H, E-16 > D]4F | DWFKFHYDKVAEKFKDAF | 372 |
| [A-5 > V, V-10 > H]4F | DWFKVFYDKHAEKFKEAF | 373 |
| [A-5 > V, V-10 > H, D-E switched]4F | EWFKVFYEKHADKFKDAF | 374 |
| [A-5 > V, V-10 > H, D-1 > E]4F | EWFKVFYDKHAEKFKEAF | 375 |
| [A-5 > V, V-10 > H, D-8 > E] 4F | DWFKVFYEKHAEKFKEAF | 376 |
| [A-5 > V, V-10 > H, E-12 > D] 4F | DWFKVFYDKHADKFKEAF | 377 |
| [A-5 > V, V-10 > H, E16 > D] 4F | DWFKVFYDKHAEKFKDAF | 378 |
| [[A-17 > H]4F | DWFKAFYDKVAEKFKEHF | 379 |
| [A-17 > H, D-E switched] 4F | EWFKAFYEKVADKFKDHF | 380 |
| [[A-17 > H, D-1 > E]4F | EWFKAFYDKVAEKFKEHF | 381 |
| [[A-17 > H, D-8 > E]4F | DWFKAFYEKVAEKFKEHF | 382 |
| [[A-17 > H, E-12 > D]4F | DWFKAFYDKVADKFKEHF | 383 |
| [[A-17 > H, E16 > D]4F | DWFKAFYDKVAEKFKDHF | 384 |
| [A-17 > F, F-18 > H] 4F | DWFKAFYDKVAEKFKEFH | 385 |
| [A-17 > F, F-18 > H, D-E switched] 4F | EWFKAFYEKVADKFKDFH | 386 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| [A-17 > F, F-18 > H, D-1 > E]-4F | EWFKAFYDKVAEKFKEFH | 387 |
| [A-17 > F, F-18 > H] 4F | DWFKAFYDKVAEKFKEFH | 388 |
| [A-17 > F, F-18 > H, D-8 > E]-4F | DWFKAFYEKVAEKFKEFH | 389 |
| [A-17 > F, F-18 > H, E-12 > D] 4F | DWFKAFYDKVADKFKEFH | 390 |
| [A-17 > F, F-18 > H], E-16 > D]-4F | DWFKAFYDKVAEKFKDFH | 391 |
| Rev-4F | FAEKFKEAVKDYFAKFWD | 392 |
| [A-2 > H]Rev4F | FHEKFKEAVKDYFAKFWD | 393 |
| Rev-[A-2 > H, D > E]-4F | FHEKFKEAVKEYFAKFWE | 394 |
| Rev-[A-2 > H, E > D]4F | FHDKFDAVKDYFAKFWD | 395 |
| [A-2 > H, D-E switched] Rev-4F | FHDKFDAVKEYFAKFWE | 396 |
| [A-2 > H, E-3 > D]Rev-4F | FHDKFKAVKDYFAKFWD | 397 |
| [A-2 > H, E-7 > D]Rev-4F | FHEKFDAVKDYFAKFWD | 398 |
| [A-2 > H, D-11 > E]Rev-4F | FHEKFKEAVKEYFAKFWD | 399 |
| [A-2 > H, D-18 > E]Rev-4F | FHEKFKEAVKDYFAKFWE | 400 |
| [F-1 > H, A-2 > F]Rev-4F | HFEKFKEAVKDYFAKFWD | 401 |
| [F-1 > H, A-2 > F, D-E switched]Rev-4F | HFDKFDAVKEYFAKFWE | 402 |
| [F-1 > H, A-2 > F, D > E]Rev-4F | HFEKFKEAVKEYFAKFWE | 403 |
| [F-1 > H, A-2 > F, E-3 > D]Rev-4F | HFDKFKAVKDYFAKFWD | 404 |
| [F-1 > H, A-2 > F, E-7 > D]Rev-4F | HFEKFDAVKDYFAKFWD | 405 |
| [F-1 > H, A-2 > F, D-11 > E]Rev-4F | HFEKFKEAVKEYFAKFWD | 406 |
| [F-1 > H, A-2 > F, D-18 > E]Rev-4F | HFEKFKEAVKDYFAKFWE | 407 |
| [A-2 > F, F-5 > H] Rev D-4F | FFEKHKEAVKDYFAKFWD | 408 |
| [A-2 > F, F-5 > H, D-E switched] Rev D-4F | FFDKHKDAVKEYFAKFWE | 409 |
| [A-2 > F, F-5 > H, D > E] Rev D-4F | FFEKHKEAVKEYFAKFWE | 410 |
| [A-2 > F, F-5 > H, E > D] Rev D-4F | FFDKHKDAVKDYFAKFWD | 411 |
| [A-2 > F, F-5 > H, E-3 > D] Rev D-4F | FFDKHKEAVKDYFAKFWD | 412 |
| [A-2 > F, F-5 > H, D-11 > E] Rev D-4F | FFEKHKEAVKEYFAKFWD | 413 |
| [A-2 > F, F-5 > H, D-18 > E] Rev D-4F | FFEKHKEAVKDYFAKFWE | 414 |
| [A-2 > V, V-9 > H] Rev D-4F | FVEKFKEAHKDYFAKFWD | 415 |
| [A-2 > V, V-9 > H, D-E switched] Rev D-4F | FVDKFKDAHKEYFAKFWE | 416 |
| [A-2 > V, V-9 > H, D > E] Rev D-4F | FVEKFKEAHKEYFAKFWE | 417 |
| [A-2 > V, V-9 > H, E > D] Rev D-4F | FVDKFDAHKDYFAKFWD | 418 |
| [A-2 > V, V-9 > H, E-3 > D] Rev D-4F | FVDKFKEAHKDYFAKFWD | 419 |
| [A-2 > V, V-9 > H, E-7 > D] Rev D-4F | FVEKFDAHKDYFAKFWD | 420 |
| [A-2 > V, V-9 > H, D-11 > E] Rev D-4F | FVEKFKEAHKEYFAKFWD | 421 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also comtemplated.

| Peptide Name | Amino Acid Sequence | SEQ ID NO. |
| --- | --- | --- |
| [A-2 > V, V-9 > H, D-18 > E] Rev D-4F | FVEKFKEAHKDYFAKFWE | 422 |
| [A-8 > H]Rev-4F | FAEKFKEHVKDYFAKFWD | 423 |
| [A-8 > H, D-E switched]Rev-4F | FADKFKDHVKEYFAKFWE | 424 |
| [A-8 > H, D > E]Rev-4F | FAEKFKEHVKEYFAKFWE | 425 |
| [A-8 > H, E > D]Rev-4F | FADKFKDHVKDYFAKFWD | 426 |
| [A-8 > H, E-3 > D]Rev-4F | FADKFKEHVKDYFAKFWD | 427 |
| [A-8 > H, E-7 > D]Rev-4F | FAEKFKDHVKDYFAKFWD | 428 |
| [A-8 > H, D-11 > E]Rev-4F | FAEKFKEHVKEYFAKFWD | 429 |
| [A-8 > H, D-18 > E]Rev-4F | FAEKFKEHVKDYFAKFWE | 430 |
| [A-8 > F, F-13 > H]Rev-4F | FAEKFKEFVKDYHAKFWD | 431 |
| [A-8 > F, F-13 > H, D-E switched]Rev-4F | FADKFKDFVKEYHAKFWE | 432 |
| [A-8 > F, F-13 > H, E-3 > D]Rev-4F | FADKFKEFVKDYHAKFWD | 433 |
| [A-8 > F, F-13 > H, E-7 > D]Rev-4F | FAEKFKDFVKDYHAKFWD | 434 |
| [A-8 > F, F-13 > H, E > D]Rev-4F | FADKFKDFVKDYHAKFWD | 435 |
| [A-8 > F, F-13 > H, D > E]Rev-4F | FAEKFKEFVKEYHAKFWE | 436 |
| [A-8 > F, F-13 > H, D-11 > E]Rev-4F | FAEKFKEFVKEYHAKFWD | 437 |
| [A-8 > F, F-13 > H, D-18 > E]Rev-4F | FAEKFKEFVKDYHAKFWE | 438 |
| [A-8 > F, F16 > H]Rev.-4F | FAEKFKEFVKDYFAKHWD | 439 |
| [A-8 > F, F16 > H, D-E switched]Rev.-4F | FADKFKDFVKEYFAKHWE | 440 |
| [A-8 > F, F16 > H, D > E]Rev.-4F | FAEKFKEFVKEYFAKHWE | 441 |
| [A-8 > F, F16 > H, E > D]Rev.-4F | FADKFKDFVKDYFAKHWD | 442 |
| [A-8 > F, F16 > H, E-3 > D]Rev.-4F | FADKFKEFVKDYFAKHWD | 443 |
| [A-8 > F, F16 > H, E-7 > D]Rev.-4F | FAEKFKDFVKDYFAKHWD | 444 |
| [A-8 > F, F16 > H, D-11 > E]Rev.-4F | FAEKFKEFVKEYFAKHWD | 445 |
| [A-8 > F, F16 > H, D-18 > E]Rev.-4F | FAEKFKEFVKDYFAKHWE | 446 |
| Rev-[D > E]-4F | FAEKFKEAVKEYFAKFWE | 447 |
| Rev-[E > D]4F | FADKFKDAVKDYFAKFWD | 448 |
| Rev-R4-4F | FAERFKEAVKDYFAKFWD | 449 |
| Rev-R6-4F | FAEKFREAVKDYFAKFWD | 450 |
| Rev-R10-4F | FAEKFKEAVRDYFAKFWD | 451 |
| Rev-R14-4F | FAEKFKEAVKDYFARFWD | 452 |
| Rev-[D > E]-4F | FAEKFKEAVKEYFAKFWE | 453 |
| Rev-[E > D]4F | FADKFKDAVKDYFAKFWD | 454 |
| Rev-R4-4F | FAERFKEAVKDYFAKFWD | 455 |
| Rev-R6-4F | FAEKFREAVKDYFAKFWD | 456 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
| --- | --- | --- |
| Rev-R10-4F | FAEKFKEAVRDYFAKFWD | 457 |
| Rev-R14-4F | FAEKFKEAVKDYFARFWD | 458 |
| Rev-[D > E]-4F | FAEKFKEAVKEYFAKFWE | 459 |
| Rev-[E > D]4F | FADKFKDAVKDYFAKFWD | 460 |
| Rev-R4-4F | FAERFREAVKDYFAKFWD | 461 |
| Rev-R6-4F | FAEKFREAVKDYFAKFWD | 462 |
| Rev-R10-4F | FAEKFKEAVRDYFAKFWD | 463 |
| Rev-R14-4F | FAEKFKEAVKDYFARFWD | 464 |
| Rev-R4-4F | FAERFREAVKDYFAKFWD | 465 |
| Rev-R6-4F | FAEKFREAVKDYFAKFWD | 466 |
| Rev-R10-4F | FAEKFKEAVRDYFAKFWD | 467 |
| Rev-R14-4F | FAEKFKEAVKDYFARFWD | 468 |
| Rev-[D > E]-4F | FAEKFKEAVKEYFAKFWE | 469 |
| Rev-[E > D]4F | FADKFKDAVKDYFAKFWD | 470 |
| Rev-R4-4F | FAERFREAVKDYFAKFWD | 471 |
| Rev-R6-4F | FAEKFREAVKDYFAKFWD | 472 |
| Rev-R10-4F | FAEKFKEAVRDYFAKFWD | 473 |
| Rev-R14-4F | FAEKFKEAVKDYFARFWD | 474 |
| Rev3F-2 | LFEKFAEAFKDYVAKWKD | 475 |
| RevR4-3F-2 | LFERFAEAFKDYVAKWKD | 476 |
| RevR10-3F2 | LFEKFAEAFRDYVAKWKD | 477 |
| RevR15-3F-2 | LFEKFAEAFKDYVARWKD | 478 |
| Rev R17-3F-2 | LFEKFAEAFKDYVAKWRD | 479 |
| Rev[D > E]3F2 | LFEKFAEAFKEYVAKWKE | 480 |
| Rev [E > D]3F-2 | LFDKFADAFKDYVAKWKD | 481 |
| Rev-[E3 > D]-3F-2 | LFDKFAEAFKDYVAKWKD | 482 |
| Rev-[E7 > D]-3F-2 | LFEKFADAFKDYVAKWKD | 483 |
| Rev[D11 > E]3F-2 | LFEKFAEAFKEYVAKWKD | 484 |
| Rev-[D18 > E]3F-2 | LFEKFAEAFKDYVAKWKE | 485 |
| Rev3F-1 | FAEKAWEFVKDYFAKLKD | 486 |
| RevR4-3F-1 | FAERAWEFVKDYFAKLKD | 487 |
| RevR10-3F-1 | FAEKAWEFVKDYFAKLKD | 488 |
| RevR15-3F-1 | FAEKAWEFVKDYFAKLKD | 489 |
| RevR17-3F-1 | FAEKAWEFVKDYFAKLRD | 490 |
| Rev[D > E]3F-1 | FAEKAWEFVKEYFAKLKE | 491 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
| --- | --- | --- |
| Rev [E > D}3F-1 | FADKAWDFVKDYFAKLKD | 492 |
| Rev [E3 > D]-3F-1 | FADKAWEFVKDYFAKLKD | 493 |
| Rev[E7 > D]3F-1 | FAEKAWDFVKDYFAKLKD | 494 |
| Rev4-[D11 > E]3F-1 | FAEKAWEFVKEYFAKLKD | 495 |
| Rev-[D18 > E]3F-1 | FAEKAWEFVKDYFAKLKE | 496 |
| Rev-5F | FFEKFKEFVKDYFAKLWD | 497 |
| Rev-[D > E]5F | FFEKFKEFVKEYFAKLWE | 498 |
| Rev-[E > D]5F | FFDKFKDFVKDYFAKLWD | 499 |
| Rev-R4-5F | FFERFKEFVKDYFAKLWD | 500 |
| Rev-R6-5F | FFEKFREFVKDYFAKLWD | 501 |
| Rev-R10-5F | FFEKFKEFVRDYFAKLWD | 502 |
| Rev-R15-5F | FFEKFKEFVKDYFARLWD | 503 |
| Rev-[E3 > D]-5F | FFDKFKEFVKDYFAKLWD | 504 |
| Rev-[E7 > D]5F | FFEKFKDFVKDYFAKLWD | 505 |
| Rev-[D11 > E]-5F | FFEKFKEFVKEYFAKLWD | 506 |
| Rev-[D18 > E]-5F | FFEKFKEFVKDYFAKLWE | 507 |
| Rev-5F-2 | FLEKFKEFVKDYFAKFWD | 508 |
| Rev-[D > E]-5F-2 | FLEKFKEFVKEYFAKFWE | 509 |
| Rev-[E > D]-5F-2 | FLDKFKEFVKDYFAKFWD | 510 |
| Rev-[E3 > D]-5F-2 | FLDKFKEFVKDYFAKFWD | 511 |
| Rev-[E7 > D]-5F-2 | FLEKFKDFVKDYFAKFWD | 512 |
| Rev4-[D11 > E]-5F-2 | FLEKFKEFVKEYFAKFWD | 513 |
| Rev-[D18 > E]-5F-2 | FLEKFKEFVKDYFAKFWE | 514 |
| Rev-R4-5F-2 | FLERFKEFVKDYFAKFWD | 515 |
| Rev-R6-5F-2 | FLEKFREFVKDYFAKFWD | 516 |
| RevR10-5F-2 | FLEKFKEFVRDYFAKFWD | 517 |
| Rev-R16-5F-2 | FLEKFKEFVKDYFARFWD | 518 |
| Rev-6F | FFEKFKEFFKDYFAKLWD | 519 |
| Rev-[D > E]-6F | FFEKFKEFFKEYFAKLWE | 520 |
| Rev-[E > D]-6F | FFDKFKDFFKDYFAKLWD | 521 |
| Rev-R4-6F | FFERFKEFFKDYFAKLWD | 522 |
| Rev-R6-6F | FFEKFREFFKDYFAKLWD | 523 |
| Rev-R10-6F | FFEKFKEFFRDYFAKLWD | 524 |
| Rev-R14-6F | FFERFKEFFKDYFARLWD | 525 |
| Rev-[E3 > D]-6F | FFDKFKEFFKDYFAKLWD | 526 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| Rev-[E7 > D]-6F | FFEKFKDFFKDYFAKLWD | 527 |
| Rev-[D11 > E]-6F | FFEKFKEFFKEYFAKLWD | 528 |
| Rev-[D18 > E]-6F | FFEKFKEFFKDYFAKLWE | 529 |
| Rev-4F | FAEKFKEAVKDYFAKFWD | 530 |
| Rev-[D > E]-4F | FAEKFKEAVKEYFAKFWE | 531 |
| Rev-[E > D]4F | FADKFKDAVKDYFAKFWD | 532 |
| Rev-R4-4F | FAERFREAVKDYFAKFWD | 533 |
| Rev-R6-4F | FAEKFREAVKDYFAKFWD | 534 |
| Rev-R10-4F | FAEKFKEAVRDYFAKFWD | 535 |
| Rev-R14-4F | FAEKFKEAVKDYFARFWD | 536 |
| 4F-2 | DKWKAVYDKFAEAFKEFF | 537 |
| [D > E]-4F-2 | EKWKAVYEKFAEAFKEFF | 538 |
| [E > D]-4F-2 | DKWKAVYDKFADAFKDFF | 539 |
| R2-4F-2 | DRWKAVYDKFAEAFKEFF | 540 |
| R4-4F-2 | DKWRAVYDKFAEAFKEFF | 541 |
| R9-4F-2 | DKWKAVYDRFAEAFKEFF | 542 |
| R14-4F-2 | DKWKAVYDKFAEAFREFF | 543 |
| Rev4F-2 | FFEKFAEAFKDYVAKWKD | 544 |
| Rev-[D > E]-4F-2 | FFEKFAEAFKEYVAKWKE | 545 |
| Rev-[E > D]-3F-2 | FFDKFADAFKDYVAKWKD | 546 |
| Rev-R4-4F-2 | FFERFAEAFKDYVAKWKD | 547 |
| Rev-R10-4F-2 | FFERFAEAFRDYVAKWKD | 548 |
| Rev-R15-4F-2 | FFEKFAEAFKDYVARWKD | 549 |
| Rev-R17-4F-2 | FFERFAEAFKDYVAKWRD | 550 |
| Rev-[E3 > D]-4F-2 | FFDKFAEAFKDYVAKWKD | 551 |
| Rev-[E7 > D]-4F-2 | FFEKFADAFKDYVAKWKD | 552 |
| Rev-[D11 > E]-4F-2 | FFERFAEAFKEYVAKWKD | 553 |
| Rev-[D18 > E]-4F-2 | FFERFAEAFKDYVAKWKE | 554 |
| Rev-7F | FFEKFKEFFKDYFAKFWD | 555 |
| Rev-[E > D]-7F | FFDKFKDFFKDYFAKFWD | 556 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| Rev-[D > E]-7F | FFEKFKEFFKEYFAKFWE | 557 |
| Rev-R4-7F | FFERFKEFFKDYFAKFWD | 558 |
| Rev-R6-7F | FFEKFREFFKDYFAKFWD | 559 |
| Rev-R10-7F | FFEKFKEFFRDYFAKFWD | 560 |
| Rev-R14-7F | FFEKFKEFFKDYFARFWD | 561 |
| Rev-[E3 > D]-7F | FFDKFKEFFKDYFAKFWD | 562 |
| Rev-[E7 > D]7F | FFEKFKDFFKDYFAKFWD | 563 |
| Rev-[D11 > E]-7F | FFEKFKEFFKEYFAKFWD | 564 |
| Rev-[D18 > E]-7F | FFEKFKEFFKDYFAKFWE | 565 |
| | EVRAKLEEQAQQIRLQAEAFQARLKSWFEPLVE | 566 |
| | EVRAKLEEQAQQIRLQAEAFQARLKSWFE | 567 |
| | EVRSKLEEAAFREFAEEFLARLKS | 568 |
| | PVLDLFRELLNELLEALKQKLK | 569 |
| | DWLKAFYDKVAEKLKEAF- P-DWAKAAYDKAAEKAKEAA | 570 |
| | EELKEKLEELKEKLEEKL-P-EELKEKLEELKEKLEEKL | 571 |
| | EELKAKLEELKAKLEEKL-P-EELKAKLEELKAKLEEKL | 572 |
| | EKLKALLEKLLAKLKELL P-EKLKALLEKLLAKLKELL | 573 |
| | EWLKELLEKLLEKLKELL-P-EWLKELLEKLLEKLKELL | 574 |
| | EKFKELLEKFLEKFKELL-P-EKFKELLEKFLEKFKELL | 575 |
| | EKLKELLEKLLELLKKLL-P-EKLKELLEKLLELLKKLL | 576 |
| | EKLKELLEKLKAKLEELL-P-EKLKELLEKLKAKLEELL | 577 |
| | EKLKELLEKLLAKLKELL-P-EKLKELLEKLLAKLKELL | 578 |
| | EKFKELLEKLLEKLKELL-P-EKFKELLEKLLEKLKELL | 579 |
| | EKLKAKLEELKAKLEELL-P-EKLKAKLEELKAKLEELL | 580 |
| | EELKELLKELLKKLEKLL-P-ELKELLKELLKKLEKLL | 581 |
| | EELKKLLEELKKLKELL-P-EELKKLLEELKKLKELL | 582 |
| | EKLKELLEKLLEKLKELL-A-EKLKELLEKLLEKLKELL | 583 |
| | EKLKELLEKLLEKLKELL-AA-EKLKELLEKLLEKLKELL | 584 |

TABLE 1-continued

Certain ApoA-I mimetic peptides that can be used for the preparation of ezetimibe associated peptides (Ez-peptides), e.g., as described herein. The table includes various class A and/or class Y peptide analogs. For each sequence listed in this table, the retro form of the sequence is also comtemplated. Thus, for example where the 6F peptide sequence DWLKAFYDKFFEKFKEFF (SEQ ID NO: 1) is shown, the retro amino acid sequence FFEKFKEFFKDYFAKLWD (SEQ ID NO: 15) is also contemplated.

| Peptide Name | Amino Acid Sequence | SEQ ID NO. |
|---|---|---|
| | EKLKAKLEELKAKLEELL-P-EKAKAALEEAKAKAEELA | 585 |
| | EKLKAKLEELKAKLEELL-P-EHAKAALEEAKCKAEELA | 586 |
| | DHLKAFYDKVACKLKEAF-P-DWAKAAYDKAAEKAKEAA | 587 |
| | DWLKAFYDKVAEKLKEAF-P-DHAKAAYDKAACKAKEAA | 588 |
| | DWLKAFYDKVACKLKEAF-P-DWAKAAYNKAAEKAKEAA | 589 |
| | DHLKAFYDKVAEKLKEAF-P-DWAKAAYDKAAEKAKEAA | 590 |
| | VLESFKVSFLSALEEYTKKLNTQ | 591 |
| (3F$^{Cπ}$) | DKWKAVYDKFAEAFKEFL | 592 |
| (3F$^{Iπ}$) | DKLKAFYDKVFEWAKEAF | 593 |

Apo-J (G* Peptides).

It was also discovered that peptides that mimic the amphipathic helical domains of apoJ are also capable of mitigating one or more symptoms of atherosclerosis and/or other pathologies described herein. Apolipoprotein J possesses a wide nonpolar face termed globular protein-like, or G* amphipathic helical domains. The class G amphipathic helix is found in globular proteins, and thus, the name class G. This class of amphipathic helix is characterized by a random distribution of positively charged and negatively charged residues on the polar face with a narrow nonpolar face. Because of the narrow nonpolar face this class does not readily associate with phospholipids. The G* of amphipathic helix possesses similar, but not identical, characteristics to the G amphipathic helix. Similar to the class G amphipathic helix, the G* class peptides possesses a random distribution of positively and negatively charged residues on the polar face. However, in contrast to the class G amphipathic helix which has a narrow nonpolar face, this class has a wide nonpolar face that allows this class to readily bind phospholipid and the class is termed G* to differentiate it from the G class of amphipathic helix.

A number of suitable G* amphipathic peptides are described U.S. Pat. Nos. 6,930,085, and 7,638,494, and in PCT Publication No: PCT/US03/09988 (WO 2003/086326) which are incorporated herein by reference for the peptides described therein. In certain embodiments the G* (apoJ) peptides used for the preparation of ezetimibe associated peptides (Ez-peptides) comprise one or more domains that have an amino acid sequence shown in Table 2 or the reverse sequence.

TABLE 2

Certain peptides related to G* amphipathic helical domains of app J that can be used for the preparation of ezetimibe associated peptides (Ez-peptides), e.g., as described herein. For each sequence listed in this table, the retro form of the sequence is also contemplated. Thus, for example where the sequence DQYYLRVTTVA (SEQ ID NO: 595) is shown, the amino acid sequence AVTTVRLYYQD (SEQ ID NO: 594) is also contemplated.

| Amino Acid Sequence | SEQ ID NO |
|---|---|
| DQYYLRVTTVA | 595 |
| ECKPCLKQTCMKFYARVCR | 596 |
| FSRASSIIDELFQD | 597 |
| IQNAVNGVKQIKTLIEKTNEE | 598 |
| LLEQLNEQFNWVSRLANL | 599 |
| LLEQLNEQFNWVSRLANLTEGE | 600 |
| LLEQLNEQFNWVSRLANLTQGE | 601 |
| LVGRQLEEFL | 602 |
| MNGDRIDSLLEN | 603 |
| NELQEMSNQGSKYVNKEIQNAVNGV | 604 |
| PCLKQTCMKFYARVCR | 605 |
| PFLEMIHEAQQAMDI | 606 |
| PGVCNETMMALWEECK | 607 |
| PKFMETVAEKALQEYRKKHRE | 608 |

TABLE 2-continued

Certain peptides related to G* amphipathic helical domains of app J that can be used for the preparation of ezetimibe associated peptides (Ez-peptides), e.g., as described herein. For each sequence listed in this table, the retro form of the sequence is also contemplated. Thus, for example where the sequence DQYYLRVTTVA (SEQ ID NO: 595) is shown, the amino acid sequence AVTTVRLYYQD (SEQ ID NO: 594) is also contemplated.

| Amino Acid Sequence | SEQ ID NO |
|---|---|
| PSGVTEVVVKLFDS | 609 |
| PSQAKLRRELDESLQVAERLTRKYNELLKSYQ | 610 |
| PTEFIREGDDD | 611 |
| QQTHMLDVMQD | 612 |
| RKTLLSNLEEAKKKKEDALNETRESETKLKEL | 613 |
| RMKDQCDKCREILSV | 614 |

ApoE Mimetic Peptides

ApoE mimetic peptides have also been demonstrated to have activities similar to those described above for ApoA-I mimetic peptides, particularly with respect to neurological and/or ocular dysfunction (see, e.g., Handattu et al. (2010) *J. Lipid Res.* 51: 3491-3499; Laskowitz et al. (2001) *Experimental Neurology* 167: 74-85; Minami et al. (2010) *Molecular Neurodegeneration,* 5:16; Bhattacharj ee et al. (2008) *Invest Ophthalmol Vis Sci.* 49: 4263-4268; Li et al. 92010) *J. Pharmacol. and Experimental Therapeutics* 334: 106-115; Klein and Yakel (2004) *Neurosci.,* 127: 563-567; Laskowitz et al. (2007) *J. of Neurotrauma* 24: 1093-1107; Christensen et al. (2011) *J. Immunol.,* 186: 2535-2542; Croy et al. 92004) *Biochemistry* 43: 7328-7335). In certain embodiments the peptides used for the preparation of ezetimibe associated peptides (Ez-peptides) comprise one or more domains that have an apoE amino acid sequence or a dual ApoE/ApoA-I sequence shown in Table 3 or the reverse sequence.

TABLE 3

Certain ApoE peptides that can be used for the preparation of ezetimibe associated peptides (Ez-peptides), e.g., as described herein. For each sequence listed in this table, the retro form of the sequence is also contemplated. Thus, for example where the sequence GIKKFLGSIWKFIKAFVG (SEQ ID NO: 616) is shown, the amino acid sequence GVFAKIFKWISGLFKKIG (SEQ ID NO: 615) is also contemplated.

| Amino Acid Sequence | SEQ ID NO |
|---|---|
| ApoE peptides: | |
| GIKKFLGSIWKFIKAFVG | 616 |
| GFKKFLGSWAKIYKAFVG | 617 |
| GFRRFLGSWARIYRAFVG | 618 |
| TEELRVRLASHLRKLRKRLL | 619 |
| TEELRVRLASHLRKLRK | 620 |
| LRVRLASHLRKLRKRLL | 621 |
| RLASHLRKLRKRLL | 622 |
| SHLRKLRKRLL | 623 |
| LRKLRKRLL | 624 |
| LRKLRKRLLLRKLRKRLL | 625 |
| LRKLRKRLLLRKLRKRLLLRKLRKRLL | 626 |
| RQIKIWFQNRRMKWKKCLRVRLASHLRKLRKRLL | 627 |

TABLE 3-continued

Certain ApoE peptides that can be used for the preparation of ezetimibe associated peptides (Ez-peptides), e.g., as described herein. For each sequence listed in this table, the retro form of the sequence is also contemplated. Thus, for example where the sequence GIKKFLGSIWKFIKAFVG (SEQ ID NO: 616) is shown, the amino acid sequence GVFAKIFKWISGLFKKIG (SEQ ID NO: 615) is also contemplated.

| Amino Acid Sequence | SEQ ID NO |
|---|---|
| LRVRLASHLRKLRKRLL | 628 |
| EELRVRLASHLRKLRKRLLRDADDLQKRLAVYEEQAQQ | 629 |
| IRLQAEAFQARLKSWFEPLVEDM | |
| CEELRVRLASHLRKLRKRLLRDADDLQKRLAVY | 630 |
| LRKLRKRLLRDADDLLRKLRKRLLRDADDL | 631 |
| TEELRVRLASHLRKLRKRLL | 632 |
| TEELRVRLASHLEKLRKRLL | 633 |
| TEELRVRLASHLRELRKRLL | 634 |
| LREKKLRVSALRTHRLELRL | 635 |
| Dual ApoE and ApoA-I mimetic peptides: | |
| LRKLRKRLLRDWLKAFYDKVAEKLKEAF | 636 |
| LRRLRRRLLRDWLKAFYDKVAEKLKEAF | 637 |
| RRRRRRRRRDWLKAFYDKVAEKLKEAF | 638 |

It has been demonstrated that in certain embodiments, linking the receptor binding domain of apolipoprotein E (apoE) to a class A amphipathic helix can enhance internalization and degradation of LDL by fibroblasts and can lower plasma cholesterol and restore endothelial function (see, e.g., Datta et al. (2000) *Biochemistry* 39: 213-220; Gupta et al. (2005) *Circulation* 111: 3112-3118).

Accordingly in certain embodiments, any of the peptides described herein, can be provided as a peptide also comprising an apoE receptor binding domain (see, e.g., SEQ ID NOs:636-638 for illustrative examples).

In various embodiments, peptides comprising an oxpholipin domain such as Arg-Glu-Dpa-Thr-Gly-Leu-Ala-Trp-Glu-Trp-Trp-Arg-Thr-Val (SEQ ID NO:639), where Dpa (3,3'-diphenyl alanine) is substituted with Trp, Phe, or Ala) are also contemplated. Oxpholipin peptides are described by Ruchala et al. (2010) *PLoS ONE* 5(4): e10181) and in PCT Publication No: PCT/US2010/046534 (WO/2011/031460), which are incorporated herein by reference for the peptides described therein and where such peptides incorporate 3,3'-diphenylalanine, this residue is substituted with Trp, Phe, or Ala.

In addition to the sequences listed in Tables 1, 2, and 3 amino acid sequences comprising 1 conservative substitution, 2 conservative substitutions, 3 conservative substitutions, 4 conservative substitutions, 5 conservative substitutions, 6 conservative substitutions, 7 conservative substitutions, 8 conservative substitutions, 9 conservative substitutions, or 10 conservative substitutions are contemplated.

The foregoing peptides are intended to be illustrative and not limiting. In view of the surprising discovery that ApoA-I mimetic peptides and other related peptides described herein can be used for the preparation of ezetimibe associated peptides (Ez-peptides), one of skill in the art will recognized that numerous other such peptides can also also be used for the preparation of ezetimibe associated peptides (Ez-peptides), e.g., to afford a similar utility.

Chemical Synthesis of apoA-I Mimetic Peptides.

In various embodiments the peptides use for the ezetimibe-associated apoA-I peptide is synthesized by any of a number of fluid or solid phase peptide synthesis techniques known to those of skill in the art. In certain embodiments the peptide is syntheized using solid phase synthesis in which the C-terminal amino acid of the sequence is attached to an insoluble support followed by sequential addition of the remaining amino acids in the sequence. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis, Biology. Vol. 2: Special Methods in Peptide Synthesis, Part A*; Merrifield et al. (1963) *J. Am. Chem. Soc.,* 85: 2149-2156, and Stewart et al. (1984) *Solid Phase Peptide Synthesis,* 2nd ed. Pierce Chem. Co., Rockford, Ill.

In one embodiment, the peptides are synthesized by the solid phase peptide synthesis procedure using a benzhyderylamine resin (Beckman Bioproducts, 0.59 mmol of $NH_2$/g of resin) as the solid support. The COOH terminal amino acid (e.g., t-butylcarbonyl-Phe) is attached to the solid support through a 4-(oxymethyl)phenacetyl group. This is a more stable linkage than the conventional benzyl ester linkage, yet the finished peptide can still be cleaved by hydrogenation. Transfer hydrogenation using formic acid as the hydrogen donor is used for this purpose. Detailed protocols used for peptide synthesis and analysis of synthesized peptides are describe in a miniprint supplement accompanying Anantharamaiah et al. (1985) *J. Biol. Chem.,* 260(16): 10248-10255.

It is noted that in the chemical synthesis of peptides, particularly peptides comprising D amino *acids, the synthesis usually produces a number of truncated peptides in addition to the desired full-length product. The purification process (e.g. HPLC) typically results in the loss of a significant amount of the full-length product.

Construction and Propagation of Transgenic Plants.

In various embodiments the ezetimibe-associated apoA-I peptide is prepared using an apoA-I mimetic pepide that is recombinantly expressed, e.g., in a plant, yeast, or animal tissue. In certain embodiments the ezetimibe-associated apoA-I peptide is prepared using the tissue of a plant (e.g., a tomato) that where said tissue contains a heterologous ApoA-I mimetic peptide expressed by the plant.

The construction and propagation of transgenic plants expressing ApoA-I peptides or mimetics thereof and suitable for the preparation of ezetimibe-associated ApoA-I peptides as described herein is detailed, inter alia, in PCT Publication No: WO 2013/148214 A1 and in Chattopadhyay et al. (2013) *J. Lipid Res.,* 54: 995-10101, and Navab et al. (2013) *J. Lipid Res.,* 54: 3403-3418. The methods typically involve constructing a vector (e.g., a plasmid vector) or a DNA fragment by operably linking a DNA sequence encoding the peptide(s) of interest (e.g., peptides comprising ApoA-I, and/or G*, and/or ApoE domain(s)) to a plant-functional promoter capable of directing the expression of the peptide in the plant and then transforming a plant cell with the plasmid vector or DNA fragment. Where preferred, the method may be extended to produce transgenic plants from the transformed cells by including a step of regenerating a transgenic plant from the transgenic plant cell. The resulting plants provide tissues, extracts of which having ApoA-I activity can be produced using the methods described herein.

Illustrative, but non-limiting methods of producing such transgenic plants are also described below.

Nucleic Acids and Vectors Expressing the Peptide(s) of Interest.

Typically, the codon usage of the nucleic acid that is to express the desired amino acid sequence(s) is selected to reflect the optimal codon usage in that plant. Methods of optimizing codon usage for expression of a nucleic acid in a particular host organism are known to those of skill in the art, and numerous software tools are available for such optimization. For example, codon tables are available from the Codon Usage Database, maintained by the Department of Plant Gene Research in Kazusa, Japan (see, e.g., www.kazusa.or.jp/codon/).

In certain embodiments the codon optimized nucleic acid sequence is incorporated into an expression vector (e.g., a plasmid). Typically the nucleic acid sequence is operably linked (put under control of) a promoter capable of directing expression of the nucleic acid sequence in the host plant.

Promoters

Promoters that are known or found to cause transcription of a foreign gene in plant cells are well known to those of skill in the art. Such promoters include, for example, promoters of viral origin and promoters of plant origin. The promoters can be constitutive or inducible, and in various embodiments, are tissue-specific promoters. In various embodiments any of these promoters are contemplated for the expression of a peptide described herein in a plant/plant tissue.

The most common promoters used for constitutive over-expression in plants are derived from plant virus sources, such as the cauliflower mosaic (CaMV) 35S promoter (Odell et al. (1985) *Nature,* 313: 810-812). This promoter, like similar virally derived promoters used in plant systems, is harvested from double-stranded DNA viral genomes, which use host nuclear RNA polymerase and do not appear to depend on any trans-acting viral gene products. The CaMV 35S promoter delivers high expression in virtually all regions of the transgenic plant, is readily obtainable in research and academic settings, and available in plant transformation vector cassettes that allow for easy subcloning of the transgene of interest. The CaMV 35S promoter can drive high levels of transgene expression in both dicots and monocots (Battraw and Hall (1990) *Plant Mol. Biol.* 15: 527-538; Benfey et al. (1990) *EMBO J.* 9: 1677-1684). In various embodiments the full-sized 35S promoter (−941 to +9 bp) (Odell et al. (1985) *Nature,* 313: 810-812) or various fragments such as a 2343 bp fragment can be used. Other viral promoters are also well known to those of skill in the art. These include, but are not limited to the cassava vein mosaic virus (CsVMV) promoter (see, e.g., Verdaguer et al. (1996) *Plant Mol. Biol.* 31: 1129-1139; Verdaguer et al. (1998) *Plant Mol. Biol.* 37: 1055-1067; Li et al. (2001) *Plant Sci.* 160: 877-887), Australian banana streak virus (BSV) promoters (see, e.g., Schenk et al. (2001) *Plant Mol. Biol.* 47: 399-412), mirabilis mosaic virus (MMV) promoter (see, e.g., Dey and Maiti (1999) *Plant Mol. Biol.* 40: 771-782), the figwort mosaic virus (FMV) promoter (see, e.g., Sanger et al. (1990) *Plant Mol. Biol.* 14: 433-443; Maiti et al. (1997) *Transgenic Res.* 6: 143-156) and the like.

Endogenous plant promoters are also used regularly to drive high constitutive levels of transgene expression (Gupta et al. (2001) *Plant Biotechnol.* 18: 275-282; Dhankher et al. (2002) *Nature Biotechnol.* 20: 1-6). A number of these strong constitutive promoters are derived from actin and ubiquitin genes. For example, the Act2 promoter was developed from the actin gene family in *Arabidopsis* (An et al. (1996) *Plant J.* 10: 107-121). The rice actin 1 gene promoter has also been developed for use in cereal systems (McElroy et al. (1991; Zhang et al. (1991) *Plant Cell* 3: 1155-1165) and drives expression in virtually all tissues except xylem when transformed back into rice. Ubiquitin promoters, for example the maize ubiquitin 1 promoter (pUbi) has provided high expression in of heterologous genes in maize protoplasts. The maize Ubi1 promoter: GUS fusion has been used in rice (Cornejo et al. (1993) *Plant Mol. Biol.* 23: 567-581). The Ubi.U4 gene promoter has also been shown to drive high expression activity (Garbarino et al. (1995) *Plant Physiol.* 109: 1371-1378).

A number of tissue-specific (e.g., specific to fruit, seed/grain, tubers/root storage systems, florets/flowers, Leaves/green tissue, anthers/pollen, and the like) are known. Illustrative, but non-limiting fruit-specific promoters include, for example promoters from the 1-aminocyclopropane-1-carboxylate (ACC) oxidase gene, the E8 gene, and polygalacturonase (PG) genes have been characterized in apple (Atkinson et al. (1998) *Plant Mol. Biol.* 38: 449-460) and tomato (Montgomery et al. (1993) *Plant Cell* 5: 1049-1062; Nicholass et al. (1995) *Plant Mol. Biol.* 28: 423-435; Deikman and Fischer (1988) *EMBO J.* 7: 3315-3320). The promoter of the tomato E8 gene has been used successfully in a number of instances to target transgene expression to fruit. The promoter of the tomato polygalacturonase gene (PG gene product accumulates during ripening and is associated with fruit softening) has been used to drive expression of heterologous genes (Fraser et al. (2002) *Eur. J. Biochem.* 270: 1365-1380). In tomato, a single gene encodes PG, and analysis of a 1.4 kb promoter fragment shows that it also directs ripening-specific expression (Montgomery et al. (1993) *Plant Cell* 5: 1049-1062). Phytoene desaturase (Pds) is the second dedicated enzyme in carotenoid biosynthesis and is also encoded by a single gene in tomato (Giuliano et al. (1993) *Plant Cell* 5: 379-387). Because carotenoids accumulate in the chloroplasts and chromoplasts, the tomato Pds promoter (2.0 kb from start of translation) drives high levels of expression in organs and developing tissues where chromoplasts are found (fruits, petals, anthers) (Corona et al. (1996) *Plant J.* 9: 505-512).

Seed-specific transgene expression has been used for a number of genetic engineering applications. Illustrative seed specific promoters include, but are not limited to the promoters of various seed storage proteins. Other seed specific promoters include for example, those from the soybean β-conglycinin (Chen et al. (1989) *Dev. Genet.* 10: 112-122; Chamberland et al. (1992) *Plant Mol. Biol.* 19: 937-949; Lessard et al. (1993) *Plant Mol. Biol.* 5: 873-885), the sunflower helianthinin genes (Nunberg et al. (1994) *Plant Cell* 6: 473-486), and the like. One of the best-characterized and most commonly used seed-specific promoters is the French bean β-phaseolin gene (see, e.g., Bustos et al. (1989) *Plant Cell* 1: 839-853; van der Geest and Hall (1997) *Plant J.* 6: 413-423). Another useful seed specific promoter is the cotton α-globulin promoter (Sunilkumar et al. (2002) *Transgenic Res.* 11: 347-359) and has been characterized in cotton, *Arabidopsis*, and tobacco. In monocots, several promoters of storage proteins include, but are not limited to the endosperm-specific hordein promoters in barley (Forde et al. (1985) *Nucleic Acids Res.* 13: 7327-7339), glutenin promoters from wheat (Lamacchia et al. (2001) *J. Exp. Bot.* 52: 243-250), the zein promoters in maize (Marzabal et al. (1998) *Plant J.* 16: 41-52), and the granule-bound starch synthase 1 (gbss1) gene in wheat (Kluth et al. (2002) *Plant Mol. Biol.* 49: 669-682).

Tubers/root storage specific promoters include, but are not limited to the potato class I patatin family members, B33 and PAT 21 (Jefferson et al. (1990; Liu et al. (1991), the potato granule-bound starch synthase (GBSS) promoter, sweet potato, sporamin and β-amylase promoters (Maeo et al. (2001) *Plant Mol. Biol.* 46: 627-637), e.g., the gSPO-A1 promoter (Ohta et al. (1991) *Mol. Gen. Genet.* 225: 369-378).

Promoters specific to legume-rhizobium-associated root nodules include promoters of genes expressed early in nodule organogenesis (ENOD genes) (see, e.g., Lauridsen et al. (1993) *Plant J.* 3: 484-492; Vijn et al. (1995) *Plant Mol. Biol.* 28: 1103-1110; Fang and Hirsch (1998) *Plant Physiol.* 116: 53-68; Hohnjec et al. (2000) *Mol. Gen. Genet.* 264: 241-250), late nodulin promoters (see, e.g., Sandal et al. (1987) *Nucleic Acids Res.* 15: 1507-1519; Stougaard et al. (1987) *EMBO J.* 6: 3565-3569), leghemoglobin promoters, the *Sesbania rostrata* leghemoglobin glb3 promoter (see, e.g., Szabados et al. (1990) *Plant Cell* 2: 973-986; Szczyglowski et al. (1996) *Plant Mol. Biol.* 31: 931-935), and the like.

Root specific promoters are described, for example, by Yamamoto et al. (1991) *Plant Cell* 3: 371-382. Non-plant root-specific promoters include the promoters of the rooting loci (rol) genes found in the Ri (root-inducing) plasmid of *A. rhizogenes* (e.g., the rolD promoter), Domain A of the CaMV 35S promoter (Benfey and Chua (1989) *Plant Cell* 2: 849-856), the TobRB7 promoter from tobacco (Yamamoto et al. (1991) *Plant Cell* 3: 371-382), and the like.

Promoters specific to leaves/green tissues include, but are not limited to, promoters from the rbcS multigene family encoding the small subunit of ribulose-1,5-bisphosphate carboxylase such as the pea rbcS-3A promoter the alfalfa rbcS promoter the Rubisco promoter, promoters from the chlorophyll a/b-binding (Cab) protein genes (e.g., CAB2 promoter) (Piechulla et al. (1998) *Plant Mol. Biol.* 38: 655-662), the alfalfa 1532 bp RAc promoter, and the like.

Illustrative, but non-limiting examples of tissue specific promoters are shown in Table 4.

Table 4 shows illustrative, but non-limiting examples of tissue specific promoters.

| Tissue | Illustrative Promoters |
| --- | --- |
| Fruit specific | Apple ACC oxidase |
| | Tomato polygalactouronidase |
| | Tomato E8 |
| | Tomato PDS |
| Green tissue specific | Pea rbcs-3A |
| | *Arabidopsis* CAB2 |
| | Alfalfa RAc |
| Nodule specific | *Vicia faba* VfEnod12 |
| | Bean NVP30 |
| | *S. rostrata* leghemoglobin |
| Root specific | *A. rhizogenes* rolD |
| | Domain A, CaMV 35S |
| | Tobacco TobRB7 |
| Tuber/storage organ specific | Potato patatin B33 |
| | Potato patatin PAT21 |
| | Potato GBSS |
| Seed specific | Bean beta-phaseolin |
| | Cotton alpha-globulin |
| | Wheat gbssl |
| | Zma10 Kz or Zmag12 (maize zein gene) |
| | Zmag12 (maize glutelin gene) |
| Seed coat specific | Pea GsGNS2 |
| Floral specific | *Chrysanthemum* UEP1 |
| | Bean CHS15 |
| | *Petunia* EPSPS |
| Pollen specific | Maize ZMC5 |
| | Tomato lat52 |
| Pistil specific | Pear PsTL1 |
| | Potato SK2 |

In certain embodiments, the peptide(s) described are expressed under the control of the CaMV promoter. As used herein, the phrase "CaMV 35S" promoter includes variations of CaMV 35S promoter, e.g. promoters derived by means of ligations with operator regions, random or controlled mutagenesis, etc.). In certain embodiments, the peptide(s) described herein are expressed under the control of the E8 promoter. In certain embodiments, the peptide(s) described herein are expressed under the control of the hybrid tomato E4/E8 plant promoter (see, e.g., U.S. Pat. No. 6,118,049).

Vectors

As indicated above, the nucleic acid encoding the peptide (s) described herein is placed in a vector (e.g., a plasmid vector) under control of the desired promoter. In certain embodiments the vector (e.g., plasmid vector) can further encode one or more selectable markers (e.g., an antibiotic resistance marker such as the npt II gene for kanamycin resistance) and markers that confer selection by hygromycin, streptomycin, spectinomycin, or phosphinotricin. Illustrative selectable markers for use in plants include, but are not limited to neomycin phosphotransferase, hygromycin phosphotransferase, dihydrofolate reductase, chloramphenicol acetyl transferase, gentamycin acetyl transferase, nopaline synthase, octopine synthase, p-galactosidase, p-glucuronidase, streptomycin phosphotransferase, bleomycin resistance, firefly luciferase, bacterial luciferase, threonine dehydratase, metallothionein il, epsp synthase, phosphinothricin acetyl transferase, acetolactate synthase, bromoxynil nitrilase, and the like.

In certain embodiments the vector can encode a signal peptide (e.g., ALPAH-Al1-*Phaseolus vulgaris*). Sequences that can be provided include, for example, a leader sequence (e.g., to allow secretion or vacuolar targeting), and translation termination signals.

More generally a number of vectors for plant cell transformation and heterologous gene expression are known to those of skill in the art. For example, the structures of a wide array of plasmids that have proven effective in (a) plant transformation and expression of heterologous genes including constructs that confer resistance to kanamycin, hygromycin, streptomycin, spectinomycin and phosphinotricin, or that confer β-glucuronidase (GUS) gene expression are described by Jones et al. (1992) *Transgenic Res.*, 1: 285-297. Binary vector constructs that carry polylinkers of the pUC and Bluescript types, plasmids that permit the expression of any heterologous reading frame from either nopaline synthase (nos) or octopine synthase (ocs) promoters, as well as the cauliflower mosaic virus 35S promoter, using either the nopaline synthase or octopine synthase 3' polyadenylation sequences, are also presented in this reference. These constructs permit a choice of orientation of the resulting transgene of interest, relative to the orientation of the selection marker gene. Most of the plasmids described by Jones et al. (supra.) are publicly/commercially available.

Illustrative and non-limiting examples of vectors include the pRL200 vector that has been used to stably transform lettuce (see, e.g., Kanamoto et al. (2006) *Transgenic Res.*, 15: 205-217), the pCAMBI1381-GUS plasmid has been used to target specific tissues in tomatoes (see, e.g., Lim et al. (2012) *Molecules and Cells* 34: 53-59), the pSB S4642 vector, the chloroplast transformation vector pLD, and the like.

Means of constructing the heterologous "gene" and incorporating it into a plasmid are well known to those of skill in the art. For example the heterologous "gene" can be chemically synthesized using a DNA synthesizer. Commercial services can also provide nucleic acid sequences synthesized to order. The construct can then be cloned into the vector using, for example, PCR cloning procedures. Methods of making the nucleic acid constructs described herein are well known to those of skill in the art, and specific methods are illustrated in the examples. Cloning and transformation methods, DNA vectors and the use of regulatory sequences are well known to the skilled artisan and may for instance be found in Current Protocols in Molecular Biology, F. M. Ausubel et al, Wiley Interscience, 2004, incorporated herein by reference.

In certain embodiments the marker genes (e.g., selectable markers) are removed from the transgenic plant. Methods of removing selectable markers are well known to those of skill in the art. In one illustrative, but non-limiting approach the marker genes are eliminated using MAT vector systems. MAT (Multi-Auto-Transformation) vectors are designed to use the oncogenes (ipt, iaaM/H, rol) of *Agrobacterium*, which control the endogenous levels of plant hormones and the cell responses to plant growth regulators, to differentiate transgenic cells, and to select marker-free transgenic plants. The oncogenes are combined with the site-specific recombination system (R/RS). At transformation, the oncogenes regenerate transgenic plants and then are removed by the R/RS system to generate marker-free transgenic plants. Protocols for the choice of a promoter for the oncogenes and the recombinase (R) gene, the state of plant materials and the tissue culture conditions are described, for example, by Ebinuman et al. (2005) *Meth. Mol. Biol.*, 286: 237-254.

Host Plant Selection

A wide variety of plant species have been genetically transformed with foreign DNA, using several different techniques to insert genes (see, e.g., Wu (1989) Pp. 35-15 In: *Plant Biotechnology*, Kung, S. and Arntzen, eds., Butterworth Publishers, Boston, Mass.; Deak et al. (1986) *Plant Cell Rep.* 5, 97-100; McCormick et al. (1986) *Plant Cell Rep.*, 5: 81-84; Shahin and Simpson (1986) *Hort. Sci.* 21: 1199-1201; Umbeck et al. (1987) *Bio/Technology* 5: 263-266; Christon et al. (1990) *Trends Biotechnol.* 8: 145-151; Datta et al. (1990) *Bio/Technology* 8: 736-740; Hinchee et al. (1988) *Bio/Technology* 6: 915-922; Raineri et al. (1990) *Bio/Technology*, 8: 33-38; Fromm et al. (1990) *Bio/Technology* 8: 833-839; and the like). Since many edible plants used by humans for food or as components of animal feed are dicotyledenous plants, in certain embodiments, it is preferred to employ dicotyledons for expression of the peptide (s) described herein, although monocotyledon transformation is also applicable especially in the production of certain grains useful for animal feed.

In certain embodiments the host plant selected for genetic transformation has edible tissue in which the peptide(s) of interest can be expressed. Thus, in various embodiments, the peptide(s) can be expressed in a part of the plant, such as the fruit, leaves, stems, seeds, or roots, which may be consumed by a human or an animal for which the peptide(s) are intended.

Various other considerations can inform selection of the host plant. It is sometimes preferred that the edible tissue of the host plant not require heating prior to consumption since the heating may reduce the effectiveness of apolipoprotein or mimetic for animal or human use. Also, it is sometimes preferred that the host plant express the peptide(s) in the form of a drinkable liquid.

In certain embodiments plants that are suitable for expression of the peptide(s) described herein include any dicotyledon or monocotyledon that is edible in part or in whole by a human or an animal. Illustrative plants include, for example, tomatoes, carrots, potatoes, apples, pears, plums, peaches, oranges, kiwis, papayas, pineapples, guava, lilikoi, starfruit, lychee, mango, grape, pomegranate, mustard greens, kale, chard, lettuce, soybean, rice, corn and other grains (e.g., wheat, rice, barley, bulgur, faro, kamut, millet, oats, quinoa, rice, rye, sorghum, spelt, teff, triticale, and the like), berries such as strawberries, blueberries, blackberries, goji berries, and raspberries, banana, rice, turnip, maize, grape, fig, plum, potato, safflower seeds, nuts (e.g., almond, walnut, pecan, peanut, cashew, macademia, hazelnut, etc.), legumes (e.g., alfalfa, clover, peas, beans (including black beans), lentils, lupins, mesquite, carob, soybeans, and the like), and the like. In certain embodiments expression in plants such as tobacco and the like, is also contemplated.

Methods of Gene Transfer into Plants

Any of a number of transformation protocols can be used to transform the plant cells and plants described herein. While certain preferred embodiments described below utilize particular transformation protocols, it will be understood by those of skill in the art that any transformation method may be utilized within the definitions and scope of the invention.

There are a number of methods for introducing foreign genes into both monocotyledenous and dicotyledenous plants (see, e.g., Potrykus (1991) *Annu. Rev. Plant Physiol, Plant Mol. Biol.* 42: 205-225; Shimamoto et al. (1989) *Nature* 338: 274-27, and the like. Methods for stable integration of exogenous DNA into plant genomic DNA include for example *agrobacterium*-mediated gene transfer, direct DNA uptake including methods for direct uptake DNA into protoplasts, DNA uptake induced by brief electric shock of plant cells, DNA injection into plant cells or tissues by particle bombardment, or by the use of micropipette systems, or by the direct incubation of DNA with germinating pollen; and the use of plant virus as gene vectors.

Plant transformation and regeneration in dicotyledons by *Agrobacterium tumefaciens* (*A. tumefaciens*) is well documented. The application of the *Agrobacterium tumefaciens* system with, for example, the leaf disc transformation method (see, e.g., Horsch et al. (1988) Pp. 1-9 In: *Plant Molecular Biology Manual* A5, Kluwer Academic Publishers, Dordrecht) permits efficient gene transfer, selection and regeneration.

Monocotyledons have also been found to be capable of genetic transformation by *Agrobacterium tumefaciens* as well as by other methods such as direct DNA uptake mediated by PEG (polyethylene glycol), or electroporation. Successful transfer of foreign genes into corn (see, e.g., Rhodes et al. (1989) *Science* 240: 204-207) and rice (see, e.g., Toriyama et al. (1988) *Bio/Technology* 6: 1072-1074; Zhang and Wu (1988) *Theor. Appl. Genet.* 76: 835-840), tomato (see, e.g., Frary and Earl (1996) *Plant Cell Rept.* 15: 235-240), as well as wheat and sorghum protoplasts, and numerous other species has been demonstrated.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. One illustrative approach is the leaf disc procedure which can be performed with any tissue explant that provides a good source for initiation of whole plant differentiation. The *Agrobacterium* system is especially viable in the creation of transgenic dicotyledenous plants.

As indicated above there are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Another method of vector transfer is the transmission of genetic material using modified plant viruses. DNA of interest is integrated into DNA viruses, and these viruses are used to infect plants at wound sites.

One method of transfection utilizing *Agrobacterium tumafaciens* is illustrated herein in the Examples. Using these teachings, numerous other plants can be similarly transformed. Those skilled in the art should recognize that there are multiple choices of *Agrobacterium* strains and plasmid construction strategies that can be used to optimize genetic transformation of plants. They will also recognize that *A. tumefaciens* may not be the only *Agrobacterium* strain used. Other *Agrobacterium* strains such as *A. rhizogenes* might be more suitable in some applications.

Methods of inoculation of the plant tissue vary depending upon the plant species and the *Agrobacterium* delivery system. A very convenient approach is the leaf disc procedure which can be performed with any tissue explant that provides a good source for initiation of whole plant differentiation. The addition of nurse tissue may be desirable under certain conditions. Other procedures such as the in vitro transformation of regenerating protoplasts with *A. tumefaciens* may be followed to obtain transformed plant cells as well.

It is noted that heterologous genes have been expressed in a wide variety of plants, particular edible plants. Thus, for example, a minimal peach chlorophyll a/b-binding protein gene (Lhcb2*Pp/) promoter (Cab19) and an enhanced mas35S CaMV promoter has been used to express heterologous genes in tomatoes (see, e.g., Bassett et al. (2007) *BMC Biotechnology* 7: 47). A 35S::PtFT1 promoter (35S CaMV promoter) has been used successfully in plums (see, e.g., Srinivasan *PLoS ONE* 7(7):e40715) and in apples (see, e.g., Trankener et al. (2010) *Planta* 232: 1309-1324). Suc2 promoter sequence of the *A. Thaliana* SUC2 gene (sucrose-H+ symporter) has also been used (Id.). Another promoter used in apples was the Pgst1 promoter from potato (see, e.g., Malnoy et al. (2006) *Transgenic Res.,* 15: 83-93). The 35S CaMV promoter has been used in apples for many years (see, e.g., Gleave (1992) *Plant Mol Biol.* 20: 1203-1207). Other promoters that are derivatives of the 35S CaMV promoter have been used in apples such as the potato proteinase inhibitor II (Pint) promoter (see, e.g., Ko et al. (2002) *J. Amer. Soc. Hort. Sci.* 127: 515-519). Butelli et al. used a binary vector (pDEL.ROS) containing both Delila and Rosea1 cDNAs from snapdragon under the control of the E8 promoter from tomato to produce tomatoes enriched in anthocyanins (see e.g., Butelli et al. (2008) *Nature Biotechnology* 26: 1301-1308). Kesanakurti et al. (2012) *Physiologia Plantarum* 146: 136-148) used the E8 promoter to produce tomato plants to transgenically produce tomato anionic peroxidase (tap1). Yang et al. (2012) *Transgenic Res.* 21: 1043-1056) demonstrated that the *Gentiana lutea* zeaxanthin epoxidase (GlZEP) promoter was highly expressed in transgenic tomato plants.

In view of the foregoing, one of skill will recognize that using the teachings and examples provided herein, any of peptides (e.g., apoA-I mimetic peptides) described herein can be expressed in an effective amount in a plant tissue with at most routine experimentation.

The resulting plant tissue that contains one or more peptides having the desired ApoA-I activity can then be concentrated suite the method described herein to produce a biologically active (ApoA-I active) plant extract.

Method of Administering Ezetimibe-Associated apoA-I Peptide Mimetics for Therapeutic and/or Prophylactic Use.

In various embodiments methods for the prophylaxis and/or treatment of various pathologies, especially pathologies characterized by an inflammatory response (see, e.g., Table 5) are provided. In certain embodiments the methods involve administering to a mammal in need thereof (e.g., a human, a non-human mammal) an ezetimibe-associated ApoA-I peptide described herein (e.g., Ez-Tg6F). In certain embodiments the ezetimibe-associated ApoA-I peptide is simply orally administered to the mammal. In certain embodiments the ezetimibe-associated ApoA-I peptide is administered in combination with a food, and/or a protein powder, and/or a nutritional supplement, and/or a "power bar", and/or a "defined diet".

In various embodiments the ezetimibe-associated ApoA-I peptides described herein are used in the prophylaxis and/or treatment of pathologies that include, but are not limited to atherosclerosis, arthritis, cancer, diabetes, hepatic fibrosis, macular degeneration, kidney disease, obesity, osteoporosis, scleroderma, systemic lupus erythematosus, transplant vasculopathy, and vascular dementia.

In certain embodiments the pathology is atherosclerosis and the administration is for the treatment of disease or is a prophylactic administration. In certain embodiments, the prophylactic administration is to a subject (e.g., a human or non-human mammal) showing one or more risk factors for atherosclerosis (e.g., obesity, family history, elevated cholesterol, hypertension, diabetes, metabolic syndrome, low levels of HDL-cholesterol, elevated levels of triglycerides, or levels of high sensitivity CRP that are in the upper half of normal or are frankly elevated, and the like).

In certain embodiments the pathology is a cancer and the administration is as a therapeutic method in its own right and/or to augment therapeutic methods and/or to reduce adverse side effects to therapeutic methods (e.g., chemotherapy, radiotherapy, etc.). Various cancers for which the administration is believed to be suitable include, but are not limited to ovarian cancer, colon cancer, myeloma or multiple myeloma, breast cancer, bone cancer, cervical cancer, brain cancer, lung cancer, skin cancer including malignant melanoma, and prostate cancer.

In certain embodiments the administration of the extract is to prevent the onset, slow the onset and/or slow the progression of Alzheimer's disease and/or other dementias.

Administration of Ez-ApoA-I Mimetic Peptides.

In certain embodiments the mammal is administered the ezetimibe-associated ApoA-I peptide (e.g., Ez-Tg6F, etc.). In certain embodiments the mammal is simply fed the ezetimibe-associated ApoA-I peptide as a powder, or in a solution or suspension, or formulated into a gel or pill. In certain embodiments the ezetimibe-associated ApoA-I peptide is combined with other dietary components (e.g., as a food ingredient) for administration to the subject.

Pills Capsules and Lozenges.

In certain embodiments the ezetimibe-associated ApoA-I peptide(s) can be formulated for direct administration to a subject. Such formulations include, for example a simple powder that can be directly administered or combined with, e.g., a drink for administration. Suitable unit dosage forms include, but are not limited to powders, tablets, pills, capsules, lozenges, bars, and the like.

Such compositions can be manufactured by means of conventional mixing, dissolving, granulating, dragee-making, levigating, emulsifying, encapsulating, entrapping or lyophilizing processes.

For oral administration, the formulations can involve combining the ezetimibe-associated ApoA-I peptide(s) with carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

Protein Powder

In certain embodiments the mammal is administered a "protein powder comprising a ezetimibe-associated ApoA-I peptide as described herein. In certain embodiments the protein powder further comprises an additional protein. Illustrative proteins include, but are not limited to whey protein (e.g., whey concentrate, whey isolate, and whey hydrolysate), casein protein (or milk protein), soy protein, egg-white protein, hemp seed protein, rice protein, pea protein, and the like.

Methods of isolating/producing protein powder are well known to those of skill in the art. Typical methods involve a crude isolation step (e.g., filtering processes to separate lactose from milk in the preparation of whey protein) followed by a concentration step, e.g., an ion exchange purification to purify the protein without denaturing it. In certain embodiments the ezetimibe-associated ApoA-I peptide(s) described herein are simply added to a commercially available protein powder.

Food or Food Ingredient Comprising a Plant or Plant Part.

In certain embodiments the mammal is administered a food or a food ingredient that is eaten before or after or in combination with the ezetimibe-associated ApoA-I peptide (s) described herein. In certain embodiments, the food is a food product that naturally comprises all or a part of the same type of plant in which the peptide is transgenically expressed. Thus, where ezetimibe-associated ApoA-I peptide comprises a transgenic tomato extract, the food may also comprise a tomato, tomato paste or sauce, and the like.

Nutritional Supplement.

In certain embodiments the ezetimibe-associated ApoA-I peptide (s) described herein are provided as a component of a nutritional supplement (e.g., a vitamin supplement, a protein supplement, etc.). Illustrative vitamin supplements include, for example, vitamin A supplements, vitamin B supplements, vitamin D supplements, vitamin C supplements, fatty acid supplements (e.g., omega 3 fatty acids), mineral supplements such as calcium, zinc, and iron, and various combinations thereof.

In certain embodiments the ezetimibe-associated ApoA-I peptide (s) described herein are provided as a component of a multivitamin formulation or combined in a multi-component package with other vitamin/FA/mineral supplements. In certain embodiments where the extract is used in such a supplement the extract, e.g., provided as a fine powder is then incorporated into a multivitamin, or tableted or encapsulated by itself. In certain embodiments the vitamin supplement comprises vitamin A, and/or vitamin B1, and/or B2, and/or B6 and/or B12, and/or vitamin C, and/or vitamin E, and/or a fatty acid.

Defined Diet/Meal Replacement Product.

In certain embodiments the ezetimibe-associated ApoA-I peptide(s) described herein are provided as a component of a "defined diet" and/or meal replacement products (MRPs). A defined diet is a diet, optionally pre-packaged, that is intended to meet all the dietary requirements of a particular subject. For example, for humans a defined diet can be a pre-determined diet designed to facilitate a particular dietary goal (e.g., weight reduction, reduction of allergens, lactose, weight gain, protein elevation, etc.). In the case of non-human mammals (e.g., canines, felines, porcines, equines, bovines, etc.) the "defined diet" can be provided in the form an animal food product. The animal food product can be designed to meet particular dietary goals, e.g., as described above for a human.

In certain embodiments, the animal food product can be provided as the component of a treatment regimen (e.g., for a farm animal, pet, etc.) afflicted with, or at risk for, a particular pathology, e.g., cancer, atherosclerosis, kidney disease, etc.

Meal replacement products are a form of defined diet, either pre-packaged powdered drink mixes or edible bars designed to replace prepared meals. MRPs are generally high in protein, low in fat, have a low to moderate amount of carbohydrates, and contain a wide array of vitamins and minerals. The majority of MRPs use whey protein, casein (often listed as calcium caseinate or micellar casein), soy protein, and/or egg albumin as protein sources. Carbohydrates are typically derived from maltodextrin, oat fiber, brown rice, and/or wheat flour. Some MRPs also contain flax oil powder as a source of essential fatty acids. MRPs can also contain other ingredients. These can include, but are not limited to creatine monohydrate, glutamine peptides, L-glutamine, calcium alpha-ketoglutarate, additional amino acids, lactoferrin, conjugated linoleic acid, and medium chain triglycerides.

In certain embodiments the "defined diet" comprises one or more food items. Each food item may be individually prepackaged. In addition, one or more of the food items may be nutritionally enhanced by fortification of vitamins and minerals and/or by incorporation of ezetimibe-associated ApoA-I peptide(s) described herein, The individual food items may be prepared by processing, e.g., mixing, precooking, cooking, freezing, dehydrating or freeze-drying, such that the meal may be maintained in a frozen or dry condition for an extended period. Additionally, an individual food item may be packaged in such a way that, before consumption, the food item must be mixed by hand or blender, cooked by placing the food component on a stove top, in an oven or microwave, or prepared by adding cool, hot or boiling water or by submerging the food item into boiling water. One or more of the food items may be shelf-stable. Preferably, a food item has a sufficiently long storage or shelf-life such that defined diet may be stored in advance of consumption. In certain embodiments a storage or shelf-life under retail conditions in a range of about six to twelve months is desirable.

In certain embodiments individual food items may be in the form of solids, semi-solids or liquids and may include, but are not limited to, soup products, protein supplements, grain foods, starch foods, fruit or vegetables foods, nutritional drinks and beverages.

In certain embodiments the ezetimibe-associated ApoA-I peptide (s) described herein are simply combined with/incorporated into the defined diet and/or meal replacement product (MRP). For example, in certain embodiments, the ezetimibe-associated ApoA-I peptide powder is added to one or more of the food components comprising the defined diet or MRP.

Power Bars.

In certain embodiments the ezetimibe-associated ApoA-I peptide (s) described herein are provided as a component of a "power bar"/energy bar. Energy bars are supplemental bars that typically contain cereals and/or dried fruit(s), and/or other high energy foods and/or fiber targeted at people that require quick energy or that are on certain weight loss regimens, but do not have time for a meal. They are different from energy drinks, which contain caffeine, whereas bars provide food energy.

Numerous power bar formulations are known to those of skill in the art. In certain embodiments the peptide comprising or consisting of one or more apolipoprotein domains is incorporated into the power bar as a protein (amino acid) component. In certain embodiments the transgenic plant or at least a portion thereof is provided as a component of the power bar. In various embodiments the plant can be provided as all or a portion of a fruit and/or fiber component of the power bar formulation.

Animal Uses.

As indicated above, in various embodiments, the ezetimibe-associated ApoA-I peptide (s) described herein are is provided as a component of an animal diet. The diet can be provided to simply maintain a healthy animal or in certain embodiments, the diet is optimized to facilitate a prophylactic or therapeutic effect.

Illustrative animal diets include, but are not limited to diets for juvenile animals, diets for normal adult animals, diets for old animals, weight loss diets, dental health diets, thyroid health diets, gastrointestinal health diets, hypoallergenic diets, kidney health diets, bladder health diets, aging diets, and the like. In certain embodiments the diet is a diet optimized for treatment of an animal with kidney disease and/or with cancer. In certain embodiments the diet is designed for administration to an animal receiving chemotherapy and/or radiotherapy.

In certain embodiments the ezetimibe-associated ApoA-I peptide(s) described herein are simply added to the diet as an additional food (e.g., amino acid) source. The extract can be incorporated into a wet animal food or a dried (e.g., pellet) animal food. In certain embodiments the extract can provides a fiber component of the diet.

Therapeutic/Prophylactic Applications of Ezetimibe-Associated ApoA-I Peptide(a).

It has been demonstrated that ezetimibe-associated ApoA-I peptide(s) described herein (e.g., Ez-Tg6F) are therapeutically and/or prophylactically effective in a number of indications characterized by an inflammatory response. Such indications include, for example atherosclerosis as described for example, in U.S. Pat. Nos. 6,664,230, 6,933, 279, 7,144,862, 7,166,578, 7,199,102 and PCT Publication Nos: PCT/US2001/026497 (WO 2002/015923), and PCT/

US2008/085409, which are incorporated herein by reference for the peptides and indications described herein.

Accordingly, it is believed that ezetimibe-associated ApoA-I peptide as described herein comprising the peptides or portions thereof are similarly effective in such indications. Thus, in certain embodiments, methods for the treatment or prophylaxis of a pathology characterized by an inflammatory response are provided where the method comprises administering to a mammal in need thereof an effective amount of a ezetimibe-associated ApoA-I peptide comprising one or more peptides from Tables 1, 2, and/or 3.

In certain embodiments the ezetimibe-associated ApoA-I peptide comprises a peptide having an amino acid sequence selected from the group consisting of

DWLKAFYDKFFEKFKEFF, (6F, SEQ ID NO: 1)

FFEKFKEFFKDYFAKLWD, (rev6F, SEQ ID NO: 15)

DWFKAFYDKVAEKFKEAF, (4F, SEQ ID NO: 6)

FAEKFKEAVKDYFAKFWD, (rev4F, SEQ ID NO: 13)

LLEQLNEQFNWVSRLANL, (SEQ ID NO: 599)
and

LVGRQLEEFL. (SEQ ID NO: 602)

An illustrative, but non-limiting list of indications/conditions for which the peptides described herein have been shown to be effective and/or are believed to be effective is shown in Table 5.

TABLE 5

Illustrative conditions in which the ezetimibe-associated peptides described herein (e.g., 4F, Ez-6F, Ez-t6F, etc.) have been shown to be or are believed to be effective. It is believed the transgenic plant extracts described herein will be similarly effective.

atherosclerosis/symptoms/consequences thereof plaque formation
    lesion formation
    myocardial infarction
    stroke
congestive heart failure
vascular function:

arteriole function
    arteriolar disease
        associated with aging
        associated with Alzheimer's disease
        associated with chronic kidney disease
        associated with hypertension
        associated with multi-infarct dementia
        associated with subarachnoid hemorrhage
    peripheral vascular disease
pulmonary disease:

chronic obstructive pulmonary disease (COPD),
    emphysema
    asthma
    idiopathic pulmonary fibrosis
    pulmonary fibrosis
    adult respiratory distress syndrome TABLE 5-continued Illustrative conditions in which the ezetimibe-associated peptides described herein (e.g., 4F, Ez-6F, Ez-t6F, etc.) have been shown to be or are believed to be effective. It is believed the transgenic plant extracts described herein will be similarly effective.

osteoporosis
Paget's disease
coronary calcification
autoimmune:

rheumatoid arthritis
        polyarteritis nodosa
        polymyalgia rheumatica
        lupus erythematosus
        multiple sclerosis
        Wegener's granulomatosis
        central nervous system vasculitis (CNSV)
        Sjögren's syndrome
        Scleroderma
        polymyositis
AIDS inflammatory response
infections:

bacterial
    fungal
    viral
    parasitic
    influenza (including avian flu)
    viral pneumonia
    endotoxic shock syndrome
    sepsis
    sepsis syndrome
    (clinical syndrome where it appears that the patient is septic
    but no organisms are recovered from the blood)
trauma/wound:

organ transplant
    transplant atherosclerosis
    transplant rejection
    corneal ulcer
    chronic/non-healing wound
    ulcerative colitis
    reperfusion injury (prevent and/or treat)
    ischemic reperfusion injury (prevent and/or treat)
    spinal cord injuries (mitigating effects)
cancers lung
    myeloma/multiple myeloma
    ovarian cancer
    breast cancer
    colon cancer
    bone cancer
    cervical cancer
    prostate cancer
osteoarthritis
inflammatory bowel disease
allergic rhinitis
cachexia
diabetes
Alzheimer's disease
implanted prosthesis
biofilm formation
Crohns' disease
Ulcerative colitis
Inflammatory bowel disease
renal failure (acute renal failure, chronic renal failure)
sickle cell disease, sickle cell crisis
amelioration of adriamycin toxicity
amelioration of anthracylin toxicity
to improve insulin sensitivity
to treat the metabolic syndrome
to increase adiponectin
to reduce abdominal fat
dermatitis, acute and chronic eczema
    psoriasis
    contact dermatitis
    scleroderma TABLE 5-continued Illustrative conditions in which the ezetimibe-associated peptides described herein (e.g., 4F, Ez-6F, Ez-t6F, etc.) have been shown to be or are believed to be effective. It is believed the transgenic plant extracts described herein will be similarly effective.

diabetes and related conditions

Type I Diabetes
Type II Diabetes
Juvenile Onset Diabetes
Prevention of the onset of diabetes
Diabetic Nephropathy
Diabetic Neuropathy
Diabetic Retinopathy
erectile dysfunction
macular degeneration
multiple sclerosis
nephropathy
neuropathy
Parkinson's Disease
peripheral vascular disease
meningitis
Specific biological activities:

increase Heme Oxygenase 1
increase extracellular superoxide dismutase
prevent endothelial sloughing
prevent the association of myeloperoxidase with ApoA-I
prevent the nitrosylation of tyrosine in ApoA-I
render HDL anti-inflammatory
improve vasoreactivity
increase the formation of pre-beta HDL
promote reverse cholesterol transport
promote reverse cholesterol transport from macrophages
synergize the action of statins It is noted that the conditions listed in Table 5 are intended to be illustrative and not limiting.

Additional Pharmacologically Active Agents.

In various embodiments pharmacologically active agents may be delivered along with the primary active agents, e.g., the ezetimibe-associated ampA-I mimetic peptides described herein. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Statins.

It is believed that administration of one or more the ezetimibe-associated ampA-I mimetic peptides described herein with one or more statins can synergistically enhance the effect of the statin(s). That is, the statins can achieve a similar efficacy at lower dosage thereby obviating potential adverse side effects (e.g. muscle wasting) associated with these drugs and/or cause the statins to be significantly more anti-inflammatory at any given dose.

The major effect of the statins is to lower LDL-cholesterol levels, and they lower LDL-cholesterol more than many other types of drugs. Statins generally inhibit an enzyme, HMG-CoA reductase, that controls the rate of cholesterol production in the body. These drugs typically lower cholesterol by slowing down the production of cholesterol and by increasing the liver's ability to remove the LDL-cholesterol already in the blood.

The large reductions in total and LDL-cholesterol produced by these drugs appears to result in large reductions in heart attacks and heart disease deaths. Thanks to their track record in these studies and their ability to lower LDL-cholesterol, statins have become the drugs most often prescribed when a person needs a cholesterol-lowering medicine. Studies using statins have reported 20 to 60 percent lower LDL-cholesterol levels in patients on these drugs. Statins also reduce elevated triglyceride levels and produce a modest increase in HDL-cholesterol. Recently it has been appreciated that statins have anti-inflammatory properties that may not be directly related to the degree of lipid lowering achieved. For example it has been found that statins decrease the plasma levels of the inflammatory marker CRP relatively independent of changes in plasma lipid levels. This anti-inflammatory activity of statins has been found to be as or more important in predicting the reduction in clinical events induced by statins than is the degree of LDL lowering.

The statins are usually given in a single dose at the evening meal or at bedtime. These medications are often given in the evening to take advantage of the fact that the body makes more cholesterol at night than during the day. In certain embodiments when combined with the ezetimibe-associated ampA-I mimetic peptides described herein the combined peptide/statin treatment regimen will also typically be given in the evening.

Suitable statins are well known to those of skill in the art. Such statins include, but are not limited to atorvastatin (Lipitor®, Pfizer), simvastatin (Zocor®, Merck0, pravastatin (Pravachol®, Bristol-Myers Squibb0, fluvastatin (Lescol®, Novartis), lovastatin (Mevacor®, Merck), rosuvastatin (Crestor®, Astra Zeneca), and Pitavastatin (Sankyo), and the like.

The combined statin/ezetimibe-associated peptide dosage can be routinely optimized for each patient. Typically statins show results after several weeks, with a maximum effect in 4 to 6 weeks. Prior to combined treatment with a statin and one of the peptides described herein, the physician would obtain routine tests for starting a statin including LDL-cholesterol and HDL-cholesterol levels. Additionally, the physician would also measure the anti-inflammatory properties of the patient's HDL and determine CRP levels with a high sensitivity assay. After about 4 to 6 weeks of combined treatment, the physician would typically repeat these tests and adjust the dosage of the medications to achieve maximum lipid lowering and maximum anti-inflammatory activity.

Beta Blockers.

In certain embodiments the ezetimibe-associated ampA-I mimetic peptides described herein can be administered in conjunction with one or more beta blockers. Suitable beta blockers include, but are not limited to cardioselective (selective beta 1 blockers), e.g., acebutolol (Sectral®), atenolol (Tenormin®), betaxolol (KERLONE®), bisoprolol (ZEBETA®), metoprolol (LOPRESSOR®), and the like. Suitable non-selective blockers (block beta 1 and beta 2 equally) include, but are not limited to carteolol (CARTROL®), nadolol (CORGARD®), penbutolol (LEVATOL®), pindolol (VISKEN®), propranolol (INDERAL®), timolol (BLOCKADREN®), labetalol (NORMODYNE®, TRANDATE®), and the like.

Suitable beta blocker thiazide diuretic combinations include, but are not limited to Lopressor HCT, ZIAC, Tenoretic, Corzide, Timolide, Inderal LA 40/25, Inderide, Normozide, and the like.

ACE Inhibitors.

In certain embodiments the ezetimibe-associated ampA-I mimetic peptides described herein can be administerd in conjunction with one or more ACE inhibitors. Suitable ACE inhibitors include, but are not limited to captopril (e.g. CAPOTEN® by Squibb), benazepril (e.g., LOTENSIN® by Novartis), enalapril (e.g., VASOTEC® by Merck), fosinopril (e.g., MONOPRIL® by Bristol-Myers), lisinopril (e.g. PRINIVIL® by Merck or ZESTRIL® by Astra-Zeneca), quinapril (e.g. ACCUPRIL® by Parke-Davis), ramipril (e.g., ALTACE® by Hoechst Marion Roussel, King Pharmaceuticals), imidapril, perindopril erbumine (e.g., ACEON® by Rhone-Polenc Rorer), trandolapril (e.g., MAVIK® by Knoll Pharmaceutical), and the like. Suitable ARES (Ace Receptor Blockers) include but are not limited to losartan (e.g. COZAAR® by Merck), irbesartan (e.g., AVAPRO® by Sanofi), candesartan (e.g., ATACAND® by Astra Merck), valsartan (e.g., DIOVAN® by Novartis), and the like.

XII. Kits.

In another embodiment this invention provides kits for amelioration of one or more symptoms of atherosclerosis and/or for the prophylactic treatment of a subject (human or animal) at risk for atherosclerosis and/or for reducing the uptake of cholesterol, and/or for ameliorating dyslipidemia, cancer, and/or a number of illnesses associated with chronic inflammation including, but not limited to, Alzheimer's disease, Crohn's disease and ulcerative colitis among others.

In various embodiments the kits will typically comprise a container containing one or more of the ezetimibe-associated peptides and/or pharmaceutical formulations thereof described herein.

In certain embodiments the kits can, optionally, further comprise one or more other agents used in the treatment of heart disease and/or atherosclerosis. Such agents include, but are not limited to, beta blockers, vasodilators, aspirin, statins, ace inhibitors or ace receptor inhibitors (ARBs) and the like, e.g. as described above.

In certain embodiments, the kits additionally include a statin (e.g. cerivastatin, atorvastatin, simvastatin, pravastatin, fluvastatin, lovastatin. rosuvastatin, pitavastatin, etc.) either formulated separately or in a combined formulation with the ezetimibe-associated peptide(s). Typically, the dosage of a statin in such a formulation can be lower than the dosage of a statin typically prescribed without the synergistic peptide.

In addition, the kits optionally include labeling and/or instructional materials providing directions (i.e., protocols) for the practice of the methods or use of the "therapeutics" or "prophylactics" of this invention. Preferred instructional materials describe the use of one or more ezetimibe-associated polypeptides described herein to mitigate one or more symptoms of atherosclerosis and/or to prevent the onset or increase of one or more of such symptoms in an individual at risk for atherosclerosis, or for reducing the uptake of cholesterol, and/or for ameliorating dyslipidemia, cancer, and/or a number of illnesses associated with chronic inflammation including, but not limited to, Alzheimer's disease, Crohn's disease and ulcerative colitis among others. The instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Examples

The following examples are offered to illustrate, but not to limit the claimed invention.

Example 1

Concentration of 6F Peptide Activity in Tomato Plant Extract

Transgenic tomatoes were constructed with the vector pBI121 containing the GUS gene (empty vector control tomatoes; EV) or transgenic tomatoes were constructed with the vector pBI121 in which the GUS gene was replaced with a sequence designed to express the apoA-I mimetic peptide 6F (D-W-L-K-A-F-Y-D-K-F-F-E-K-F-K-E-F-F, Seq ID NO:1) (Tg6F) and grown, freeze-dried and ground into powder as previously described (Chattopadhyay et al. (2013) *J. Lipid Res.*, 54: 995-10101). Ten grams of freeze-dried tomato powder from EV and ten grams of freeze-dried tomato powder from Tg6F tomatoes were thoroughly mixed an incubated for 24 hours in 250 mL of ethyl acetate (HPLC grade from Fisher Scientific, catalogue number E195-4) containing 5% glacial acetic acid (HPLC grade from Fisher Scientific, catalogue number (A35-500). The liquid phase was collected and dried under argon gas. The remaining solids were dissolved in 20 mL of distilled water and then lyophilized. The final extracts were weighed and stored at −20° C. until use. The weight of the final extract from EV was 300 mg and the weight of the final Tg6F extract was 310 mg.

Example 2

Preparation of Ezetimibe-Associated 6F Peptide and Use Thereof to Reduce Plasma Total Cholesterol Female LDLR null mice age 5-8 months (n=20 per group) were fed standard mouse chow (Chow) or a Western diet high in cholesterol and fat (WD) or were fed WD+0.06% by weight of a freeze-dried concentrate of transgenic tomatoes expressing the apoA-I mimetic peptide 6F, which was prepared as previously described (see, e.g., Chattopadhyay et al. (2015) *Pharma. Res. Per.* 3: e00154; Chattopadhyay et al. (2016) *J. Lipid Res.* 57: 832-847; PCT Pub. Nos: WO 2013/148214 (PCT/US2013/031037), WO 2015/175968 (PCT/US2015/031134)) (Tg6F), or the mice were fed WD with Ezetimibe added to give a daily dose of 10 mg/kg body weight/day (WD+Ezetimibe), or the mice were fed WD with Tg6F added at 0.06% by weight plus Ezetimibe (each added separately to the diet) to give a daily dose of Ezetimibe of 10 mg/kg body weight; the Tg6F and Ezetimibe were mixed into WD as described previously (Chattopadhyay et al. (2016) *J. Lipid. Res.* 57: 832-847) (Combined Formulation), or the mice were fed WD to which was added ezetimibe-associated transgenic 6F peptide (Ez-tg6F) at 0.06% Tg6F by weight containing sufficient Ezetimibe to give a daily dose of 10 mg/kg body weight/day that was prepared as described herein. Specifically, the ezetimibe-associated Tg6F peptide (Ez-Tg6F) was made by adding the ezetimibe directly to a solution of ethyl acetate 5% acetic acid that had been incubated overnight at room temperature with freeze-dried tomato powder obtained from transgenic tomatoes expressing the 6F peptide, and which had been removed to a separate vessel as described previously (see, e.g., Chattopadhyay et al. (2015) *Pharma. Res. Per.* 3: e00154; Chattopadhyay et al. (2016) *J. Lipid. Res.* 57: 832-847) prior to addition of the ezetimibe. After the addition of the ezetimibe, the solution was incubated at room temperature with gentle mixing for two hours prior to processing and addition of the resulting freeze-dried powder to WD as previously described (Chattopadhyay et al. (2016) *J. Lipid. Res.* 57: 832-847). After feeding the diets for two weeks, the mice were bled and total plasma cholesterol levels were determined as described (Id.). NS=Not Significant. The total cholesterol for each treatment is shown in FIG. 1.

Figure 2:
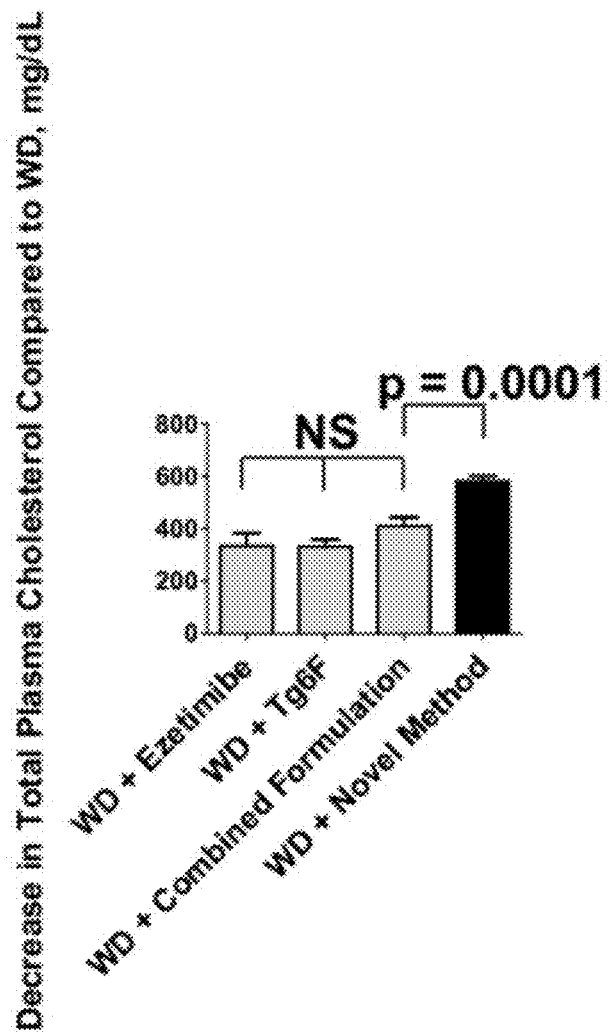
FIG. 2 shows the decrease in plasma total cholesterol compared to WD. The data in FIG. 1 were calculated to show the decrease in plasma total cholesterol compared to WD.

FIG. 2 shows the decrease in plasma total cholesterol for each condition in FIG. 1 compared to WD.

Figure 3:
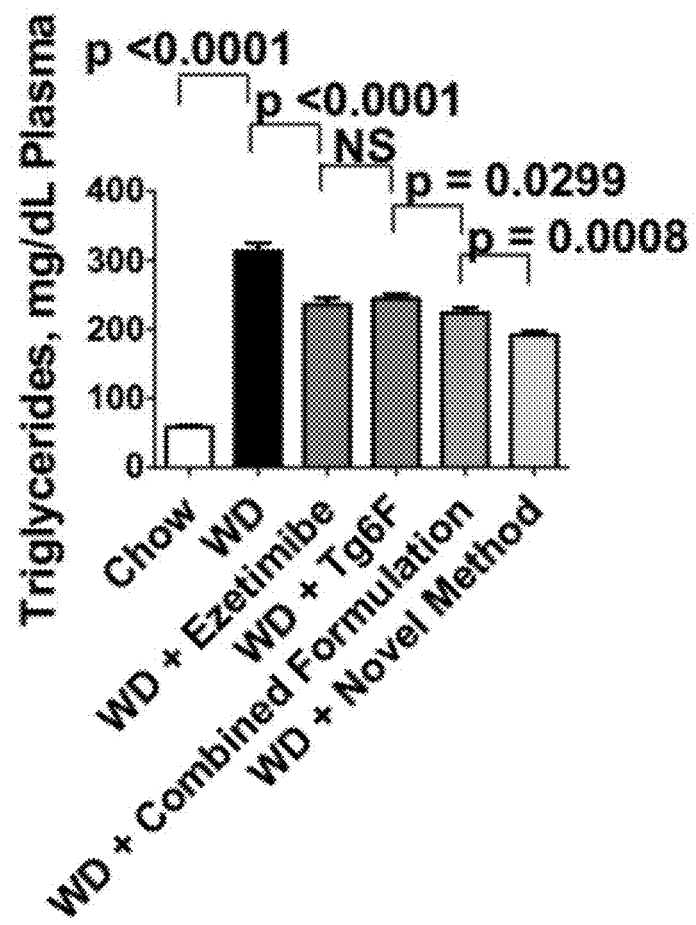
FIG. 3 shows plasma triglycerides. The plasma from the mice in FIG. 1 was analyzed for triglycerides as described (see, e.g., Chattopadhyay et al. (2015) *Pharma. Res. Per.* 3: e00154; Chattopadhyay et al. (2016) *J. Lipid. Res.* 57: 832-847).

FIG. 3 shows plasma triglyceride levels in the mice. in the example shown there was a significant reduction in plasma triglyceride levels when Tg6F and ezetimibe were fed to the mice as a combined formulation, but there was an even greater decrease in plasma triglyceride levels when the same doses of Tg6F and ezetimibe were administered as Ez-Tg6F after preparation by the methods described herein.

Figure 4:
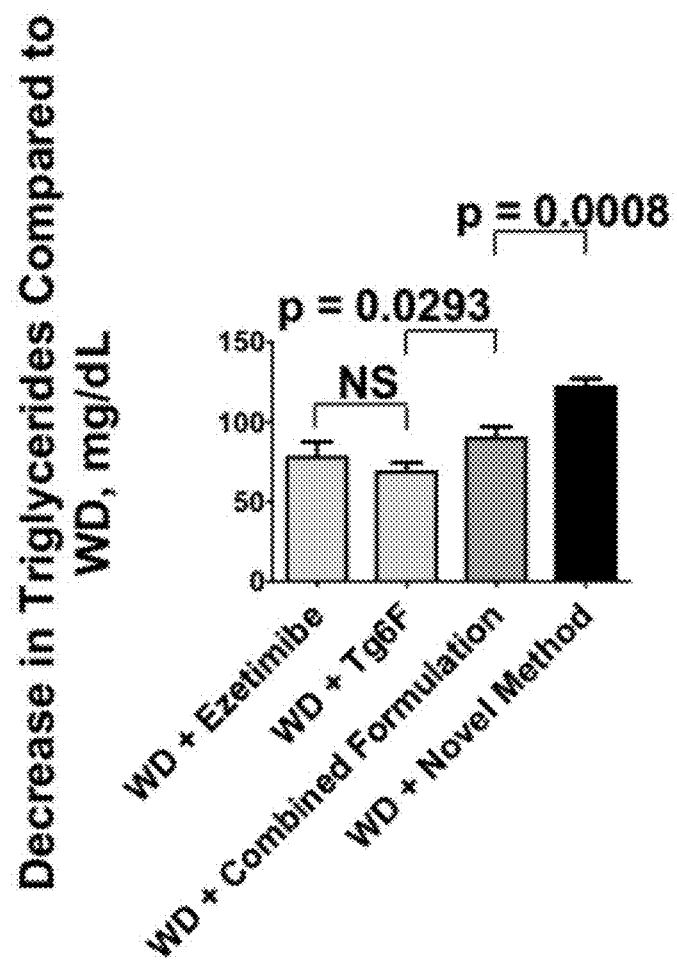
FIG. 4 shows the decrease in plasma triglycerides. The data in FIG. 3 were calculated to show the decrease in plasma triglycerides compared to WD.

FIG. 4 shows the decrease in plasma triglycerides for each condition in FIG. 3 compared to WD.

Figure 5:
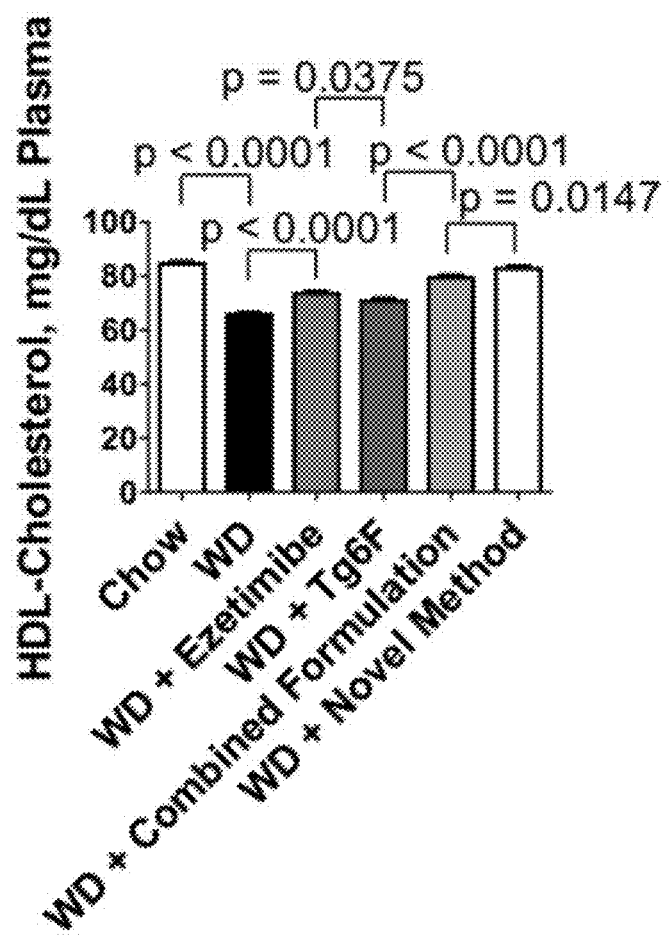
FIG. 5 shows plasma HDL cholesterol. The plasma from the mice in FIG. 1 was analyzed for HDL-cholesterol as described (see, e.g., Chattopadhyay et al. (2015) *Pharma. Res. Per.* 3: e00154; Chattopadhyay et al. (2016) *J. Lipid. Res.* 57: 832-847).

FIG. 5 shows the plasma HDL-cholesterol levels for the mice. In the example shown there was a significant increase in plasma HDL-cholesterol levels when Tg6F and ezetimibe were fed to the mice as a combined formulation, but there was an even greater increase in plasma HDL-cholesterol levels when the same doses of Tg6F and Ezetimibe were administered as Ez-Tg6F prepared as described herein.

Figure 6:
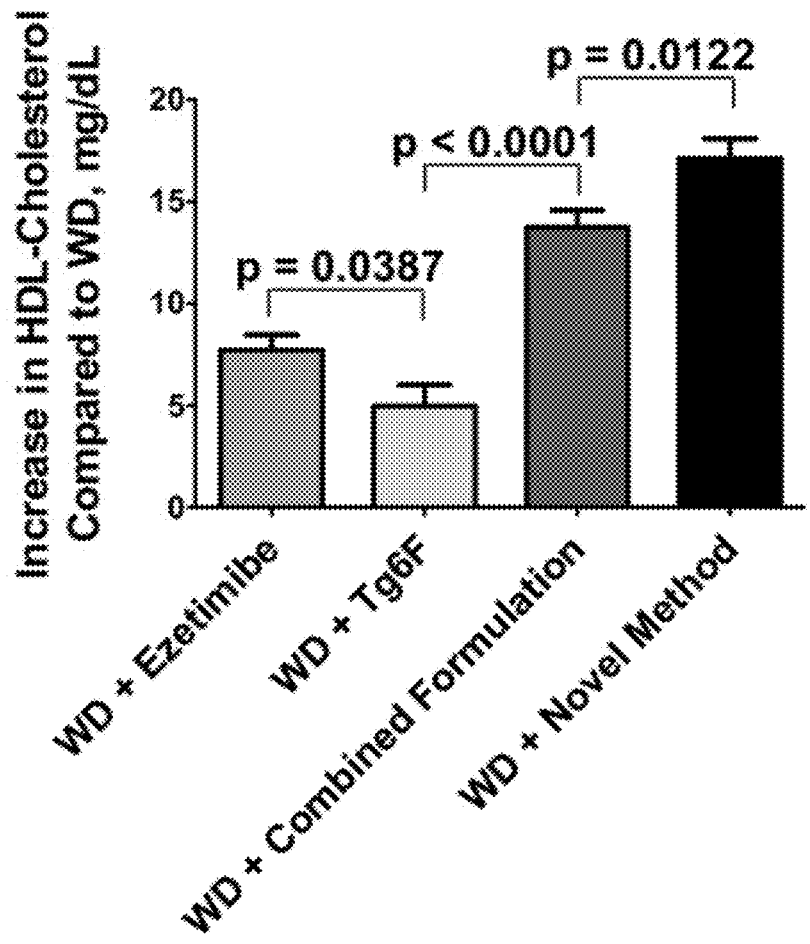
FIG. 6 shows the increase in plasma HDL-cholesterol compared to WD. The data in FIG. 5 were calculated to show the increase in plasma HDL-cholesterol compared to WD.

FIG. 6 shows the increase in plasma HDL-cholesterol for each condition in FIG. 5 compared to WD.

Figure 7:
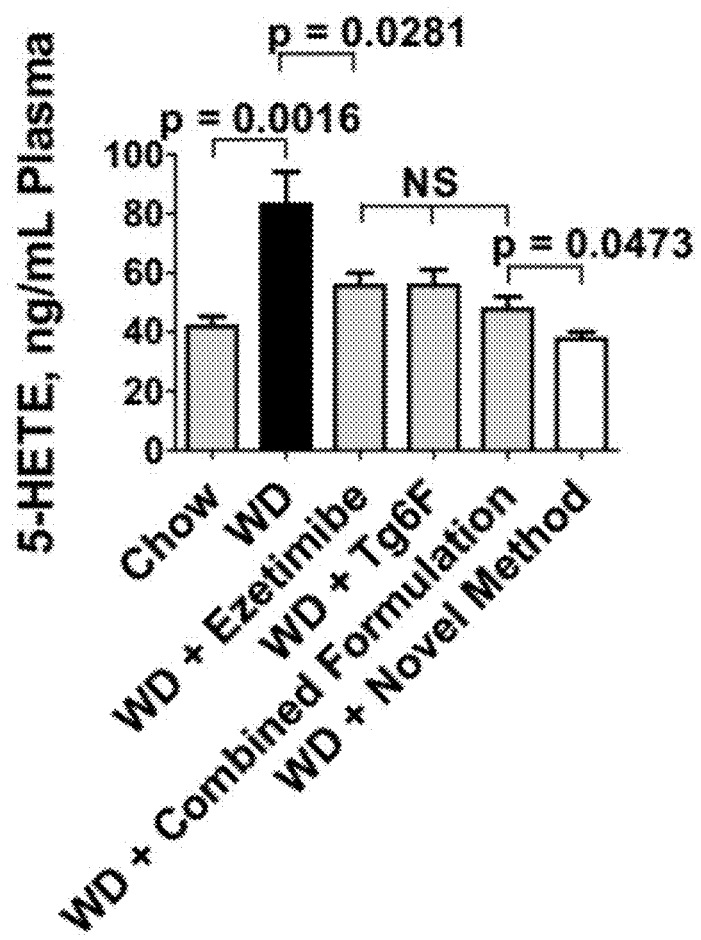
FIG. 7 shows plasma 5-HETE levels. The plasma from the mice in FIG. 1 was analyzed for 5-HETE as described (see, e.g., Navab et al. (2012) *J. Lipid Res.*, 53: 437-445).

FIG. 7 shows plasma 5-HETE levels for the mice described in FIG. 1. In the example shown, the separate addition of Tg6F and Ezetimibe to the diet which was fed to the mice as a combined formulation did not significantly reduce plasma 5-HETE levels beyond the addition of either agent alone, but the addition to the diet of the same doses of Tg6F and Ezetimibe as Ez-Tg6F prepared as described herein, was significantly more effective in reducing plasma 5-HETE levels than either agent added alone.

Figure 8:
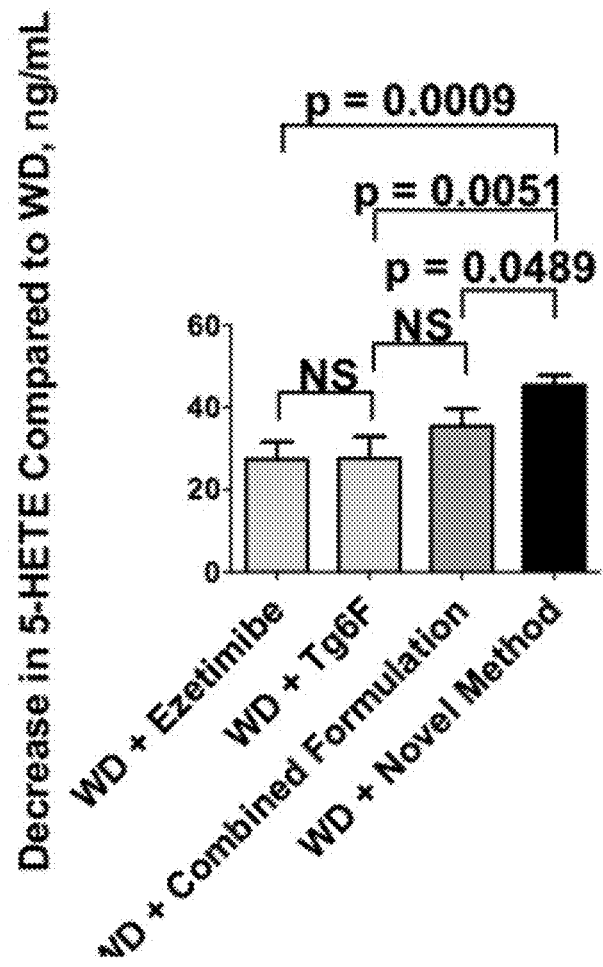
FIG. 8 shows the decrease in plasma 5-HETE levels compared to WD. The data in FIG. 7 were calculated to show the decrease in plasma 5-HETE levels compared to WD.

FIG. 8 shows the decrease in plasma 5-HETE levels for each condition in FIG. 7 compared to WD.

Figure 9:
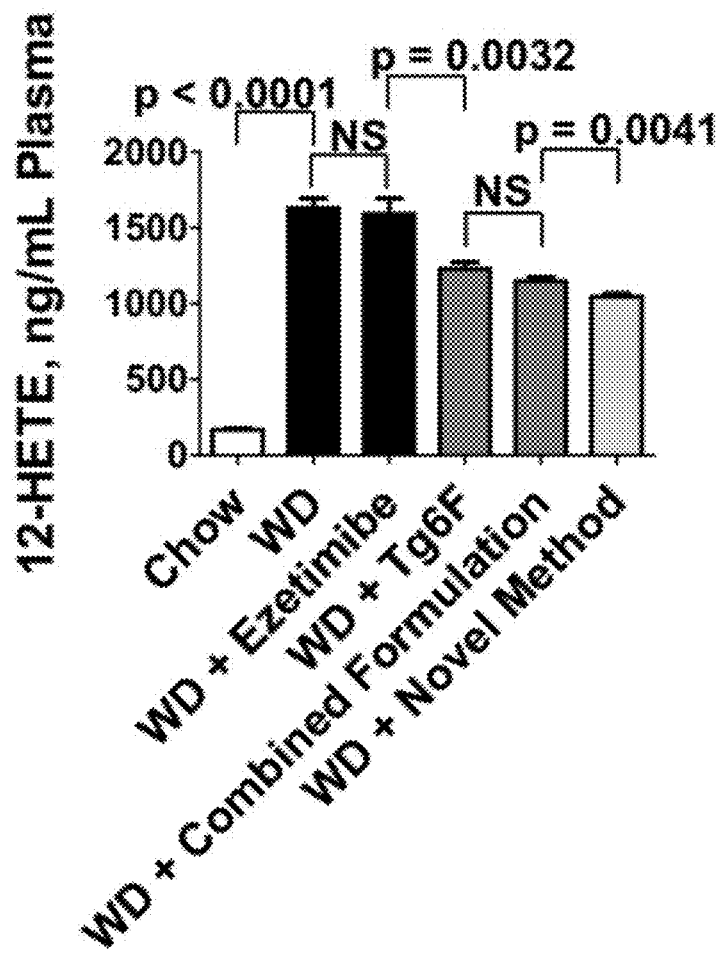
FIG. 9 shows plasma 12-HETE levels. The plasma from the mice in FIG. 1 was analyzed for 12-HETE as described (see, e.g., Navab et al. (2012) *J. Lipid Res.*, 53: 437-445).

FIG. 9 shows plasma 12-HETE levels for the mice described in FIG. 1. In the example shown, the addition of Ezetimibe as a single agent was without effect but the addition of Tg6F as a single agent significantly reduced plasma 12-HETE levels. The separate addition of Tg6F and Ezetimibe to the diet which was fed to the mice as a combined formulation did not significantly reduce plasma 12-HETE levels beyond the addition of Tg6F alone, but the addition to the diet of the same doses of Ez-Tg6F prepared as described herein, was significantly more effective in reducing plasma 12-HETE levels than either Ezetimibe or Tg6F added as a single agent.

Figure 10:
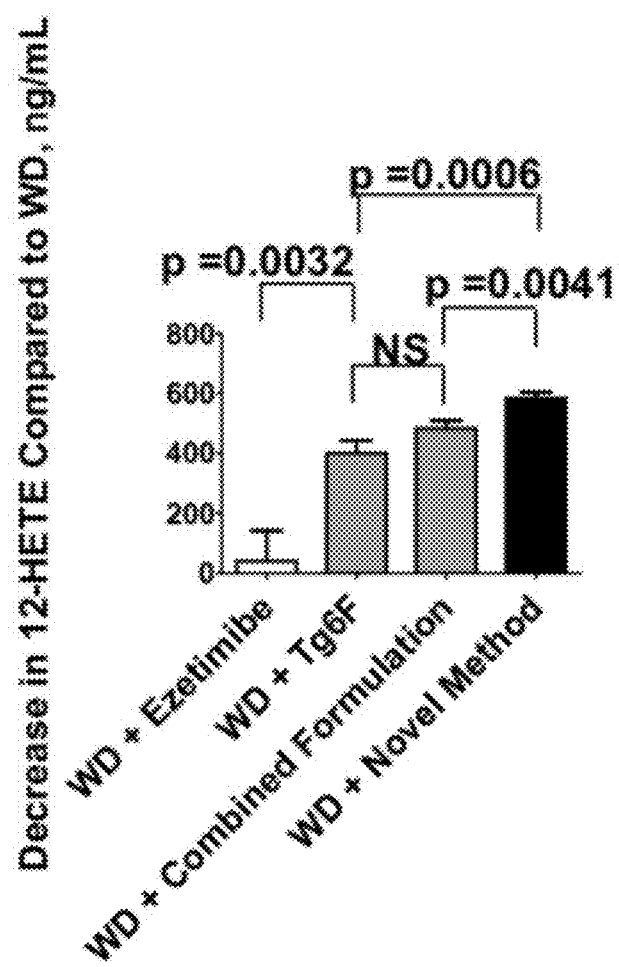
FIG. 10 shows the decrease in plasma 12-HETE compared to WD. The data in FIG. 9 were calculated to show the decrease in plasma 12-HETE compared to WD.

FIG. 10 shows the decrease in plasma 12-HETE levels for each condition in FIG. 9 compared to WD.

Figure 11:
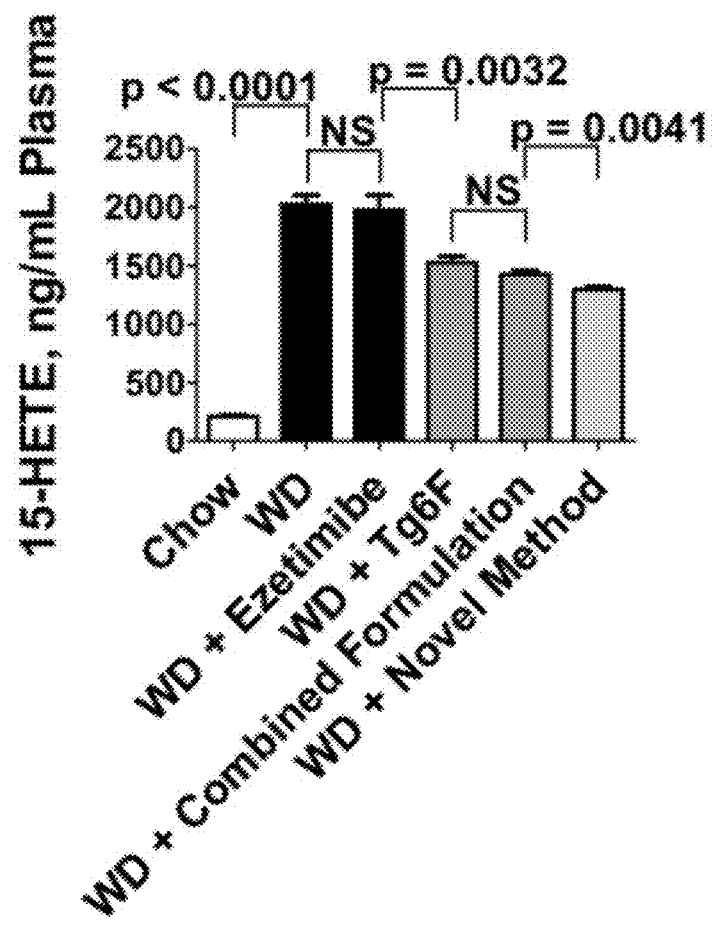
FIG. 11 shows plasma 15-HETE levels. The plasma from the mice in FIG. 1 was analyzed for 15-HETE as described (see, e.g., Navab et al. (2012) *J. Lipid Res.*, 53: 437-445).

FIG. 11 shows plasma 15-HETE levels for the mice described in FIG. 1. In the example shown, the addition of Ezetimibe as a single agent was without effect but the addition of Tg6F as a single agent significantly reduced plasma 15-HETE levels. The separate addition of Tg6F and Ezetimibe to the diet which was fed to the mice as a combined formulation did not significantly reduce plasma 15-HETE levels beyond the addition of Tg6F alone, but the addition to the diet of the same doses of Tg6F and Ezetimibe as Ez-Tg6F, prepared as described herein, was significantly more effective in reducing plasma 15-HETE levels than either Ezetimibe or Tg6F added as a single agent.

Figure 12:
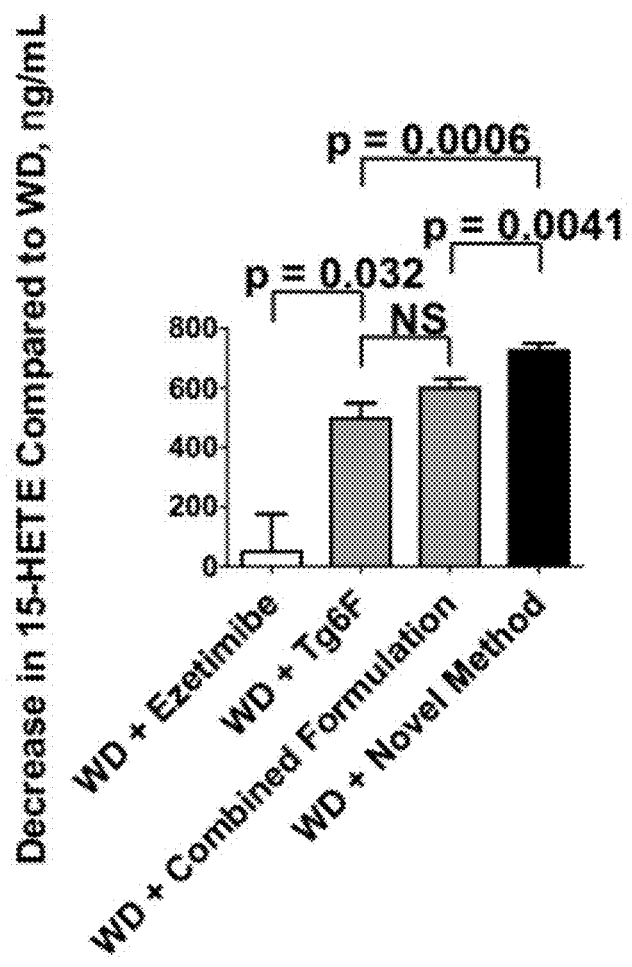
FIG. 12 shows the decrease in plasma 15-HETE compared to WD. The data in FIG. 11 were calculated to show the decrease in plasma 15-HETE compared to WD.

FIG. 12 shows the decrease in plasma 15-HETE levels for each condition in FIG. 11 compared to WD.

Figure 13:
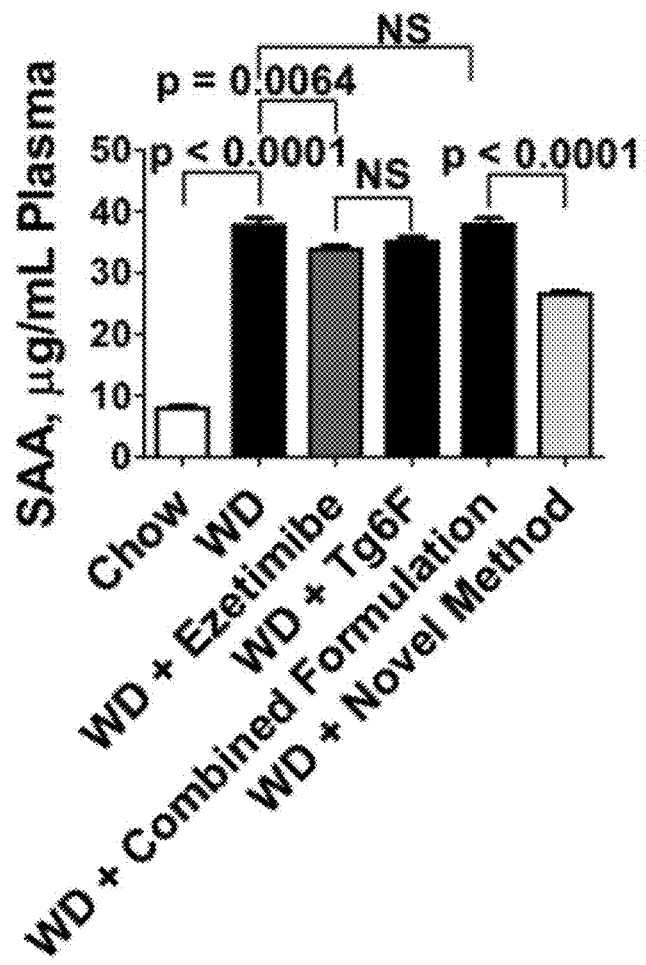
FIG. 13 shows plasma SAA levels. The plasma from the mice in FIG. 1 was analyzed for SAA as described as described (see, e.g., Chattopadhyay et al. (2015) *Pharma. Res. Per.* 3: e00154; Chattopadhyay et al. (2016) *J. Lipid. Res.* 57: 832-847).

FIG. 13 shows plasma SAA levels for the mice described in FIG. 1. In the example shown, the separate addition of both Tg6F and Ezetimibe to the diet, which was fed to the mice as a combined formulation did not significantly reduce plasma SAA levels. In contrast, the reduction in plasma SAA levels achieved by addition to the diet of the same doses of Tg6F and Ezetimibe as Ez-Tg6F, prepared as described herein, was highly significant.

Figure 14:
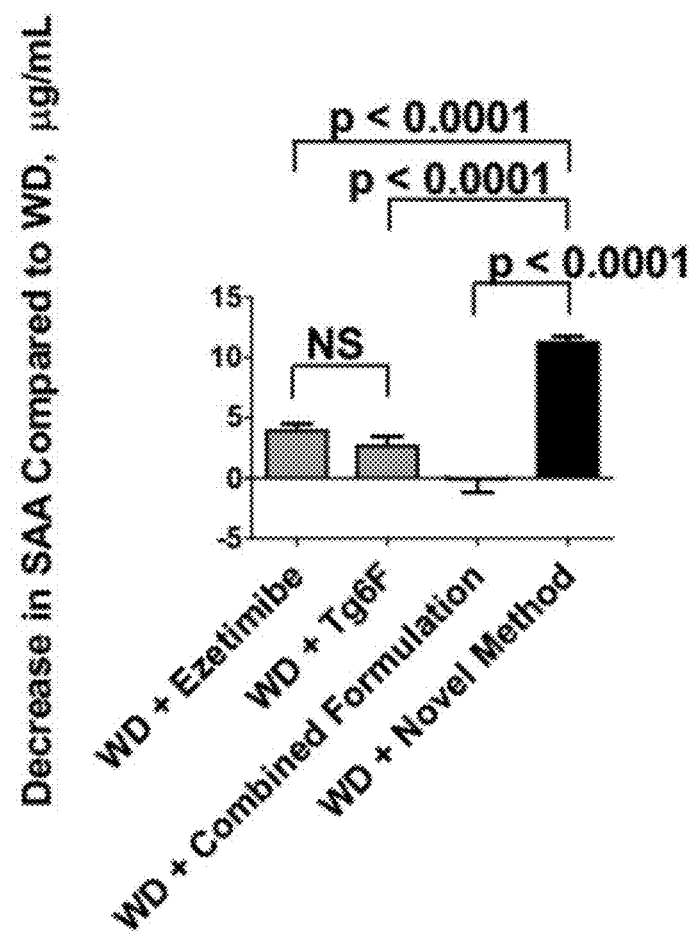
FIG. 14 shows the decrease in plasma SAA compared to WD. The data in FIG. 13 were calculated to show the decrease in plasma 15-HETE compared to WD.

FIG. 14 shows the decrease in plasma SAA levels for each condition in FIG. 13 compared to WD.

The data in FIGS. 1-14 demonstrate a significant improvement in efficacy by using ezetimibe-associated apoA-I peptides as described herein (e.g., Ez-Tg6F) compared to using a combined formulation of the same doses of Tg6F and Ezetimibe.

Example 3

Ezetimibe Enhances ApoA-I Mimetic Tg6F Amelioration of Dyslipidemia and Systemic Inflammation Abbreviations in Example 3

The following abbreviations are used in this example: 4F: the peptide Ac-D-W-F-K-A-F-Y-D-K-V-A-E-K-F-K-E-A-F-NH$_2$ (SEQ ID NO:6); 6F: the peptide D-W-L-K-A-F-Y-D-K-F-F-E-K-F-K-E-F-F (SEQ ID NO:1) without end blocking groups; ABC: ATP-binding cassette; EV: transgenic tomatoes expressing a control marker protein: β-glucuronidase; HETE: hydroxyeicosatetraenoic acid; LDLR: Low density lipoprotein receptor; LysoPC: lysophosphatidylcholine; LysoPC 18:0: LysoPC with stearic acid at sn-1 and a hydroxyl group at sn-2; LysoPC 18:1: LysoPC with oleic acid at sn-1 and a hydroxyl group at sn-2; LysoPC 20:4: LysoPC with arachidonic acid at sn-1 and a hydroxyl group at sn-2; NPC1L1: Niemann-Pick C1-like 1; PC: phosphatidylcholine; SAA: serum amyloid A; TICE: transintestinal cholesterol efflux; Tg6F: transgenic tomatoes expressing the 6F peptide; and WD: Western diet.

Summary of Example 3

As described in this Example, Ezetimibe or a concentrate of transgenic tomatoes expressing the 6F peptide (Tg6F) were added as single agents to a Western diet (WD) and fed to LDLR null mice providing Ezetimibe at 10 mg/kg/day or Tg6F at 0.06% by weight of diet. After two weeks, plasma lipid levels and serum amyloid A (SAA) were determined. As single agents, Ezetimibe and Tg6F were equally effective in reducing plasma levels of total cholesterol, triglycerides, 5-HETE, and SAA and were equally effective in increasing plasma HDL-cholesterol levels. When both were added to WD at the same doses (Combined Formulation), in general, the resulting values were significantly better compared to adding them as single agents. Surprisingly, when Ezetimibe was added during the preparation of the Tg6F concentrate and the resulting concentrate containing both Ezetimibe and Tg6F was added to WD (Novel Method), the decrease in plasma total cholesterol, triglycerides, 5-HETE, 12-HETE, 15-HETE, and SAA was significantly greater as was the increase in plasma HDL-cholesterol levels compared to administering the same doses as single agents or in the Combined Formulation. We conclude that Ezetimibe and Tg6F prepared by the Novel Method likely results in an Ezetimibe-Tg6F associated peptide that may have significant therapeutic potential.

Background of Example 3

We previously reported that an oral apoA-I mimetic peptide (4F) when synthesized from all D-amino acids (D-4F) improved HDL anti-inflammatory properties and reduced aortic atherosclerosis in mouse models without significantly altering plasma cholesterol concentrations (Navab et al. (2002) *Circ.* 105:290-292.). In a subsequent publication we reported that the D-4F peptide synergized with statins to render HDL anti-inflammatory and cause lesion regression in old apoE null mice (Navab et al. (2005) *Arterioscler. Thromb. Vasc. Biol.* 25: 1426-1432). In these studies, total plasma cholesterol levels were not significantly altered, but HDL-cholesterol levels, plasma apoA-I levels and paraoxonase-1 (PON) activity were significantly increased (Id). In humans, at high doses (but not at low doses), oral D-4F improved HDL anti-inflammatory properties without altering plasma cholesterol levels (Bloedon et al. (2008) *J. Lipid Res.* 49: 1344-1352). Thus, the 4F peptide did not significantly alter plasma cholesterol levels, but improved HDL anti-inflammatory properties and aortic atherosclerosis.

In contrast to the 4F peptide, a related peptide with two additional phenylalanine residues on the hydrophobic face of the class A amphipathic helix (6F) when expressed as a transgene in tomatoes and fed as freeze-dried tomato powder (Tg6F) significantly reduced plasma cholesterol and triglycerides and serum amyloid A (SAA) levels, increased plasma HDL-cholesterol levels and PON activity and decreased aortic atherosclerosis in mice (Chattopadhyay et al. (2013) *J. Lipid Res.* 54: 995-1010).

When the 4F peptide was synthesized from all D-amino acids and administered orally, low levels of peptide were found in the plasma of mice and humans (Navab et al. (2002) *Circ.* 105:290-292; Bloedon et al. (2008) *J. Lipid Res.* 49: 1344-1352; Navab et al. (2004) *Circ.* 109:3215-3220). When the 4F peptide was synthesized from all L-amino acids and administered orally to mice, little to none of the peptide was detected in plasma (Navab et al. (2002) *Circ.* 105:290-292). Nonetheless when the 4F peptide synthesized from all L-amino acids was incorporated into mouse chow at high doses, the peptide was efficacious in a mouse model of ovarian cancer (Su et al. (2010) *Proc. Natl. Acad. Sci. USA*, 107: 19997-20002). Directly comparing the 4F peptide synthesized from all D-amino acids with 4F peptide synthesized from all L-amino acids when both were administered by injection at the same dose in cholesterol-fed rabbits, revealed no difference in efficacy (Van Lenten et al. (2007) *J Lipid Res.* 48: 2344-2353). Administration of low doses of 4F peptide synthesized from all L-amino acids when administered by injection yielded high plasma levels of peptide, but did not improve HDL function (Watson et al. (2011) *J. Lipid Res.* 52: 361-373).

As a result of the discrepancy between the study in humans in which the 4F peptide was administered orally and was found to be efficacious at high doses despite extremely low levels of peptide in the plasma (Bloedon et al. (2008) *J. Lipid Res.* 49: 1344-1352), and the study in humans in which the 4F peptide was administered at low doses by injection and was not found to be efficacious despite very high levels of peptide in the plasma (Watson et al. (2011) *J. Lipid Res.* 52: 361-373), additional studies were performed in mice. These studies demonstrated that the dose of peptide administered, and not the peptide plasma level determined efficacy regardless of the route of administration (Navab et al. (2011) *J Lipid Res.* 52: 1200-1210; Navab et al. (2012) *J. Lipid Res.* 53: 437-446). These studies (Id.) also demonstrated that the dose required for efficacy was far above the highest dose tested in the human clinical trials that did not demonstrate efficacy (Watson et al. (2011) *J. Lipid Res.* 52: 361-373). Subsequently, our laboratory reported that intravenous administration of either D-4F or L-4F results in a remarkable targeting of the peptide to the proximal small intestine where it is transported into the intestinal lumen by the process of transintestinal cholesterol efflux (TICE) (Meriwether et al. (2016) *J Lipid Res.* 57: 1175-1193). Based on our data, we concluded that the 4F peptide functions as a modulator of the TICE pathway and suggests that the anti-inflammatory functions of 4F may be a partial consequence of the codependent intestinal transport of both 4F and cholesterol (Id.).

Nakano et al. (Nakano et al. (2016) *PLoS ONE* 11: e0152207) reported that Ezetimibe promotes TICE by targeting the Niemann-Pick C1-like 1 (NPC1L1) protein, which blocks internalization of cholesterol from the brush border membrane causing cholesterol in the brush border membrane to exit by diffusion into the lumen of the small intestine or be pumped out into the lumen of the small intestine by ATP-binding cassette (ABC) protein complex ABC5/G8 (Chang and Chang (2008) *Cell Metabolism.* 7: 469-471). Since both the 4F apoA-I mimetic peptide and Ezetimibe have been reported to promote TICE (Meriwether et al. (2016) *J Lipid Res.* 57: 1175-1193; Nakano et al. (2016) *PLoS ONE* 11: e0152207), and both Ezetimibe and Tg6F lower plasma cholesterol levels, it seemed reasonable to determine if Ezetimibe would enhance the amelioration of dyslipidemia and systemic inflammation by Tg6F. We report here that is indeed the case. Additionally, we report a novel method for preparing Tg6F and Ezetimibe for oral administration that is significantly better than adding them separately to a Western diet (WD) and feeding them as a combined formulation to LDLR null mice.

Materials and Methods

Materials

Transgenic tomatoes expressing the 6F peptide (Tg6F) and control transgenic tomatoes (EV) that express a marker protein (β-glucuronidase) instead of the 6F peptid were grown and processed as described previously (Chattopadhyay et al. (2016) J. Lipid Res. 57: 832-847). Ezetimibe was purchased from Cayman Chemical Company, Ann Arbor, Mich. (Catalogue No. 16331). All other materials were purchased from sources previously described (Id.).

Mice and Diets

LDLR-null mice originally purchased from Jackson Laboratories on a C57BL/6J background were obtained from the breeding colony of the Department of Laboratory and Animal Medicine at the David Geffen School of Medicine at UCLA. The gender and age of the mice are stated in the legend to each figure. The mice were maintained on standard mouse chow (Ralston Purina) before being switched to a Western diet WD (Teklad, Harlan, catalog #TD88137).

Single Agents and the Combined Formulation

In experiments in which Tg6F or EV or Ezetimibe were administered as single agents, the EV or Tg6F concentrate was added to WD at 0.06% by weight or Ezetimibe was added to WD to give a final dose of 10 mg/kg body weight/day. The EV or Tg6F concentrate or Ezetimibe was mixed into the diets as described (Chattopadhyay et al. (2015) Pharma. Res. Per. 3: e00154). In experiments in which the EV or Tg6F concentrates and Ezetimibe were both added to WD, each was added separately to WD at the same dose as used for the single agents, and each was mixed into the diet as described (Id.). Hereafter, the separate addition of the Tg6F concentrate and Ezetimibe to WD is referred to as the "Combined Formulation" to distinguish it from the "Novel Method" described below.

A Novel Method

In some experiments in which Tg6 and Ezetimibe were both administered, instead of adding Tg6F and Ezetimibe separately to WD as described above for the "Combined Formulation", Ezetimibe was added to the supernatant of ethyl acetate with 5% acetic acid that had been incubated overnight with the freeze-dried transgenic 6F tomato powder as previously described (Chattopadhyay et al. (2016) *J. Lipid Res.* 57: 832-847; Chattopadhyay et al. (2015) *Pharma. Res. Per.* 3: e00154). The amount of Ezetimibe added to the supernatant provided 10 mg/kg body weight per day of Ezetimibe in the final preparation. After addition of Ezetimibe to the supernatant, the mixture was incubated at room temperature with gentle mixing for periods ranging from 2-hours to overnight as indicated in the Figure legends. Subsequently, the ethyl acetate was removed as described (Id.), the resulting powder was re-suspended in water and freeze-dried (Chattopadhyay et al. (2016) *J. Lipid Res.* 57: 832-847). The final freeze-dried tomato powder containing the 6F peptide together with Ezetimibe is hereafter referred to as "Novel Method" to distinguish it from the "Combined Formulation". The final Novel Method freeze-dried tomato powder was mixed into to the diet as described (Chattopadhyay et al. (2016) *J. Lipid Res.* 57: 832-847; Chattopadhyay et al. (2015) *Pharma. Res. Per.* 3: e00154), and fed to the mice to give them the same dose each day of Tg6F (0.06% of diet by weight) and Ezetimibe (10 mg/kg body weight) as was the case when the agents were administered singly or as the Combined Formulation. Each day the mice ate all of the food administered for each condition; there was no difference in food consumption between groups.

At the end of the treatment periods, the mice were fasted overnight in clean cages with new bedding, and following blood collection for plasma determinations, and prior to harvesting of organs, the mice were perfused under anesthesia to remove all blood (Chattopadhyay et al. (2013) *J. Lipid Res.* 54: 995-1010; Navab et al. (2013) *J. Lipid Res.* 54: 3403-3418), and organs were harvested and washed as described previously (Id.). All mouse studies were approved by the Animal Research Committee at UCLA.

Assays

Plasma lipids, and serum amyloid A (SAA) levels were determined and LC-MS/MS was performed as described (Navab et al. (2012) *J. Lipid Res.* 53: 437-446; Chattopadhyay et al. (2016) *J. Lipid Res.* 57: 832-847; Chattopadhyay et al. (2015) *Pharma. Res. Per.* 3: e00154). Determination of neutral sterols in the feces was performed as described (Meriwether et al. (2016) *J Lipid Res.* 57: 1175-1193).

Statistical Analysis

Statistical analyses were performed initially by ANOVA. After determining that statistically significant differences were present by ANOVA, further comparisons were made by unpaired two-tailed t-test. All statistical analyses were performed using Graph-Pad Prism version 5.03 (GraphPad Software, San Diego, Calif.). Statistical significance was considered achieved if P<0.05.

Results

Figure 15:
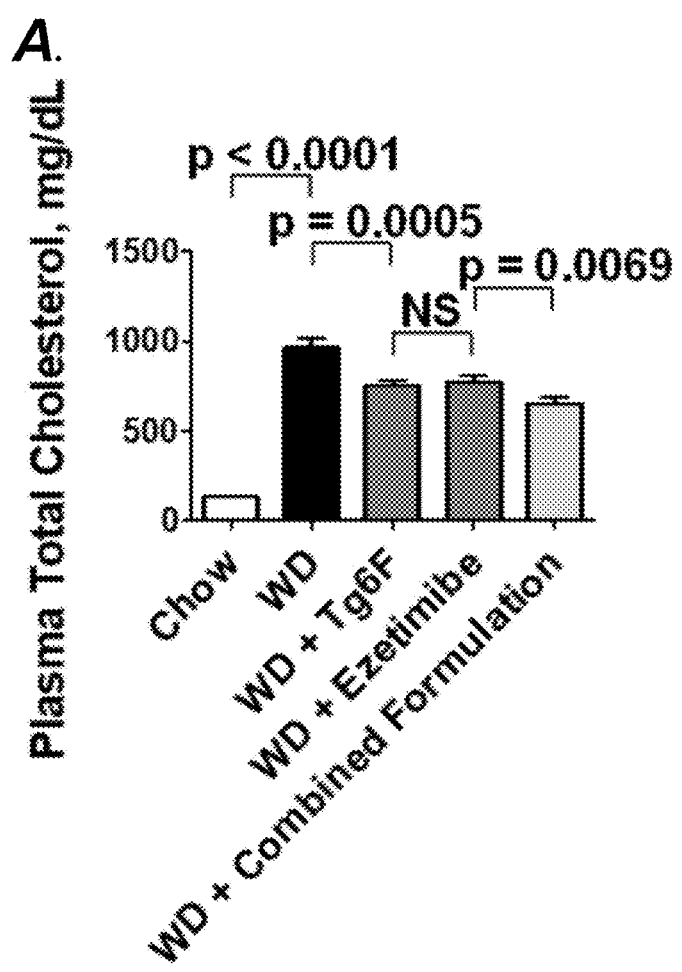
FIG. 15, panels A-F, shows that addition of either Ezetimibe or Tg6F to WD ameliorated dyslipidemia in LDLR null mice and addition of both to WD (Combined Formulation) was significantly better than addition of either agent alone. Female LDLR null mice age 3-6 months (n=20-28 per group) were fed standard mouse chow (Chow) or a Western diet (WD) or the mice were fed WD+0.06% by weight of Tg6F concentrate, which was prepared as described in Methods, or the mice were fed WD with Ezetimibe added to give a daily dose of 10 mg/kg body weight (WD+Ezetimibe) or the mice were fed WD with Tg6F added at 0.06% by weight plus Ezetimibe (each added separately to the diet) to give a daily dose of Ezetimibe of 10 mg/kg body weight as described in Methods for the Combined Formulation. After feeding the diets for two weeks the mice were bled and plasma lipid levels were determined as described in Methods. Panel A) Plasma total cholesterol levels. Panel B) The decrease in plasma cholesterol compared to WD for each treatment. Panel C) Plasma triglyceride levels. Panel D) The decrease in plasma triglycerides compared to WD for each treatment. Panel E) Plasma HDL-Cholesterol levels. Panel F) The Increase in plasma HDL-Cholesterol compared to WD for each treatment. The data shown are Mean±SEM. NS=Not significant.

Addition of Either Ezetimibe or Tg6F to WD Ameliorated Dyslipidemia in LDLR Null Mice and Addition of Both to WD (Combined Formulation) was Significantly Better than Addition of Either Agent Alone We previously reported that a dose of Tg6F of 0.06% by weight of diet was near maximal for ameliorating dyslipidemia in LDLR null mice on WD (Chattopadhyay et al. (2015) *Pharma. Res. Per.* 3: e00154). Therefore, we tested Tg6F at 0.06% by weight added to WD. In cholesterol-fed monkeys the $ED_{50}$ value (the median effective dose) of Ezetimibe for inhibiting the rise in plasma cholesterol levels was 0.5 µg/kg/day (17). In mice the $ED_{50}$ value for Ezetimibe was reported to be 700 µg/kg/day (Publication 29480958T REV 14 by Merck/Schering-Plough Pharmaceuticals. 2007. Zetia (Ezetimibe) tablets. www.accessdata.fda-.gov/drugsatfda_docs/label/2008/021445s019lbl.pdf). The recommended dose for a human is 10 mg daily (0.14 mg/kg/day for a 70 Kg human) (Id.). We tested Ezetimibe at a dose of 10 mg/kg/day, a dose equal to or greater than the highest dose used in mice that we found in the literature (Nakano et al. (2016) *PLoS ONE* 11: e0152207; Publication 29480958T REV 14 by Merck/Schering-Plough Pharmaceuticals. 2007. Zetia (Ezetimibe) tablets. www.accessdata.fda-.gov/drugsatfda_docs/label/2008/021445s019lbl.pdf; Davis et al. (2001) *Arterioscle.r Thromb. Vasc. Biol.* 21:2032-2038; Altmann et al. (2014) *Sic. Transl. Med.* 303:1201-1204). As shown in the experiment described in FIG. 15, adding either Tg6F or Ezetimibe to WD significantly ameliorated dyslipidemia, and adding both to WD at the same dose (Combined Formulation) further significantly ameliorated dyslipidemia. FIG. 15, panel A shows the results for total plasma cholesterol levels, and FIG. 15, panel B presents the data plotted to show the decrease in plasma cholesterol compared to WD for each treatment. FIG. 15, panel C shows the results for plasma triglyceride levels, and FIG. 15, panel D presents the data plotted to show the decrease in plasma triglycerides compared to WD for each treatment. FIG. 15, panel D shows the results for plasma HDL-Cholesterol levels, and FIG. 15, panel E presents the data plotted to show the increase in plasma HDL-Cholesterol compared to WD for each treatment. In this experiment Tg6F and Ezetimibe were not different as single agents except for HDL-Cholesterol where Tg6F was superior to Ezetimibe as a single agent. In each case the Combined Formulation was significantly better than the single agents.

Adding both Tg6F and Ezetimibe to WD (Combined Formulation) ameliorated dyslipidemia, reduced plasma levels of lysophosphatidylcholine (LysoPC), and reduced Serum Amyloid A (SAA) levels in LDLR null mice significantly more than adding the single agents. In contrast, adding the same dose of Ezetimibe and a control transgenic tomato concentrate (EV) that does not contain the 6F peptide to WD was no more effective than Ezetimibe as a single agent—

Figure 16:
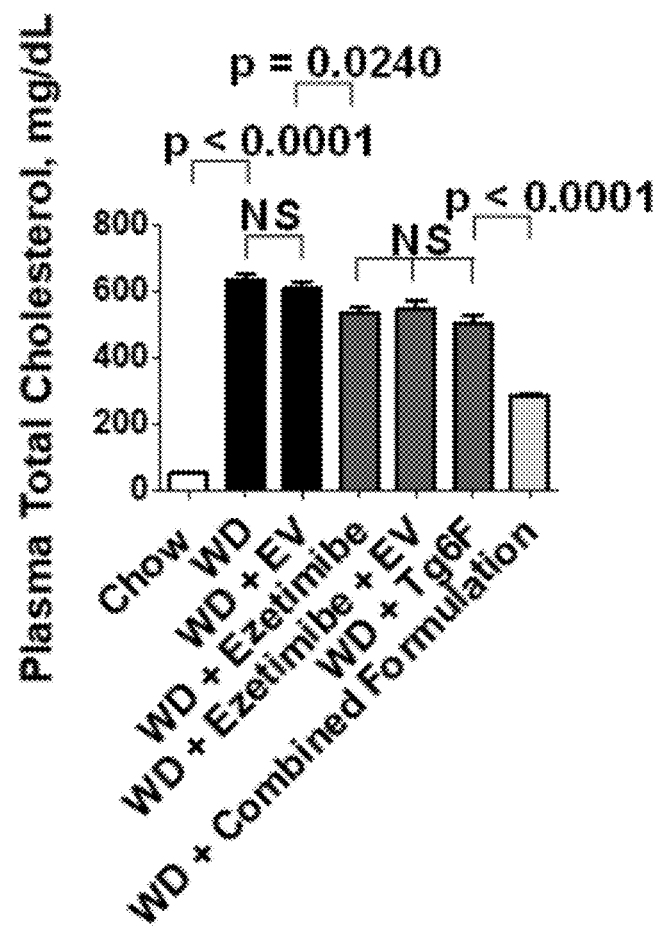
FIG. 16, panels A-N, shows that the enhanced effectiveness of the Combined Formulation depends on the presence of the 6F peptide in Tg6F. Female LDLR null mice age 4-7 months (n=20 per group) were fed standard mouse chow (Chow) or a Western diet (WD) or the mice were fed WD+0.06% by weight of a control transgenic tomato concentrate that does not contain the 6F peptide (EV) as described in Methods, or the mice were fed WD with Ezetimibe added to give a daily dose of 10 mg/kg body weight (WD+Ezetimibe) or the mice were fed WD+Ezetimibe+0.06% by weight of EV (WD+Ezetimibe+ EV), or the mice were fed WD with Tg6F added at 0.06% by weight (WD+Tg6F), or the mice were fed Tg6F added at 0.06% by weight plus Ezetimibe (each added separately to the diet) to give a daily dose of Ezetimibe of 10 mg/kg body weight (WD+Combined Formulation) as described in Methods. After feeding the diets for two weeks the mice were bled and plasma lipid levels, plasma levels of lysophosphatidylcholine (LysoPC), and plasma levels of Serum Amyloid A (SAA) were determined as described in Example 3 Methods. Panel A) Plasma total cholesterol levels. Panel B) The decrease in plasma cholesterol compared to WD for each treatment. Panel C) Plasma triglyceride levels. Panel D) The decrease in plasma triglycerides compared to WD for each treatment. Panel E) Plasma HDL-Cholesterol levels. Panel F) The Increase in plasma HDL-Cholesterol compared to WD for each treatment. Panel G) Plasma LysoPC 18:0 levels. Panel H) The decrease in plasma LysoPC 18:0 levels compared to WD for each treatment. Panel I) Plasma LysoPC 18:1 levels. Panel J) The decrease in plasma LysoPC 18:1 levels compared to WD for each treatment. Panel K) Plasma LysoPC 20:4 levels. Panel L) The decrease in plasma LysoPC 20:4 levels compared to WD for each treatment. Panel M) Plasma SAA levels. Panel N) The decrease in plasma SAA levels compared to WD for each treatment. The data shown are Mean±SEM. NS=Not significant.

As shown in FIG. 16, panels A-F, the Combined Formulation was significantly more effective in ameliorating dyslipidemia compared to adding Tg6F or Ezetimibe to WD as single agents. However, adding a control transgenic tomato concentrate (EV) that does not contain the 6F peptide to WD together with the same dose of Ezetimibe as contained in the Combined Formulation did not significantly ameliorate dyslipidemia beyond that achieved by adding Ezetimibe to WD as a single agent. Similar results were seen for changes in LysoPC 18:0 (FIG. 16, panels G and H), LysoPC 18:1 (FIG. 16, panels I and J), LysoPC 20:4 (FIG. 16, panels K and L), and plasma SAA levels (FIG. 16, panels M and N). We conclude that the enhanced effectiveness of adding both Tg6F and Ezetimibe to WD (Combined Formulation) compared to the single agents is due to the presence of the 6F peptide in Tg6F.

A Novel Method for Administering Tg6F and Ezetimibe Together that is Significantly More Effective Compared to Adding them Separately to WD as in the Combined Formulation Instead of adding Tg6F and Ezetimibe separately to WD as in the Combined Formulation, we added Ezetimibe during the preparation of the Tg6F concentrate. In making the Tg6F concentrate, freeze-dried tomato powder from transgenic 6F tomatoes are incubated at room temperature in ethyl acetate with 5% acetic acid (Chattopadhyay et al. (2015) *Pharma. Res. Per.* 3: e00154). After an overnight incubation the supernatant contains the 6F peptide, which is recovered by removing the ethyl acetate. The resulting solids are re-suspended in water and subjected to a final freeze drying that results in a uniform fluffy tomato powder that by weight is 37-fold more active than the starting material (Id.). Surprisingly, we found that after the overnight incubation, if we added Ezetimibe to the supernatant and incubated it for 2 hours prior to removing the ethyl acetate with 5% acetic acid, the final resulting lyophilized tomato powder containing Ezetimibe and the 6F peptide was significantly more effective when added to WD than the same dose of Tg6F and Ezetimibe added in the Combined Formulation (i.e., both added separately to WD). In the experiment described in FIG. 17, the Combined Formulation demonstrated a non-significant trend for improving some measurements compared to the results obtained with Tg6F and Ezetimibe added as single agents. However, using the Novel Method for administering Tg6F and Ezetimibe together in WD was significantly more effective than adding Tg6F or Ezetimibe as single agents to WD or adding both separately to WD (Combined Formulation).

Figure 17:
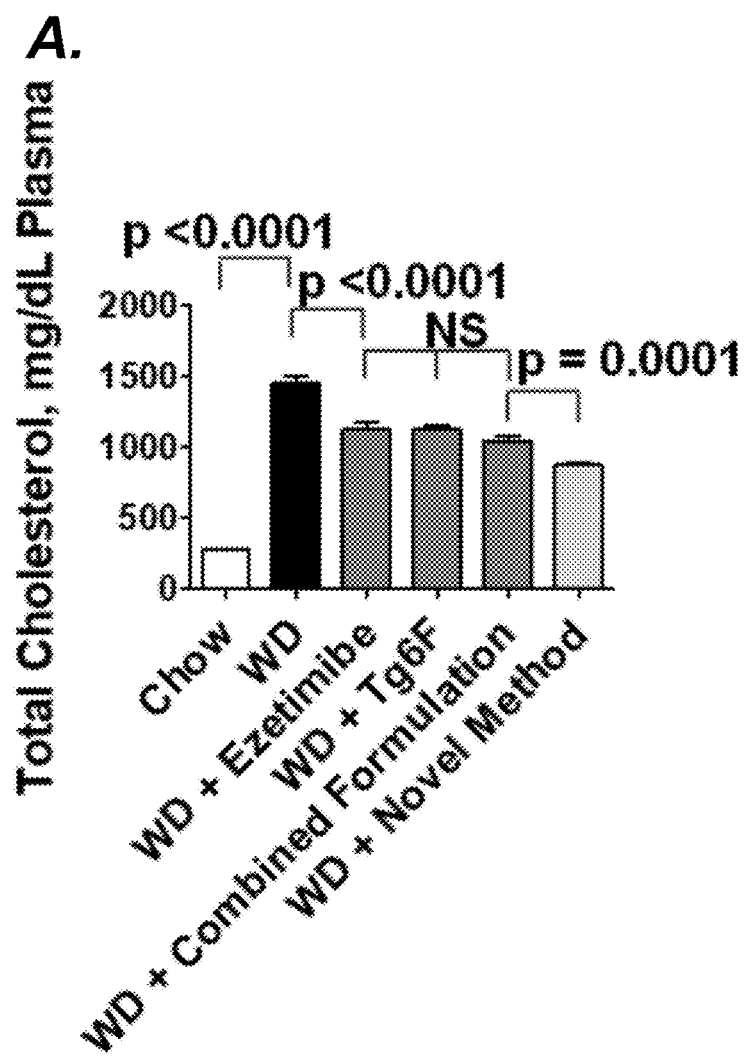
FIG. 17, panels A-N, shows a novel method for administering Tg6F and Ezetimibe together is significantly more effective compared to adding them separately to WD as in the Combined Formulation. Female LDLR null mice age 5-8 months (n=20 per group) were fed standard mouse chow (Chow), or a Western diet (WD), or the mice were fed WD with Ezetimibe added to give a daily dose of 10 mg/kg body weight (WD+Ezetimibe), or the mice were fed WD with Tg6F added at 0.06% by weight of diet (WD+Tg6F), or the mice were fed Tg6F added at 0.06% by weight of diet plus Ezetimibe (each added separately to the diet) to give a daily dose of Ezetimibe of 10 mg/kg body weight (WD+Combined Formulation), or using the Novel Method described in Methods the mice were fed WD containing Tg6F at 0.06% by weight of diet and Ezetimibe sufficient to provide the mice with 10 mg/kg/day (WD+Novel Method). After feeding the diets for two weeks, the mice were bled and plasma lipid levels, plasma levels of hydroxyeicosatetraenoic acid (HETE), and plasma levels of Serum Amyloid A (SAA) were determined as described in Methods. Panel A) Plasma total cholesterol levels. Panel B) The decrease in plasma cholesterol compared to WD for each treatment. Panel C) Plasma triglyceride levels. Panel D) The decrease in plasma triglycerides compared to WD for each treatment. Panel E) Plasma HDL-Cholesterol levels. Panel F) The Increase in plasma HDL-Cholesterol compared to WD for each treatment. Panel G) Plasma 5-HETE levels. Panel H) The decrease in plasma 5-HETE levels compared to WD for each treatment. Panel I) Plasma 12-HETE levels. Panel J) The decrease in plasma 12-HETE levels compared to WD for each treatment. Panel K) Plasma 15-HETE levels. Panel L) The decrease in plasma 15-HETE levels compared to WD for each treatment. Panel M) Plasma SAA levels. Panel N) The decrease in plasma SAA levels compared to WD for each treatment. The data shown are Mean±SEM. NS=Not significant.

FIG. 17, panels A-F, shows the results for the effect of each treatment on dyslipidemia in the LDLR null mice. FIG. 17, panels G-L show the results of each treatment on plasma hydroxyeicosatetraenoic acid levels. FIG. 17, panels M and N show the results of each treatment on plasma SAA levels.

Figure 18:
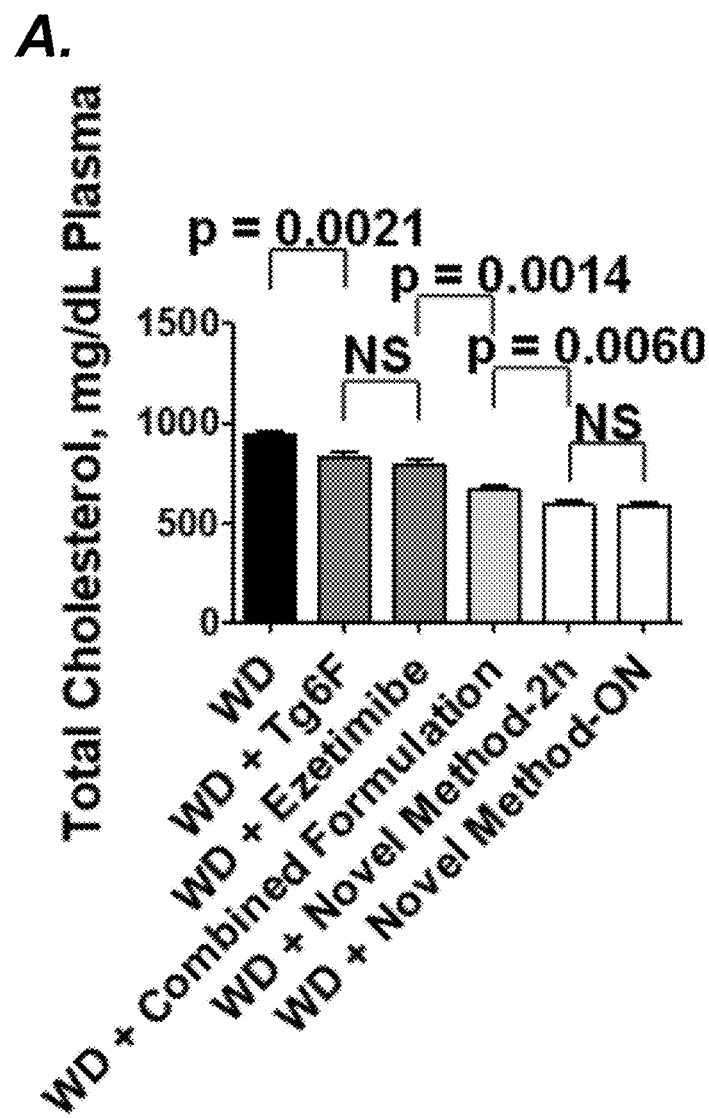
FIG. 18, panels A-F, shows that incubating Ezetimibe in the ethyl acetate with 5% acetic acid Tg6F supernatant for 2 hours or overnight gave similar results. Female LDLR null mice age 8-10 months (n=20 per group) were fed standard mouse chow (Chow), or a Western diet (WD), or the mice were fed WD with Ezetimibe added to give a daily dose of 10 mg/kg body weight (WD+Ezetimibe), or the mice were fed WD with Tg6F added at 0.06% by weight of diet (WD+Tg6F), or the mice were fed Tg6F added at 0.06% by weight of diet plus Ezetimibe (each added separately to the diet) to give a daily dose of Ezetimibe of 10 mg/kg body weight (WD+Combined Formulation), or the mice were fed WD containing Tg6F at 0.06% by weight of diet and Ezetimibe sufficient to provide the mice with 10 mg/kg/day that had been prepared by the Novel Method with Ezetimibe incubated in the ethyl acetate with 5% acetic acid supernatant for 2 hours (WD+Novel Method-2h) or the Ezetimibe was incubated in the ethyl acetate with 5% acetic acid supernatant overnight (WD+Novel Method-ON) as described in Methods. After feeding the diets for two weeks, the mice were bled and plasma lipid levels and plasma levels of Serum Amyloid A (SAA) were determined as described in Methods. Panel A) Plasma total cholesterol levels. Panel B) The decrease in plasma cholesterol compared to WD for each treatment. Panel C) Plasma triglyceride levels. Panel D) The decrease in plasma triglycerides compared to WD for each treatment. Panel E) Plasma SAA levels. Panel F) The decrease in plasma SAA levels compared to WD for each treatment. The data shown are Mean±SEM. NS=Not significant.
Figure 19:
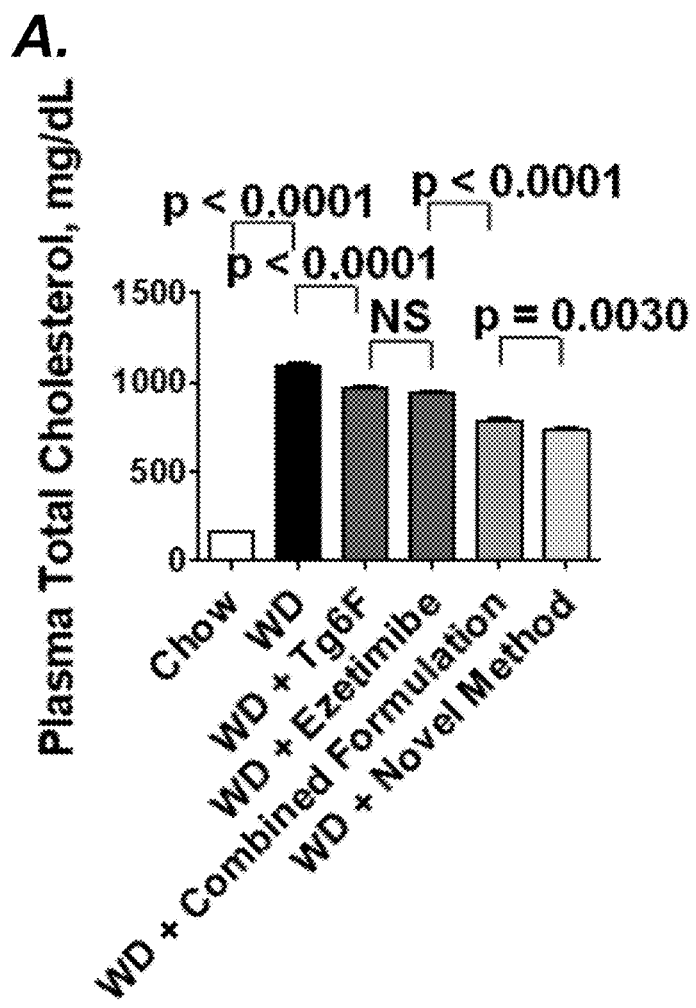
FIG. 19, panels A-H, shows that the novel method for administering Tg6F and Ezetimibe together is significantly more effective compared to adding them separately to WD (Combined Formulation) in old mice. Female LDLR null mice age 9-12 months (n=25 per group) were fed standard mouse chow (Chow), or a Western diet (WD), or the mice were fed WD with Ezetimibe added to give a daily dose of 10 mg/kg body weight (WD+Ezetimibe), or the mice were fed WD with Tg6F added at 0.06% by weight of diet (WD+Tg6F), or the mice were fed Tg6F added at 0.06% by weight of diet plus Ezetimibe (each added separately to the diet) to give a daily dose of Ezetimibe of 10 mg/kg body weight (WD+Combined Formulation), or using the Novel Method described in Methods (2 hour incubation of Ezetimibe in the ethyl acetate with 5% acetic acid supernatant) the mice were fed WD containing Tg6F at 0.06% by weight of diet and Ezetimibe sufficient to provide the mice with 10 mg/kg/day (WD+Novel Method). After feeding the diets for two weeks, the mice were bled and plasma lipid levels and plasma levels of Serum Amyloid A (SAA) were determined as described in Methods. Panel A) Plasma total cholesterol levels. Panel B) The decrease in plasma cholesterol compared to WD for each treatment. Panel C) Plasma triglyceride levels. Panel D) The decrease in plasma triglycerides compared to WD for each treatment. Panel E) Plasma HDL-Cholesterol levels. Panel F) The Increase in plasma HDL-Cholesterol compared to WD for each treatment. Panel G) Plasma SAA levels. Panel H) The decrease in plasma SAA levels compared to WD for each treatment. The data shown are Mean±SEM. NS=Not significant.

FIG. 18 demonstrates that incubating Ezetimibe in the ethyl acetate with 5% acetic acid supernatant for 2 hours or incubating overnight gave similar results. FIGS. 4 and 5 demonstrate that the Novel Method was superior to the Combined Formulation in old mice (up to one year of age).

Discussion

Adding Ezetimibe or Tg6F as Single Agents to WD—

Each parameter measured was significantly improved by Tg6F added to WD as a single agent. In five out of five experiments adding either Ezetimibe or Tg6F to WD improved plasma total cholesterol and triglyceride levels. In four out of four experiments in which HDL-cholesterol was measured, adding either Ezetimibe or Tg6F as a single agent to WD significantly increased the levels. In four out of four experiments in which SAA was measured, adding Ezetimibe or Tg6F as a single agent to WD significantly decreased the levels. In the experiment in which plasma HETE levels were measured adding either Ezetimibe or Tg6F as a single agent to WD significantly decreased plasma levels of 5-HETE (FIG. 17, panels G and H). In this experiment, adding Tg6F as a single agent to WD also significantly decreased plasma levels of 12-HETE and 15-HETE, but adding Ezetimibe as a single agent to WD failed to significantly decrease plasma 12-HETE and 15-HETE levels (FIG. 17, panels I-L). The levels of 12-HETE and 15-HETE in the mouse are determined primarily by 12/15-lipoxygenase activity while the levels of 5-HETE are determined by the activity of 5-lipoxygenase. From our studies, we cannot determine why Ezetimibe effectively reduced the levels of 5-HETE, while not significantly altering 12-HETE or 15-HETE levels.

In the experiment in which plasma LysoPC levels were measured, adding Ezetimibe or Tg6F as single agents to WD failed to significantly alter plasma levels of LysoPC 18:0 (FIG. 16, panels G and H). We previously reported that when LDLR null mice were fed WD, Tg6F failed to decrease plasma LysoPC 18:0 levels, but did reduce plasma LysoPC 18:1 levels (Chattopadhyay et al. (2016) *J. Lipid Res.* 57: 832-847). Consistent with this previous report (Id.) adding either Tg6F or Ezetimibe to WD as single agents significantly decreased plasma levels of LysoPC 18:1 (FIG. 16, panels I and J) and also significantly reduced plasma levels of LysoPC 20:4 (FIG. 16, panels K and L).

Thus, with the exception of the case for plasma 12-HETE and 15-HETE levels, adding Ezetimibe or Tg6F to WD as single agents gave comparable results at near maximal doses for each.

Adding Both Ezetimibe and Tg6F Separately to WD (Combined Formulation)

While Ezetimibe and Tg6F were effective when added as single agents at near maximal doses to WD, adding both of them to WD separately at the same doses (Combined Formulation), in general, resulted in significantly greater effectiveness. In four out of five experiments the Combined Formulation was significantly better than either agent alone in reducing plasma total cholesterol levels. In one experiment the mice receiving the Combined Formulation showed a trend for a decrease in plasma total cholesterol compared to the mice receiving the single agents, but the difference did not reach statistical significance (FIG. 17, panels A and B). In five out of five experiments, the Combined Formulation was significantly better than either agent alone in reducing plasma triglyceride levels. In four out of four experiments, the Combined Formulation was significantly better than either agent alone in increasing plasma HDL-cholesterol levels. In three out four experiments, the Combined Formulation was significantly better than either agent alone in decreasing plasma SAA levels. In one experiment the values for plasma SAA for the mice receiving the Combined Formulation were slightly but significantly higher than the case for the single agents (FIG. 17, panels M and N). While neither Ezetimibe or Tg6F as single agents significantly altered plasma LysoPC 18:0 levels, the Combined Formulation significantly reduced plasma LysoPC 18:0 levels (FIGS. 16G and 16H). The Combined Formulation was also significantly better than either agent alone in further reducing plasma levels of LysoPC 18:1 (FIGS. 16I and 16J) and plasma levels of LysoPC 20:4 (FIG. 16, panels K and L). While showing a trend toward lower levels of plasma 5-HETE the values for the Combined formulation were not significantly different from those obtained with the single agents (FIG. 17, panels G and H). Similarly, the values for the Combined Formulation were not significantly different from that obtained by adding Tg6F as a single agent for plasma 12-HETE (FIG. 17, panels I and J) and plasma 15-HETE (FIG. 17, panels K and L); as noted above, Ezetimibe as a single agent did not significantly alter plasma 12-HETE or 15-HETE levels.

We previously reported (Chattopadhyay et al. (2015) *Pharma. Res. Per.* 3: e00154) that adding to WD concentrate from control transgenic tomatoes (EV) that expressed a marker protein instead of the 6F peptide was significantly less effective compared to adding concentrate from transgenic tomatoes expressing the 6F peptide (Tg6F) to WD. As shown in FIG. 16, separately adding Ezetimibe and the control EV concentrate to WD was no more effective than adding Ezetimibe as a single agent. In contrast, as noted above, separately adding Ezetimibe and Tg6F to WD (Combined Formulation) was significantly more effective in lowering plasma levels of total cholesterol, triglycerides, LysoPC 18:0, LysoPC 18:1, LysoPC 20:4, and SAA and increasing plasma HDL-cholesterol levels (FIG. 16). Thus, we conclude that the 6F peptide is responsible for the enhanced effectiveness of the combined formulation.

A Novel Method for Increasing the Effectiveness of Adding Ezetimibe and Tg6F to WD Adding Ezetimibe and Tg6F separately to WD was in general (but not always) significantly more effective than adding the single agents to WD as discussed above. It was a surprising finding that adding Ezetimibe to the ethyl acetate with 5% acetic acid supernatant during the preparation of the Tg6F concentrate resulted in a final preparation that when added to WD was significantly more effective compared to the single agents or the Combined Formulation. In three out three experiments, despite the diet containing the same amount of Ezetimibe and Tg6F, plasma total cholesterol, plasma triglyceride and plasma SAA levels were significantly lower with the Novel Method compared to the administration of the single agents or the Combined Formulation. In two out of two experiments in which HDL-cholesterol was measured, plasma HDL-cholesterol levels were significantly higher with the Novel Method compared to the administration of the single agents or the Combined Formulation. Plasma 5-HETE, 12-HETE and 15-HETE levels were significantly lower with the Novel Method compared to the administration of the single agents or the Combined Formulation.

What explains the increased effectiveness of the Novel Method? There are several possibilities. During the preparation of the final concentrate there might be the formation of a covalent or non-covalent new molecule that is more effective. Another possibility is that during the preparation of the concentrate the tomato polyphenols together with the 6F peptide form micelles, which the Ezetimibe inserts into resulting in better targeting of Ezetimibe and Tg6F in the small intestine. While not being bound to a particular mechanism, the the data are clear that the Novel Method described herein results in a significantly more active preparation that likely is due to the formation of an Ezetimibe-T6F associated peptide. Based on the data presented here, we believe that the Ezetimibe-T6F associated peptide may have therapeutic potential for treating dyslipidemia and systemic inflammation. Based on our previous work (Id.) we believe that the Ezetimibe-T6F associated peptide also may have therapeutic potential for treating cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of preparing an ezetimibe-associated apoA-I mimetic peptide, said method comprising:
   incubating ezetimibe and an apoA-I mimetic peptide comprising the amino acid sequence DWLKAFYDKFFEKFKEFF (SEQ ID NO:1), in a solution comprising ethyl acetate and acetic acid or in a solution comprising ethyl lactate and lactic acid; and
   drying said solution to provide a dry ezetimibe-associated apoA-I mimetic peptide wherein said ezetimibe-associated apoA-I mimetic peptide, when fed to a mammal, lowers plasma total cholesterol to a greater amount than a mixed ezetimibe apoA-I mimetic peptide formulation containing the same amounts of ezetimibe and apoA-I mimetic peptide.

2. The method of claim 1, wherein said incubating comprises incubating 1:10 ezetimibe: apoA-I mimetic peptide by weight.

3. The method of claim 1, wherein said drying comprises:
   drying said solution to produce a dry residue;
   resuspending said residue in water to provide a resuspended mixture; and
   drying the resuspended mixture to provide a dry powder extract comprising ezetimibe-associated apoA-I mimetic peptide.

4. The method of claim 3, wherein said drying the resuspended mixture comprises lyophilizing said mixture to provide said dry powder extract.

5. The method of claim 3, wherein said resuspending comprises re-suspending said residue in distilled water.

6. The method of claim 3, wherein said resuspending comprises re-suspending said residue in de-ionized water.

7. The method of claim 3, wherein said resuspending comprises re-suspending said residue in food-grade water.

8. The method of claim 1, wherein the incubating peptide with ezetimibe is for at least about 10 minutes, or at least about 15 minutes, or at least about 30 minutes, or at least about 45 minutes, or at least about 1 hr, or at least about 1.5 hrs, or at least about 2 hrs, or at least about 3 hrs, or at least about 4 hrs, or at least about 5 hours, or at least about 6 hrs, or at least about 12 hours, or at least about 1 day.

9. The method of claim 1, wherein said incubating comprises incubating said ezetimibe and said apoA-I mimetic peptide in a solution comprising ethyl acetate and acetic acid.

10. The method of claim 9, wherein said solution comprises about 5% acetic acid.

11. The method of claim 9, wherein said solution comprises about 1% to about 25% acetic acid.

12. The method of claim 1, wherein said incubating comprises incubating said ezetimibe and said apoA-I mimetic peptide in a solution comprising ethyl lactate and lactic acid.

13. The method of claim 12, wherein said solution comprises about 5% lactic acid.

14. The method of claim 12, wherein said solution comprises about 1% to about 25% lactic acid.

15. The method of claim 1, wherein:
said apoA-I mimetic peptide is a chemically synthesized peptide; or
said apoA-I mimetic peptide is a peptide recombinantly expressed in a plant cell.

16. The method of claim 15, wherein said apoA-I mimetic peptide is provided as a tissue of a transgenic plant wherein said tissue contains the ApoA-I mimetic peptide expressed by said plant.

17. The method of claim 16, wherein:
said tissue is provided as a substantially dry powder;
said powder is mixed with said solution comprising ethyl acetate and acetic acid or with said solution comprising ethyl lactate and lactic acid, to form an extraction mixture; and
said extraction mixture is incubated before addition of said ezetimibe.

18. The method of claim 16, wherein said providing tissue comprises providing said tissue as a freeze-dried powder.

19. The method of claim 16, wherein said tissue of a transgenic plant comprises tissue of a tomato plant.

20. The method of claim 17, wherein said extraction mixture is incubated for at least about 15 minutes.

21. The method of claim 17, wherein said extraction mixture is incubated overnight.

22. The method of claim 1, wherein said ezetimibe-associated apoA-I mimetic peptide is effective to decrease plasma total cholesterol in a mammal, and/or to decrease plasma triglyceride in said mammal, and/or to decrease plasma 5-HETE in said mammal, and/or to decrease plasma 12-HETE in said mammal, and/or to decrease plasma 15-HETE in said mammal, and/or to decrease SAA levels in said mammal, and/or to increase plasma paraoxonase activity in said mammal, and/or to decrease plasma levels of lyophosphatidic acid (LPA) in a mammal when fed to said mammal alone or as a component of a food or diet.

23. The method of claim 1, wherein:
said ezetimibe-associated apoA-I mimetic peptide, when fed to a mammal, lowers plasma triglyceride, and/or raises plasma HDL cholesterol to a greater amount than a mixed ezetimibe apoA-I mimetic peptide formulation containing the same amounts of ezetimibe and apoA-I mimetic peptide; and/or
said ezetimibe-associated apoA-I mimetic peptide, when fed to a mammal, lowers plasma 5-HETE to a greater amount than a mixed ezetimibe apoA-I mimetic peptide formulation containing the same amounts of ezetimibe and apoA-I mimetic peptide; and/or
said ezetimibe-associated apoA-I mimetic peptide, when fed to a mammal, lowers plasma 12-HETE to a greater amount than a mixed ezetimibe apoA-I mimetic peptide formulation containing the same amounts of ezetimibe and apoA-I mimetic peptide; and/or
said ezetimibe-associated apoA-I mimetic peptide, when fed to a mammal, lowers plasma 15-HETE to a greater amount than a mixed ezetimibe apoA-I mimetic peptide formulation containing the same amounts of ezetimibe and apoA-I mimetic peptide; and/or
said ezetimibe-associated apoA-I mimetic peptide, when fed to a mammal, lowers plasma SAA to a greater amount than a mixed ezetimibe apoA-I mimetic peptide formulation containing the same amounts of ezetimibe and apoA-I mimetic peptide.

24. The method of claim 1, wherein said incubating is for about 2 hrs.

25. The method of claim 1, wherein said incubating is at room temperature.

26. The method of claim 1, wherein said apoA-I mimetic peptide is a peptide recombinantly expressed in a plant cell.

* * * * *

SEQUENCE LISTING

```
<160> NUMBER OF SEQ ID NOS: 639

<210> SEQ ID NO 1
<211> LENGTH: 18
<212> TYPE: PRT
<213> ORGANISM: Artificial
<220> FEATURE:
<223> OTHER INFORMATION: Synthetic peptide

<400> SEQUENCE: 1

Asp Trp Leu Lys Ala Phe Tyr Asp Lys Phe Phe Glu Lys Phe Lys Glu
1               5                   10                  15

Phe Phe

<210> SEQ ID NO 2
<211> LENGTH: 18
<212> TYPE: PRT
<213> ORGANISM: Artificial
<220> FEATURE:
<223> OTHER INFORMATION: Synthetic peptide

<400> SEQUENCE: 2

Asp Trp Leu Lys Ala Phe Tyr Asp Lys Val Ala Glu Lys Leu Lys Glu
1               5                   10                  15

Ala Phe

<210> SEQ ID NO 3
<211> LENGTH: 18
<212> TYPE: PRT
<213> ORGANISM: Artificial
<220> FEATURE:
<223> OTHER INFORMATION: Synthetic peptide
```

```
<400> SEQUENCE: 3

Asp Trp Leu Lys Ala Phe Tyr Asp Lys Val Ala Glu Lys Leu Lys Glu
1               5                   10                  15

Ala Phe

<210> SEQ ID NO 4
<211> LENGTH: 18
<212> TYPE: PRT
<213> ORGANISM: Artificial
<220> FEATURE:
<223> OTHER INFORMATION: Synthetic peptide

<400> SEQUENCE: 4

Asp Trp Phe Lys Ala Phe Tyr Asp Lys Val Ala Glu Lys Leu Lys Glu
1               5                   10                  15

Ala Phe

<210> SEQ ID NO 5
<211> LENGTH: 18
<212> TYPE: PRT
<213> ORGANISM: Artificial
<220> FEATURE:
<223> OTHER INFORMATION: Synthetic peptide

<400> SEQUENCE: 5

Asp Trp Leu Lys Ala Phe Tyr Asp Lys Val Ala Glu Lys Phe Lys Glu
1               5                   10                  15

Ala Phe

<210> SEQ ID NO 6
<211> LENGTH: 18
<212> TYPE: PRT
<213> ORGANISM: Artificial
<220> FEATURE:
<223> OTHER INFORMATION: Synthetic peptide

<400> SEQUENCE: 6

Asp Trp Phe Lys Ala Phe Tyr Asp Lys Val Ala Glu Lys Phe Lys Glu
1               5                   10                  15

Ala Phe

<210> SEQ ID NO 7
<211> LENGTH: 18
<212> TYPE: PRT
<213> ORGANISM: Artificial
<220> FEATURE:
<223> OTHER INFORMATION: Synthetic peptide

<400> SEQUENCE: 7

Asp Trp Leu Lys Ala Phe Tyr Asp Lys Val Phe Glu Lys Phe Lys Glu
1               5                   10                  15

Phe Phe

<210> SEQ ID NO 8
<211> LENGTH: 18
<212> TYPE: PRT
<213> ORGANISM: Artificial
<220> FEATURE:
<223> OTHER INFORMATION: Synthetic peptide

<400> SEQUENCE: 8

Asp Trp Phe Lys Ala Phe Tyr Asp Lys Phe Phe Glu Lys Phe Lys Glu
1               5                   10                  15
```

Phe Phe

<210> SEQ ID NO 9
<211> LENGTH: 18
<212> TYPE: PRT
<213> ORGANISM: Artificial
<220> FEATURE:
<223> OTHER INFORMATION: Synthetic peptide

<400> SEQUENCE: 9

Asp Trp Leu Lys Ala Phe Tyr Asp Lys Val Ala Glu Lys Leu Lys Glu
1               5                   10                  15

Phe Phe

<210> SEQ ID NO 10
<211> LENGTH: 18
<212> TYPE: PRT
<213> ORGANISM: Artificial
<220> FEATURE:
<223> OTHER INFORMATION: Synthetic peptide

<400> SEQUENCE: 10

Phe Ala Glu Lys Leu Lys Glu Ala Val Lys Asp Tyr Phe Ala Lys Leu
1               5                   10                  15

Trp Asp

<210> SEQ ID NO 11
<211> LENGTH: 18
<212> TYPE: PRT
<213> ORGANISM: Artificial
<220> FEATURE:
<223> OTHER INFORMATION: Synthetic peptide

<400> SEQUENCE: 11

Phe Ala Glu Lys Leu Lys Glu Ala Val Lys Asp Tyr Phe Ala Lys Leu
1               5                   10                  15

Trp Asp

<210> SEQ ID NO 12
<211> LENGTH: 18
<212> TYPE: PRT
<213> ORGANISM: Artificial
<220> FEATURE:
<223> OTHER INFORMATION: Synthetic peptide

<400> SEQUENCE: 12

Phe Ala Glu Lys Leu Lys Glu Ala Val Lys Asp Tyr Phe Ala Lys Phe
1               5                   10                  15

Trp Asp

<210> SEQ ID NO 13
<211> LENGTH: 18
<212> TYPE: PRT
<213> ORGANISM: Artificial
<220> FEATURE:
<223> OTHER INFORMATION: Synthetic peptide

<400> SEQUENCE: 13

Phe Ala Glu Lys Phe Lys Glu Ala Val Lys Asp Tyr Phe Ala Lys Phe
1               5                   10                  15

Trp Asp

<210> SEQ ID NO 14
<211> LENGTH: 18
<212> TYPE: PRT
<213> ORGANISM: Artificial
<220> FEATURE:
<223> OTHER INFORMATION: Synthetic peptide

<400> SEQUENCE: 14

```
Phe Phe Glu Lys Phe Lys Glu Phe Val Lys Asp Tyr Phe Ala Lys Leu
1               5                   10                  15

Trp Asp
```

<210> SEQ ID NO 15
<211> LENGTH: 18
<212> TYPE: PRT
<213> ORGANISM: Artificial
<220> FEATURE:
<223> OTHER INFORMATION: Synthetic peptide

<400> SEQUENCE: 15

```
Phe Phe Glu Lys Phe Lys Glu Phe Phe Lys Asp Tyr Phe Ala Lys Leu
1               5                   10                  15

Trp Asp
```

<210> SEQ ID NO 16
<211> LENGTH: 18
<212> TYPE: PRT
<213> ORGANISM: Artificial
<220> FEATURE:
<223> OTHER INFORMATION: Synthetic peptide

<400> SEQUENCE: 16

```
Phe Phe Glu Lys Phe Lys Glu Phe Phe Lys Asp Tyr Phe Ala Lys Phe
1               5                   10                  15

Trp Asp
```

<210> SEQ ID NO 17
<211> LENGTH: 18
<212> TYPE: PRT
<213> ORGANISM: Artificial
<220> FEATURE:
<223> OTHER INFORMATION: Synthetic peptide

<400> SEQUENCE: 17

```
Asp Trp Leu Lys Ala Phe Tyr Asp Lys Val Phe Glu Lys Phe Lys Glu
1               5                   10                  15

Ala Phe
```

<210> SEQ ID NO 18
<211> LENGTH: 18
<212> TYPE: PRT
<213> ORGANISM: Artificial
<220> FEATURE:
<223> OTHER INFORMATION: Synthetic peptide

<400> SEQUENCE: 18

```
Asp Trp Leu Lys Ala Phe Tyr Asp Lys Val Phe Glu Lys Leu Lys Glu
1               5                   10                  15

Phe Phe
```

<210> SEQ ID NO 19
<211> LENGTH: 18
<212> TYPE: PRT
<213> ORGANISM: Artificial

<220> FEATURE:
<223> OTHER INFORMATION: Synthetic peptide

<400> SEQUENCE: 19

Asp Trp Leu Lys Ala Phe Tyr Asp Lys Val Ala Glu Lys Phe Lys Glu
1               5                   10                  15

Phe Phe

<210> SEQ ID NO 20
<211> LENGTH: 18
<212> TYPE: PRT
<213> ORGANISM: Artificial
<220> FEATURE:
<223> OTHER INFORMATION: Synthetic peptide

<400> SEQUENCE: 20

Asp Trp Leu Lys Ala Phe Tyr Asp Lys Val Phe Glu Lys Phe Lys Glu
1               5                   10                  15

Phe Phe

<210> SEQ ID NO 21
<211> LENGTH: 18
<212> TYPE: PRT
<213> ORGANISM: Artificial
<220> FEATURE:
<223> OTHER INFORMATION: Synthetic peptide

<400> SEQUENCE: 21

Glu Trp Leu Lys Leu Phe Tyr Glu Lys Val Leu Glu Lys Phe Lys Glu
1               5                   10                  15

Ala Phe

<210> SEQ ID NO 22
<211> LENGTH: 18
<212> TYPE: PRT
<213> ORGANISM: Artificial
<220> FEATURE:
<223> OTHER INFORMATION: Synthetic peptide

<400> SEQUENCE: 22

Glu Trp Leu Lys Ala Phe Tyr Asp Lys Val Ala Glu Lys Phe Lys Glu
1               5                   10                  15

Ala Phe

<210> SEQ ID NO 23
<211> LENGTH: 18
<212> TYPE: PRT
<213> ORGANISM: Artificial
<220> FEATURE:
<223> OTHER INFORMATION: Synthetic peptide

<400> SEQUENCE: 23

Glu Trp Leu Lys Ala Phe Tyr Asp Lys Val Ala Glu Lys Leu Lys Glu
1               5                   10                  15

Phe Phe

<210> SEQ ID NO 24
<211> LENGTH: 18
<212> TYPE: PRT
<213> ORGANISM: Artificial
<220> FEATURE:
<223> OTHER INFORMATION: Synthetic peptide

<400> SEQUENCE: 24

```
Glu Trp Leu Lys Ala Phe Tyr Asp Lys Val Phe Glu Lys Phe Lys Glu
1               5                   10                  15

Ala Phe

<210> SEQ ID NO 25
<211> LENGTH: 18
<212> TYPE: PRT
<213> ORGANISM: Artificial
<220> FEATURE:
<223> OTHER INFORMATION: Synthetic peptide

<400> SEQUENCE: 25

Glu Trp Leu Lys Ala Phe Tyr Asp Lys Val Phe Glu Lys Leu Lys Glu
1               5                   10                  15

Phe Phe

<210> SEQ ID NO 26
<211> LENGTH: 18
<212> TYPE: PRT
<213> ORGANISM: Artificial
<220> FEATURE:
<223> OTHER INFORMATION: Synthetic peptide

<400> SEQUENCE: 26

Glu Trp Leu Lys Ala Phe Tyr Asp Lys Val Ala Glu Lys Phe Lys Glu
1               5                   10                  15

Phe Phe

<210> SEQ ID NO 27
<211> LENGTH: 18
<212> TYPE: PRT
<213> ORGANISM: Artificial
<220> FEATURE:
<223> OTHER INFORMATION: Synthetic peptide

<400> SEQUENCE: 27

Glu Trp Leu Lys Ala Phe Tyr Asp Lys Val Phe Glu Lys Phe Lys Glu
1               5                   10                  15

Phe Phe

<210> SEQ ID NO 28
<211> LENGTH: 14
<212> TYPE: PRT
<213> ORGANISM: Artificial
<220> FEATURE:
<223> OTHER INFORMATION: Synthetic peptide

<400> SEQUENCE: 28

Ala Phe Tyr Asp Lys Val Ala Glu Lys Leu Lys Glu Ala Phe
1               5                   10

<210> SEQ ID NO 29
<211> LENGTH: 14
<212> TYPE: PRT
<213> ORGANISM: Artificial
<220> FEATURE:
<223> OTHER INFORMATION: Synthetic peptide

<400> SEQUENCE: 29

Ala Phe Tyr Asp Lys Val Ala Glu Lys Phe Lys Glu Ala Phe
1               5                   10

<210> SEQ ID NO 30
```

```
<211> LENGTH: 14
<212> TYPE: PRT
<213> ORGANISM: Artificial
<220> FEATURE:
<223> OTHER INFORMATION: Synthetic peptide

<400> SEQUENCE: 30

Ala Phe Tyr Asp Lys Val Ala Glu Lys Phe Lys Glu Ala Phe
1               5                   10

<210> SEQ ID NO 31
<211> LENGTH: 14
<212> TYPE: PRT
<213> ORGANISM: Artificial
<220> FEATURE:
<223> OTHER INFORMATION: Synthetic peptide

<400> SEQUENCE: 31

Ala Phe Tyr Asp Lys Phe Phe Glu Lys Phe Lys Glu Phe Phe
1               5                   10

<210> SEQ ID NO 32
<211> LENGTH: 14
<212> TYPE: PRT
<213> ORGANISM: Artificial
<220> FEATURE:
<223> OTHER INFORMATION: Synthetic peptide

<400> SEQUENCE: 32

Ala Phe Tyr Asp Lys Phe Phe Glu Lys Phe Lys Glu Phe Phe
1               5                   10

<210> SEQ ID NO 33
<211> LENGTH: 14
<212> TYPE: PRT
<213> ORGANISM: Artificial
<220> FEATURE:
<223> OTHER INFORMATION: Synthetic peptide

<400> SEQUENCE: 33

Ala Phe Tyr Asp Lys Val Ala Glu Lys Phe Lys Glu Ala Phe
1               5                   10

<210> SEQ ID NO 34
<211> LENGTH: 14
<212> TYPE: PRT
<213> ORGANISM: Artificial
<220> FEATURE:
<223> OTHER INFORMATION: Synthetic peptide

<400> SEQUENCE: 34

Ala Phe Tyr Asp Lys Val Ala Glu Lys Leu Lys Glu Phe Phe
1               5                   10

<210> SEQ ID NO 35
<211> LENGTH: 14
<212> TYPE: PRT
<213> ORGANISM: Artificial
<220> FEATURE:
<223> OTHER INFORMATION: Synthetic peptide

<400> SEQUENCE: 35

Ala Phe Tyr Asp Lys Val Phe Glu Lys Phe Lys Glu Ala Phe
1               5                   10

<210> SEQ ID NO 36
<211> LENGTH: 14
```

```
<212> TYPE: PRT
<213> ORGANISM: Artificial
<220> FEATURE:
<223> OTHER INFORMATION: Synthetic peptide

<400> SEQUENCE: 36

Ala Phe Tyr Asp Lys Val Phe Glu Lys Leu Lys Glu Phe Phe
1               5                   10

<210> SEQ ID NO 37
<211> LENGTH: 14
<212> TYPE: PRT
<213> ORGANISM: Artificial
<220> FEATURE:
<223> OTHER INFORMATION: Synthetic peptide

<400> SEQUENCE: 37

Ala Phe Tyr Asp Lys Val Ala Glu Lys Phe Lys Glu Phe Phe
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide

<400> SEQUENCE: 38

Lys Ala Phe Tyr Asp Lys Val Phe Glu Lys Phe Lys Glu Phe
1               5                   10

<210> SEQ ID NO 39
<211> LENGTH: 14
<212> TYPE: PRT
<213> ORGANISM: Artificial
<220> FEATURE:
<223> OTHER INFORMATION: Synthetic peptide

<400> SEQUENCE: 39

Leu Phe Tyr Glu Lys Val Leu Glu Lys Phe Lys Glu Ala Phe
1               5                   10

<210> SEQ ID NO 40
<211> LENGTH: 14
<212> TYPE: PRT
<213> ORGANISM: Artificial
<220> FEATURE:
<223> OTHER INFORMATION: Synthetic peptide

<400> SEQUENCE: 40

Ala Phe Tyr Asp Lys Val Ala Glu Lys Phe Lys Glu Ala Phe
1               5                   10

<210> SEQ ID NO 41
<211> LENGTH: 14
<212> TYPE: PRT
<213> ORGANISM: Artificial
<220> FEATURE:
<223> OTHER INFORMATION: Synthetic peptide

<400> SEQUENCE: 41

Ala Phe Tyr Asp Lys Val Ala Glu Lys Leu Lys Glu Phe Phe
1               5                   10

<210> SEQ ID NO 42
<211> LENGTH: 14
<212> TYPE: PRT
```

```
<213> ORGANISM: Artificial
<220> FEATURE:
<223> OTHER INFORMATION: Synthetic peptide

<400> SEQUENCE: 42

Ala Phe Tyr Asp Lys Val Phe Glu Lys Phe Lys Glu Ala Phe
1               5                   10

<210> SEQ ID NO 43
<211> LENGTH: 14
<212> TYPE: PRT
<213> ORGANISM: Artificial
<220> FEATURE:
<223> OTHER INFORMATION: Synthetic peptide

<400> SEQUENCE: 43

Ala Phe Tyr Asp Lys Val Phe Glu Lys Leu Lys Glu Phe Phe
1               5                   10

<210> SEQ ID NO 44
<211> LENGTH: 14
<212> TYPE: PRT
<213> ORGANISM: Artificial
<220> FEATURE:
<223> OTHER INFORMATION: Synthetic peptide

<400> SEQUENCE: 44

Ala Phe Tyr Asp Lys Val Ala Glu Lys Phe Lys Glu Phe Phe
1               5                   10

<210> SEQ ID NO 45
<211> LENGTH: 14
<212> TYPE: PRT
<213> ORGANISM: Artificial
<220> FEATURE:
<223> OTHER INFORMATION: Synthetic peptide

<400> SEQUENCE: 45

Ala Phe Tyr Asp Lys Val Phe Glu Lys Phe Lys Glu Phe Phe
1               5                   10

<210> SEQ ID NO 46
<211> LENGTH: 18
<212> TYPE: PRT
<213> ORGANISM: Artificial
<220> FEATURE:
<223> OTHER INFORMATION: Synthetic peptide

<400> SEQUENCE: 46

Asp Trp Leu Lys Ala Leu Tyr Asp Lys Val Ala Glu Lys Leu Lys Glu
1               5                   10                  15

Ala Leu

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Asp Trp Phe Lys Ala Phe Tyr Glu Lys Val Ala Glu Lys Leu Lys Glu
1               5                   10                  15

Phe Phe
```

```
<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Asp Trp Phe Lys Ala Phe Tyr Glu Lys Phe Phe Glu Lys Phe Lys Glu
1               5                   10                  15

Phe Phe

<210> SEQ ID NO 49
<211> LENGTH: 18
<212> TYPE: PRT
<213> ORGANISM: Artificial
<220> FEATURE:
<223> OTHER INFORMATION: Synthetic peptide

<400> SEQUENCE: 49

Glu Trp Leu Lys Ala Leu Tyr Glu Lys Val Ala Glu Lys Leu Lys Glu
1               5                   10                  15

Ala Leu

<210> SEQ ID NO 50
<211> LENGTH: 18
<212> TYPE: PRT
<213> ORGANISM: Artificial
<220> FEATURE:
<223> OTHER INFORMATION: Synthetic peptide

<400> SEQUENCE: 50

Glu Trp Leu Lys Ala Phe Tyr Glu Lys Val Ala Glu Lys Leu Lys Glu
1               5                   10                  15

Ala Phe

<210> SEQ ID NO 51
<211> LENGTH: 18
<212> TYPE: PRT
<213> ORGANISM: Artificial
<220> FEATURE:
<223> OTHER INFORMATION: Synthetic peptide

<400> SEQUENCE: 51

Glu Trp Phe Lys Ala Phe Tyr Glu Lys Val Ala Glu Lys Leu Lys Glu
1               5                   10                  15

Phe Phe

<210> SEQ ID NO 52
<211> LENGTH: 18
<212> TYPE: PRT
<213> ORGANISM: Artificial
<220> FEATURE:
<223> OTHER INFORMATION: Synthetic peptide

<400> SEQUENCE: 52

Glu Trp Leu Lys Ala Phe Tyr Glu Lys Val Phe Glu Lys Phe Lys Glu
1               5                   10                  15

Phe Phe

<210> SEQ ID NO 53
<211> LENGTH: 18
<212> TYPE: PRT
<213> ORGANISM: Artificial
```

<220> FEATURE:
<223> OTHER INFORMATION: Synthetic peptide

<400> SEQUENCE: 53

Glu Trp Leu Lys Ala Phe Tyr Glu Lys Phe Phe Glu Lys Phe Lys Glu
1               5                   10                  15

Phe Phe

<210> SEQ ID NO 54
<211> LENGTH: 18
<212> TYPE: PRT
<213> ORGANISM: Artificial
<220> FEATURE:
<223> OTHER INFORMATION: Synthetic peptide

<400> SEQUENCE: 54

Glu Trp Phe Lys Ala Phe Tyr Glu Lys Phe Phe Glu Lys Phe Lys Glu
1               5                   10                  15

Phe Phe

<210> SEQ ID NO 55
<211> LENGTH: 18
<212> TYPE: PRT
<213> ORGANISM: Artificial
<220> FEATURE:
<223> OTHER INFORMATION: Synthetic peptide

<400> SEQUENCE: 55

Asp Phe Leu Lys Ala Trp Tyr Asp Lys Val Ala Glu Lys Leu Lys Glu
1               5                   10                  15

Ala Trp

<210> SEQ ID NO 56
<211> LENGTH: 18
<212> TYPE: PRT
<213> ORGANISM: Artificial
<220> FEATURE:
<223> OTHER INFORMATION: Synthetic peptide

<400> SEQUENCE: 56

Glu Phe Leu Lys Ala Trp Tyr Glu Lys Val Ala Glu Lys Leu Lys Glu
1               5                   10                  15

Ala Trp

<210> SEQ ID NO 57
<211> LENGTH: 18
<212> TYPE: PRT
<213> ORGANISM: Artificial
<220> FEATURE:
<223> OTHER INFORMATION: Synthetic peptide

<400> SEQUENCE: 57

Asp Phe Trp Lys Ala Trp Tyr Asp Lys Val Ala Glu Lys Leu Lys Glu
1               5                   10                  15

Trp Trp

<210> SEQ ID NO 58
<211> LENGTH: 18
<212> TYPE: PRT
<213> ORGANISM: Artificial
<220> FEATURE:
<223> OTHER INFORMATION: Synthetic peptide

<400> SEQUENCE: 58

Glu Phe Trp Lys Ala Trp Tyr Glu Lys Val Ala Glu Lys Leu Lys Glu
1               5                   10                  15

Trp Trp

<210> SEQ ID NO 59
<211> LENGTH: 18
<212> TYPE: PRT
<213> ORGANISM: Artificial
<220> FEATURE:
<223> OTHER INFORMATION: Synthetic peptide

<400> SEQUENCE: 59

Asp Lys Leu Lys Ala Phe Tyr Asp Lys Val Phe Glu Trp Ala Lys Glu
1               5                   10                  15

Ala Phe

<210> SEQ ID NO 60
<211> LENGTH: 18
<212> TYPE: PRT
<213> ORGANISM: Artificial
<220> FEATURE:
<223> OTHER INFORMATION: Synthetic peptide

<400> SEQUENCE: 60

Asp Lys Trp Lys Ala Val Tyr Asp Lys Phe Ala Glu Ala Phe Lys Glu
1               5                   10                  15

Phe Leu

<210> SEQ ID NO 61
<211> LENGTH: 18
<212> TYPE: PRT
<213> ORGANISM: Artificial
<220> FEATURE:
<223> OTHER INFORMATION: Synthetic peptide

<400> SEQUENCE: 61

Glu Lys Leu Lys Ala Phe Tyr Glu Lys Val Phe Glu Trp Ala Lys Glu
1               5                   10                  15

Ala Phe

<210> SEQ ID NO 62
<211> LENGTH: 18
<212> TYPE: PRT
<213> ORGANISM: Artificial
<220> FEATURE:
<223> OTHER INFORMATION: Synthetic peptide

<400> SEQUENCE: 62

Glu Lys Trp Lys Ala Val Tyr Glu Lys Phe Ala Glu Ala Phe Lys Glu
1               5                   10                  15

Phe Leu

<210> SEQ ID NO 63
<211> LENGTH: 18
<212> TYPE: PRT
<213> ORGANISM: Artificial
<220> FEATURE:
<223> OTHER INFORMATION: Synthetic peptide

<400> SEQUENCE: 63

Asp Trp Leu Lys Ala Phe Val Asp Lys Phe Ala Glu Lys Phe Lys Glu
1               5                   10                  15

Ala Tyr

<210> SEQ ID NO 64
<211> LENGTH: 18
<212> TYPE: PRT
<213> ORGANISM: Artificial
<220> FEATURE:
<223> OTHER INFORMATION: Synthetic peptide

<400> SEQUENCE: 64

Glu Lys Trp Lys Ala Val Tyr Glu Lys Phe Ala Glu Ala Phe Lys Glu
1               5                   10                  15

Phe Leu

<210> SEQ ID NO 65
<211> LENGTH: 18
<212> TYPE: PRT
<213> ORGANISM: Artificial
<220> FEATURE:
<223> OTHER INFORMATION: Synthetic peptide

<400> SEQUENCE: 65

Asp Trp Leu Lys Ala Phe Val Tyr Asp Lys Val Phe Lys Leu Lys Glu
1               5                   10                  15

Phe Phe

<210> SEQ ID NO 66
<211> LENGTH: 18
<212> TYPE: PRT
<213> ORGANISM: Artificial
<220> FEATURE:
<223> OTHER INFORMATION: Synthetic peptide

<400> SEQUENCE: 66

Glu Trp Leu Lys Ala Phe Val Tyr Glu Lys Val Phe Lys Leu Lys Glu
1               5                   10                  15

Phe Phe

<210> SEQ ID NO 67
<211> LENGTH: 18
<212> TYPE: PRT
<213> ORGANISM: Artificial
<220> FEATURE:
<223> OTHER INFORMATION: Synthetic peptide

<400> SEQUENCE: 67

Asp Trp Leu Arg Ala Phe Tyr Asp Lys Val Ala Glu Lys Leu Lys Glu
1               5                   10                  15

Ala Phe

<210> SEQ ID NO 68
<211> LENGTH: 18
<212> TYPE: PRT
<213> ORGANISM: Artificial
<220> FEATURE:
<223> OTHER INFORMATION: Synthetic peptide

<400> SEQUENCE: 68

Glu Trp Leu Arg Ala Phe Tyr Glu Lys Val Ala Glu Lys Leu Lys Glu
1               5                   10                  15

Ala Phe

<210> SEQ ID NO 69

```
<211> LENGTH: 18
<212> TYPE: PRT
<213> ORGANISM: Artificial
<220> FEATURE:
<223> OTHER INFORMATION: Synthetic peptide

<400> SEQUENCE: 69

Asp Trp Leu Lys Ala Phe Tyr Asp Arg Val Ala Glu Lys Leu Lys Glu
1               5                   10                  15

Ala Phe

<210> SEQ ID NO 70
<211> LENGTH: 18
<212> TYPE: PRT
<213> ORGANISM: Artificial
<220> FEATURE:
<223> OTHER INFORMATION: Synthetic peptide

<400> SEQUENCE: 70

Glu Trp Leu Lys Ala Phe Tyr Glu Arg Val Ala Glu Lys Leu Lys Glu
1               5                   10                  15

Ala Phe

<210> SEQ ID NO 71
<211> LENGTH: 18
<212> TYPE: PRT
<213> ORGANISM: Artificial
<220> FEATURE:
<223> OTHER INFORMATION: Synthetic peptide

<400> SEQUENCE: 71

Asp Trp Leu Lys Ala Phe Tyr Asp Lys Val Ala Glu Arg Leu Lys Glu
1               5                   10                  15

Ala Phe

<210> SEQ ID NO 72
<211> LENGTH: 18
<212> TYPE: PRT
<213> ORGANISM: Artificial
<220> FEATURE:
<223> OTHER INFORMATION: Synthetic peptide

<400> SEQUENCE: 72

Glu Trp Leu Lys Ala Phe Tyr Glu Lys Val Ala Glu Arg Leu Lys Glu
1               5                   10                  15

Ala Phe

<210> SEQ ID NO 73
<211> LENGTH: 18
<212> TYPE: PRT
<213> ORGANISM: Artificial
<220> FEATURE:
<223> OTHER INFORMATION: Synthetic peptide

<400> SEQUENCE: 73

Asp Trp Leu Lys Ala Phe Tyr Asp Lys Val Ala Glu Lys Leu Arg Glu
1               5                   10                  15

Ala Phe

<210> SEQ ID NO 74
<211> LENGTH: 18
<212> TYPE: PRT
<213> ORGANISM: Artificial
<220> FEATURE:
```

```
<223> OTHER INFORMATION: Synthetic peptide

<400> SEQUENCE: 74

Glu Trp Leu Lys Ala Phe Tyr Glu Lys Val Ala Glu Lys Leu Arg Glu
1               5                   10                  15

Ala Phe

<210> SEQ ID NO 75
<211> LENGTH: 18
<212> TYPE: PRT
<213> ORGANISM: Artificial
<220> FEATURE:
<223> OTHER INFORMATION: Synthetic peptide

<400> SEQUENCE: 75

Asp Trp Leu Lys Ala Phe Tyr Asp Arg Val Ala Glu Arg Leu Lys Glu
1               5                   10                  15

Ala Phe

<210> SEQ ID NO 76
<211> LENGTH: 18
<212> TYPE: PRT
<213> ORGANISM: Artificial
<220> FEATURE:
<223> OTHER INFORMATION: Synthetic peptide

<400> SEQUENCE: 76

Glu Trp Leu Lys Ala Phe Tyr Glu Arg Val Ala Glu Arg Leu Lys Glu
1               5                   10                  15

Ala Phe

<210> SEQ ID NO 77
<211> LENGTH: 18
<212> TYPE: PRT
<213> ORGANISM: Artificial
<220> FEATURE:
<223> OTHER INFORMATION: Synthetic peptide

<400> SEQUENCE: 77

Asp Trp Leu Arg Ala Phe Tyr Asp Lys Val Ala Glu Lys Leu Arg Glu
1               5                   10                  15

Ala Phe

<210> SEQ ID NO 78
<211> LENGTH: 18
<212> TYPE: PRT
<213> ORGANISM: Artificial
<220> FEATURE:
<223> OTHER INFORMATION: Synthetic peptide

<400> SEQUENCE: 78

Glu Trp Leu Arg Ala Phe Tyr Glu Lys Val Ala Glu Lys Leu Arg Glu
1               5                   10                  15

Ala Phe

<210> SEQ ID NO 79
<211> LENGTH: 18
<212> TYPE: PRT
<213> ORGANISM: Artificial
<220> FEATURE:
<223> OTHER INFORMATION: Synthetic peptide

<400> SEQUENCE: 79
```

Asp Trp Leu Arg Ala Phe Tyr Asp Arg Val Ala Glu Lys Leu Lys Glu
1               5                   10                  15

Ala Phe

<210> SEQ ID NO 80
<211> LENGTH: 18
<212> TYPE: PRT
<213> ORGANISM: Artificial
<220> FEATURE:
<223> OTHER INFORMATION: Synthetic peptide

<400> SEQUENCE: 80

Glu Trp Leu Arg Ala Phe Tyr Glu Arg Val Ala Glu Lys Leu Lys Glu
1               5                   10                  15

Ala Phe

<210> SEQ ID NO 81
<211> LENGTH: 18
<212> TYPE: PRT
<213> ORGANISM: Artificial
<220> FEATURE:
<223> OTHER INFORMATION: Synthetic peptide

<400> SEQUENCE: 81

Asp Trp Leu Lys Ala Phe Tyr Asp Lys Val Ala Glu Arg Leu Arg Glu
1               5                   10                  15

Ala Phe

<210> SEQ ID NO 82
<211> LENGTH: 18
<212> TYPE: PRT
<213> ORGANISM: Artificial
<220> FEATURE:
<223> OTHER INFORMATION: Synthetic peptide

<400> SEQUENCE: 82

Glu Trp Leu Lys Ala Phe Tyr Glu Lys Val Ala Glu Arg Leu Arg Glu
1               5                   10                  15

Ala Phe

<210> SEQ ID NO 83
<211> LENGTH: 18
<212> TYPE: PRT
<213> ORGANISM: Artificial
<220> FEATURE:
<223> OTHER INFORMATION: Synthetic peptide

<400> SEQUENCE: 83

Asp Trp Leu Arg Ala Phe Tyr Asp Lys Val Ala Glu Arg Leu Lys Glu
1               5                   10                  15

Ala Phe

<210> SEQ ID NO 84
<211> LENGTH: 18
<212> TYPE: PRT
<213> ORGANISM: Artificial
<220> FEATURE:
<223> OTHER INFORMATION: Synthetic peptide

<400> SEQUENCE: 84

Glu Trp Leu Arg Ala Phe Tyr Glu Lys Val Ala Glu Arg Leu Lys Glu
1               5                   10                  15

Ala Phe

<210> SEQ ID NO 85
<211> LENGTH: 37
<212> TYPE: PRT
<213> ORGANISM: Artificial
<220> FEATURE:
<223> OTHER INFORMATION: Synthetic peptide

<400> SEQUENCE: 85

```
Asp Trp Leu Lys Ala Phe Tyr Asp Lys Val Ala Glu Lys Leu Lys Glu
1               5                   10                  15

Ala Phe Pro Asp Trp Leu Lys Ala Phe Tyr Asp Lys Val Ala Glu Lys
                20                  25                  30

Leu Lys Glu Ala Phe
        35
```

<210> SEQ ID NO 86
<211> LENGTH: 37
<212> TYPE: PRT
<213> ORGANISM: Artificial
<220> FEATURE:
<223> OTHER INFORMATION: Synthetic peptide

<400> SEQUENCE: 86

```
Asp Trp Leu Lys Ala Phe Tyr Asp Lys Val Ala Glu Lys Leu Lys Glu
1               5                   10                  15

Phe Phe Pro Asp Trp Leu Lys Ala Phe Tyr Asp Lys Val Ala Glu Lys
                20                  25                  30

Leu Lys Glu Phe Phe
        35
```

<210> SEQ ID NO 87
<211> LENGTH: 37
<212> TYPE: PRT
<213> ORGANISM: Artificial
<220> FEATURE:
<223> OTHER INFORMATION: Synthetic peptide

<400> SEQUENCE: 87

```
Asp Trp Phe Lys Ala Phe Tyr Asp Lys Val Ala Glu Lys Leu Lys Glu
1               5                   10                  15

Ala Phe Pro Asp Trp Phe Lys Ala Phe Tyr Asp Lys Val Ala Glu Lys
                20                  25                  30

Leu Lys Glu Ala Phe
        35
```

<210> SEQ ID NO 88
<211> LENGTH: 37
<212> TYPE: PRT
<213> ORGANISM: Artificial
<220> FEATURE:
<223> OTHER INFORMATION: Synthetic peptide

<400> SEQUENCE: 88

```
Asp Lys Leu Lys Ala Phe Tyr Asp Lys Val Phe Glu Trp Ala Lys Glu
1               5                   10                  15

Ala Phe Pro Asp Lys Leu Lys Ala Phe Tyr Asp Lys Val Phe Glu Trp
                20                  25                  30

Leu Lys Glu Ala Phe
        35
```

<210> SEQ ID NO 89

<211> LENGTH: 37
<212> TYPE: PRT
<213> ORGANISM: Artificial
<220> FEATURE:
<223> OTHER INFORMATION: Synthetic peptide

<400> SEQUENCE: 89

Asp Lys Trp Lys Ala Val Tyr Asp Lys Phe Ala Glu Ala Phe Lys Glu
1               5                   10                  15

Phe Leu Pro Asp Lys Trp Lys Ala Val Tyr Asp Lys Phe Ala Glu Ala
                20                  25                  30

Phe Lys Glu Phe Leu
        35

<210> SEQ ID NO 90
<211> LENGTH: 37
<212> TYPE: PRT
<213> ORGANISM: Artificial
<220> FEATURE:
<223> OTHER INFORMATION: Synthetic peptide

<400> SEQUENCE: 90

Asp Trp Phe Lys Ala Phe Tyr Asp Lys Val Ala Glu Lys Phe Lys Glu
1               5                   10                  15

Ala Phe Pro Asp Trp Phe Lys Ala Phe Tyr Asp Lys Val Ala Glu Lys
                20                  25                  30

Phe Lys Glu Ala Phe
        35

<210> SEQ ID NO 91
<211> LENGTH: 37
<212> TYPE: PRT
<213> ORGANISM: Artificial
<220> FEATURE:
<223> OTHER INFORMATION: Synthetic peptide

<400> SEQUENCE: 91

Asp Trp Leu Lys Ala Phe Val Tyr Asp Lys Val Phe Lys Leu Lys Glu
1               5                   10                  15

Phe Phe Pro Asp Trp Leu Lys Ala Phe Val Tyr Asp Lys Val Phe Lys
                20                  25                  30

Leu Lys Glu Phe Phe
        35

<210> SEQ ID NO 92
<211> LENGTH: 37
<212> TYPE: PRT
<213> ORGANISM: Artificial
<220> FEATURE:
<223> OTHER INFORMATION: Synthetic peptide

<400> SEQUENCE: 92

Asp Trp Leu Lys Ala Phe Tyr Asp Lys Phe Ala Glu Lys Phe Lys Glu
1               5                   10                  15

Phe Phe Pro Asp Trp Leu Lys Ala Phe Tyr Asp Lys Phe Ala Glu Lys
                20                  25                  30

Phe Lys Glu Phe Phe
        35

<210> SEQ ID NO 93
<211> LENGTH: 18
<212> TYPE: PRT
<213> ORGANISM: Artificial

<220> FEATURE:
<223> OTHER INFORMATION: Synthetic peptide

<400> SEQUENCE: 93

Glu Trp Phe Lys Ala Phe Tyr Glu Lys Val Ala Glu Lys Phe Lys Glu
1               5                   10                  15
Ala Phe

<210> SEQ ID NO 94
<211> LENGTH: 14
<212> TYPE: PRT
<213> ORGANISM: Artificial
<220> FEATURE:
<223> OTHER INFORMATION: Synthetic peptide

<400> SEQUENCE: 94

Asp Trp Phe Lys Ala Phe Tyr Asp Lys Val Ala Glu Lys Phe
1               5                   10

<210> SEQ ID NO 95
<211> LENGTH: 14
<212> TYPE: PRT
<213> ORGANISM: Artificial
<220> FEATURE:
<223> OTHER INFORMATION: Synthetic peptide

<400> SEQUENCE: 95

Phe Lys Ala Phe Tyr Asp Lys Val Ala Glu Lys Phe Lys Glu
1               5                   10

<210> SEQ ID NO 96
<211> LENGTH: 14
<212> TYPE: PRT
<213> ORGANISM: Artificial
<220> FEATURE:
<223> OTHER INFORMATION: Synthetic peptide

<400> SEQUENCE: 96

Phe Lys Ala Phe Tyr Glu Lys Val Ala Glu Lys Phe Lys Glu
1               5                   10

<210> SEQ ID NO 97
<211> LENGTH: 14
<212> TYPE: PRT
<213> ORGANISM: Artificial
<220> FEATURE:
<223> OTHER INFORMATION: Synthetic peptide

<400> SEQUENCE: 97

Phe Lys Ala Phe Tyr Asp Lys Val Ala Glu Lys Phe Lys Glu
1               5                   10

<210> SEQ ID NO 98
<211> LENGTH: 14
<212> TYPE: PRT
<213> ORGANISM: Artificial
<220> FEATURE:
<223> OTHER INFORMATION: Synthetic peptide

<400> SEQUENCE: 98

Phe Lys Ala Phe Tyr Glu Lys Val Ala Glu Lys Phe Lys Glu
1               5                   10

<210> SEQ ID NO 99
<211> LENGTH: 18
<212> TYPE: PRT

```
<213> ORGANISM: Artificial
<220> FEATURE:
<223> OTHER INFORMATION: Synthetic peptide

<400> SEQUENCE: 99

Asp Trp Phe Lys Ala Phe Tyr Asp Lys Val Ala Glu Lys Phe Lys Glu
1               5                   10                  15

Ala Phe

<210> SEQ ID NO 100
<211> LENGTH: 18
<212> TYPE: PRT
<213> ORGANISM: Artificial
<220> FEATURE:
<223> OTHER INFORMATION: Synthetic peptide

<400> SEQUENCE: 100

Glu Trp Phe Lys Ala Phe Tyr Glu Lys Val Ala Glu Lys Phe Lys Glu
1               5                   10                  15

Ala Phe

<210> SEQ ID NO 101
<211> LENGTH: 14
<212> TYPE: PRT
<213> ORGANISM: Artificial
<220> FEATURE:
<223> OTHER INFORMATION: Synthetic peptide

<400> SEQUENCE: 101

Ala Phe Tyr Asp Lys Val Ala Glu Lys Phe Lys Glu Ala Phe
1               5                   10

<210> SEQ ID NO 102
<211> LENGTH: 14
<212> TYPE: PRT
<213> ORGANISM: Artificial
<220> FEATURE:
<223> OTHER INFORMATION: Synthetic peptide

<400> SEQUENCE: 102

Asp Trp Phe Lys Ala Phe Tyr Asp Lys Val Ala Glu Lys Phe
1               5                   10

<210> SEQ ID NO 103
<211> LENGTH: 18
<212> TYPE: PRT
<213> ORGANISM: Artificial
<220> FEATURE:
<223> OTHER INFORMATION: Synthetic peptide

<400> SEQUENCE: 103

Asp Trp Leu Lys Ala Phe Tyr Asp Lys Val Phe Glu Lys Phe Lys Glu
1               5                   10                  15

Phe Phe

<210> SEQ ID NO 104
<211> LENGTH: 18
<212> TYPE: PRT
<213> ORGANISM: Artificial
<220> FEATURE:
<223> OTHER INFORMATION: Synthetic peptide

<400> SEQUENCE: 104

Glu Trp Leu Lys Ala Phe Tyr Glu Lys Val Phe Glu Lys Phe Lys Glu
1               5                   10                  15
```

Phe Phe

<210> SEQ ID NO 105
<211> LENGTH: 14
<212> TYPE: PRT
<213> ORGANISM: Artificial
<220> FEATURE:
<223> OTHER INFORMATION: Synthetic peptide

<400> SEQUENCE: 105

Ala Phe Tyr Asp Lys Val Phe Glu Lys Phe Lys Glu Phe Phe
1               5                   10

<210> SEQ ID NO 106
<211> LENGTH: 14
<212> TYPE: PRT
<213> ORGANISM: Artificial
<220> FEATURE:
<223> OTHER INFORMATION: Synthetic peptide

<400> SEQUENCE: 106

Ala Phe Tyr Glu Lys Val Phe Glu Lys Phe Lys Glu Phe Phe
1               5                   10

<210> SEQ ID NO 107
<211> LENGTH: 14
<212> TYPE: PRT
<213> ORGANISM: Artificial
<220> FEATURE:
<223> OTHER INFORMATION: Synthetic peptide

<400> SEQUENCE: 107

Asp Trp Leu Lys Ala Phe Tyr Asp Lys Val Phe Glu Lys Phe
1               5                   10

<210> SEQ ID NO 108
<211> LENGTH: 14
<212> TYPE: PRT
<213> ORGANISM: Artificial
<220> FEATURE:
<223> OTHER INFORMATION: Synthetic peptide

<400> SEQUENCE: 108

Glu Trp Leu Lys Ala Phe Tyr Glu Lys Val Phe Glu Lys Phe
1               5                   10

<210> SEQ ID NO 109
<211> LENGTH: 14
<212> TYPE: PRT
<213> ORGANISM: Artificial
<220> FEATURE:
<223> OTHER INFORMATION: Synthetic peptide

<400> SEQUENCE: 109

Leu Lys Ala Phe Tyr Asp Lys Val Phe Glu Lys Phe Lys Glu
1               5                   10

<210> SEQ ID NO 110
<211> LENGTH: 14
<212> TYPE: PRT
<213> ORGANISM: Artificial
<220> FEATURE:
<223> OTHER INFORMATION: Synthetic peptide

<400> SEQUENCE: 110

Leu Lys Ala Phe Tyr Glu Lys Val Phe Glu Lys Phe Lys Glu

```
<210> SEQ ID NO 111
<211> LENGTH: 18
<212> TYPE: PRT
<213> ORGANISM: Artificial
<220> FEATURE:
<223> OTHER INFORMATION: Synthetic peptide

<400> SEQUENCE: 111

Glu Trp Phe Lys Ala Phe Tyr Glu Lys Val Ala Asp Lys Phe Lys Asp
1               5                   10                  15

Ala Phe

<210> SEQ ID NO 112
<211> LENGTH: 18
<212> TYPE: PRT
<213> ORGANISM: Artificial
<220> FEATURE:
<223> OTHER INFORMATION: Synthetic peptide

<400> SEQUENCE: 112

Glu Trp Phe Lys Ala Phe Tyr Asp Lys Val Ala Asp Lys Phe Lys Glu
1               5                   10                  15

Ala Phe

<210> SEQ ID NO 113
<211> LENGTH: 18
<212> TYPE: PRT
<213> ORGANISM: Artificial
<220> FEATURE:
<223> OTHER INFORMATION: Synthetic peptide

<400> SEQUENCE: 113

Asp Trp Phe Lys Ala Phe Tyr Glu Lys Val Ala Asp Lys Phe Lys Glu
1               5                   10                  15

Ala Phe

<210> SEQ ID NO 114
<211> LENGTH: 18
<212> TYPE: PRT
<213> ORGANISM: Artificial
<220> FEATURE:
<223> OTHER INFORMATION: Synthetic peptide

<400> SEQUENCE: 114

Asp Trp Phe Lys Ala Phe Tyr Glu Lys Val Ala Glu Lys Phe Lys Asp
1               5                   10                  15

Ala Phe

<210> SEQ ID NO 115
<211> LENGTH: 18
<212> TYPE: PRT
<213> ORGANISM: Artificial
<220> FEATURE:
<223> OTHER INFORMATION: Synthetic peptide

<400> SEQUENCE: 115

Asp Phe Trp Lys Ala Phe Tyr Asp Lys Val Ala Glu Lys Phe Lys Glu
1               5                   10                  15

Ala Phe

<210> SEQ ID NO 116
```

```
<211> LENGTH: 18
<212> TYPE: PRT
<213> ORGANISM: Artificial
<220> FEATURE:
<223> OTHER INFORMATION: Synthetic peptide

<400> SEQUENCE: 116

Glu Phe Trp Lys Ala Phe Tyr Glu Lys Val Ala Asp Lys Phe Lys Asp
1               5                   10                  15

Ala Phe

<210> SEQ ID NO 117
<211> LENGTH: 18
<212> TYPE: PRT
<213> ORGANISM: Artificial
<220> FEATURE:
<223> OTHER INFORMATION: Synthetic peptide

<400> SEQUENCE: 117

Glu Phe Trp Lys Ala Phe Tyr Asp Lys Val Ala Asp Lys Phe Lys Glu
1               5                   10                  15

Ala Phe

<210> SEQ ID NO 118
<211> LENGTH: 18
<212> TYPE: PRT
<213> ORGANISM: Artificial
<220> FEATURE:
<223> OTHER INFORMATION: Synthetic peptide

<400> SEQUENCE: 118

Asp Phe Trp Lys Ala Phe Tyr Glu Lys Val Ala Asp Lys Phe Lys Glu
1               5                   10                  15

Ala Phe

<210> SEQ ID NO 119
<211> LENGTH: 18
<212> TYPE: PRT
<213> ORGANISM: Artificial
<220> FEATURE:
<223> OTHER INFORMATION: Synthetic peptide

<400> SEQUENCE: 119

Asp Phe Trp Lys Ala Phe Tyr Glu Lys Val Ala Glu Lys Phe Lys Asp
1               5                   10                  15

Ala Phe

<210> SEQ ID NO 120
<211> LENGTH: 18
<212> TYPE: PRT
<213> ORGANISM: Artificial
<220> FEATURE:
<223> OTHER INFORMATION: Synthetic peptide

<400> SEQUENCE: 120

Asp Trp Phe Lys Ala Tyr Phe Asp Lys Val Ala Glu Lys Phe Lys Glu
1               5                   10                  15

Ala Phe

<210> SEQ ID NO 121
<211> LENGTH: 18
<212> TYPE: PRT
<213> ORGANISM: Artificial
<220> FEATURE:
```

<223> OTHER INFORMATION: Synthetic peptide

<400> SEQUENCE: 121

Glu Trp Phe Lys Ala Tyr Phe Glu Lys Val Ala Asp Lys Phe Lys Asp
1               5                   10                  15

Ala Phe

<210> SEQ ID NO 122
<211> LENGTH: 18
<212> TYPE: PRT
<213> ORGANISM: Artificial
<220> FEATURE:
<223> OTHER INFORMATION: Synthetic peptide

<400> SEQUENCE: 122

Glu Trp Phe Lys Ala Tyr Phe Asp Lys Val Ala Asp Lys Phe Lys Glu
1               5                   10                  15

Ala Phe

<210> SEQ ID NO 123
<211> LENGTH: 18
<212> TYPE: PRT
<213> ORGANISM: Artificial
<220> FEATURE:
<223> OTHER INFORMATION: Synthetic peptide

<400> SEQUENCE: 123

Asp Trp Phe Lys Ala Tyr Phe Glu Lys Val Ala Asp Lys Phe Lys Glu
1               5                   10                  15

Ala Phe

<210> SEQ ID NO 124
<211> LENGTH: 18
<212> TYPE: PRT
<213> ORGANISM: Artificial
<220> FEATURE:
<223> OTHER INFORMATION: Synthetic peptide

<400> SEQUENCE: 124

Asp Trp Phe Lys Ala Tyr Phe Glu Lys Val Ala Glu Lys Phe Lys Asp
1               5                   10                  15

Ala Phe

<210> SEQ ID NO 125
<211> LENGTH: 18
<212> TYPE: PRT
<213> ORGANISM: Artificial
<220> FEATURE:
<223> OTHER INFORMATION: Synthetic peptide

<400> SEQUENCE: 125

Asp Trp Phe Lys Ala Phe Val Asp Lys Tyr Ala Glu Lys Phe Lys Glu
1               5                   10                  15

Ala Phe

<210> SEQ ID NO 126
<211> LENGTH: 18
<212> TYPE: PRT
<213> ORGANISM: Artificial
<220> FEATURE:
<223> OTHER INFORMATION: Synthetic peptide

<400> SEQUENCE: 126

```
Glu Trp Phe Lys Ala Phe Val Glu Lys Tyr Ala Asp Lys Phe Lys Asp
1               5                   10                  15

Ala Phe

<210> SEQ ID NO 127
<211> LENGTH: 18
<212> TYPE: PRT
<213> ORGANISM: Artificial
<220> FEATURE:
<223> OTHER INFORMATION: Synthetic peptide

<400> SEQUENCE: 127

Glu Trp Phe Lys Ala Phe Val Asp Lys Tyr Ala Asp Lys Phe Lys Glu
1               5                   10                  15

Ala Phe

<210> SEQ ID NO 128
<211> LENGTH: 18
<212> TYPE: PRT
<213> ORGANISM: Artificial
<220> FEATURE:
<223> OTHER INFORMATION: Synthetic peptide

<400> SEQUENCE: 128

Asp Trp Phe Lys Ala Phe Val Glu Lys Tyr Ala Asp Lys Phe Lys Glu
1               5                   10                  15

Ala Phe

<210> SEQ ID NO 129
<211> LENGTH: 18
<212> TYPE: PRT
<213> ORGANISM: Artificial
<220> FEATURE:
<223> OTHER INFORMATION: Synthetic peptide

<400> SEQUENCE: 129

Asp Trp Phe Lys Ala Phe Val Glu Lys Tyr Ala Glu Lys Phe Lys Asp
1               5                   10                  15

Ala Phe

<210> SEQ ID NO 130
<211> LENGTH: 18
<212> TYPE: PRT
<213> ORGANISM: Artificial
<220> FEATURE:
<223> OTHER INFORMATION: Synthetic peptide

<400> SEQUENCE: 130

Asp Trp Phe Lys Ala Phe Tyr Asp Lys Ala Val Glu Lys Phe Lys Glu
1               5                   10                  15

Ala Phe

<210> SEQ ID NO 131
<211> LENGTH: 18
<212> TYPE: PRT
<213> ORGANISM: Artificial
<220> FEATURE:
<223> OTHER INFORMATION: Synthetic peptide

<400> SEQUENCE: 131

Glu Trp Phe Lys Ala Phe Tyr Glu Lys Ala Val Asp Lys Phe Lys Asp
1               5                   10                  15

Ala Phe
```

<210> SEQ ID NO 132
<211> LENGTH: 18
<212> TYPE: PRT
<213> ORGANISM: Artificial
<220> FEATURE:
<223> OTHER INFORMATION: Synthetic peptide

<400> SEQUENCE: 132

Glu Trp Phe Lys Ala Phe Tyr Asp Lys Ala Val Asp Lys Phe Lys Glu
1               5                   10                  15

Ala Phe

<210> SEQ ID NO 133
<211> LENGTH: 18
<212> TYPE: PRT
<213> ORGANISM: Artificial
<220> FEATURE:
<223> OTHER INFORMATION: Synthetic peptide

<400> SEQUENCE: 133

Asp Trp Phe Lys Ala Phe Tyr Glu Lys Ala Val Asp Lys Phe Lys Glu
1               5                   10                  15

Ala Phe

<210> SEQ ID NO 134
<211> LENGTH: 18
<212> TYPE: PRT
<213> ORGANISM: Artificial
<220> FEATURE:
<223> OTHER INFORMATION: Synthetic peptide

<400> SEQUENCE: 134

Asp Trp Phe Lys Ala Phe Tyr Glu Lys Ala Val Glu Lys Phe Lys Asp
1               5                   10                  15

Ala Phe

<210> SEQ ID NO 135
<211> LENGTH: 18
<212> TYPE: PRT
<213> ORGANISM: Artificial
<220> FEATURE:
<223> OTHER INFORMATION: Synthetic peptide

<400> SEQUENCE: 135

Asp Trp Phe Lys Ala Phe Tyr Asp Lys Val Phe Glu Lys Ala Lys Glu
1               5                   10                  15

Ala Phe

<210> SEQ ID NO 136
<211> LENGTH: 18
<212> TYPE: PRT
<213> ORGANISM: Artificial
<220> FEATURE:
<223> OTHER INFORMATION: Synthetic peptide

<400> SEQUENCE: 136

Glu Trp Phe Lys Ala Phe Tyr Glu Lys Val Phe Asp Lys Ala Lys Asp
1               5                   10                  15

Ala Phe

<210> SEQ ID NO 137
<211> LENGTH: 18

```
<212> TYPE: PRT
<213> ORGANISM: Artificial
<220> FEATURE:
<223> OTHER INFORMATION: Synthetic peptide

<400> SEQUENCE: 137

Glu Trp Phe Lys Ala Phe Tyr Asp Lys Val Phe Asp Lys Ala Lys Glu
1               5                   10                  15

Ala Phe

<210> SEQ ID NO 138
<211> LENGTH: 18
<212> TYPE: PRT
<213> ORGANISM: Artificial
<220> FEATURE:
<223> OTHER INFORMATION: Synthetic peptide

<400> SEQUENCE: 138

Asp Trp Phe Lys Ala Phe Tyr Glu Lys Val Phe Asp Lys Ala Lys Glu
1               5                   10                  15

Ala Phe

<210> SEQ ID NO 139
<211> LENGTH: 18
<212> TYPE: PRT
<213> ORGANISM: Artificial
<220> FEATURE:
<223> OTHER INFORMATION: Synthetic peptide

<400> SEQUENCE: 139

Asp Trp Phe Lys Ala Phe Tyr Glu Lys Val Phe Glu Lys Ala Lys Asp
1               5                   10                  15

Ala Phe

<210> SEQ ID NO 140
<211> LENGTH: 18
<212> TYPE: PRT
<213> ORGANISM: Artificial
<220> FEATURE:
<223> OTHER INFORMATION: Synthetic peptide

<400> SEQUENCE: 140

Asp Trp Phe Lys Ala Phe Tyr Asp Lys Val Ala Glu Lys Ala Lys Glu
1               5                   10                  15

Phe Phe

<210> SEQ ID NO 141
<211> LENGTH: 18
<212> TYPE: PRT
<213> ORGANISM: Artificial
<220> FEATURE:
<223> OTHER INFORMATION: Synthetic peptide

<400> SEQUENCE: 141

Glu Trp Phe Lys Ala Phe Tyr Glu Lys Val Ala Asp Lys Ala Lys Asp
1               5                   10                  15

Phe Phe

<210> SEQ ID NO 142
<211> LENGTH: 18
<212> TYPE: PRT
<213> ORGANISM: Artificial
<220> FEATURE:
<223> OTHER INFORMATION: Synthetic peptide
```

<400> SEQUENCE: 142

Glu Trp Phe Lys Ala Phe Tyr Asp Lys Val Ala Asp Lys Ala Lys Glu
1               5                   10                  15

Phe Phe

<210> SEQ ID NO 143
<211> LENGTH: 18
<212> TYPE: PRT
<213> ORGANISM: Artificial
<220> FEATURE:
<223> OTHER INFORMATION: Synthetic peptide

<400> SEQUENCE: 143

Asp Trp Phe Lys Ala Phe Tyr Glu Lys Val Ala Asp Lys Ala Lys Glu
1               5                   10                  15

Phe Phe

<210> SEQ ID NO 144
<211> LENGTH: 18
<212> TYPE: PRT
<213> ORGANISM: Artificial
<220> FEATURE:
<223> OTHER INFORMATION: Synthetic peptide

<400> SEQUENCE: 144

Asp Trp Phe Lys Ala Phe Tyr Glu Lys Val Ala Glu Lys Ala Lys Asp
1               5                   10                  15

Phe Phe

<210> SEQ ID NO 145
<211> LENGTH: 18
<212> TYPE: PRT
<213> ORGANISM: Artificial
<220> FEATURE:
<223> OTHER INFORMATION: Synthetic peptide

<400> SEQUENCE: 145

Asp Trp Phe Lys Ala Phe Tyr Asp Lys Val Ala Glu Lys Phe Lys Glu
1               5                   10                  15

Phe Ala

<210> SEQ ID NO 146
<211> LENGTH: 18
<212> TYPE: PRT
<213> ORGANISM: Artificial
<220> FEATURE:
<223> OTHER INFORMATION: Synthetic peptide

<400> SEQUENCE: 146

Glu Trp Phe Lys Ala Phe Tyr Glu Lys Val Ala Asp Lys Phe Lys Asp
1               5                   10                  15

Phe Ala

<210> SEQ ID NO 147
<211> LENGTH: 18
<212> TYPE: PRT
<213> ORGANISM: Artificial
<220> FEATURE:
<223> OTHER INFORMATION: Synthetic peptide

<400> SEQUENCE: 147

Glu Trp Phe Lys Ala Phe Tyr Asp Lys Val Ala Asp Lys Phe Lys Glu

```
1               5                  10                 15

Phe Ala

<210> SEQ ID NO 148
<211> LENGTH: 18
<212> TYPE: PRT
<213> ORGANISM: Artificial
<220> FEATURE:
<223> OTHER INFORMATION: Synthetic peptide

<400> SEQUENCE: 148

Asp Trp Phe Lys Ala Phe Tyr Glu Lys Val Ala Asp Lys Phe Lys Glu
1               5                  10                 15

Phe Ala

<210> SEQ ID NO 149
<211> LENGTH: 18
<212> TYPE: PRT
<213> ORGANISM: Artificial
<220> FEATURE:
<223> OTHER INFORMATION: Synthetic peptide

<400> SEQUENCE: 149

Asp Trp Phe Lys Ala Phe Tyr Glu Lys Val Ala Glu Lys Phe Lys Asp
1               5                  10                 15

Phe Ala

<210> SEQ ID NO 150
<211> LENGTH: 18
<212> TYPE: PRT
<213> ORGANISM: Artificial
<220> FEATURE:
<223> OTHER INFORMATION: Synthetic peptide

<400> SEQUENCE: 150

Asp Ala Phe Lys Ala Phe Tyr Asp Lys Val Ala Glu Lys Phe Lys Glu
1               5                  10                 15

Trp Phe

<210> SEQ ID NO 151
<211> LENGTH: 18
<212> TYPE: PRT
<213> ORGANISM: Artificial
<220> FEATURE:
<223> OTHER INFORMATION: Synthetic peptide

<400> SEQUENCE: 151

Glu Ala Phe Lys Ala Phe Tyr Glu Lys Val Ala Asp Lys Phe Lys Asp
1               5                  10                 15

Trp Phe

<210> SEQ ID NO 152
<211> LENGTH: 18
<212> TYPE: PRT
<213> ORGANISM: Artificial
<220> FEATURE:
<223> OTHER INFORMATION: Synthetic peptide

<400> SEQUENCE: 152

Glu Ala Phe Lys Ala Phe Tyr Asp Lys Val Ala Asp Lys Phe Lys Glu
1               5                  10                 15

Trp Phe
```

```
<210> SEQ ID NO 153
<211> LENGTH: 18
<212> TYPE: PRT
<213> ORGANISM: Artificial
<220> FEATURE:
<223> OTHER INFORMATION: Synthetic peptide

<400> SEQUENCE: 153

Asp Ala Phe Lys Ala Phe Tyr Glu Lys Val Ala Asp Lys Phe Lys Glu
1               5                   10                  15

Trp Phe

<210> SEQ ID NO 154
<211> LENGTH: 18
<212> TYPE: PRT
<213> ORGANISM: Artificial
<220> FEATURE:
<223> OTHER INFORMATION: Synthetic peptide

<400> SEQUENCE: 154

Asp Ala Phe Lys Ala Phe Tyr Glu Lys Val Ala Glu Lys Phe Lys Asp
1               5                   10                  15

Trp Phe

<210> SEQ ID NO 155
<211> LENGTH: 18
<212> TYPE: PRT
<213> ORGANISM: Artificial
<220> FEATURE:
<223> OTHER INFORMATION: Synthetic peptide

<400> SEQUENCE: 155

Asp Ala Phe Lys Ala Phe Tyr Asp Lys Val Trp Glu Lys Phe Lys Glu
1               5                   10                  15

Ala Phe

<210> SEQ ID NO 156
<211> LENGTH: 18
<212> TYPE: PRT
<213> ORGANISM: Artificial
<220> FEATURE:
<223> OTHER INFORMATION: Synthetic peptide

<400> SEQUENCE: 156

Glu Ala Phe Lys Ala Phe Tyr Glu Lys Val Trp Asp Lys Phe Lys Asp
1               5                   10                  15

Ala Phe

<210> SEQ ID NO 157
<211> LENGTH: 18
<212> TYPE: PRT
<213> ORGANISM: Artificial
<220> FEATURE:
<223> OTHER INFORMATION: Synthetic peptide

<400> SEQUENCE: 157

Glu Ala Phe Lys Ala Phe Tyr Asp Lys Val Trp Asp Lys Phe Lys Glu
1               5                   10                  15

Ala Phe

<210> SEQ ID NO 158
<211> LENGTH: 18
<212> TYPE: PRT
```

```
<213> ORGANISM: Artificial
<220> FEATURE:
<223> OTHER INFORMATION: Synthetic peptide

<400> SEQUENCE: 158

Asp Ala Phe Lys Ala Phe Tyr Glu Lys Val Trp Asp Lys Phe Lys Glu
1               5                   10                  15

Ala Phe

<210> SEQ ID NO 159
<211> LENGTH: 18
<212> TYPE: PRT
<213> ORGANISM: Artificial
<220> FEATURE:
<223> OTHER INFORMATION: Synthetic peptide

<400> SEQUENCE: 159

Asp Ala Phe Lys Ala Phe Tyr Glu Lys Val Trp Glu Lys Phe Lys Asp
1               5                   10                  15

Ala Phe

<210> SEQ ID NO 160
<211> LENGTH: 18
<212> TYPE: PRT
<213> ORGANISM: Artificial
<220> FEATURE:
<223> OTHER INFORMATION: Synthetic peptide

<400> SEQUENCE: 160

Asp Tyr Phe Lys Ala Phe Trp Asp Lys Val Ala Glu Lys Phe Lys Glu
1               5                   10                  15

Ala Phe

<210> SEQ ID NO 161
<211> LENGTH: 18
<212> TYPE: PRT
<213> ORGANISM: Artificial
<220> FEATURE:
<223> OTHER INFORMATION: Synthetic peptide

<400> SEQUENCE: 161

Glu Tyr Phe Lys Ala Phe Trp Glu Lys Val Ala Asp Lys Phe Lys Asp
1               5                   10                  15

Ala Phe

<210> SEQ ID NO 162
<211> LENGTH: 18
<212> TYPE: PRT
<213> ORGANISM: Artificial
<220> FEATURE:
<223> OTHER INFORMATION: Synthetic peptide

<400> SEQUENCE: 162

Glu Tyr Phe Lys Ala Phe Trp Asp Lys Val Ala Asp Lys Phe Lys Glu
1               5                   10                  15

Ala Phe

<210> SEQ ID NO 163
<211> LENGTH: 18
<212> TYPE: PRT
<213> ORGANISM: Artificial
<220> FEATURE:
<223> OTHER INFORMATION: Synthetic peptide
```

```
<400> SEQUENCE: 163

Asp Tyr Phe Lys Ala Phe Trp Glu Lys Val Ala Asp Lys Phe Lys Glu
1               5                   10                  15

Ala Phe

<210> SEQ ID NO 164
<211> LENGTH: 18
<212> TYPE: PRT
<213> ORGANISM: Artificial
<220> FEATURE:
<223> OTHER INFORMATION: Synthetic peptide

<400> SEQUENCE: 164

Asp Tyr Phe Lys Ala Phe Trp Glu Lys Val Ala Glu Lys Phe Lys Asp
1               5                   10                  15

Ala Phe

<210> SEQ ID NO 165
<211> LENGTH: 18
<212> TYPE: PRT
<213> ORGANISM: Artificial
<220> FEATURE:
<223> OTHER INFORMATION: Synthetic peptide

<400> SEQUENCE: 165

Asp Trp Ala Lys Ala Phe Tyr Asp Lys Val Ala Glu Lys Phe Lys Glu
1               5                   10                  15

Phe Phe

<210> SEQ ID NO 166
<211> LENGTH: 18
<212> TYPE: PRT
<213> ORGANISM: Artificial
<220> FEATURE:
<223> OTHER INFORMATION: Synthetic peptide

<400> SEQUENCE: 166

Glu Trp Ala Lys Ala Phe Tyr Glu Lys Val Ala Asp Lys Phe Lys Asp
1               5                   10                  15

Phe Phe

<210> SEQ ID NO 167
<211> LENGTH: 18
<212> TYPE: PRT
<213> ORGANISM: Artificial
<220> FEATURE:
<223> OTHER INFORMATION: Synthetic peptide

<400> SEQUENCE: 167

Glu Trp Ala Lys Ala Phe Tyr Asp Lys Val Ala Asp Lys Phe Lys Glu
1               5                   10                  15

Phe Phe

<210> SEQ ID NO 168
<211> LENGTH: 18
<212> TYPE: PRT
<213> ORGANISM: Artificial
<220> FEATURE:
<223> OTHER INFORMATION: Synthetic peptide

<400> SEQUENCE: 168

Asp Trp Ala Lys Ala Phe Tyr Glu Lys Val Ala Asp Lys Phe Lys Glu
1               5                   10                  15
```

Phe Phe

<210> SEQ ID NO 169
<211> LENGTH: 18
<212> TYPE: PRT
<213> ORGANISM: Artificial
<220> FEATURE:
<223> OTHER INFORMATION: Synthetic peptide

<400> SEQUENCE: 169

Asp Trp Ala Lys Ala Phe Tyr Glu Lys Val Ala Glu Lys Phe Lys Asp
1               5                   10                  15

Phe Phe

<210> SEQ ID NO 170
<211> LENGTH: 18
<212> TYPE: PRT
<213> ORGANISM: Artificial
<220> FEATURE:
<223> OTHER INFORMATION: Synthetic peptide

<400> SEQUENCE: 170

Asp Trp Phe Lys Ala Ala Tyr Asp Lys Val Ala Glu Lys Phe Lys Glu
1               5                   10                  15

Phe Phe

<210> SEQ ID NO 171
<211> LENGTH: 18
<212> TYPE: PRT
<213> ORGANISM: Artificial
<220> FEATURE:
<223> OTHER INFORMATION: Synthetic peptide

<400> SEQUENCE: 171

Glu Trp Phe Lys Ala Ala Tyr Glu Lys Val Ala Asp Lys Phe Lys Asp
1               5                   10                  15

Phe Phe

<210> SEQ ID NO 172
<211> LENGTH: 18
<212> TYPE: PRT
<213> ORGANISM: Artificial
<220> FEATURE:
<223> OTHER INFORMATION: Synthetic peptide

<400> SEQUENCE: 172

Glu Trp Phe Lys Ala Ala Tyr Asp Lys Val Ala Asp Lys Phe Lys Glu
1               5                   10                  15

Phe Phe

<210> SEQ ID NO 173
<211> LENGTH: 18
<212> TYPE: PRT
<213> ORGANISM: Artificial
<220> FEATURE:
<223> OTHER INFORMATION: Synthetic peptide

<400> SEQUENCE: 173

Asp Trp Phe Lys Ala Ala Tyr Glu Lys Val Ala Asp Lys Phe Lys Glu
1               5                   10                  15

Phe Phe

```
<210> SEQ ID NO 174
<211> LENGTH: 18
<212> TYPE: PRT
<213> ORGANISM: Artificial
<220> FEATURE:
<223> OTHER INFORMATION: Synthetic peptide

<400> SEQUENCE: 174

Asp Trp Phe Lys Ala Ala Tyr Glu Lys Val Ala Glu Lys Phe Lys Asp
1               5                   10                  15

Phe Phe

<210> SEQ ID NO 175
<211> LENGTH: 18
<212> TYPE: PRT
<213> ORGANISM: Artificial
<220> FEATURE:
<223> OTHER INFORMATION: Synthetic peptide

<400> SEQUENCE: 175

Asp Trp Phe Lys Ala Phe Ala Asp Lys Val Ala Glu Lys Phe Lys Glu
1               5                   10                  15

Tyr Phe

<210> SEQ ID NO 176
<211> LENGTH: 18
<212> TYPE: PRT
<213> ORGANISM: Artificial
<220> FEATURE:
<223> OTHER INFORMATION: Synthetic peptide

<400> SEQUENCE: 176

Glu Trp Phe Lys Ala Phe Ala Glu Lys Val Ala Asp Lys Phe Lys Asp
1               5                   10                  15

Tyr Phe

<210> SEQ ID NO 177
<211> LENGTH: 18
<212> TYPE: PRT
<213> ORGANISM: Artificial
<220> FEATURE:
<223> OTHER INFORMATION: Synthetic peptide

<400> SEQUENCE: 177

Glu Trp Phe Lys Ala Phe Ala Asp Lys Val Ala Asp Lys Phe Lys Glu
1               5                   10                  15

Tyr Phe

<210> SEQ ID NO 178
<211> LENGTH: 18
<212> TYPE: PRT
<213> ORGANISM: Artificial
<220> FEATURE:
<223> OTHER INFORMATION: Synthetic peptide

<400> SEQUENCE: 178

Asp Trp Phe Lys Ala Phe Ala Glu Lys Val Ala Asp Lys Phe Lys Glu
1               5                   10                  15

Tyr Phe

<210> SEQ ID NO 179
<211> LENGTH: 18
<212> TYPE: PRT
<213> ORGANISM: Artificial
```

<220> FEATURE:
<223> OTHER INFORMATION: Synthetic peptide

<400> SEQUENCE: 179

Asp Trp Phe Lys Ala Phe Ala Glu Lys Val Ala Glu Lys Phe Lys Asp
1               5                   10                  15

Tyr Phe

<210> SEQ ID NO 180
<211> LENGTH: 18
<212> TYPE: PRT
<213> ORGANISM: Artificial
<220> FEATURE:
<223> OTHER INFORMATION: Synthetic peptide

<400> SEQUENCE: 180

Asp Trp Phe Lys Ala Phe Tyr Asp Lys Ala Ala Glu Lys Phe Lys Glu
1               5                   10                  15

Val Phe

<210> SEQ ID NO 181
<211> LENGTH: 18
<212> TYPE: PRT
<213> ORGANISM: Artificial
<220> FEATURE:
<223> OTHER INFORMATION: Synthetic peptide

<400> SEQUENCE: 181

Glu Trp Phe Lys Ala Phe Tyr Glu Lys Ala Ala Asp Lys Phe Lys Asp
1               5                   10                  15

Val Phe

<210> SEQ ID NO 182
<211> LENGTH: 18
<212> TYPE: PRT
<213> ORGANISM: Artificial
<220> FEATURE:
<223> OTHER INFORMATION: Synthetic peptide

<400> SEQUENCE: 182

Glu Trp Phe Lys Ala Phe Tyr Asp Lys Ala Ala Asp Lys Phe Lys Glu
1               5                   10                  15

Val Phe

<210> SEQ ID NO 183
<211> LENGTH: 18
<212> TYPE: PRT
<213> ORGANISM: Artificial
<220> FEATURE:
<223> OTHER INFORMATION: Synthetic peptide

<400> SEQUENCE: 183

Asp Trp Phe Lys Ala Phe Tyr Glu Lys Ala Ala Asp Lys Phe Lys Glu
1               5                   10                  15

Val Phe

<210> SEQ ID NO 184
<211> LENGTH: 18
<212> TYPE: PRT
<213> ORGANISM: Artificial
<220> FEATURE:
<223> OTHER INFORMATION: Synthetic peptide

<400> SEQUENCE: 184

```
Asp Trp Phe Lys Ala Phe Tyr Glu Lys Ala Ala Glu Lys Phe Lys Asp
1               5                   10                  15

Val Phe
```

<210> SEQ ID NO 185
<211> LENGTH: 18
<212> TYPE: PRT
<213> ORGANISM: Artificial
<220> FEATURE:
<223> OTHER INFORMATION: Synthetic peptide

<400> SEQUENCE: 185

```
Asp Trp Tyr Lys Ala Phe Phe Asp Lys Val Ala Glu Lys Phe Lys Glu
1               5                   10                  15

Ala Phe
```

<210> SEQ ID NO 186
<211> LENGTH: 18
<212> TYPE: PRT
<213> ORGANISM: Artificial
<220> FEATURE:
<223> OTHER INFORMATION: Synthetic peptide

<400> SEQUENCE: 186

```
Glu Trp Tyr Lys Ala Phe Phe Glu Lys Val Ala Asp Lys Phe Lys Asp
1               5                   10                  15

Ala Phe
```

<210> SEQ ID NO 187
<211> LENGTH: 18
<212> TYPE: PRT
<213> ORGANISM: Artificial
<220> FEATURE:
<223> OTHER INFORMATION: Synthetic peptide

<400> SEQUENCE: 187

```
Glu Trp Tyr Lys Ala Phe Phe Asp Lys Val Ala Asp Lys Phe Lys Glu
1               5                   10                  15

Ala Phe
```

<210> SEQ ID NO 188
<211> LENGTH: 18
<212> TYPE: PRT
<213> ORGANISM: Artificial
<220> FEATURE:
<223> OTHER INFORMATION: Synthetic peptide

<400> SEQUENCE: 188

```
Asp Trp Tyr Lys Ala Phe Phe Glu Lys Val Ala Asp Lys Phe Lys Glu
1               5                   10                  15

Ala Phe
```

<210> SEQ ID NO 189
<211> LENGTH: 18
<212> TYPE: PRT
<213> ORGANISM: Artificial
<220> FEATURE:
<223> OTHER INFORMATION: Synthetic peptide

<400> SEQUENCE: 189

```
Asp Trp Tyr Lys Ala Phe Phe Glu Lys Val Ala Glu Lys Phe Lys Asp
1               5                   10                  15
```

Ala Phe

<210> SEQ ID NO 190
<211> LENGTH: 18
<212> TYPE: PRT
<213> ORGANISM: Artificial
<220> FEATURE:
<223> OTHER INFORMATION: Synthetic peptide

<400> SEQUENCE: 190

Asp Trp Val Lys Ala Phe Tyr Asp Lys Phe Ala Glu Lys Phe Lys Glu
1               5                   10                  15

Ala Phe

<210> SEQ ID NO 191
<211> LENGTH: 18
<212> TYPE: PRT
<213> ORGANISM: Artificial
<220> FEATURE:
<223> OTHER INFORMATION: Synthetic peptide

<400> SEQUENCE: 191

Glu Trp Val Lys Ala Phe Tyr Glu Lys Phe Ala Asp Lys Phe Lys Asp
1               5                   10                  15

Ala Phe

<210> SEQ ID NO 192
<211> LENGTH: 18
<212> TYPE: PRT
<213> ORGANISM: Artificial
<220> FEATURE:
<223> OTHER INFORMATION: Synthetic peptide

<400> SEQUENCE: 192

Glu Trp Val Lys Ala Phe Tyr Asp Lys Phe Ala Asp Lys Phe Lys Glu
1               5                   10                  15

Ala Phe

<210> SEQ ID NO 193
<211> LENGTH: 18
<212> TYPE: PRT
<213> ORGANISM: Artificial
<220> FEATURE:
<223> OTHER INFORMATION: Synthetic peptide

<400> SEQUENCE: 193

Asp Trp Val Lys Ala Phe Tyr Glu Lys Phe Ala Asp Lys Phe Lys Glu
1               5                   10                  15

Ala Phe

<210> SEQ ID NO 194
<211> LENGTH: 18
<212> TYPE: PRT
<213> ORGANISM: Artificial
<220> FEATURE:
<223> OTHER INFORMATION: Synthetic peptide

<400> SEQUENCE: 194

Asp Trp Val Lys Ala Phe Tyr Glu Lys Phe Ala Glu Lys Phe Lys Asp
1               5                   10                  15

Ala Phe

<210> SEQ ID NO 195

```
<211> LENGTH: 18
<212> TYPE: PRT
<213> ORGANISM: Artificial
<220> FEATURE:
<223> OTHER INFORMATION: Synthetic peptide

<400> SEQUENCE: 195

Asp Trp Phe Lys Ala Phe Phe Asp Lys Val Ala Glu Lys Tyr Lys Glu
1               5                   10                  15
Ala Phe

<210> SEQ ID NO 196
<211> LENGTH: 18
<212> TYPE: PRT
<213> ORGANISM: Artificial
<220> FEATURE:
<223> OTHER INFORMATION: Synthetic peptide

<400> SEQUENCE: 196

Glu Trp Phe Lys Ala Phe Phe Glu Lys Val Ala Asp Lys Tyr Lys Asp
1               5                   10                  15
Ala Phe

<210> SEQ ID NO 197
<211> LENGTH: 18
<212> TYPE: PRT
<213> ORGANISM: Artificial
<220> FEATURE:
<223> OTHER INFORMATION: Synthetic peptide

<400> SEQUENCE: 197

Glu Trp Phe Lys Ala Phe Phe Asp Lys Val Ala Asp Lys Tyr Lys Glu
1               5                   10                  15
Ala Phe

<210> SEQ ID NO 198
<211> LENGTH: 18
<212> TYPE: PRT
<213> ORGANISM: Artificial
<220> FEATURE:
<223> OTHER INFORMATION: Synthetic peptide

<400> SEQUENCE: 198

Asp Trp Phe Lys Ala Phe Phe Glu Lys Val Ala Asp Lys Tyr Lys Glu
1               5                   10                  15
Ala Phe

<210> SEQ ID NO 199
<211> LENGTH: 18
<212> TYPE: PRT
<213> ORGANISM: Artificial
<220> FEATURE:
<223> OTHER INFORMATION: Synthetic peptide

<400> SEQUENCE: 199

Asp Trp Phe Lys Ala Phe Phe Glu Lys Val Ala Asp Lys Tyr Lys Glu
1               5                   10                  15
Ala Phe

<210> SEQ ID NO 200
<211> LENGTH: 18
<212> TYPE: PRT
<213> ORGANISM: Artificial
<220> FEATURE:
```

<223> OTHER INFORMATION: Synthetic peptide

<400> SEQUENCE: 200

Asp Trp Phe Lys Ala Phe Phe Asp Lys Val Ala Glu Lys Phe Lys Glu
1               5                   10                  15

Ala Tyr

<210> SEQ ID NO 201
<211> LENGTH: 18
<212> TYPE: PRT
<213> ORGANISM: Artificial
<220> FEATURE:
<223> OTHER INFORMATION: Synthetic peptide

<400> SEQUENCE: 201

Glu Trp Phe Lys Ala Phe Phe Glu Lys Val Ala Asp Lys Phe Lys Asp
1               5                   10                  15

Ala Tyr

<210> SEQ ID NO 202
<211> LENGTH: 18
<212> TYPE: PRT
<213> ORGANISM: Artificial
<220> FEATURE:
<223> OTHER INFORMATION: Synthetic peptide

<400> SEQUENCE: 202

Glu Trp Phe Lys Ala Phe Phe Asp Lys Val Ala Asp Lys Phe Lys Glu
1               5                   10                  15

Ala Tyr

<210> SEQ ID NO 203
<211> LENGTH: 18
<212> TYPE: PRT
<213> ORGANISM: Artificial
<220> FEATURE:
<223> OTHER INFORMATION: Synthetic peptide

<400> SEQUENCE: 203

Asp Trp Phe Lys Ala Phe Phe Glu Lys Val Ala Asp Lys Phe Lys Glu
1               5                   10                  15

Ala Tyr

<210> SEQ ID NO 204
<211> LENGTH: 18
<212> TYPE: PRT
<213> ORGANISM: Artificial
<220> FEATURE:
<223> OTHER INFORMATION: Synthetic peptide

<400> SEQUENCE: 204

Asp Trp Phe Lys Ala Phe Phe Glu Lys Val Ala Glu Lys Phe Lys Asp
1               5                   10                  15

Ala Tyr

<210> SEQ ID NO 205
<211> LENGTH: 18
<212> TYPE: PRT
<213> ORGANISM: Artificial
<220> FEATURE:
<223> OTHER INFORMATION: Synthetic peptide

<400> SEQUENCE: 205

Asp Trp Phe Lys Ala Phe Tyr Asp Lys Phe Ala Glu Lys Phe Lys Glu
1               5                   10                  15

Ala Val

<210> SEQ ID NO 206
<211> LENGTH: 18
<212> TYPE: PRT
<213> ORGANISM: Artificial
<220> FEATURE:
<223> OTHER INFORMATION: Synthetic peptide

<400> SEQUENCE: 206

Glu Trp Phe Lys Ala Phe Tyr Glu Lys Phe Ala Asp Lys Phe Lys Asp
1               5                   10                  15

Ala Val

<210> SEQ ID NO 207
<211> LENGTH: 18
<212> TYPE: PRT
<213> ORGANISM: Artificial
<220> FEATURE:
<223> OTHER INFORMATION: Synthetic peptide

<400> SEQUENCE: 207

Glu Trp Phe Lys Ala Phe Tyr Asp Lys Phe Ala Asp Lys Phe Lys Glu
1               5                   10                  15

Ala Val

<210> SEQ ID NO 208
<211> LENGTH: 18
<212> TYPE: PRT
<213> ORGANISM: Artificial
<220> FEATURE:
<223> OTHER INFORMATION: Synthetic peptide

<400> SEQUENCE: 208

Asp Trp Phe Lys Ala Phe Tyr Glu Lys Phe Ala Asp Lys Phe Lys Glu
1               5                   10                  15

Ala Val

<210> SEQ ID NO 209
<211> LENGTH: 18
<212> TYPE: PRT
<213> ORGANISM: Artificial
<220> FEATURE:
<223> OTHER INFORMATION: Synthetic peptide

<400> SEQUENCE: 209

Asp Trp Phe Lys Ala Phe Tyr Glu Lys Phe Ala Glu Lys Phe Lys Asp
1               5                   10                  15

Ala Val

<210> SEQ ID NO 210
<211> LENGTH: 18
<212> TYPE: PRT
<213> ORGANISM: Artificial
<220> FEATURE:
<223> OTHER INFORMATION: Synthetic peptide

<400> SEQUENCE: 210

Asp Lys Phe Lys Ala Phe Tyr Asp Lys Val Ala Glu Lys Phe Trp Glu
1               5                   10                  15

Ala Phe

<210> SEQ ID NO 211
<211> LENGTH: 18
<212> TYPE: PRT
<213> ORGANISM: Artificial
<220> FEATURE:
<223> OTHER INFORMATION: Synthetic peptide

<400> SEQUENCE: 211

Glu Lys Phe Lys Ala Phe Tyr Glu Lys Val Ala Asp Lys Phe Trp Asp
1               5                   10                  15

Ala Phe

<210> SEQ ID NO 212
<211> LENGTH: 18
<212> TYPE: PRT
<213> ORGANISM: Artificial
<220> FEATURE:
<223> OTHER INFORMATION: Synthetic peptide

<400> SEQUENCE: 212

Glu Lys Phe Lys Ala Phe Tyr Asp Lys Val Ala Asp Lys Phe Trp Glu
1               5                   10                  15

Ala Phe

<210> SEQ ID NO 213
<211> LENGTH: 18
<212> TYPE: PRT
<213> ORGANISM: Artificial
<220> FEATURE:
<223> OTHER INFORMATION: Synthetic peptide

<400> SEQUENCE: 213

Asp Lys Phe Lys Ala Phe Tyr Glu Lys Val Ala Asp Lys Phe Trp Glu
1               5                   10                  15

Ala Phe

<210> SEQ ID NO 214
<211> LENGTH: 18
<212> TYPE: PRT
<213> ORGANISM: Artificial
<220> FEATURE:
<223> OTHER INFORMATION: Synthetic peptide

<400> SEQUENCE: 214

Asp Lys Phe Lys Ala Phe Tyr Glu Lys Val Ala Glu Lys Phe Trp Asp
1               5                   10                  15

Ala Phe

<210> SEQ ID NO 215
<211> LENGTH: 18
<212> TYPE: PRT
<213> ORGANISM: Artificial
<220> FEATURE:
<223> OTHER INFORMATION: Synthetic peptide

<400> SEQUENCE: 215

Asp Lys Trp Lys Ala Phe Tyr Asp Lys Val Ala Glu Lys Phe Phe Glu
1               5                   10                  15

Ala Phe

<210> SEQ ID NO 216
<211> LENGTH: 18

<212> TYPE: PRT
<213> ORGANISM: Artificial
<220> FEATURE:
<223> OTHER INFORMATION: Synthetic peptide

<400> SEQUENCE: 216

Glu Lys Trp Lys Ala Phe Tyr Glu Lys Val Ala Asp Lys Phe Phe Asp
1               5                   10                  15

Ala Phe

<210> SEQ ID NO 217
<211> LENGTH: 18
<212> TYPE: PRT
<213> ORGANISM: Artificial
<220> FEATURE:
<223> OTHER INFORMATION: Synthetic peptide

<400> SEQUENCE: 217

Glu Lys Trp Lys Ala Phe Tyr Asp Lys Val Ala Asp Lys Phe Phe Glu
1               5                   10                  15

Ala Phe

<210> SEQ ID NO 218
<211> LENGTH: 18
<212> TYPE: PRT
<213> ORGANISM: Artificial
<220> FEATURE:
<223> OTHER INFORMATION: Synthetic peptide

<400> SEQUENCE: 218

Asp Lys Trp Lys Ala Phe Tyr Glu Lys Val Ala Asp Lys Phe Phe Glu
1               5                   10                  15

Ala Phe

<210> SEQ ID NO 219
<211> LENGTH: 18
<212> TYPE: PRT
<213> ORGANISM: Artificial
<220> FEATURE:
<223> OTHER INFORMATION: Synthetic peptide

<400> SEQUENCE: 219

Asp Lys Trp Lys Ala Phe Tyr Glu Lys Val Ala Glu Lys Phe Phe Asp
1               5                   10                  15

Ala Phe

<210> SEQ ID NO 220
<211> LENGTH: 18
<212> TYPE: PRT
<213> ORGANISM: Artificial
<220> FEATURE:
<223> OTHER INFORMATION: Synthetic peptide

<400> SEQUENCE: 220

Asp Lys Phe Lys Ala Phe Tyr Asp Lys Trp Ala Glu Val Phe Lys Glu
1               5                   10                  15

Ala Phe

<210> SEQ ID NO 221
<211> LENGTH: 18
<212> TYPE: PRT
<213> ORGANISM: Artificial
<220> FEATURE:
<223> OTHER INFORMATION: Synthetic peptide

```
<400> SEQUENCE: 221

Glu Lys Phe Lys Ala Phe Tyr Glu Lys Trp Ala Asp Val Phe Lys Asp
1               5                   10                  15

Ala Phe

<210> SEQ ID NO 222
<211> LENGTH: 18
<212> TYPE: PRT
<213> ORGANISM: Artificial
<220> FEATURE:
<223> OTHER INFORMATION: Synthetic peptide

<400> SEQUENCE: 222

Glu Lys Phe Lys Ala Phe Tyr Asp Lys Trp Ala Asp Val Phe Lys Glu
1               5                   10                  15

Ala Phe

<210> SEQ ID NO 223
<211> LENGTH: 18
<212> TYPE: PRT
<213> ORGANISM: Artificial
<220> FEATURE:
<223> OTHER INFORMATION: Synthetic peptide

<400> SEQUENCE: 223

Asp Lys Phe Lys Ala Phe Tyr Glu Lys Trp Ala Asp Val Phe Lys Glu
1               5                   10                  15

Ala Phe

<210> SEQ ID NO 224
<211> LENGTH: 18
<212> TYPE: PRT
<213> ORGANISM: Artificial
<220> FEATURE:
<223> OTHER INFORMATION: Synthetic peptide

<400> SEQUENCE: 224

Asp Lys Phe Lys Ala Phe Tyr Glu Lys Trp Ala Glu Val Phe Lys Asp
1               5                   10                  15

Ala Phe

<210> SEQ ID NO 225
<211> LENGTH: 18
<212> TYPE: PRT
<213> ORGANISM: Artificial
<220> FEATURE:
<223> OTHER INFORMATION: Synthetic peptide

<400> SEQUENCE: 225

Asp Lys Phe Lys Ala Phe Tyr Asp Lys Val Ala Glu Phe Trp Lys Glu
1               5                   10                  15

Ala Phe

<210> SEQ ID NO 226
<211> LENGTH: 18
<212> TYPE: PRT
<213> ORGANISM: Artificial
<220> FEATURE:
<223> OTHER INFORMATION: Synthetic peptide

<400> SEQUENCE: 226

Glu Lys Phe Lys Ala Phe Tyr Glu Lys Val Ala Asp Phe Trp Lys Asp
```

```
1               5                   10                  15

Ala Phe

<210> SEQ ID NO 227
<211> LENGTH: 18
<212> TYPE: PRT
<213> ORGANISM: Artificial
<220> FEATURE:
<223> OTHER INFORMATION: Synthetic peptide

<400> SEQUENCE: 227

Glu Lys Phe Lys Ala Phe Tyr Asp Lys Val Ala Asp Phe Trp Lys Glu
1               5                   10                  15

Ala Phe

<210> SEQ ID NO 228
<211> LENGTH: 18
<212> TYPE: PRT
<213> ORGANISM: Artificial
<220> FEATURE:
<223> OTHER INFORMATION: Synthetic peptide

<400> SEQUENCE: 228

Asp Lys Phe Lys Ala Phe Tyr Glu Lys Val Ala Asp Phe Trp Lys Glu
1               5                   10                  15

Ala Phe

<210> SEQ ID NO 229
<211> LENGTH: 18
<212> TYPE: PRT
<213> ORGANISM: Artificial
<220> FEATURE:
<223> OTHER INFORMATION: Synthetic peptide

<400> SEQUENCE: 229

Asp Lys Phe Lys Ala Phe Tyr Glu Lys Val Ala Glu Phe Trp Lys Asp
1               5                   10                  15

Ala Phe

<210> SEQ ID NO 230
<211> LENGTH: 18
<212> TYPE: PRT
<213> ORGANISM: Artificial
<220> FEATURE:
<223> OTHER INFORMATION: Synthetic peptide

<400> SEQUENCE: 230

Phe Ala Glu Lys Phe Lys Glu Ala Val Lys Asp Tyr Phe Ala Lys Phe
1               5                   10                  15

Trp Asp

<210> SEQ ID NO 231
<211> LENGTH: 18
<212> TYPE: PRT
<213> ORGANISM: Artificial
<220> FEATURE:
<223> OTHER INFORMATION: Synthetic peptide

<400> SEQUENCE: 231

Phe Ala Asp Lys Phe Lys Asp Ala Val Lys Glu Tyr Phe Ala Lys Phe
1               5                   10                  15

Trp Glu
```

<210> SEQ ID NO 232
<211> LENGTH: 18
<212> TYPE: PRT
<213> ORGANISM: Artificial
<220> FEATURE:
<223> OTHER INFORMATION: Synthetic peptide

<400> SEQUENCE: 232

Phe Ala Asp Lys Phe Lys Glu Ala Val Lys Asp Tyr Phe Ala Lys Phe
1               5                   10                  15

Trp Glu

<210> SEQ ID NO 233
<211> LENGTH: 18
<212> TYPE: PRT
<213> ORGANISM: Artificial
<220> FEATURE:
<223> OTHER INFORMATION: Synthetic peptide

<400> SEQUENCE: 233

Phe Ala Glu Lys Phe Lys Asp Ala Val Lys Glu Tyr Phe Ala Lys Phe
1               5                   10                  15

Trp Asp

<210> SEQ ID NO 234
<211> LENGTH: 18
<212> TYPE: PRT
<213> ORGANISM: Artificial
<220> FEATURE:
<223> OTHER INFORMATION: Synthetic peptide

<400> SEQUENCE: 234

Phe Ala Glu Lys Phe Lys Asp Ala Val Lys Asp Tyr Phe Ala Lys Phe
1               5                   10                  15

Trp Glu

<210> SEQ ID NO 235
<211> LENGTH: 18
<212> TYPE: PRT
<213> ORGANISM: Artificial
<220> FEATURE:
<223> OTHER INFORMATION: Synthetic peptide

<400> SEQUENCE: 235

Phe Trp Glu Lys Phe Lys Glu Ala Val Lys Asp Tyr Phe Ala Lys Phe
1               5                   10                  15

Ala Asp

<210> SEQ ID NO 236
<211> LENGTH: 18
<212> TYPE: PRT
<213> ORGANISM: Artificial
<220> FEATURE:
<223> OTHER INFORMATION: Synthetic peptide

<400> SEQUENCE: 236

Phe Trp Asp Lys Phe Lys Asp Ala Val Lys Glu Tyr Phe Ala Lys Phe
1               5                   10                  15

Ala Glu

<210> SEQ ID NO 237
<211> LENGTH: 18
<212> TYPE: PRT

```
<213> ORGANISM: Artificial
<220> FEATURE:
<223> OTHER INFORMATION: Synthetic peptide

<400> SEQUENCE: 237

Phe Ala Asp Lys Phe Lys Glu Ala Val Lys Asp Tyr Phe Ala Lys Phe
1               5                   10                  15
Trp Glu

<210> SEQ ID NO 238
<211> LENGTH: 18
<212> TYPE: PRT
<213> ORGANISM: Artificial
<220> FEATURE:
<223> OTHER INFORMATION: Synthetic peptide

<400> SEQUENCE: 238

Phe Ala Glu Lys Phe Lys Asp Ala Val Lys Glu Tyr Phe Ala Lys Phe
1               5                   10                  15
Trp Asp

<210> SEQ ID NO 239
<211> LENGTH: 18
<212> TYPE: PRT
<213> ORGANISM: Artificial
<220> FEATURE:
<223> OTHER INFORMATION: Synthetic peptide

<400> SEQUENCE: 239

Phe Ala Glu Lys Phe Lys Asp Ala Val Lys Asp Tyr Phe Ala Lys Phe
1               5                   10                  15
Trp Glu

<210> SEQ ID NO 240
<211> LENGTH: 18
<212> TYPE: PRT
<213> ORGANISM: Artificial
<220> FEATURE:
<223> OTHER INFORMATION: Synthetic peptide

<400> SEQUENCE: 240

Phe Phe Glu Lys Phe Lys Glu Ala Val Lys Asp Tyr Phe Ala Lys Ala
1               5                   10                  15
Trp Asp

<210> SEQ ID NO 241
<211> LENGTH: 18
<212> TYPE: PRT
<213> ORGANISM: Artificial
<220> FEATURE:
<223> OTHER INFORMATION: Synthetic peptide

<400> SEQUENCE: 241

Phe Phe Asp Lys Phe Lys Asp Ala Val Lys Glu Tyr Phe Ala Lys Ala
1               5                   10                  15
Trp Glu

<210> SEQ ID NO 242
<211> LENGTH: 18
<212> TYPE: PRT
<213> ORGANISM: Artificial
<220> FEATURE:
<223> OTHER INFORMATION: Synthetic peptide
```

<400> SEQUENCE: 242

Phe Phe Asp Lys Phe Lys Glu Ala Val Lys Asp Tyr Phe Ala Lys Ala
1               5                   10                  15

Trp Glu

<210> SEQ ID NO 243
<211> LENGTH: 18
<212> TYPE: PRT
<213> ORGANISM: Artificial
<220> FEATURE:
<223> OTHER INFORMATION: Synthetic peptide

<400> SEQUENCE: 243

Phe Phe Glu Lys Phe Lys Asp Ala Val Lys Glu Tyr Phe Ala Lys Ala
1               5                   10                  15

Trp Asp

<210> SEQ ID NO 244
<211> LENGTH: 18
<212> TYPE: PRT
<213> ORGANISM: Artificial
<220> FEATURE:
<223> OTHER INFORMATION: Synthetic peptide

<400> SEQUENCE: 244

Phe Phe Glu Lys Phe Lys Asp Ala Val Lys Asp Tyr Phe Ala Lys Ala
1               5                   10                  15

Trp Glu

<210> SEQ ID NO 245
<211> LENGTH: 18
<212> TYPE: PRT
<213> ORGANISM: Artificial
<220> FEATURE:
<223> OTHER INFORMATION: Synthetic peptide

<400> SEQUENCE: 245

Phe Ala Glu Lys Ala Lys Glu Phe Val Lys Asp Tyr Phe Ala Lys Phe
1               5                   10                  15

Trp Asp

<210> SEQ ID NO 246
<211> LENGTH: 18
<212> TYPE: PRT
<213> ORGANISM: Artificial
<220> FEATURE:
<223> OTHER INFORMATION: Synthetic peptide

<400> SEQUENCE: 246

Phe Ala Asp Lys Ala Lys Asp Phe Val Lys Glu Tyr Phe Ala Lys Phe
1               5                   10                  15

Trp Glu

<210> SEQ ID NO 247
<211> LENGTH: 18
<212> TYPE: PRT
<213> ORGANISM: Artificial
<220> FEATURE:
<223> OTHER INFORMATION: Synthetic peptide

<400> SEQUENCE: 247

Phe Ala Asp Lys Ala Lys Glu Phe Val Lys Asp Tyr Phe Ala Lys Phe
1               5                   10                  15

Trp Glu

<210> SEQ ID NO 248
<211> LENGTH: 18
<212> TYPE: PRT
<213> ORGANISM: Artificial
<220> FEATURE:
<223> OTHER INFORMATION: Synthetic peptide

<400> SEQUENCE: 248

Phe Ala Glu Lys Ala Lys Asp Phe Val Lys Glu Tyr Phe Ala Lys Phe
1               5                   10                  15

Trp Asp

<210> SEQ ID NO 249
<211> LENGTH: 18
<212> TYPE: PRT
<213> ORGANISM: Artificial
<220> FEATURE:
<223> OTHER INFORMATION: Synthetic peptide

<400> SEQUENCE: 249

Phe Ala Glu Lys Ala Lys Asp Phe Val Lys Asp Tyr Phe Ala Lys Phe
1               5                   10                  15

Trp Glu

<210> SEQ ID NO 250
<211> LENGTH: 18
<212> TYPE: PRT
<213> ORGANISM: Artificial
<220> FEATURE:
<223> OTHER INFORMATION: Synthetic peptide

<400> SEQUENCE: 250

Phe Ala Glu Lys Phe Lys Glu Val Ala Lys Asp Tyr Phe Ala Lys Phe
1               5                   10                  15

Trp Asp

<210> SEQ ID NO 251
<211> LENGTH: 18
<212> TYPE: PRT
<213> ORGANISM: Artificial
<220> FEATURE:
<223> OTHER INFORMATION: Synthetic peptide

<400> SEQUENCE: 251

Phe Ala Asp Lys Phe Lys Asp Val Ala Lys Glu Tyr Phe Ala Lys Phe
1               5                   10                  15

Trp Glu

<210> SEQ ID NO 252
<211> LENGTH: 18
<212> TYPE: PRT
<213> ORGANISM: Artificial
<220> FEATURE:
<223> OTHER INFORMATION: Synthetic peptide

<400> SEQUENCE: 252

Phe Ala Asp Lys Phe Lys Glu Val Ala Lys Asp Tyr Phe Ala Lys Phe
1               5                   10                  15

Trp Glu

-continued

```
<210> SEQ ID NO 253
<211> LENGTH: 18
<212> TYPE: PRT
<213> ORGANISM: Artificial
<220> FEATURE:
<223> OTHER INFORMATION: Synthetic peptide

<400> SEQUENCE: 253

Phe Ala Glu Lys Phe Lys Asp Val Ala Lys Glu Tyr Phe Ala Lys Phe
1               5                   10                  15

Trp Asp

<210> SEQ ID NO 254
<211> LENGTH: 18
<212> TYPE: PRT
<213> ORGANISM: Artificial
<220> FEATURE:
<223> OTHER INFORMATION: Synthetic peptide

<400> SEQUENCE: 254

Phe Ala Glu Lys Phe Lys Asp Val Ala Lys Asp Tyr Phe Ala Lys Phe
1               5                   10                  15

Trp Glu

<210> SEQ ID NO 255
<211> LENGTH: 18
<212> TYPE: PRT
<213> ORGANISM: Artificial
<220> FEATURE:
<223> OTHER INFORMATION: Synthetic peptide

<400> SEQUENCE: 255

Phe Ala Glu Lys Phe Lys Glu Ala Tyr Lys Asp Val Phe Ala Lys Phe
1               5                   10                  15

Trp Asp

<210> SEQ ID NO 256
<211> LENGTH: 18
<212> TYPE: PRT
<213> ORGANISM: Artificial
<220> FEATURE:
<223> OTHER INFORMATION: Synthetic peptide

<400> SEQUENCE: 256

Phe Ala Asp Lys Phe Lys Asp Ala Tyr Lys Glu Val Phe Ala Lys Phe
1               5                   10                  15

Trp Glu

<210> SEQ ID NO 257
<211> LENGTH: 18
<212> TYPE: PRT
<213> ORGANISM: Artificial
<220> FEATURE:
<223> OTHER INFORMATION: Synthetic peptide

<400> SEQUENCE: 257

Phe Ala Asp Lys Phe Lys Glu Ala Tyr Lys Asp Val Phe Ala Lys Phe
1               5                   10                  15

Trp Glu

<210> SEQ ID NO 258
<211> LENGTH: 18
<212> TYPE: PRT
<213> ORGANISM: Artificial
```

-continued

<220> FEATURE:
<223> OTHER INFORMATION: Synthetic peptide

<400> SEQUENCE: 258

Phe Ala Glu Lys Phe Lys Asp Ala Tyr Lys Glu Val Phe Ala Lys Phe
1               5                   10                  15

Trp Asp

<210> SEQ ID NO 259
<211> LENGTH: 18
<212> TYPE: PRT
<213> ORGANISM: Artificial
<220> FEATURE:
<223> OTHER INFORMATION: Synthetic peptide

<400> SEQUENCE: 259

Phe Ala Glu Lys Phe Lys Asp Ala Tyr Lys Asp Val Phe Ala Lys Phe
1               5                   10                  15

Trp Glu

<210> SEQ ID NO 260
<211> LENGTH: 18
<212> TYPE: PRT
<213> ORGANISM: Artificial
<220> FEATURE:
<223> OTHER INFORMATION: Synthetic peptide

<400> SEQUENCE: 260

Phe Ala Glu Lys Phe Lys Glu Ala Val Lys Asp Phe Tyr Ala Lys Phe
1               5                   10                  15

Trp Asp

<210> SEQ ID NO 261
<211> LENGTH: 18
<212> TYPE: PRT
<213> ORGANISM: Artificial
<220> FEATURE:
<223> OTHER INFORMATION: Synthetic peptide

<400> SEQUENCE: 261

Phe Ala Asp Lys Phe Lys Asp Ala Val Lys Glu Phe Tyr Ala Lys Phe
1               5                   10                  15

Trp Glu

<210> SEQ ID NO 262
<211> LENGTH: 18
<212> TYPE: PRT
<213> ORGANISM: Artificial
<220> FEATURE:
<223> OTHER INFORMATION: Synthetic peptide

<400> SEQUENCE: 262

Phe Ala Asp Lys Phe Lys Glu Ala Val Lys Asp Phe Tyr Ala Lys Phe
1               5                   10                  15

Trp Glu

<210> SEQ ID NO 263
<211> LENGTH: 18
<212> TYPE: PRT
<213> ORGANISM: Artificial
<220> FEATURE:
<223> OTHER INFORMATION: Synthetic peptide

<400> SEQUENCE: 263

```
Phe Ala Glu Lys Phe Lys Asp Ala Val Lys Glu Phe Tyr Ala Lys Phe
1               5                   10                  15

Trp Asp

<210> SEQ ID NO 264
<211> LENGTH: 18
<212> TYPE: PRT
<213> ORGANISM: Artificial
<220> FEATURE:
<223> OTHER INFORMATION: Synthetic peptide

<400> SEQUENCE: 264

Phe Ala Glu Lys Phe Lys Asp Ala Val Lys Asp Phe Tyr Ala Lys Phe
1               5                   10                  15

Trp Glu

<210> SEQ ID NO 265
<211> LENGTH: 18
<212> TYPE: PRT
<213> ORGANISM: Artificial
<220> FEATURE:
<223> OTHER INFORMATION: Synthetic peptide

<400> SEQUENCE: 265

Phe Ala Glu Lys Phe Trp Glu Ala Val Lys Asp Tyr Phe Ala Lys Phe
1               5                   10                  15

Lys Asp

<210> SEQ ID NO 266
<211> LENGTH: 18
<212> TYPE: PRT
<213> ORGANISM: Artificial
<220> FEATURE:
<223> OTHER INFORMATION: Synthetic peptide

<400> SEQUENCE: 266

Phe Ala Asp Lys Phe Trp Asp Ala Val Lys Glu Tyr Phe Ala Lys Phe
1               5                   10                  15

Lys Glu

<210> SEQ ID NO 267
<211> LENGTH: 18
<212> TYPE: PRT
<213> ORGANISM: Artificial
<220> FEATURE:
<223> OTHER INFORMATION: Synthetic peptide

<400> SEQUENCE: 267

Phe Ala Asp Lys Phe Trp Glu Ala Val Lys Asp Tyr Phe Ala Lys Phe
1               5                   10                  15

Lys Glu

<210> SEQ ID NO 268
<211> LENGTH: 18
<212> TYPE: PRT
<213> ORGANISM: Artificial
<220> FEATURE:
<223> OTHER INFORMATION: Synthetic peptide

<400> SEQUENCE: 268

Phe Ala Glu Lys Phe Trp Asp Ala Val Lys Glu Tyr Phe Ala Lys Phe
1               5                   10                  15
```

Lys Asp

<210> SEQ ID NO 269
<211> LENGTH: 18
<212> TYPE: PRT
<213> ORGANISM: Artificial
<220> FEATURE:
<223> OTHER INFORMATION: Synthetic peptide

<400> SEQUENCE: 269

Phe Ala Glu Lys Phe Trp Asp Ala Val Lys Asp Tyr Phe Ala Lys Phe
1               5                   10                  15

Lys Glu

<210> SEQ ID NO 270
<211> LENGTH: 18
<212> TYPE: PRT
<213> ORGANISM: Artificial
<220> FEATURE:
<223> OTHER INFORMATION: Synthetic peptide

<400> SEQUENCE: 270

Ala Phe Glu Lys Phe Lys Glu Ala Val Lys Asp Tyr Phe Ala Lys Phe
1               5                   10                  15

Trp Asp

<210> SEQ ID NO 271
<211> LENGTH: 18
<212> TYPE: PRT
<213> ORGANISM: Artificial
<220> FEATURE:
<223> OTHER INFORMATION: Synthetic peptide

<400> SEQUENCE: 271

Ala Phe Asp Lys Phe Lys Asp Ala Val Lys Glu Tyr Phe Ala Lys Phe
1               5                   10                  15

Trp Glu

<210> SEQ ID NO 272
<211> LENGTH: 18
<212> TYPE: PRT
<213> ORGANISM: Artificial
<220> FEATURE:
<223> OTHER INFORMATION: Synthetic peptide

<400> SEQUENCE: 272

Ala Phe Asp Lys Phe Lys Glu Ala Val Lys Asp Tyr Phe Ala Lys Phe
1               5                   10                  15

Trp Glu

<210> SEQ ID NO 273
<211> LENGTH: 18
<212> TYPE: PRT
<213> ORGANISM: Artificial
<220> FEATURE:
<223> OTHER INFORMATION: Synthetic peptide

<400> SEQUENCE: 273

Ala Phe Glu Lys Phe Lys Asp Ala Val Lys Glu Tyr Phe Ala Lys Phe
1               5                   10                  15

Trp Asp

<210> SEQ ID NO 274

```
<211> LENGTH: 18
<212> TYPE: PRT
<213> ORGANISM: Artificial
<220> FEATURE:
<223> OTHER INFORMATION: Synthetic peptide

<400> SEQUENCE: 274

Ala Phe Glu Lys Phe Lys Asp Ala Val Lys Asp Tyr Phe Ala Lys Phe
1               5                   10                  15

Trp Glu

<210> SEQ ID NO 275
<211> LENGTH: 18
<212> TYPE: PRT
<213> ORGANISM: Artificial
<220> FEATURE:
<223> OTHER INFORMATION: Synthetic peptide

<400> SEQUENCE: 275

Val Ala Glu Lys Phe Lys Glu Ala Phe Lys Asp Tyr Phe Ala Lys Phe
1               5                   10                  15

Trp Asp

<210> SEQ ID NO 276
<211> LENGTH: 18
<212> TYPE: PRT
<213> ORGANISM: Artificial
<220> FEATURE:
<223> OTHER INFORMATION: Synthetic peptide

<400> SEQUENCE: 276

Val Ala Asp Lys Phe Lys Asp Ala Phe Lys Glu Tyr Phe Ala Lys Phe
1               5                   10                  15

Trp Glu

<210> SEQ ID NO 277
<211> LENGTH: 18
<212> TYPE: PRT
<213> ORGANISM: Artificial
<220> FEATURE:
<223> OTHER INFORMATION: Synthetic peptide

<400> SEQUENCE: 277

Val Ala Asp Lys Phe Lys Glu Ala Phe Lys Asp Tyr Phe Ala Lys Phe
1               5                   10                  15

Trp Glu

<210> SEQ ID NO 278
<211> LENGTH: 18
<212> TYPE: PRT
<213> ORGANISM: Artificial
<220> FEATURE:
<223> OTHER INFORMATION: Synthetic peptide

<400> SEQUENCE: 278

Val Ala Glu Lys Phe Lys Asp Ala Phe Lys Glu Tyr Phe Ala Lys Phe
1               5                   10                  15

Trp Asp

<210> SEQ ID NO 279
<211> LENGTH: 18
<212> TYPE: PRT
<213> ORGANISM: Artificial
<220> FEATURE:
```

```
<223> OTHER INFORMATION: Synthetic peptide

<400> SEQUENCE: 279

Val Ala Glu Lys Phe Lys Asp Ala Phe Lys Asp Tyr Phe Ala Lys Phe
1               5                   10                  15

Trp Glu

<210> SEQ ID NO 280
<211> LENGTH: 18
<212> TYPE: PRT
<213> ORGANISM: Artificial
<220> FEATURE:
<223> OTHER INFORMATION: Synthetic peptide

<400> SEQUENCE: 280

Tyr Ala Glu Lys Phe Lys Glu Ala Val Lys Asp Phe Phe Ala Lys Phe
1               5                   10                  15

Trp Asp

<210> SEQ ID NO 281
<211> LENGTH: 18
<212> TYPE: PRT
<213> ORGANISM: Artificial
<220> FEATURE:
<223> OTHER INFORMATION: Synthetic peptide

<400> SEQUENCE: 281

Tyr Ala Asp Lys Phe Lys Asp Ala Val Lys Glu Phe Phe Ala Lys Phe
1               5                   10                  15

Trp Glu

<210> SEQ ID NO 282
<211> LENGTH: 18
<212> TYPE: PRT
<213> ORGANISM: Artificial
<220> FEATURE:
<223> OTHER INFORMATION: Synthetic peptide

<400> SEQUENCE: 282

Tyr Ala Asp Lys Phe Lys Glu Ala Val Lys Asp Phe Phe Ala Lys Phe
1               5                   10                  15

Trp Glu

<210> SEQ ID NO 283
<211> LENGTH: 18
<212> TYPE: PRT
<213> ORGANISM: Artificial
<220> FEATURE:
<223> OTHER INFORMATION: Synthetic peptide

<400> SEQUENCE: 283

Tyr Ala Glu Lys Phe Lys Asp Ala Val Lys Glu Phe Phe Ala Lys Phe
1               5                   10                  15

Trp Asp

<210> SEQ ID NO 284
<211> LENGTH: 18
<212> TYPE: PRT
<213> ORGANISM: Artificial
<220> FEATURE:
<223> OTHER INFORMATION: Synthetic peptide

<400> SEQUENCE: 284
```

Tyr Ala Glu Lys Phe Lys Asp Ala Val Lys Asp Phe Phe Ala Lys Phe
1               5                   10                  15

Trp Glu

<210> SEQ ID NO 285
<211> LENGTH: 18
<212> TYPE: PRT
<213> ORGANISM: Artificial
<220> FEATURE:
<223> OTHER INFORMATION: Synthetic peptide

<400> SEQUENCE: 285

Ala Ala Glu Lys Phe Lys Glu Phe Val Lys Asp Tyr Phe Ala Lys Phe
1               5                   10                  15

Trp Asp

<210> SEQ ID NO 286
<211> LENGTH: 18
<212> TYPE: PRT
<213> ORGANISM: Artificial
<220> FEATURE:
<223> OTHER INFORMATION: Synthetic peptide

<400> SEQUENCE: 286

Ala Ala Asp Lys Phe Lys Asp Phe Val Lys Glu Tyr Phe Ala Lys Phe
1               5                   10                  15

Trp Glu

<210> SEQ ID NO 287
<211> LENGTH: 18
<212> TYPE: PRT
<213> ORGANISM: Artificial
<220> FEATURE:
<223> OTHER INFORMATION: Synthetic peptide

<400> SEQUENCE: 287

Ala Ala Asp Lys Phe Lys Glu Phe Val Lys Asp Tyr Phe Ala Lys Phe
1               5                   10                  15

Trp Glu

<210> SEQ ID NO 288
<211> LENGTH: 18
<212> TYPE: PRT
<213> ORGANISM: Artificial
<220> FEATURE:
<223> OTHER INFORMATION: Synthetic peptide

<400> SEQUENCE: 288

Ala Ala Glu Lys Phe Lys Asp Phe Val Lys Glu Tyr Phe Ala Lys Phe
1               5                   10                  15

Trp Asp

<210> SEQ ID NO 289
<211> LENGTH: 18
<212> TYPE: PRT
<213> ORGANISM: Artificial
<220> FEATURE:
<223> OTHER INFORMATION: Synthetic peptide

<400> SEQUENCE: 289

Ala Ala Glu Lys Phe Lys Asp Phe Val Lys Asp Tyr Phe Ala Lys Phe
1               5                   10                  15

Trp Glu

-continued

```
<210> SEQ ID NO 290
<211> LENGTH: 18
<212> TYPE: PRT
<213> ORGANISM: Artificial
<220> FEATURE:
<223> OTHER INFORMATION: Synthetic peptide

<400> SEQUENCE: 290

Phe Phe Glu Lys Ala Lys Glu Ala Val Lys Asp Tyr Phe Ala Lys Phe
1               5                   10                  15

Trp Asp

<210> SEQ ID NO 291
<211> LENGTH: 18
<212> TYPE: PRT
<213> ORGANISM: Artificial
<220> FEATURE:
<223> OTHER INFORMATION: Synthetic peptide

<400> SEQUENCE: 291

Phe Phe Asp Lys Ala Lys Asp Ala Val Lys Glu Tyr Phe Ala Lys Phe
1               5                   10                  15

Trp Glu

<210> SEQ ID NO 292
<211> LENGTH: 18
<212> TYPE: PRT
<213> ORGANISM: Artificial
<220> FEATURE:
<223> OTHER INFORMATION: Synthetic peptide

<400> SEQUENCE: 292

Phe Phe Asp Lys Ala Lys Glu Ala Val Lys Asp Tyr Phe Ala Lys Phe
1               5                   10                  15

Trp Glu

<210> SEQ ID NO 293
<211> LENGTH: 18
<212> TYPE: PRT
<213> ORGANISM: Artificial
<220> FEATURE:
<223> OTHER INFORMATION: Synthetic peptide

<400> SEQUENCE: 293

Phe Phe Glu Lys Ala Lys Asp Ala Val Lys Glu Tyr Phe Ala Lys Phe
1               5                   10                  15

Trp Asp

<210> SEQ ID NO 294
<211> LENGTH: 18
<212> TYPE: PRT
<213> ORGANISM: Artificial
<220> FEATURE:
<223> OTHER INFORMATION: Synthetic peptide

<400> SEQUENCE: 294

Phe Phe Glu Lys Ala Lys Asp Ala Val Lys Asp Tyr Phe Ala Lys Phe
1               5                   10                  15

Trp Glu

<210> SEQ ID NO 295
<211> LENGTH: 18
```

<212> TYPE: PRT
<213> ORGANISM: Artificial
<220> FEATURE:
<223> OTHER INFORMATION: Synthetic peptide

<400> SEQUENCE: 295

Phe Tyr Glu Lys Phe Lys Glu Ala Val Lys Asp Ala Phe Ala Lys Phe
1               5                   10                  15

Trp Asp

<210> SEQ ID NO 296
<211> LENGTH: 18
<212> TYPE: PRT
<213> ORGANISM: Artificial
<220> FEATURE:
<223> OTHER INFORMATION: Synthetic peptide

<400> SEQUENCE: 296

Phe Tyr Asp Lys Phe Lys Asp Ala Val Lys Glu Ala Phe Ala Lys Phe
1               5                   10                  15

Trp Glu

<210> SEQ ID NO 297
<211> LENGTH: 18
<212> TYPE: PRT
<213> ORGANISM: Artificial
<220> FEATURE:
<223> OTHER INFORMATION: Synthetic peptide

<400> SEQUENCE: 297

Phe Tyr Asp Lys Phe Lys Glu Ala Val Lys Asp Ala Phe Ala Lys Phe
1               5                   10                  15

Trp Glu

<210> SEQ ID NO 298
<211> LENGTH: 18
<212> TYPE: PRT
<213> ORGANISM: Artificial
<220> FEATURE:
<223> OTHER INFORMATION: Synthetic peptide

<400> SEQUENCE: 298

Phe Tyr Glu Lys Phe Lys Asp Ala Val Lys Glu Ala Phe Ala Lys Phe
1               5                   10                  15

Trp Asp

<210> SEQ ID NO 299
<211> LENGTH: 18
<212> TYPE: PRT
<213> ORGANISM: Artificial
<220> FEATURE:
<223> OTHER INFORMATION: Synthetic peptide

<400> SEQUENCE: 299

Phe Tyr Glu Lys Phe Lys Asp Ala Val Lys Asp Ala Phe Ala Lys Phe
1               5                   10                  15

Trp Glu

<210> SEQ ID NO 300
<211> LENGTH: 18
<212> TYPE: PRT
<213> ORGANISM: Artificial
<220> FEATURE:
<223> OTHER INFORMATION: Synthetic peptide -continued

```
<400> SEQUENCE: 300

Phe Val Glu Lys Phe Lys Glu Ala Ala Lys Asp Tyr Phe Ala Lys Phe
1               5                   10                  15

Trp Asp

<210> SEQ ID NO 301
<211> LENGTH: 18
<212> TYPE: PRT
<213> ORGANISM: Artificial
<220> FEATURE:
<223> OTHER INFORMATION: Synthetic peptide

<400> SEQUENCE: 301

Phe Val Asp Lys Phe Lys Asp Ala Ala Lys Glu Tyr Phe Ala Lys Phe
1               5                   10                  15

Trp Glu

<210> SEQ ID NO 302
<211> LENGTH: 18
<212> TYPE: PRT
<213> ORGANISM: Artificial
<220> FEATURE:
<223> OTHER INFORMATION: Synthetic peptide

<400> SEQUENCE: 302

Phe Val Asp Lys Phe Lys Glu Ala Ala Lys Asp Tyr Phe Ala Lys Phe
1               5                   10                  15

Trp Glu

<210> SEQ ID NO 303
<211> LENGTH: 18
<212> TYPE: PRT
<213> ORGANISM: Artificial
<220> FEATURE:
<223> OTHER INFORMATION: Synthetic peptide

<400> SEQUENCE: 303

Phe Val Glu Lys Phe Lys Asp Ala Ala Lys Glu Tyr Phe Ala Lys Phe
1               5                   10                  15

Trp Asp

<210> SEQ ID NO 304
<211> LENGTH: 18
<212> TYPE: PRT
<213> ORGANISM: Artificial
<220> FEATURE:
<223> OTHER INFORMATION: Synthetic peptide

<400> SEQUENCE: 304

Phe Val Glu Lys Phe Lys Asp Ala Ala Lys Asp Tyr Phe Ala Lys Phe
1               5                   10                  15

Trp Glu

<210> SEQ ID NO 305
<211> LENGTH: 18
<212> TYPE: PRT
<213> ORGANISM: Artificial
<220> FEATURE:
<223> OTHER INFORMATION: Synthetic peptide

<400> SEQUENCE: 305

Phe Ala Glu Lys Tyr Lys Glu Ala Val Lys Asp Phe Phe Ala Lys Phe
```

-continued

```
1               5                   10                  15

Trp Asp

<210> SEQ ID NO 306
<211> LENGTH: 18
<212> TYPE: PRT
<213> ORGANISM: Artificial
<220> FEATURE:
<223> OTHER INFORMATION: Synthetic peptide

<400> SEQUENCE: 306

Phe Ala Asp Lys Tyr Lys Asp Ala Val Lys Glu Phe Phe Ala Lys Phe
1               5                   10                  15

Trp Glu

<210> SEQ ID NO 307
<211> LENGTH: 18
<212> TYPE: PRT
<213> ORGANISM: Artificial
<220> FEATURE:
<223> OTHER INFORMATION: Synthetic peptide

<400> SEQUENCE: 307

Phe Ala Asp Lys Tyr Lys Glu Ala Val Lys Asp Phe Phe Ala Lys Phe
1               5                   10                  15

Trp Glu

<210> SEQ ID NO 308
<211> LENGTH: 18
<212> TYPE: PRT
<213> ORGANISM: Artificial
<220> FEATURE:
<223> OTHER INFORMATION: Synthetic peptide

<400> SEQUENCE: 308

Phe Ala Glu Lys Tyr Lys Asp Ala Val Lys Glu Phe Phe Ala Lys Phe
1               5                   10                  15

Trp Asp

<210> SEQ ID NO 309
<211> LENGTH: 18
<212> TYPE: PRT
<213> ORGANISM: Artificial
<220> FEATURE:
<223> OTHER INFORMATION: Synthetic peptide

<400> SEQUENCE: 309

Phe Ala Glu Lys Tyr Lys Asp Ala Val Lys Asp Phe Phe Ala Lys Phe
1               5                   10                  15

Trp Glu

<210> SEQ ID NO 310
<211> LENGTH: 18
<212> TYPE: PRT
<213> ORGANISM: Artificial
<220> FEATURE:
<223> OTHER INFORMATION: Synthetic peptide

<400> SEQUENCE: 310

Phe Ala Glu Lys Val Lys Glu Ala Phe Lys Asp Tyr Phe Ala Lys Phe
1               5                   10                  15

Trp Asp
```

<210> SEQ ID NO 311
<211> LENGTH: 18
<212> TYPE: PRT
<213> ORGANISM: Artificial
<220> FEATURE:
<223> OTHER INFORMATION: Synthetic peptide

<400> SEQUENCE: 311

Phe Ala Asp Lys Val Lys Asp Ala Phe Lys Glu Tyr Phe Ala Lys Phe
1               5                   10                  15

Trp Glu

<210> SEQ ID NO 312
<211> LENGTH: 18
<212> TYPE: PRT
<213> ORGANISM: Artificial
<220> FEATURE:
<223> OTHER INFORMATION: Synthetic peptide

<400> SEQUENCE: 312

Phe Ala Asp Lys Val Lys Glu Ala Phe Lys Asp Tyr Phe Ala Lys Phe
1               5                   10                  15

Trp Glu

<210> SEQ ID NO 313
<211> LENGTH: 18
<212> TYPE: PRT
<213> ORGANISM: Artificial
<220> FEATURE:
<223> OTHER INFORMATION: Synthetic peptide

<400> SEQUENCE: 313

Phe Ala Glu Lys Val Lys Asp Ala Phe Lys Glu Tyr Phe Ala Lys Phe
1               5                   10                  15

Trp Asp

<210> SEQ ID NO 314
<211> LENGTH: 18
<212> TYPE: PRT
<213> ORGANISM: Artificial
<220> FEATURE:
<223> OTHER INFORMATION: Synthetic peptide

<400> SEQUENCE: 314

Phe Ala Glu Lys Val Lys Asp Ala Phe Lys Asp Tyr Phe Ala Lys Phe
1               5                   10                  15

Trp Glu

<210> SEQ ID NO 315
<211> LENGTH: 18
<212> TYPE: PRT
<213> ORGANISM: Artificial
<220> FEATURE:
<223> OTHER INFORMATION: Synthetic peptide

<400> SEQUENCE: 315

Phe Ala Glu Lys Phe Lys Glu Tyr Val Lys Asp Ala Phe Ala Lys Phe
1               5                   10                  15

Trp Asp

<210> SEQ ID NO 316
<211> LENGTH: 18
<212> TYPE: PRT

<213> ORGANISM: Artificial
<220> FEATURE:
<223> OTHER INFORMATION: Synthetic peptide

<400> SEQUENCE: 316

Phe Ala Asp Lys Phe Lys Asp Tyr Val Lys Glu Ala Phe Ala Lys Phe
1               5                   10                  15

Trp Glu

<210> SEQ ID NO 317
<211> LENGTH: 18
<212> TYPE: PRT
<213> ORGANISM: Artificial
<220> FEATURE:
<223> OTHER INFORMATION: Synthetic peptide

<400> SEQUENCE: 317

Phe Ala Asp Lys Phe Lys Glu Tyr Val Lys Asp Ala Phe Ala Lys Phe
1               5                   10                  15

Trp Glu

<210> SEQ ID NO 318
<211> LENGTH: 18
<212> TYPE: PRT
<213> ORGANISM: Artificial
<220> FEATURE:
<223> OTHER INFORMATION: Synthetic peptide

<400> SEQUENCE: 318

Phe Ala Glu Lys Phe Lys Asp Tyr Val Lys Glu Ala Phe Ala Lys Phe
1               5                   10                  15

Trp Asp

<210> SEQ ID NO 319
<211> LENGTH: 18
<212> TYPE: PRT
<213> ORGANISM: Artificial
<220> FEATURE:
<223> OTHER INFORMATION: Synthetic peptide

<400> SEQUENCE: 319

Phe Ala Glu Lys Phe Lys Asp Tyr Val Lys Asp Ala Phe Ala Lys Phe
1               5                   10                  15

Trp Glu

<210> SEQ ID NO 320
<211> LENGTH: 18
<212> TYPE: PRT
<213> ORGANISM: Artificial
<220> FEATURE:
<223> OTHER INFORMATION: Synthetic peptide

<400> SEQUENCE: 320

Phe Ala Glu Lys Phe Lys Glu Ala Phe Lys Asp Tyr Val Ala Lys Phe
1               5                   10                  15

Trp Asp

<210> SEQ ID NO 321
<211> LENGTH: 18
<212> TYPE: PRT
<213> ORGANISM: Artificial
<220> FEATURE:
<223> OTHER INFORMATION: Synthetic peptide

```
<400> SEQUENCE: 321

Phe Ala Asp Lys Phe Lys Asp Ala Phe Lys Glu Tyr Val Ala Lys Phe
1               5                   10                  15

Trp Glu

<210> SEQ ID NO 322
<211> LENGTH: 18
<212> TYPE: PRT
<213> ORGANISM: Artificial
<220> FEATURE:
<223> OTHER INFORMATION: Synthetic peptide

<400> SEQUENCE: 322

Phe Ala Asp Lys Phe Lys Glu Ala Phe Lys Asp Tyr Val Ala Lys Phe
1               5                   10                  15

Trp Glu

<210> SEQ ID NO 323
<211> LENGTH: 18
<212> TYPE: PRT
<213> ORGANISM: Artificial
<220> FEATURE:
<223> OTHER INFORMATION: Synthetic peptide

<400> SEQUENCE: 323

Phe Ala Glu Lys Phe Lys Asp Ala Phe Lys Glu Tyr Val Ala Lys Phe
1               5                   10                  15

Trp Asp

<210> SEQ ID NO 324
<211> LENGTH: 18
<212> TYPE: PRT
<213> ORGANISM: Artificial
<220> FEATURE:
<223> OTHER INFORMATION: Synthetic peptide

<400> SEQUENCE: 324

Phe Ala Glu Lys Phe Lys Asp Ala Phe Lys Asp Tyr Val Ala Lys Phe
1               5                   10                  15

Trp Glu

<210> SEQ ID NO 325
<211> LENGTH: 18
<212> TYPE: PRT
<213> ORGANISM: Artificial
<220> FEATURE:
<223> OTHER INFORMATION: Synthetic peptide

<400> SEQUENCE: 325

Phe Ala Glu Lys Phe Lys Glu Ala Phe Lys Asp Tyr Phe Ala Lys Val
1               5                   10                  15

Trp Asp

<210> SEQ ID NO 326
<211> LENGTH: 18
<212> TYPE: PRT
<213> ORGANISM: Artificial
<220> FEATURE:
<223> OTHER INFORMATION: Synthetic peptide

<400> SEQUENCE: 326

Phe Ala Asp Lys Phe Lys Asp Ala Phe Lys Glu Tyr Phe Ala Lys Val
1               5                   10                  15
```

```
Trp Glu

<210> SEQ ID NO 327
<211> LENGTH: 18
<212> TYPE: PRT
<213> ORGANISM: Artificial
<220> FEATURE:
<223> OTHER INFORMATION: Synthetic peptide

<400> SEQUENCE: 327

Phe Ala Asp Lys Phe Lys Glu Ala Phe Lys Asp Tyr Phe Ala Lys Val
1               5                   10                  15

Trp Glu

<210> SEQ ID NO 328
<211> LENGTH: 18
<212> TYPE: PRT
<213> ORGANISM: Artificial
<220> FEATURE:
<223> OTHER INFORMATION: Synthetic peptide

<400> SEQUENCE: 328

Phe Ala Glu Lys Phe Lys Asp Ala Phe Lys Glu Tyr Phe Ala Lys Val
1               5                   10                  15

Trp Asp

<210> SEQ ID NO 329
<211> LENGTH: 18
<212> TYPE: PRT
<213> ORGANISM: Artificial
<220> FEATURE:
<223> OTHER INFORMATION: Synthetic peptide

<400> SEQUENCE: 329

Phe Ala Glu Lys Phe Lys Asp Ala Phe Lys Asp Tyr Phe Ala Lys Val
1               5                   10                  15

Trp Glu

<210> SEQ ID NO 330
<211> LENGTH: 18
<212> TYPE: PRT
<213> ORGANISM: Artificial
<220> FEATURE:
<223> OTHER INFORMATION: Synthetic peptide

<400> SEQUENCE: 330

Phe Ala Glu Lys Phe Lys Glu Ala Val Lys Asp Phe Phe Ala Lys Tyr
1               5                   10                  15

Trp Asp

<210> SEQ ID NO 331
<211> LENGTH: 18
<212> TYPE: PRT
<213> ORGANISM: Artificial
<220> FEATURE:
<223> OTHER INFORMATION: Synthetic peptide

<400> SEQUENCE: 331

Phe Ala Asp Lys Phe Lys Asp Ala Val Lys Glu Phe Phe Ala Lys Tyr
1               5                   10                  15

Trp Glu
```

```
<210> SEQ ID NO 332
<211> LENGTH: 18
<212> TYPE: PRT
<213> ORGANISM: Artificial
<220> FEATURE:
<223> OTHER INFORMATION: Synthetic peptide

<400> SEQUENCE: 332

Phe Ala Asp Lys Phe Lys Glu Ala Val Lys Asp Phe Phe Ala Lys Tyr
1               5                   10                  15

Trp Glu

<210> SEQ ID NO 333
<211> LENGTH: 18
<212> TYPE: PRT
<213> ORGANISM: Artificial
<220> FEATURE:
<223> OTHER INFORMATION: Synthetic peptide

<400> SEQUENCE: 333

Phe Ala Glu Lys Phe Lys Asp Ala Val Lys Glu Phe Phe Ala Lys Tyr
1               5                   10                  15

Trp Asp

<210> SEQ ID NO 334
<211> LENGTH: 18
<212> TYPE: PRT
<213> ORGANISM: Artificial
<220> FEATURE:
<223> OTHER INFORMATION: Synthetic peptide

<400> SEQUENCE: 334

Phe Ala Glu Lys Phe Lys Asp Ala Val Lys Asp Phe Phe Ala Lys Tyr
1               5                   10                  15

Trp Glu

<210> SEQ ID NO 335
<211> LENGTH: 18
<212> TYPE: PRT
<213> ORGANISM: Artificial
<220> FEATURE:
<223> OTHER INFORMATION: Synthetic peptide

<400> SEQUENCE: 335

Trp Ala Glu Lys Phe Phe Glu Ala Val Lys Asp Tyr Phe Ala Lys Phe
1               5                   10                  15

Lys Asp

<210> SEQ ID NO 336
<211> LENGTH: 18
<212> TYPE: PRT
<213> ORGANISM: Artificial
<220> FEATURE:
<223> OTHER INFORMATION: Synthetic peptide

<400> SEQUENCE: 336

Trp Ala Asp Lys Phe Phe Asp Ala Val Lys Glu Tyr Phe Ala Lys Phe
1               5                   10                  15

Lys Glu

<210> SEQ ID NO 337
<211> LENGTH: 18
<212> TYPE: PRT
<213> ORGANISM: Artificial
```

-continued

<220> FEATURE:
<223> OTHER INFORMATION: Synthetic peptide

<400> SEQUENCE: 337

Trp Ala Asp Lys Phe Phe Glu Ala Val Lys Asp Tyr Phe Ala Lys Phe
1               5                   10                  15

Lys Glu

<210> SEQ ID NO 338
<211> LENGTH: 18
<212> TYPE: PRT
<213> ORGANISM: Artificial
<220> FEATURE:
<223> OTHER INFORMATION: Synthetic peptide

<400> SEQUENCE: 338

Trp Ala Glu Lys Phe Phe Asp Ala Val Lys Glu Tyr Phe Ala Lys Phe
1               5                   10                  15

Lys Asp

<210> SEQ ID NO 339
<211> LENGTH: 18
<212> TYPE: PRT
<213> ORGANISM: Artificial
<220> FEATURE:
<223> OTHER INFORMATION: Synthetic peptide

<400> SEQUENCE: 339

Trp Ala Glu Lys Phe Phe Asp Ala Val Lys Asp Tyr Phe Ala Lys Phe
1               5                   10                  15

Lys Glu

<210> SEQ ID NO 340
<211> LENGTH: 18
<212> TYPE: PRT
<213> ORGANISM: Artificial
<220> FEATURE:
<223> OTHER INFORMATION: Synthetic peptide

<400> SEQUENCE: 340

Phe Ala Glu Lys Trp Phe Glu Ala Val Lys Asp Tyr Phe Ala Lys Phe
1               5                   10                  15

Lys Asp

<210> SEQ ID NO 341
<211> LENGTH: 18
<212> TYPE: PRT
<213> ORGANISM: Artificial
<220> FEATURE:
<223> OTHER INFORMATION: Synthetic peptide

<400> SEQUENCE: 341

Phe Ala Asp Lys Trp Phe Asp Ala Val Lys Glu Tyr Phe Ala Lys Phe
1               5                   10                  15

Lys Glu

<210> SEQ ID NO 342
<211> LENGTH: 18
<212> TYPE: PRT
<213> ORGANISM: Artificial
<220> FEATURE:
<223> OTHER INFORMATION: Synthetic peptide

<400> SEQUENCE: 342

```
Phe Ala Asp Lys Trp Phe Glu Ala Val Lys Asp Tyr Phe Ala Lys Phe
1               5                   10                  15

Lys Glu
```

<210> SEQ ID NO 343
<211> LENGTH: 18
<212> TYPE: PRT
<213> ORGANISM: Artificial
<220> FEATURE:
<223> OTHER INFORMATION: Synthetic peptide

<400> SEQUENCE: 343

```
Phe Ala Glu Lys Trp Phe Asp Ala Val Lys Glu Tyr Phe Ala Lys Phe
1               5                   10                  15

Lys Asp
```

<210> SEQ ID NO 344
<211> LENGTH: 18
<212> TYPE: PRT
<213> ORGANISM: Artificial
<220> FEATURE:
<223> OTHER INFORMATION: Synthetic peptide

<400> SEQUENCE: 344

```
Phe Ala Glu Lys Trp Phe Asp Ala Val Lys Asp Tyr Phe Ala Lys Phe
1               5                   10                  15

Lys Glu
```

<210> SEQ ID NO 345
<211> LENGTH: 18
<212> TYPE: PRT
<213> ORGANISM: Artificial
<220> FEATURE:
<223> OTHER INFORMATION: Synthetic peptide

<400> SEQUENCE: 345

```
Phe Ala Glu Lys Phe Val Glu Ala Trp Lys Asp Tyr Phe Ala Lys Phe
1               5                   10                  15

Lys Asp
```

<210> SEQ ID NO 346
<211> LENGTH: 18
<212> TYPE: PRT
<213> ORGANISM: Artificial
<220> FEATURE:
<223> OTHER INFORMATION: Synthetic peptide

<400> SEQUENCE: 346

```
Phe Ala Asp Lys Phe Val Asp Ala Trp Lys Glu Tyr Phe Ala Lys Phe
1               5                   10                  15

Lys Glu
```

<210> SEQ ID NO 347
<211> LENGTH: 18
<212> TYPE: PRT
<213> ORGANISM: Artificial
<220> FEATURE:
<223> OTHER INFORMATION: Synthetic peptide

<400> SEQUENCE: 347

```
Phe Ala Asp Lys Phe Val Glu Ala Trp Lys Asp Tyr Phe Ala Lys Phe
1               5                   10                  15
```

Lys Glu

<210> SEQ ID NO 348
<211> LENGTH: 18
<212> TYPE: PRT
<213> ORGANISM: Artificial
<220> FEATURE:
<223> OTHER INFORMATION: Synthetic peptide

<400> SEQUENCE: 348

Phe Ala Glu Lys Phe Val Asp Ala Trp Lys Glu Tyr Phe Ala Lys Phe
1               5                   10                  15

Lys Asp

<210> SEQ ID NO 349
<211> LENGTH: 18
<212> TYPE: PRT
<213> ORGANISM: Artificial
<220> FEATURE:
<223> OTHER INFORMATION: Synthetic peptide

<400> SEQUENCE: 349

Phe Ala Glu Lys Phe Val Asp Ala Trp Lys Asp Tyr Phe Ala Lys Phe
1               5                   10                  15

Lys Glu

<210> SEQ ID NO 350
<211> LENGTH: 18
<212> TYPE: PRT
<213> ORGANISM: Artificial
<220> FEATURE:
<223> OTHER INFORMATION: Synthetic peptide

<400> SEQUENCE: 350

Phe Tyr Glu Lys Phe Ala Glu Ala Val Lys Asp Trp Phe Ala Lys Phe
1               5                   10                  15

Lys Asp

<210> SEQ ID NO 351
<211> LENGTH: 18
<212> TYPE: PRT
<213> ORGANISM: Artificial
<220> FEATURE:
<223> OTHER INFORMATION: Synthetic peptide

<400> SEQUENCE: 351

Phe Tyr Asp Lys Phe Ala Asp Ala Val Lys Glu Trp Phe Ala Lys Phe
1               5                   10                  15

Lys Glu

<210> SEQ ID NO 352
<211> LENGTH: 18
<212> TYPE: PRT
<213> ORGANISM: Artificial
<220> FEATURE:
<223> OTHER INFORMATION: Synthetic peptide

<400> SEQUENCE: 352

Phe Tyr Asp Lys Phe Ala Glu Ala Val Lys Asp Trp Phe Ala Lys Phe
1               5                   10                  15

Lys Glu

<210> SEQ ID NO 353

<211> LENGTH: 18
<212> TYPE: PRT
<213> ORGANISM: Artificial
<220> FEATURE:
<223> OTHER INFORMATION: Synthetic peptide

<400> SEQUENCE: 353

Phe Tyr Glu Lys Phe Ala Asp Ala Val Lys Glu Trp Phe Ala Lys Phe
1               5                   10                  15
Lys Asp

<210> SEQ ID NO 354
<211> LENGTH: 18
<212> TYPE: PRT
<213> ORGANISM: Artificial
<220> FEATURE:
<223> OTHER INFORMATION: Synthetic peptide

<400> SEQUENCE: 354

Phe Tyr Glu Lys Phe Ala Asp Ala Val Lys Asp Trp Phe Ala Lys Phe
1               5                   10                  15
Lys Glu

<210> SEQ ID NO 355
<211> LENGTH: 18
<212> TYPE: PRT
<213> ORGANISM: Artificial
<220> FEATURE:
<223> OTHER INFORMATION: Synthetic peptide

<400> SEQUENCE: 355

Asp Trp Phe Lys His Phe Tyr Asp Lys Val Ala Glu Lys Phe Lys Glu
1               5                   10                  15
Ala Phe

<210> SEQ ID NO 356
<211> LENGTH: 18
<212> TYPE: PRT
<213> ORGANISM: Artificial
<220> FEATURE:
<223> OTHER INFORMATION: Synthetic peptide

<400> SEQUENCE: 356

Glu Trp Phe Lys His Phe Tyr Glu Lys Val Ala Asp Lys Phe Lys Asp
1               5                   10                  15
Ala Phe

<210> SEQ ID NO 357
<211> LENGTH: 18
<212> TYPE: PRT
<213> ORGANISM: Artificial
<220> FEATURE:
<223> OTHER INFORMATION: Synthetic peptide

<400> SEQUENCE: 357

Glu Trp Phe Lys His Phe Tyr Asp Lys Val Ala Glu Lys Phe Lys Glu
1               5                   10                  15
Ala Phe

<210> SEQ ID NO 358
<211> LENGTH: 18
<212> TYPE: PRT
<213> ORGANISM: Artificial
<220> FEATURE:

<223> OTHER INFORMATION: Synthetic peptide

<400> SEQUENCE: 358

Asp Trp Phe Lys His Phe Tyr Glu Lys Val Ala Glu Lys Phe Lys Glu
1               5                   10                  15

Ala Phe

<210> SEQ ID NO 359
<211> LENGTH: 18
<212> TYPE: PRT
<213> ORGANISM: Artificial
<220> FEATURE:
<223> OTHER INFORMATION: Synthetic peptide

<400> SEQUENCE: 359

Asp Trp Phe Lys His Phe Tyr Asp Lys Val Ala Asp Lys Phe Lys Glu
1               5                   10                  15

Ala Phe

<210> SEQ ID NO 360
<211> LENGTH: 18
<212> TYPE: PRT
<213> ORGANISM: Artificial
<220> FEATURE:
<223> OTHER INFORMATION: Synthetic peptide

<400> SEQUENCE: 360

Asp Trp Phe Lys His Phe Tyr Asp Lys Val Ala Glu Lys Phe Lys Asp
1               5                   10                  15

Ala Phe

<210> SEQ ID NO 361
<211> LENGTH: 18
<212> TYPE: PRT
<213> ORGANISM: Artificial
<220> FEATURE:
<223> OTHER INFORMATION: Synthetic peptide

<400> SEQUENCE: 361

Asp Trp His Lys Phe Phe Tyr Asp Lys Val Ala Glu Lys Phe Lys Glu
1               5                   10                  15

Ala Phe

<210> SEQ ID NO 362
<211> LENGTH: 18
<212> TYPE: PRT
<213> ORGANISM: Artificial
<220> FEATURE:
<223> OTHER INFORMATION: Synthetic peptide

<400> SEQUENCE: 362

Glu Trp His Lys Phe Phe Tyr Glu Lys Val Ala Asp Lys Phe Lys Asp
1               5                   10                  15

Ala Phe

<210> SEQ ID NO 363
<211> LENGTH: 18
<212> TYPE: PRT
<213> ORGANISM: Artificial
<220> FEATURE:
<223> OTHER INFORMATION: Synthetic peptide

<400> SEQUENCE: 363

Glu Trp His Lys Phe Phe Tyr Asp Lys Val Ala Glu Lys Phe Lys Glu
1               5                   10                  15

Ala Phe

<210> SEQ ID NO 364
<211> LENGTH: 18
<212> TYPE: PRT
<213> ORGANISM: Artificial
<220> FEATURE:
<223> OTHER INFORMATION: Synthetic peptide

<400> SEQUENCE: 364

Asp Trp His Lys Phe Phe Tyr Glu Lys Val Ala Glu Lys Phe Lys Glu
1               5                   10                  15

Ala Phe

<210> SEQ ID NO 365
<211> LENGTH: 18
<212> TYPE: PRT
<213> ORGANISM: Artificial
<220> FEATURE:
<223> OTHER INFORMATION: Synthetic peptide

<400> SEQUENCE: 365

Asp Trp His Lys Phe Phe Tyr Asp Lys Val Ala Asp Lys Phe Lys Glu
1               5                   10                  15

Ala Phe

<210> SEQ ID NO 366
<211> LENGTH: 18
<212> TYPE: PRT
<213> ORGANISM: Artificial
<220> FEATURE:
<223> OTHER INFORMATION: Synthetic peptide

<400> SEQUENCE: 366

Asp Trp His Lys Phe Phe Tyr Asp Lys Val Ala Glu Lys Phe Lys Asp
1               5                   10                  15

Ala Phe

<210> SEQ ID NO 367
<211> LENGTH: 18
<212> TYPE: PRT
<213> ORGANISM: Artificial
<220> FEATURE:
<223> OTHER INFORMATION: Synthetic peptide

<400> SEQUENCE: 367

Asp Trp Phe Lys Phe His Tyr Asp Lys Val Ala Glu Lys Phe Lys Glu
1               5                   10                  15

Ala Phe

<210> SEQ ID NO 368
<211> LENGTH: 18
<212> TYPE: PRT
<213> ORGANISM: Artificial
<220> FEATURE:
<223> OTHER INFORMATION: Synthetic peptide

<400> SEQUENCE: 368

Glu Trp Phe Lys Phe His Tyr Glu Lys Val Ala Asp Lys Phe Lys Asp
1               5                   10                  15

Ala Phe

```
<210> SEQ ID NO 369
<211> LENGTH: 18
<212> TYPE: PRT
<213> ORGANISM: Artificial
<220> FEATURE:
<223> OTHER INFORMATION: Synthetic peptide

<400> SEQUENCE: 369

Glu Trp Phe Lys Phe His Tyr Asp Lys Val Ala Glu Lys Phe Lys Glu
1               5                   10                  15

Ala Phe

<210> SEQ ID NO 370
<211> LENGTH: 18
<212> TYPE: PRT
<213> ORGANISM: Artificial
<220> FEATURE:
<223> OTHER INFORMATION: Synthetic peptide

<400> SEQUENCE: 370

Asp Trp Phe Lys Phe His Tyr Glu Lys Val Ala Glu Lys Phe Lys Glu
1               5                   10                  15

Ala Phe

<210> SEQ ID NO 371
<211> LENGTH: 18
<212> TYPE: PRT
<213> ORGANISM: Artificial
<220> FEATURE:
<223> OTHER INFORMATION: Synthetic peptide

<400> SEQUENCE: 371

Asp Trp Phe Lys Phe His Tyr Asp Lys Val Ala Asp Lys Phe Lys Glu
1               5                   10                  15

Ala Phe

<210> SEQ ID NO 372
<211> LENGTH: 18
<212> TYPE: PRT
<213> ORGANISM: Artificial
<220> FEATURE:
<223> OTHER INFORMATION: Synthetic peptide

<400> SEQUENCE: 372

Asp Trp Phe Lys Phe His Tyr Asp Lys Val Ala Glu Lys Phe Lys Asp
1               5                   10                  15

Ala Phe

<210> SEQ ID NO 373
<211> LENGTH: 18
<212> TYPE: PRT
<213> ORGANISM: Artificial
<220> FEATURE:
<223> OTHER INFORMATION: Synthetic peptide

<400> SEQUENCE: 373

Asp Trp Phe Lys Val Phe Tyr Asp Lys His Ala Glu Lys Phe Lys Glu
1               5                   10                  15

Ala Phe

<210> SEQ ID NO 374
<211> LENGTH: 18
```

<212> TYPE: PRT
<213> ORGANISM: Artificial
<220> FEATURE:
<223> OTHER INFORMATION: Synthetic peptide

<400> SEQUENCE: 374

Glu Trp Phe Lys Val Phe Tyr Glu Lys His Ala Asp Lys Phe Lys Asp
1               5                   10                  15

Ala Phe

<210> SEQ ID NO 375
<211> LENGTH: 18
<212> TYPE: PRT
<213> ORGANISM: Artificial
<220> FEATURE:
<223> OTHER INFORMATION: Synthetic peptide

<400> SEQUENCE: 375

Glu Trp Phe Lys Val Phe Tyr Asp Lys His Ala Glu Lys Phe Lys Glu
1               5                   10                  15

Ala Phe

<210> SEQ ID NO 376
<211> LENGTH: 18
<212> TYPE: PRT
<213> ORGANISM: Artificial
<220> FEATURE:
<223> OTHER INFORMATION: Synthetic peptide

<400> SEQUENCE: 376

Asp Trp Phe Lys Val Phe Tyr Glu Lys His Ala Glu Lys Phe Lys Glu
1               5                   10                  15

Ala Phe

<210> SEQ ID NO 377
<211> LENGTH: 18
<212> TYPE: PRT
<213> ORGANISM: Artificial
<220> FEATURE:
<223> OTHER INFORMATION: Synthetic peptide

<400> SEQUENCE: 377

Asp Trp Phe Lys Val Phe Tyr Asp Lys His Ala Asp Lys Phe Lys Glu
1               5                   10                  15

Ala Phe

<210> SEQ ID NO 378
<211> LENGTH: 18
<212> TYPE: PRT
<213> ORGANISM: Artificial
<220> FEATURE:
<223> OTHER INFORMATION: Synthetic peptide

<400> SEQUENCE: 378

Asp Trp Phe Lys Val Phe Tyr Asp Lys His Ala Glu Lys Phe Lys Asp
1               5                   10                  15

Ala Phe

<210> SEQ ID NO 379
<211> LENGTH: 18
<212> TYPE: PRT
<213> ORGANISM: Artificial
<220> FEATURE:
<223> OTHER INFORMATION: Synthetic peptide

<400> SEQUENCE: 379

Asp Trp Phe Lys Ala Phe Tyr Asp Lys Val Ala Glu Lys Phe Lys Glu
1               5                   10                  15

His Phe

<210> SEQ ID NO 380
<211> LENGTH: 18
<212> TYPE: PRT
<213> ORGANISM: Artificial
<220> FEATURE:
<223> OTHER INFORMATION: Synthetic peptide

<400> SEQUENCE: 380

Glu Trp Phe Lys Ala Phe Tyr Glu Lys Val Ala Asp Lys Phe Lys Asp
1               5                   10                  15

His Phe

<210> SEQ ID NO 381
<211> LENGTH: 18
<212> TYPE: PRT
<213> ORGANISM: Artificial
<220> FEATURE:
<223> OTHER INFORMATION: Synthetic peptide

<400> SEQUENCE: 381

Glu Trp Phe Lys Ala Phe Tyr Asp Lys Val Ala Glu Lys Phe Lys Glu
1               5                   10                  15

His Phe

<210> SEQ ID NO 382
<211> LENGTH: 18
<212> TYPE: PRT
<213> ORGANISM: Artificial
<220> FEATURE:
<223> OTHER INFORMATION: Synthetic peptide

<400> SEQUENCE: 382

Asp Trp Phe Lys Ala Phe Tyr Glu Lys Val Ala Glu Lys Phe Lys Glu
1               5                   10                  15

His Phe

<210> SEQ ID NO 383
<211> LENGTH: 18
<212> TYPE: PRT
<213> ORGANISM: Artificial
<220> FEATURE:
<223> OTHER INFORMATION: Synthetic peptide

<400> SEQUENCE: 383

Asp Trp Phe Lys Ala Phe Tyr Asp Lys Val Ala Asp Lys Phe Lys Glu
1               5                   10                  15

His Phe

<210> SEQ ID NO 384
<211> LENGTH: 18
<212> TYPE: PRT
<213> ORGANISM: Artificial
<220> FEATURE:
<223> OTHER INFORMATION: Synthetic peptide

<400> SEQUENCE: 384

Asp Trp Phe Lys Ala Phe Tyr Asp Lys Val Ala Glu Lys Phe Lys Asp

```
1               5                   10                  15

His Phe

<210> SEQ ID NO 385
<211> LENGTH: 18
<212> TYPE: PRT
<213> ORGANISM: Artificial
<220> FEATURE:
<223> OTHER INFORMATION: Synthetic peptide

<400> SEQUENCE: 385

Asp Trp Phe Lys Ala Phe Tyr Asp Lys Val Ala Glu Lys Phe Lys Glu
1               5                   10                  15

Phe His

<210> SEQ ID NO 386
<211> LENGTH: 18
<212> TYPE: PRT
<213> ORGANISM: Artificial
<220> FEATURE:
<223> OTHER INFORMATION: Synthetic peptide

<400> SEQUENCE: 386

Glu Trp Phe Lys Ala Phe Tyr Glu Lys Val Ala Asp Lys Phe Lys Asp
1               5                   10                  15

Phe His

<210> SEQ ID NO 387
<211> LENGTH: 18
<212> TYPE: PRT
<213> ORGANISM: Artificial
<220> FEATURE:
<223> OTHER INFORMATION: Synthetic peptide

<400> SEQUENCE: 387

Glu Trp Phe Lys Ala Phe Tyr Asp Lys Val Ala Glu Lys Phe Lys Glu
1               5                   10                  15

Phe His

<210> SEQ ID NO 388
<211> LENGTH: 18
<212> TYPE: PRT
<213> ORGANISM: Artificial
<220> FEATURE:
<223> OTHER INFORMATION: Synthetic peptide

<400> SEQUENCE: 388

Asp Trp Phe Lys Ala Phe Tyr Asp Lys Val Ala Glu Lys Phe Lys Glu
1               5                   10                  15

Phe His

<210> SEQ ID NO 389
<211> LENGTH: 18
<212> TYPE: PRT
<213> ORGANISM: Artificial
<220> FEATURE:
<223> OTHER INFORMATION: Synthetic peptide

<400> SEQUENCE: 389

Asp Trp Phe Lys Ala Phe Tyr Glu Lys Val Ala Glu Lys Phe Lys Glu
1               5                   10                  15

Phe His
```

<210> SEQ ID NO 390
<211> LENGTH: 18
<212> TYPE: PRT
<213> ORGANISM: Artificial
<220> FEATURE:
<223> OTHER INFORMATION: Synthetic peptide

<400> SEQUENCE: 390

Asp Trp Phe Lys Ala Phe Tyr Asp Lys Val Ala Glu Lys Phe Lys Glu
1               5                   10                  15

Phe His

<210> SEQ ID NO 391
<211> LENGTH: 18
<212> TYPE: PRT
<213> ORGANISM: Artificial
<220> FEATURE:
<223> OTHER INFORMATION: Synthetic peptide

<400> SEQUENCE: 391

Asp Trp Phe Lys Ala Phe Tyr Asp Lys Val Ala Glu Lys Phe Lys Asp
1               5                   10                  15

Phe His

<210> SEQ ID NO 392
<211> LENGTH: 18
<212> TYPE: PRT
<213> ORGANISM: Artificial
<220> FEATURE:
<223> OTHER INFORMATION: Synthetic peptide

<400> SEQUENCE: 392

Phe Ala Glu Lys Phe Lys Glu Ala Val Lys Asp Tyr Phe Ala Lys Phe
1               5                   10                  15

Trp Asp

<210> SEQ ID NO 393
<211> LENGTH: 18
<212> TYPE: PRT
<213> ORGANISM: Artificial
<220> FEATURE:
<223> OTHER INFORMATION: Synthetic peptide

<400> SEQUENCE: 393

Phe His Glu Lys Phe Lys Glu Ala Val Lys Asp Tyr Phe Ala Lys Phe
1               5                   10                  15

Trp Asp

<210> SEQ ID NO 394
<211> LENGTH: 18
<212> TYPE: PRT
<213> ORGANISM: Artificial
<220> FEATURE:
<223> OTHER INFORMATION: Synthetic peptide

<400> SEQUENCE: 394

Phe His Glu Lys Phe Lys Glu Ala Val Lys Glu Tyr Phe Ala Lys Phe
1               5                   10                  15

Trp Glu

<210> SEQ ID NO 395
<211> LENGTH: 18
<212> TYPE: PRT

-continued

```
<213> ORGANISM: Artificial
<220> FEATURE:
<223> OTHER INFORMATION: Synthetic peptide

<400> SEQUENCE: 395

Phe His Asp Lys Phe Lys Asp Ala Val Lys Asp Tyr Phe Ala Lys Phe
1               5                   10                  15

Trp Asp

<210> SEQ ID NO 396
<211> LENGTH: 18
<212> TYPE: PRT
<213> ORGANISM: Artificial
<220> FEATURE:
<223> OTHER INFORMATION: Synthetic peptide

<400> SEQUENCE: 396

Phe His Asp Lys Phe Lys Asp Ala Val Lys Glu Tyr Phe Ala Lys Phe
1               5                   10                  15

Trp Glu

<210> SEQ ID NO 397
<211> LENGTH: 18
<212> TYPE: PRT
<213> ORGANISM: Artificial
<220> FEATURE:
<223> OTHER INFORMATION: Synthetic peptide

<400> SEQUENCE: 397

Phe His Asp Lys Phe Lys Glu Ala Val Lys Asp Tyr Phe Ala Lys Phe
1               5                   10                  15

Trp Asp

<210> SEQ ID NO 398
<211> LENGTH: 18
<212> TYPE: PRT
<213> ORGANISM: Artificial
<220> FEATURE:
<223> OTHER INFORMATION: Synthetic peptide

<400> SEQUENCE: 398

Phe His Glu Lys Phe Lys Asp Ala Val Lys Asp Tyr Phe Ala Lys Phe
1               5                   10                  15

Trp Asp

<210> SEQ ID NO 399
<211> LENGTH: 18
<212> TYPE: PRT
<213> ORGANISM: Artificial
<220> FEATURE:
<223> OTHER INFORMATION: Synthetic peptide

<400> SEQUENCE: 399

Phe His Glu Lys Phe Lys Glu Ala Val Lys Glu Tyr Phe Ala Lys Phe
1               5                   10                  15

Trp Asp

<210> SEQ ID NO 400
<211> LENGTH: 18
<212> TYPE: PRT
<213> ORGANISM: Artificial
<220> FEATURE:
<223> OTHER INFORMATION: Synthetic peptide
```

```
<400> SEQUENCE: 400

Phe His Glu Lys Phe Lys Glu Ala Val Lys Asp Tyr Phe Ala Lys Phe
1               5                   10                  15

Trp Glu

<210> SEQ ID NO 401
<211> LENGTH: 18
<212> TYPE: PRT
<213> ORGANISM: Artificial
<220> FEATURE:
<223> OTHER INFORMATION: Synthetic peptide

<400> SEQUENCE: 401

His Phe Glu Lys Phe Lys Glu Ala Val Lys Asp Tyr Phe Ala Lys Phe
1               5                   10                  15

Trp Asp

<210> SEQ ID NO 402
<211> LENGTH: 18
<212> TYPE: PRT
<213> ORGANISM: Artificial
<220> FEATURE:
<223> OTHER INFORMATION: Synthetic peptide

<400> SEQUENCE: 402

His Phe Asp Lys Phe Lys Asp Ala Val Lys Glu Tyr Phe Ala Lys Phe
1               5                   10                  15

Trp Glu

<210> SEQ ID NO 403
<211> LENGTH: 18
<212> TYPE: PRT
<213> ORGANISM: Artificial
<220> FEATURE:
<223> OTHER INFORMATION: Synthetic peptide

<400> SEQUENCE: 403

His Phe Glu Lys Phe Lys Glu Ala Val Lys Glu Tyr Phe Ala Lys Phe
1               5                   10                  15

Trp Glu

<210> SEQ ID NO 404
<211> LENGTH: 18
<212> TYPE: PRT
<213> ORGANISM: Artificial
<220> FEATURE:
<223> OTHER INFORMATION: Synthetic peptide

<400> SEQUENCE: 404

His Phe Asp Lys Phe Lys Glu Ala Val Lys Asp Tyr Phe Ala Lys Phe
1               5                   10                  15

Trp Asp

<210> SEQ ID NO 405
<211> LENGTH: 18
<212> TYPE: PRT
<213> ORGANISM: Artificial
<220> FEATURE:
<223> OTHER INFORMATION: Synthetic peptide

<400> SEQUENCE: 405

His Phe Glu Lys Phe Lys Asp Ala Val Lys Asp Tyr Phe Ala Lys Phe
1               5                   10                  15
```

Trp Asp

<210> SEQ ID NO 406
<211> LENGTH: 18
<212> TYPE: PRT
<213> ORGANISM: Artificial
<220> FEATURE:
<223> OTHER INFORMATION: Synthetic peptide

<400> SEQUENCE: 406

His Phe Glu Lys Phe Lys Glu Ala Val Lys Glu Tyr Phe Ala Lys Phe
1               5                   10                  15

Trp Asp

<210> SEQ ID NO 407
<211> LENGTH: 18
<212> TYPE: PRT
<213> ORGANISM: Artificial
<220> FEATURE:
<223> OTHER INFORMATION: Synthetic peptide

<400> SEQUENCE: 407

His Phe Glu Lys Phe Lys Glu Ala Val Lys Asp Tyr Phe Ala Lys Phe
1               5                   10                  15

Trp Glu

<210> SEQ ID NO 408
<211> LENGTH: 18
<212> TYPE: PRT
<213> ORGANISM: Artificial
<220> FEATURE:
<223> OTHER INFORMATION: Synthetic peptide

<400> SEQUENCE: 408

Phe Phe Glu Lys His Lys Glu Ala Val Lys Asp Tyr Phe Ala Lys Phe
1               5                   10                  15

Trp Asp

<210> SEQ ID NO 409
<211> LENGTH: 18
<212> TYPE: PRT
<213> ORGANISM: Artificial
<220> FEATURE:
<223> OTHER INFORMATION: Synthetic peptide

<400> SEQUENCE: 409

Phe Phe Asp Lys His Lys Asp Ala Val Lys Glu Tyr Phe Ala Lys Phe
1               5                   10                  15

Trp Glu

<210> SEQ ID NO 410
<211> LENGTH: 18
<212> TYPE: PRT
<213> ORGANISM: Artificial
<220> FEATURE:
<223> OTHER INFORMATION: Synthetic peptide

<400> SEQUENCE: 410

Phe Phe Glu Lys His Lys Glu Ala Val Lys Glu Tyr Phe Ala Lys Phe
1               5                   10                  15

Trp Glu

```
<210> SEQ ID NO 411
<211> LENGTH: 18
<212> TYPE: PRT
<213> ORGANISM: Artificial
<220> FEATURE:
<223> OTHER INFORMATION: Synthetic peptide

<400> SEQUENCE: 411

Phe Phe Asp Lys His Lys Asp Ala Val Lys Asp Tyr Phe Ala Lys Phe
1               5                   10                  15

Trp Asp

<210> SEQ ID NO 412
<211> LENGTH: 18
<212> TYPE: PRT
<213> ORGANISM: Artificial
<220> FEATURE:
<223> OTHER INFORMATION: Synthetic peptide

<400> SEQUENCE: 412

Phe Phe Asp Lys His Lys Glu Ala Val Lys Asp Tyr Phe Ala Lys Phe
1               5                   10                  15

Trp Asp

<210> SEQ ID NO 413
<211> LENGTH: 18
<212> TYPE: PRT
<213> ORGANISM: Artificial
<220> FEATURE:
<223> OTHER INFORMATION: Synthetic peptide

<400> SEQUENCE: 413

Phe Phe Glu Lys His Lys Glu Ala Val Lys Glu Tyr Phe Ala Lys Phe
1               5                   10                  15

Trp Asp

<210> SEQ ID NO 414
<211> LENGTH: 18
<212> TYPE: PRT
<213> ORGANISM: Artificial
<220> FEATURE:
<223> OTHER INFORMATION: Synthetic peptide

<400> SEQUENCE: 414

Phe Phe Glu Lys His Lys Glu Ala Val Lys Asp Tyr Phe Ala Lys Phe
1               5                   10                  15

Trp Glu

<210> SEQ ID NO 415
<211> LENGTH: 18
<212> TYPE: PRT
<213> ORGANISM: Artificial
<220> FEATURE:
<223> OTHER INFORMATION: Synthetic peptide

<400> SEQUENCE: 415

Phe Val Glu Lys Phe Lys Glu Ala His Lys Asp Tyr Phe Ala Lys Phe
1               5                   10                  15

Trp Asp

<210> SEQ ID NO 416
<211> LENGTH: 18
<212> TYPE: PRT
<213> ORGANISM: Artificial
```

<220> FEATURE:
<223> OTHER INFORMATION: Synthetic peptide

<400> SEQUENCE: 416

Phe Val Asp Lys Phe Lys Asp Ala His Lys Glu Tyr Phe Ala Lys Phe
1               5                   10                  15

Trp Glu

<210> SEQ ID NO 417
<211> LENGTH: 18
<212> TYPE: PRT
<213> ORGANISM: Artificial
<220> FEATURE:
<223> OTHER INFORMATION: Synthetic peptide

<400> SEQUENCE: 417

Phe Val Glu Lys Phe Lys Glu Ala His Lys Glu Tyr Phe Ala Lys Phe
1               5                   10                  15

Trp Glu

<210> SEQ ID NO 418
<211> LENGTH: 18
<212> TYPE: PRT
<213> ORGANISM: Artificial
<220> FEATURE:
<223> OTHER INFORMATION: Synthetic peptide

<400> SEQUENCE: 418

Phe Val Asp Lys Phe Lys Asp Ala His Lys Asp Tyr Phe Ala Lys Phe
1               5                   10                  15

Trp Asp

<210> SEQ ID NO 419
<211> LENGTH: 18
<212> TYPE: PRT
<213> ORGANISM: Artificial
<220> FEATURE:
<223> OTHER INFORMATION: Synthetic peptide

<400> SEQUENCE: 419

Phe Val Asp Lys Phe Lys Glu Ala His Lys Asp Tyr Phe Ala Lys Phe
1               5                   10                  15

Trp Asp

<210> SEQ ID NO 420
<211> LENGTH: 18
<212> TYPE: PRT
<213> ORGANISM: Artificial
<220> FEATURE:
<223> OTHER INFORMATION: Synthetic peptide

<400> SEQUENCE: 420

Phe Val Glu Lys Phe Lys Asp Ala His Lys Asp Tyr Phe Ala Lys Phe
1               5                   10                  15

Trp Asp

<210> SEQ ID NO 421
<211> LENGTH: 18
<212> TYPE: PRT
<213> ORGANISM: Artificial
<220> FEATURE:
<223> OTHER INFORMATION: Synthetic peptide

<400> SEQUENCE: 421

Phe Val Glu Lys Phe Lys Glu Ala His Lys Glu Tyr Phe Ala Lys Phe
1               5                   10                  15

Trp Asp

<210> SEQ ID NO 422
<211> LENGTH: 18
<212> TYPE: PRT
<213> ORGANISM: Artificial
<220> FEATURE:
<223> OTHER INFORMATION: Synthetic peptide

<400> SEQUENCE: 422

Phe Val Glu Lys Phe Lys Glu Ala His Lys Asp Tyr Phe Ala Lys Phe
1               5                   10                  15

Trp Glu

<210> SEQ ID NO 423
<211> LENGTH: 18
<212> TYPE: PRT
<213> ORGANISM: Artificial
<220> FEATURE:
<223> OTHER INFORMATION: Synthetic peptide

<400> SEQUENCE: 423

Phe Ala Glu Lys Phe Lys Glu His Val Lys Asp Tyr Phe Ala Lys Phe
1               5                   10                  15

Trp Asp

<210> SEQ ID NO 424
<211> LENGTH: 18
<212> TYPE: PRT
<213> ORGANISM: Artificial
<220> FEATURE:
<223> OTHER INFORMATION: Synthetic peptide

<400> SEQUENCE: 424

Phe Ala Asp Lys Phe Lys Asp His Val Lys Glu Tyr Phe Ala Lys Phe
1               5                   10                  15

Trp Glu

<210> SEQ ID NO 425
<211> LENGTH: 18
<212> TYPE: PRT
<213> ORGANISM: Artificial
<220> FEATURE:
<223> OTHER INFORMATION: Synthetic peptide

<400> SEQUENCE: 425

Phe Ala Glu Lys Phe Lys Glu His Val Lys Glu Tyr Phe Ala Lys Phe
1               5                   10                  15

Trp Glu

<210> SEQ ID NO 426
<211> LENGTH: 18
<212> TYPE: PRT
<213> ORGANISM: Artificial
<220> FEATURE:
<223> OTHER INFORMATION: Synthetic peptide

<400> SEQUENCE: 426

Phe Ala Asp Lys Phe Lys Asp His Val Lys Asp Tyr Phe Ala Lys Phe
1               5                   10                  15

Trp Asp

<210> SEQ ID NO 427
<211> LENGTH: 18
<212> TYPE: PRT
<213> ORGANISM: Artificial
<220> FEATURE:
<223> OTHER INFORMATION: Synthetic peptide

<400> SEQUENCE: 427

Phe Ala Asp Lys Phe Lys Glu His Val Lys Asp Tyr Phe Ala Lys Phe
1               5                   10                  15

Trp Asp

<210> SEQ ID NO 428
<211> LENGTH: 18
<212> TYPE: PRT
<213> ORGANISM: Artificial
<220> FEATURE:
<223> OTHER INFORMATION: Synthetic peptide

<400> SEQUENCE: 428

Phe Ala Glu Lys Phe Lys Asp His Val Lys Asp Tyr Phe Ala Lys Phe
1               5                   10                  15

Trp Asp

<210> SEQ ID NO 429
<211> LENGTH: 18
<212> TYPE: PRT
<213> ORGANISM: Artificial
<220> FEATURE:
<223> OTHER INFORMATION: Synthetic peptide

<400> SEQUENCE: 429

Phe Ala Glu Lys Phe Lys Glu His Val Lys Glu Tyr Phe Ala Lys Phe
1               5                   10                  15

Trp Asp

<210> SEQ ID NO 430
<211> LENGTH: 18
<212> TYPE: PRT
<213> ORGANISM: Artificial
<220> FEATURE:
<223> OTHER INFORMATION: Synthetic peptide

<400> SEQUENCE: 430

Phe Ala Glu Lys Phe Lys Glu His Val Lys Asp Tyr Phe Ala Lys Phe
1               5                   10                  15

Trp Glu

<210> SEQ ID NO 431
<211> LENGTH: 18
<212> TYPE: PRT
<213> ORGANISM: Artificial
<220> FEATURE:
<223> OTHER INFORMATION: Synthetic peptide

<400> SEQUENCE: 431

Phe Ala Glu Lys Phe Lys Glu Phe Val Lys Asp Tyr His Ala Lys Phe
1               5                   10                  15

Trp Asp

<210> SEQ ID NO 432

```
<211> LENGTH: 18
<212> TYPE: PRT
<213> ORGANISM: Artificial
<220> FEATURE:
<223> OTHER INFORMATION: Synthetic peptide

<400> SEQUENCE: 432

Phe Ala Asp Lys Phe Lys Asp Phe Val Lys Glu Tyr His Ala Lys Phe
1               5                   10                  15

Trp Glu

<210> SEQ ID NO 433
<211> LENGTH: 18
<212> TYPE: PRT
<213> ORGANISM: Artificial
<220> FEATURE:
<223> OTHER INFORMATION: Synthetic peptide

<400> SEQUENCE: 433

Phe Ala Asp Lys Phe Lys Glu Phe Val Lys Asp Tyr His Ala Lys Phe
1               5                   10                  15

Trp Asp

<210> SEQ ID NO 434
<211> LENGTH: 18
<212> TYPE: PRT
<213> ORGANISM: Artificial
<220> FEATURE:
<223> OTHER INFORMATION: Synthetic peptide

<400> SEQUENCE: 434

Phe Ala Glu Lys Phe Lys Asp Phe Val Lys Asp Tyr His Ala Lys Phe
1               5                   10                  15

Trp Asp

<210> SEQ ID NO 435
<211> LENGTH: 18
<212> TYPE: PRT
<213> ORGANISM: Artificial
<220> FEATURE:
<223> OTHER INFORMATION: Synthetic peptide

<400> SEQUENCE: 435

Phe Ala Asp Lys Phe Lys Asp Phe Val Lys Asp Tyr His Ala Lys Phe
1               5                   10                  15

Trp Asp

<210> SEQ ID NO 436
<211> LENGTH: 18
<212> TYPE: PRT
<213> ORGANISM: Artificial
<220> FEATURE:
<223> OTHER INFORMATION: Synthetic peptide

<400> SEQUENCE: 436

Phe Ala Glu Lys Phe Lys Glu Phe Val Lys Glu Tyr His Ala Lys Phe
1               5                   10                  15

Trp Glu

<210> SEQ ID NO 437
<211> LENGTH: 18
<212> TYPE: PRT
<213> ORGANISM: Artificial
<220> FEATURE:
```

<223> OTHER INFORMATION: Synthetic peptide

<400> SEQUENCE: 437

Phe Ala Glu Lys Phe Lys Glu Phe Val Lys Glu Tyr His Ala Lys Phe
1               5                   10                  15

Trp Asp

<210> SEQ ID NO 438
<211> LENGTH: 18
<212> TYPE: PRT
<213> ORGANISM: Artificial
<220> FEATURE:
<223> OTHER INFORMATION: Synthetic peptide

<400> SEQUENCE: 438

Phe Ala Glu Lys Phe Lys Glu Phe Val Lys Asp Tyr His Ala Lys Phe
1               5                   10                  15

Trp Glu

<210> SEQ ID NO 439
<211> LENGTH: 18
<212> TYPE: PRT
<213> ORGANISM: Artificial
<220> FEATURE:
<223> OTHER INFORMATION: Synthetic peptide

<400> SEQUENCE: 439

Phe Ala Glu Lys Phe Lys Glu Phe Val Lys Asp Tyr Phe Ala Lys His
1               5                   10                  15

Trp Asp

<210> SEQ ID NO 440
<211> LENGTH: 18
<212> TYPE: PRT
<213> ORGANISM: Artificial
<220> FEATURE:
<223> OTHER INFORMATION: Synthetic peptide

<400> SEQUENCE: 440

Phe Ala Asp Lys Phe Lys Asp Phe Val Lys Glu Tyr Phe Ala Lys His
1               5                   10                  15

Trp Glu

<210> SEQ ID NO 441
<211> LENGTH: 18
<212> TYPE: PRT
<213> ORGANISM: Artificial
<220> FEATURE:
<223> OTHER INFORMATION: Synthetic peptide

<400> SEQUENCE: 441

Phe Ala Glu Lys Phe Lys Glu Phe Val Lys Glu Tyr Phe Ala Lys His
1               5                   10                  15

Trp Glu

<210> SEQ ID NO 442
<211> LENGTH: 18
<212> TYPE: PRT
<213> ORGANISM: Artificial
<220> FEATURE:
<223> OTHER INFORMATION: Synthetic peptide

<400> SEQUENCE: 442

Phe Ala Asp Lys Phe Lys Asp Phe Val Lys Asp Tyr Phe Ala Lys His
1               5                   10                  15

Trp Asp

<210> SEQ ID NO 443
<211> LENGTH: 18
<212> TYPE: PRT
<213> ORGANISM: Artificial
<220> FEATURE:
<223> OTHER INFORMATION: Synthetic peptide

<400> SEQUENCE: 443

Phe Ala Asp Lys Phe Lys Glu Phe Val Lys Asp Tyr Phe Ala Lys His
1               5                   10                  15

Trp Asp

<210> SEQ ID NO 444
<211> LENGTH: 18
<212> TYPE: PRT
<213> ORGANISM: Artificial
<220> FEATURE:
<223> OTHER INFORMATION: Synthetic peptide

<400> SEQUENCE: 444

Phe Ala Glu Lys Phe Lys Asp Phe Val Lys Asp Tyr Phe Ala Lys His
1               5                   10                  15

Trp Asp

<210> SEQ ID NO 445
<211> LENGTH: 18
<212> TYPE: PRT
<213> ORGANISM: Artificial
<220> FEATURE:
<223> OTHER INFORMATION: Synthetic peptide

<400> SEQUENCE: 445

Phe Ala Glu Lys Phe Lys Glu Phe Val Lys Glu Tyr Phe Ala Lys His
1               5                   10                  15

Trp Asp

<210> SEQ ID NO 446
<211> LENGTH: 18
<212> TYPE: PRT
<213> ORGANISM: Artificial
<220> FEATURE:
<223> OTHER INFORMATION: Synthetic peptide

<400> SEQUENCE: 446

Phe Ala Glu Lys Phe Lys Glu Phe Val Lys Asp Tyr Phe Ala Lys His
1               5                   10                  15

Trp Glu

<210> SEQ ID NO 447
<211> LENGTH: 18
<212> TYPE: PRT
<213> ORGANISM: Artificial
<220> FEATURE:
<223> OTHER INFORMATION: Synthetic peptide

<400> SEQUENCE: 447

Phe Ala Glu Lys Phe Lys Glu Ala Val Lys Glu Tyr Phe Ala Lys Phe
1               5                   10                  15

Trp Glu

<210> SEQ ID NO 448
<211> LENGTH: 18
<212> TYPE: PRT
<213> ORGANISM: Artificial
<220> FEATURE:
<223> OTHER INFORMATION: Synthetic peptide

<400> SEQUENCE: 448

Phe Ala Asp Lys Phe Lys Asp Ala Val Lys Asp Tyr Phe Ala Lys Phe
1               5                   10                  15

Trp Asp

<210> SEQ ID NO 449
<211> LENGTH: 18
<212> TYPE: PRT
<213> ORGANISM: Artificial
<220> FEATURE:
<223> OTHER INFORMATION: Synthetic peptide

<400> SEQUENCE: 449

Phe Ala Glu Arg Phe Arg Glu Ala Val Lys Asp Tyr Phe Ala Lys Phe
1               5                   10                  15

Trp Asp

<210> SEQ ID NO 450
<211> LENGTH: 18
<212> TYPE: PRT
<213> ORGANISM: Artificial
<220> FEATURE:
<223> OTHER INFORMATION: Synthetic peptide

<400> SEQUENCE: 450

Phe Ala Glu Lys Phe Arg Glu Ala Val Lys Asp Tyr Phe Ala Lys Phe
1               5                   10                  15

Trp Asp

<210> SEQ ID NO 451
<211> LENGTH: 18
<212> TYPE: PRT
<213> ORGANISM: Artificial
<220> FEATURE:
<223> OTHER INFORMATION: Synthetic peptide

<400> SEQUENCE: 451

Phe Ala Glu Lys Phe Lys Glu Ala Val Arg Asp Tyr Phe Ala Lys Phe
1               5                   10                  15

Trp Asp

<210> SEQ ID NO 452
<211> LENGTH: 18
<212> TYPE: PRT
<213> ORGANISM: Artificial
<220> FEATURE:
<223> OTHER INFORMATION: Synthetic peptide

<400> SEQUENCE: 452

Phe Ala Glu Lys Phe Lys Glu Ala Val Lys Asp Tyr Phe Ala Arg Phe
1               5                   10                  15

Trp Asp

<210> SEQ ID NO 453
<211> LENGTH: 18

<212> TYPE: PRT
<213> ORGANISM: Artificial
<220> FEATURE:
<223> OTHER INFORMATION: Synthetic peptide

<400> SEQUENCE: 453

Phe Ala Glu Lys Phe Lys Glu Ala Val Lys Glu Tyr Phe Ala Lys Phe
1               5                   10                  15
Trp Glu

<210> SEQ ID NO 454
<211> LENGTH: 18
<212> TYPE: PRT
<213> ORGANISM: Artificial
<220> FEATURE:
<223> OTHER INFORMATION: Synthetic peptide

<400> SEQUENCE: 454

Phe Ala Asp Lys Phe Lys Asp Ala Val Lys Asp Tyr Phe Ala Lys Phe
1               5                   10                  15
Trp Asp

<210> SEQ ID NO 455
<211> LENGTH: 18
<212> TYPE: PRT
<213> ORGANISM: Artificial
<220> FEATURE:
<223> OTHER INFORMATION: Synthetic peptide

<400> SEQUENCE: 455

Phe Ala Glu Arg Phe Arg Glu Ala Val Lys Asp Tyr Phe Ala Lys Phe
1               5                   10                  15
Trp Asp

<210> SEQ ID NO 456
<211> LENGTH: 18
<212> TYPE: PRT
<213> ORGANISM: Artificial
<220> FEATURE:
<223> OTHER INFORMATION: Synthetic peptide

<400> SEQUENCE: 456

Phe Ala Glu Lys Phe Arg Glu Ala Val Lys Asp Tyr Phe Ala Lys Phe
1               5                   10                  15
Trp Asp

<210> SEQ ID NO 457
<211> LENGTH: 18
<212> TYPE: PRT
<213> ORGANISM: Artificial
<220> FEATURE:
<223> OTHER INFORMATION: Synthetic peptide

<400> SEQUENCE: 457

Phe Ala Glu Lys Phe Lys Glu Ala Val Arg Asp Tyr Phe Ala Lys Phe
1               5                   10                  15
Trp Asp

<210> SEQ ID NO 458
<211> LENGTH: 18
<212> TYPE: PRT
<213> ORGANISM: Artificial
<220> FEATURE:
<223> OTHER INFORMATION: Synthetic peptide -continued

<400> SEQUENCE: 458

Phe Ala Glu Lys Phe Lys Glu Ala Val Lys Asp Tyr Phe Ala Arg Phe
1               5                   10                  15

Trp Asp

<210> SEQ ID NO 459
<211> LENGTH: 18
<212> TYPE: PRT
<213> ORGANISM: Artificial
<220> FEATURE:
<223> OTHER INFORMATION: Synthetic peptide

<400> SEQUENCE: 459

Phe Ala Glu Lys Phe Lys Glu Ala Val Lys Glu Tyr Phe Ala Lys Phe
1               5                   10                  15

Trp Glu

<210> SEQ ID NO 460
<211> LENGTH: 18
<212> TYPE: PRT
<213> ORGANISM: Artificial
<220> FEATURE:
<223> OTHER INFORMATION: Synthetic peptide

<400> SEQUENCE: 460

Phe Ala Asp Lys Phe Lys Asp Ala Val Lys Asp Tyr Phe Ala Lys Phe
1               5                   10                  15

Trp Asp

<210> SEQ ID NO 461
<211> LENGTH: 18
<212> TYPE: PRT
<213> ORGANISM: Artificial
<220> FEATURE:
<223> OTHER INFORMATION: Synthetic peptide

<400> SEQUENCE: 461

Phe Ala Glu Arg Phe Arg Glu Ala Val Lys Asp Tyr Phe Ala Lys Phe
1               5                   10                  15

Trp Asp

<210> SEQ ID NO 462
<211> LENGTH: 18
<212> TYPE: PRT
<213> ORGANISM: Artificial
<220> FEATURE:
<223> OTHER INFORMATION: Synthetic peptide

<400> SEQUENCE: 462

Phe Ala Glu Lys Phe Arg Glu Ala Val Lys Asp Tyr Phe Ala Lys Phe
1               5                   10                  15

Trp Asp

<210> SEQ ID NO 463
<211> LENGTH: 18
<212> TYPE: PRT
<213> ORGANISM: Artificial
<220> FEATURE:
<223> OTHER INFORMATION: Synthetic peptide

<400> SEQUENCE: 463

Phe Ala Glu Lys Phe Lys Glu Ala Val Arg Asp Tyr Phe Ala Lys Phe

-continued

```
1               5                   10                  15

Trp Asp

<210> SEQ ID NO 464
<211> LENGTH: 18
<212> TYPE: PRT
<213> ORGANISM: Artificial
<220> FEATURE:
<223> OTHER INFORMATION: Synthetic peptide

<400> SEQUENCE: 464

Phe Ala Glu Lys Phe Lys Glu Ala Val Lys Asp Tyr Phe Ala Arg Phe
1               5                   10                  15

Trp Asp

<210> SEQ ID NO 465
<211> LENGTH: 18
<212> TYPE: PRT
<213> ORGANISM: Artificial
<220> FEATURE:
<223> OTHER INFORMATION: Synthetic peptide

<400> SEQUENCE: 465

Phe Ala Glu Arg Phe Arg Glu Ala Val Lys Asp Tyr Phe Ala Lys Phe
1               5                   10                  15

Trp Asp

<210> SEQ ID NO 466
<211> LENGTH: 18
<212> TYPE: PRT
<213> ORGANISM: Artificial
<220> FEATURE:
<223> OTHER INFORMATION: Synthetic peptide

<400> SEQUENCE: 466

Phe Ala Glu Lys Phe Arg Glu Ala Val Lys Asp Tyr Phe Ala Lys Phe
1               5                   10                  15

Trp Asp

<210> SEQ ID NO 467
<211> LENGTH: 18
<212> TYPE: PRT
<213> ORGANISM: Artificial
<220> FEATURE:
<223> OTHER INFORMATION: Synthetic peptide

<400> SEQUENCE: 467

Phe Ala Glu Lys Phe Lys Glu Ala Val Arg Asp Tyr Phe Ala Lys Phe
1               5                   10                  15

Trp Asp

<210> SEQ ID NO 468
<211> LENGTH: 18
<212> TYPE: PRT
<213> ORGANISM: Artificial
<220> FEATURE:
<223> OTHER INFORMATION: Synthetic peptide

<400> SEQUENCE: 468

Phe Ala Glu Lys Phe Lys Glu Ala Val Lys Asp Tyr Phe Ala Arg Phe
1               5                   10                  15

Trp Asp
```

```
<210> SEQ ID NO 469
<211> LENGTH: 18
<212> TYPE: PRT
<213> ORGANISM: Artificial
<220> FEATURE:
<223> OTHER INFORMATION: Synthetic peptide

<400> SEQUENCE: 469

Phe Ala Glu Lys Phe Lys Glu Ala Val Lys Glu Tyr Phe Ala Lys Phe
1               5                   10                  15

Trp Glu

<210> SEQ ID NO 470
<211> LENGTH: 18
<212> TYPE: PRT
<213> ORGANISM: Artificial
<220> FEATURE:
<223> OTHER INFORMATION: Synthetic peptide

<400> SEQUENCE: 470

Phe Ala Asp Lys Phe Lys Asp Ala Val Lys Asp Tyr Phe Ala Lys Phe
1               5                   10                  15

Trp Asp

<210> SEQ ID NO 471
<211> LENGTH: 18
<212> TYPE: PRT
<213> ORGANISM: Artificial
<220> FEATURE:
<223> OTHER INFORMATION: Synthetic peptide

<400> SEQUENCE: 471

Phe Ala Glu Arg Phe Arg Glu Ala Val Lys Asp Tyr Phe Ala Lys Phe
1               5                   10                  15

Trp Asp

<210> SEQ ID NO 472
<211> LENGTH: 18
<212> TYPE: PRT
<213> ORGANISM: Artificial
<220> FEATURE:
<223> OTHER INFORMATION: Synthetic peptide

<400> SEQUENCE: 472

Phe Ala Glu Lys Phe Arg Glu Ala Val Lys Asp Tyr Phe Ala Lys Phe
1               5                   10                  15

Trp Asp

<210> SEQ ID NO 473
<211> LENGTH: 18
<212> TYPE: PRT
<213> ORGANISM: Artificial
<220> FEATURE:
<223> OTHER INFORMATION: Synthetic peptide

<400> SEQUENCE: 473

Phe Ala Glu Lys Phe Lys Glu Ala Val Arg Asp Tyr Phe Ala Lys Phe
1               5                   10                  15

Trp Asp

<210> SEQ ID NO 474
<211> LENGTH: 18
<212> TYPE: PRT
```

<213> ORGANISM: Artificial
<220> FEATURE:
<223> OTHER INFORMATION: Synthetic peptide

<400> SEQUENCE: 474

Phe Ala Glu Lys Phe Lys Glu Ala Val Lys Asp Tyr Phe Ala Arg Phe
1               5                   10                  15

Trp Asp

<210> SEQ ID NO 475
<211> LENGTH: 18
<212> TYPE: PRT
<213> ORGANISM: Artificial
<220> FEATURE:
<223> OTHER INFORMATION: Synthetic peptide

<400> SEQUENCE: 475

Leu Phe Glu Lys Phe Ala Glu Ala Phe Lys Asp Tyr Val Ala Lys Trp
1               5                   10                  15

Lys Asp

<210> SEQ ID NO 476
<211> LENGTH: 18
<212> TYPE: PRT
<213> ORGANISM: Artificial
<220> FEATURE:
<223> OTHER INFORMATION: Synthetic peptide

<400> SEQUENCE: 476

Leu Phe Glu Arg Phe Ala Glu Ala Phe Lys Asp Tyr Val Ala Lys Trp
1               5                   10                  15

Lys Asp

<210> SEQ ID NO 477
<211> LENGTH: 18
<212> TYPE: PRT
<213> ORGANISM: Artificial
<220> FEATURE:
<223> OTHER INFORMATION: Synthetic peptide

<400> SEQUENCE: 477

Leu Phe Glu Lys Phe Ala Glu Ala Phe Arg Asp Tyr Val Ala Lys Trp
1               5                   10                  15

Lys Asp

<210> SEQ ID NO 478
<211> LENGTH: 18
<212> TYPE: PRT
<213> ORGANISM: Artificial
<220> FEATURE:
<223> OTHER INFORMATION: Synthetic peptide

<400> SEQUENCE: 478

Leu Phe Glu Lys Phe Ala Glu Ala Phe Lys Asp Tyr Val Ala Arg Trp
1               5                   10                  15

Lys Asp

<210> SEQ ID NO 479
<211> LENGTH: 18
<212> TYPE: PRT
<213> ORGANISM: Artificial
<220> FEATURE:
<223> OTHER INFORMATION: Synthetic peptide

```
<400> SEQUENCE: 479

Leu Phe Glu Lys Phe Ala Glu Ala Phe Lys Asp Tyr Val Ala Lys Trp
1               5                   10                  15

Arg Asp

<210> SEQ ID NO 480
<211> LENGTH: 18
<212> TYPE: PRT
<213> ORGANISM: Artificial
<220> FEATURE:
<223> OTHER INFORMATION: Synthetic peptide

<400> SEQUENCE: 480

Leu Phe Glu Lys Phe Ala Glu Ala Phe Lys Glu Tyr Val Ala Lys Trp
1               5                   10                  15

Lys Glu

<210> SEQ ID NO 481
<211> LENGTH: 18
<212> TYPE: PRT
<213> ORGANISM: Artificial
<220> FEATURE:
<223> OTHER INFORMATION: Synthetic peptide

<400> SEQUENCE: 481

Leu Phe Asp Lys Phe Ala Asp Ala Phe Lys Asp Tyr Val Ala Lys Trp
1               5                   10                  15

Lys Asp

<210> SEQ ID NO 482
<211> LENGTH: 18
<212> TYPE: PRT
<213> ORGANISM: Artificial
<220> FEATURE:
<223> OTHER INFORMATION: Synthetic peptide

<400> SEQUENCE: 482

Leu Phe Asp Lys Phe Ala Glu Ala Phe Lys Asp Tyr Val Ala Lys Trp
1               5                   10                  15

Lys Asp

<210> SEQ ID NO 483
<211> LENGTH: 18
<212> TYPE: PRT
<213> ORGANISM: Artificial
<220> FEATURE:
<223> OTHER INFORMATION: Synthetic peptide

<400> SEQUENCE: 483

Leu Phe Glu Lys Phe Ala Asp Ala Phe Lys Asp Tyr Val Ala Lys Trp
1               5                   10                  15

Lys Asp

<210> SEQ ID NO 484
<211> LENGTH: 18
<212> TYPE: PRT
<213> ORGANISM: Artificial
<220> FEATURE:
<223> OTHER INFORMATION: Synthetic peptide

<400> SEQUENCE: 484

Leu Phe Glu Lys Phe Ala Glu Ala Phe Lys Glu Tyr Val Ala Lys Trp
1               5                   10                  15
```

<210> SEQ ID NO 485
<211> LENGTH: 18
<212> TYPE: PRT
<213> ORGANISM: Artificial
<220> FEATURE:
<223> OTHER INFORMATION: Synthetic peptide

<400> SEQUENCE: 485

Leu Phe Glu Lys Phe Ala Glu Ala Phe Lys Asp Tyr Val Ala Lys Trp
1               5                   10                  15

Lys Glu

<210> SEQ ID NO 486
<211> LENGTH: 18
<212> TYPE: PRT
<213> ORGANISM: Artificial
<220> FEATURE:
<223> OTHER INFORMATION: Synthetic peptide

<400> SEQUENCE: 486

Phe Ala Glu Lys Ala Trp Glu Phe Val Lys Asp Tyr Phe Ala Lys Leu
1               5                   10                  15

Lys Asp

<210> SEQ ID NO 487
<211> LENGTH: 18
<212> TYPE: PRT
<213> ORGANISM: Artificial
<220> FEATURE:
<223> OTHER INFORMATION: Synthetic peptide

<400> SEQUENCE: 487

Phe Ala Glu Arg Ala Trp Glu Phe Val Lys Asp Tyr Phe Ala Lys Leu
1               5                   10                  15

Lys Asp

<210> SEQ ID NO 488
<211> LENGTH: 18
<212> TYPE: PRT
<213> ORGANISM: Artificial
<220> FEATURE:
<223> OTHER INFORMATION: Synthetic peptide

<400> SEQUENCE: 488

Phe Ala Glu Lys Ala Trp Glu Phe Val Lys Asp Tyr Phe Ala Lys Leu
1               5                   10                  15

Lys Asp

<210> SEQ ID NO 489
<211> LENGTH: 18
<212> TYPE: PRT
<213> ORGANISM: Artificial
<220> FEATURE:
<223> OTHER INFORMATION: Synthetic peptide

<400> SEQUENCE: 489

Phe Ala Glu Lys Ala Trp Glu Phe Val Lys Asp Tyr Phe Ala Lys Leu
1               5                   10                  15

Lys Asp

```
<210> SEQ ID NO 490
<211> LENGTH: 18
<212> TYPE: PRT
<213> ORGANISM: Artificial
<220> FEATURE:
<223> OTHER INFORMATION: Synthetic peptide

<400> SEQUENCE: 490

Phe Ala Glu Lys Ala Trp Glu Phe Val Lys Asp Tyr Phe Ala Lys Leu
1               5                   10                  15

Arg Asp

<210> SEQ ID NO 491
<211> LENGTH: 18
<212> TYPE: PRT
<213> ORGANISM: Artificial
<220> FEATURE:
<223> OTHER INFORMATION: Synthetic peptide

<400> SEQUENCE: 491

Phe Ala Glu Lys Ala Trp Glu Phe Val Lys Glu Tyr Phe Ala Lys Leu
1               5                   10                  15

Lys Glu

<210> SEQ ID NO 492
<211> LENGTH: 18
<212> TYPE: PRT
<213> ORGANISM: Artificial
<220> FEATURE:
<223> OTHER INFORMATION: Synthetic peptide

<400> SEQUENCE: 492

Phe Ala Asp Lys Ala Trp Asp Phe Val Lys Asp Tyr Phe Ala Lys Leu
1               5                   10                  15

Lys Asp

<210> SEQ ID NO 493
<211> LENGTH: 18
<212> TYPE: PRT
<213> ORGANISM: Artificial
<220> FEATURE:
<223> OTHER INFORMATION: Synthetic peptide

<400> SEQUENCE: 493

Phe Ala Asp Lys Ala Trp Glu Phe Val Lys Asp Tyr Phe Ala Lys Leu
1               5                   10                  15

Lys Asp

<210> SEQ ID NO 494
<211> LENGTH: 18
<212> TYPE: PRT
<213> ORGANISM: Artificial
<220> FEATURE:
<223> OTHER INFORMATION: Synthetic peptide

<400> SEQUENCE: 494

Phe Ala Glu Lys Ala Trp Asp Phe Val Lys Asp Tyr Phe Ala Lys Leu
1               5                   10                  15

Lys Asp

<210> SEQ ID NO 495
<211> LENGTH: 18
<212> TYPE: PRT
<213> ORGANISM: Artificial
```

<220> FEATURE:
<223> OTHER INFORMATION: Synthetic peptide

<400> SEQUENCE: 495

Phe Ala Glu Lys Ala Trp Glu Phe Val Lys Glu Tyr Phe Ala Lys Leu
1               5                   10                  15

Lys Asp

<210> SEQ ID NO 496
<211> LENGTH: 18
<212> TYPE: PRT
<213> ORGANISM: Artificial
<220> FEATURE:
<223> OTHER INFORMATION: Synthetic peptide

<400> SEQUENCE: 496

Phe Ala Glu Lys Ala Trp Glu Phe Val Lys Asp Tyr Phe Ala Lys Leu
1               5                   10                  15

Lys Glu

<210> SEQ ID NO 497
<211> LENGTH: 18
<212> TYPE: PRT
<213> ORGANISM: Artificial
<220> FEATURE:
<223> OTHER INFORMATION: Synthetic peptide

<400> SEQUENCE: 497

Phe Phe Glu Lys Phe Lys Glu Phe Val Lys Asp Tyr Phe Ala Lys Leu
1               5                   10                  15

Trp Asp

<210> SEQ ID NO 498
<211> LENGTH: 18
<212> TYPE: PRT
<213> ORGANISM: Artificial
<220> FEATURE:
<223> OTHER INFORMATION: Synthetic peptide

<400> SEQUENCE: 498

Phe Phe Glu Lys Phe Lys Glu Phe Val Lys Glu Tyr Phe Ala Lys Leu
1               5                   10                  15

Trp Glu

<210> SEQ ID NO 499
<211> LENGTH: 18
<212> TYPE: PRT
<213> ORGANISM: Artificial
<220> FEATURE:
<223> OTHER INFORMATION: Synthetic peptide

<400> SEQUENCE: 499

Phe Phe Asp Lys Phe Lys Asp Phe Val Lys Asp Tyr Phe Ala Lys Leu
1               5                   10                  15

Trp Asp

<210> SEQ ID NO 500
<211> LENGTH: 18
<212> TYPE: PRT
<213> ORGANISM: Artificial
<220> FEATURE:
<223> OTHER INFORMATION: Synthetic peptide

<400> SEQUENCE: 500

Phe Phe Glu Arg Phe Lys Glu Phe Val Lys Asp Tyr Phe Ala Lys Leu
1               5                   10                  15

Trp Asp

<210> SEQ ID NO 501
<211> LENGTH: 18
<212> TYPE: PRT
<213> ORGANISM: Artificial
<220> FEATURE:
<223> OTHER INFORMATION: Synthetic peptide

<400> SEQUENCE: 501

Phe Phe Glu Lys Phe Arg Glu Phe Val Lys Asp Tyr Phe Ala Lys Leu
1               5                   10                  15

Trp Asp

<210> SEQ ID NO 502
<211> LENGTH: 18
<212> TYPE: PRT
<213> ORGANISM: Artificial
<220> FEATURE:
<223> OTHER INFORMATION: Synthetic peptide

<400> SEQUENCE: 502

Phe Phe Glu Lys Phe Lys Glu Phe Val Arg Asp Tyr Phe Ala Lys Leu
1               5                   10                  15

Trp Asp

<210> SEQ ID NO 503
<211> LENGTH: 18
<212> TYPE: PRT
<213> ORGANISM: Artificial
<220> FEATURE:
<223> OTHER INFORMATION: Synthetic peptide

<400> SEQUENCE: 503

Phe Phe Glu Lys Phe Lys Glu Phe Val Lys Asp Tyr Phe Ala Arg Leu
1               5                   10                  15

Trp Asp

<210> SEQ ID NO 504
<211> LENGTH: 18
<212> TYPE: PRT
<213> ORGANISM: Artificial
<220> FEATURE:
<223> OTHER INFORMATION: Synthetic peptide

<400> SEQUENCE: 504

Phe Phe Asp Lys Phe Lys Glu Phe Val Lys Asp Tyr Phe Ala Lys Leu
1               5                   10                  15

Trp Asp

<210> SEQ ID NO 505
<211> LENGTH: 18
<212> TYPE: PRT
<213> ORGANISM: Artificial
<220> FEATURE:
<223> OTHER INFORMATION: Synthetic peptide

<400> SEQUENCE: 505

Phe Phe Glu Lys Phe Lys Asp Phe Val Lys Asp Tyr Phe Ala Lys Leu
1               5                   10                  15

Trp Asp

<210> SEQ ID NO 506
<211> LENGTH: 18
<212> TYPE: PRT
<213> ORGANISM: Artificial
<220> FEATURE:
<223> OTHER INFORMATION: Synthetic peptide

<400> SEQUENCE: 506

Phe Phe Glu Lys Phe Lys Glu Phe Val Lys Glu Tyr Phe Ala Lys Leu
1               5                   10                  15

Trp Asp

<210> SEQ ID NO 507
<211> LENGTH: 18
<212> TYPE: PRT
<213> ORGANISM: Artificial
<220> FEATURE:
<223> OTHER INFORMATION: Synthetic peptide

<400> SEQUENCE: 507

Phe Phe Glu Lys Phe Lys Glu Phe Val Lys Asp Tyr Phe Ala Lys Leu
1               5                   10                  15

Trp Glu

<210> SEQ ID NO 508
<211> LENGTH: 18
<212> TYPE: PRT
<213> ORGANISM: Artificial
<220> FEATURE:
<223> OTHER INFORMATION: Synthetic peptide

<400> SEQUENCE: 508

Phe Leu Glu Lys Phe Lys Glu Phe Val Lys Asp Tyr Phe Ala Lys Phe
1               5                   10                  15

Trp Asp

<210> SEQ ID NO 509
<211> LENGTH: 18
<212> TYPE: PRT
<213> ORGANISM: Artificial
<220> FEATURE:
<223> OTHER INFORMATION: Synthetic peptide

<400> SEQUENCE: 509

Phe Leu Glu Lys Phe Lys Glu Phe Val Lys Glu Tyr Phe Ala Lys Phe
1               5                   10                  15

Trp Glu

<210> SEQ ID NO 510
<211> LENGTH: 18
<212> TYPE: PRT
<213> ORGANISM: Artificial
<220> FEATURE:
<223> OTHER INFORMATION: Synthetic peptide

<400> SEQUENCE: 510

Phe Leu Asp Lys Phe Lys Glu Phe Val Lys Asp Tyr Phe Ala Lys Phe
1               5                   10                  15

Trp Asp

<210> SEQ ID NO 511

```
<211> LENGTH: 18
<212> TYPE: PRT
<213> ORGANISM: Artificial
<220> FEATURE:
<223> OTHER INFORMATION: Synthetic peptide

<400> SEQUENCE: 511

Phe Leu Asp Lys Phe Lys Glu Phe Val Lys Asp Tyr Phe Ala Lys Phe
1               5                   10                  15

Trp Asp

<210> SEQ ID NO 512
<211> LENGTH: 18
<212> TYPE: PRT
<213> ORGANISM: Artificial
<220> FEATURE:
<223> OTHER INFORMATION: Synthetic peptide

<400> SEQUENCE: 512

Phe Leu Glu Lys Phe Lys Asp Phe Val Lys Asp Tyr Phe Ala Lys Phe
1               5                   10                  15

Trp Asp

<210> SEQ ID NO 513
<211> LENGTH: 18
<212> TYPE: PRT
<213> ORGANISM: Artificial
<220> FEATURE:
<223> OTHER INFORMATION: Synthetic peptide

<400> SEQUENCE: 513

Phe Leu Glu Lys Phe Lys Glu Phe Val Lys Glu Tyr Phe Ala Lys Phe
1               5                   10                  15

Trp Asp

<210> SEQ ID NO 514
<211> LENGTH: 18
<212> TYPE: PRT
<213> ORGANISM: Artificial
<220> FEATURE:
<223> OTHER INFORMATION: Synthetic peptide

<400> SEQUENCE: 514

Phe Leu Glu Lys Phe Lys Glu Phe Val Lys Asp Tyr Phe Ala Lys Phe
1               5                   10                  15

Trp Glu

<210> SEQ ID NO 515
<211> LENGTH: 18
<212> TYPE: PRT
<213> ORGANISM: Artificial
<220> FEATURE:
<223> OTHER INFORMATION: Synthetic peptide

<400> SEQUENCE: 515

Phe Leu Glu Arg Phe Lys Glu Phe Val Lys Asp Tyr Phe Ala Lys Phe
1               5                   10                  15

Trp Asp

<210> SEQ ID NO 516
<211> LENGTH: 18
<212> TYPE: PRT
<213> ORGANISM: Artificial
<220> FEATURE:
```

<223> OTHER INFORMATION: Synthetic peptide

<400> SEQUENCE: 516

Phe Leu Glu Lys Phe Arg Glu Phe Val Lys Asp Tyr Phe Ala Lys Phe
1               5                   10                  15

Trp Asp

<210> SEQ ID NO 517
<211> LENGTH: 18
<212> TYPE: PRT
<213> ORGANISM: Artificial
<220> FEATURE:
<223> OTHER INFORMATION: Synthetic peptide

<400> SEQUENCE: 517

Phe Leu Glu Lys Phe Lys Glu Phe Val Arg Asp Tyr Phe Ala Lys Phe
1               5                   10                  15

Trp Asp

<210> SEQ ID NO 518
<211> LENGTH: 18
<212> TYPE: PRT
<213> ORGANISM: Artificial
<220> FEATURE:
<223> OTHER INFORMATION: Synthetic peptide

<400> SEQUENCE: 518

Phe Leu Glu Lys Phe Lys Glu Phe Val Lys Asp Tyr Phe Ala Arg Phe
1               5                   10                  15

Trp Asp

<210> SEQ ID NO 519
<211> LENGTH: 18
<212> TYPE: PRT
<213> ORGANISM: Artificial
<220> FEATURE:
<223> OTHER INFORMATION: Synthetic peptide

<400> SEQUENCE: 519

Phe Phe Glu Lys Phe Lys Glu Phe Phe Lys Asp Tyr Phe Ala Lys Leu
1               5                   10                  15

Trp Asp

<210> SEQ ID NO 520
<211> LENGTH: 18
<212> TYPE: PRT
<213> ORGANISM: Artificial
<220> FEATURE:
<223> OTHER INFORMATION: Synthetic peptide

<400> SEQUENCE: 520

Phe Phe Glu Lys Phe Lys Glu Phe Phe Lys Glu Tyr Phe Ala Lys Leu
1               5                   10                  15

Trp Glu

<210> SEQ ID NO 521
<211> LENGTH: 18
<212> TYPE: PRT
<213> ORGANISM: Artificial
<220> FEATURE:
<223> OTHER INFORMATION: Synthetic peptide

<400> SEQUENCE: 521

Phe Phe Asp Lys Phe Lys Asp Phe Phe Lys Asp Tyr Phe Ala Lys Leu
1               5                   10                  15

Trp Asp

<210> SEQ ID NO 522
<211> LENGTH: 18
<212> TYPE: PRT
<213> ORGANISM: Artificial
<220> FEATURE:
<223> OTHER INFORMATION: Synthetic peptide

<400> SEQUENCE: 522

Phe Phe Glu Arg Phe Lys Glu Phe Phe Lys Asp Tyr Phe Ala Lys Leu
1               5                   10                  15

Trp Asp

<210> SEQ ID NO 523
<211> LENGTH: 18
<212> TYPE: PRT
<213> ORGANISM: Artificial
<220> FEATURE:
<223> OTHER INFORMATION: Synthetic peptide

<400> SEQUENCE: 523

Phe Phe Glu Lys Phe Arg Glu Phe Phe Lys Asp Tyr Phe Ala Lys Leu
1               5                   10                  15

Trp Asp

<210> SEQ ID NO 524
<211> LENGTH: 18
<212> TYPE: PRT
<213> ORGANISM: Artificial
<220> FEATURE:
<223> OTHER INFORMATION: Synthetic peptide

<400> SEQUENCE: 524

Phe Phe Glu Lys Phe Lys Glu Phe Phe Arg Asp Tyr Phe Ala Lys Leu
1               5                   10                  15

Trp Asp

<210> SEQ ID NO 525
<211> LENGTH: 18
<212> TYPE: PRT
<213> ORGANISM: Artificial
<220> FEATURE:
<223> OTHER INFORMATION: Synthetic peptide

<400> SEQUENCE: 525

Phe Phe Glu Arg Phe Lys Glu Phe Phe Lys Asp Tyr Phe Ala Arg Leu
1               5                   10                  15

Trp Asp

<210> SEQ ID NO 526
<211> LENGTH: 18
<212> TYPE: PRT
<213> ORGANISM: Artificial
<220> FEATURE:
<223> OTHER INFORMATION: Synthetic peptide

<400> SEQUENCE: 526

Phe Phe Asp Lys Phe Lys Glu Phe Phe Lys Asp Tyr Phe Ala Lys Leu
1               5                   10                  15

Trp Asp

<210> SEQ ID NO 527
<211> LENGTH: 18
<212> TYPE: PRT
<213> ORGANISM: Artificial
<220> FEATURE:
<223> OTHER INFORMATION: Synthetic peptide

<400> SEQUENCE: 527

Phe Phe Glu Lys Phe Lys Asp Phe Phe Lys Asp Tyr Phe Ala Lys Leu
1               5                   10                  15

Trp Asp

<210> SEQ ID NO 528
<211> LENGTH: 18
<212> TYPE: PRT
<213> ORGANISM: Artificial
<220> FEATURE:
<223> OTHER INFORMATION: Synthetic peptide

<400> SEQUENCE: 528

Phe Phe Glu Lys Phe Lys Glu Phe Phe Lys Glu Tyr Phe Ala Lys Leu
1               5                   10                  15

Trp Asp

<210> SEQ ID NO 529
<211> LENGTH: 18
<212> TYPE: PRT
<213> ORGANISM: Artificial
<220> FEATURE:
<223> OTHER INFORMATION: Synthetic peptide

<400> SEQUENCE: 529

Phe Phe Glu Lys Phe Lys Glu Phe Phe Lys Asp Tyr Phe Ala Lys Leu
1               5                   10                  15

Trp Glu

<210> SEQ ID NO 530
<211> LENGTH: 18
<212> TYPE: PRT
<213> ORGANISM: Artificial
<220> FEATURE:
<223> OTHER INFORMATION: Synthetic peptide

<400> SEQUENCE: 530

Phe Ala Glu Lys Phe Lys Glu Ala Val Lys Asp Tyr Phe Ala Lys Phe
1               5                   10                  15

Trp Asp

<210> SEQ ID NO 531
<211> LENGTH: 18
<212> TYPE: PRT
<213> ORGANISM: Artificial
<220> FEATURE:
<223> OTHER INFORMATION: Synthetic peptide

<400> SEQUENCE: 531

Phe Ala Glu Lys Phe Lys Glu Ala Val Lys Glu Tyr Phe Ala Lys Phe
1               5                   10                  15

Trp Glu

<210> SEQ ID NO 532
<211> LENGTH: 18

<212> TYPE: PRT
<213> ORGANISM: Artificial
<220> FEATURE:
<223> OTHER INFORMATION: Synthetic peptide

<400> SEQUENCE: 532

Phe Ala Asp Lys Phe Lys Asp Ala Val Lys Asp Tyr Phe Ala Lys Phe
1               5                   10                  15

Trp Asp

<210> SEQ ID NO 533
<211> LENGTH: 18
<212> TYPE: PRT
<213> ORGANISM: Artificial
<220> FEATURE:
<223> OTHER INFORMATION: Synthetic peptide

<400> SEQUENCE: 533

Phe Ala Glu Arg Phe Arg Glu Ala Val Lys Asp Tyr Phe Ala Lys Phe
1               5                   10                  15

Trp Asp

<210> SEQ ID NO 534
<211> LENGTH: 18
<212> TYPE: PRT
<213> ORGANISM: Artificial
<220> FEATURE:
<223> OTHER INFORMATION: Synthetic peptide

<400> SEQUENCE: 534

Phe Ala Glu Lys Phe Arg Glu Ala Val Lys Asp Tyr Phe Ala Lys Phe
1               5                   10                  15

Trp Asp

<210> SEQ ID NO 535
<211> LENGTH: 18
<212> TYPE: PRT
<213> ORGANISM: Artificial
<220> FEATURE:
<223> OTHER INFORMATION: Synthetic peptide

<400> SEQUENCE: 535

Phe Ala Glu Lys Phe Lys Glu Ala Val Arg Asp Tyr Phe Ala Lys Phe
1               5                   10                  15

Trp Asp

<210> SEQ ID NO 536
<211> LENGTH: 18
<212> TYPE: PRT
<213> ORGANISM: Artificial
<220> FEATURE:
<223> OTHER INFORMATION: Synthetic peptide

<400> SEQUENCE: 536

Phe Ala Glu Lys Phe Lys Glu Ala Val Lys Asp Tyr Phe Ala Arg Phe
1               5                   10                  15

Trp Asp

<210> SEQ ID NO 537
<211> LENGTH: 18
<212> TYPE: PRT
<213> ORGANISM: Artificial
<220> FEATURE:
<223> OTHER INFORMATION: Synthetic peptide

```
<400> SEQUENCE: 537

Asp Lys Trp Lys Ala Val Tyr Asp Lys Phe Ala Glu Ala Phe Lys Glu
1               5                   10                  15

Phe Phe

<210> SEQ ID NO 538
<211> LENGTH: 18
<212> TYPE: PRT
<213> ORGANISM: Artificial
<220> FEATURE:
<223> OTHER INFORMATION: Synthetic peptide

<400> SEQUENCE: 538

Glu Lys Trp Lys Ala Val Tyr Glu Lys Phe Ala Glu Ala Phe Lys Glu
1               5                   10                  15

Phe Phe

<210> SEQ ID NO 539
<211> LENGTH: 18
<212> TYPE: PRT
<213> ORGANISM: Artificial
<220> FEATURE:
<223> OTHER INFORMATION: Synthetic peptide

<400> SEQUENCE: 539

Asp Lys Trp Lys Ala Val Tyr Asp Lys Phe Ala Asp Ala Phe Lys Asp
1               5                   10                  15

Phe Phe

<210> SEQ ID NO 540
<211> LENGTH: 18
<212> TYPE: PRT
<213> ORGANISM: Artificial
<220> FEATURE:
<223> OTHER INFORMATION: Synthetic peptide

<400> SEQUENCE: 540

Asp Arg Trp Lys Ala Val Tyr Asp Lys Phe Ala Glu Ala Phe Lys Glu
1               5                   10                  15

Phe Phe

<210> SEQ ID NO 541
<211> LENGTH: 18
<212> TYPE: PRT
<213> ORGANISM: Artificial
<220> FEATURE:
<223> OTHER INFORMATION: Synthetic peptide

<400> SEQUENCE: 541

Asp Lys Trp Arg Ala Val Tyr Asp Lys Phe Ala Glu Ala Phe Lys Glu
1               5                   10                  15

Phe Phe

<210> SEQ ID NO 542
<211> LENGTH: 18
<212> TYPE: PRT
<213> ORGANISM: Artificial
<220> FEATURE:
<223> OTHER INFORMATION: Synthetic peptide

<400> SEQUENCE: 542

Asp Lys Trp Lys Ala Val Tyr Asp Arg Phe Ala Glu Ala Phe Lys Glu
```

```
1               5                   10                  15

Phe Phe

<210> SEQ ID NO 543
<211> LENGTH: 18
<212> TYPE: PRT
<213> ORGANISM: Artificial
<220> FEATURE:
<223> OTHER INFORMATION: Synthetic peptide

<400> SEQUENCE: 543

Asp Lys Trp Lys Ala Val Tyr Asp Lys Phe Ala Glu Ala Phe Arg Glu
1               5                   10                  15

Phe Phe

<210> SEQ ID NO 544
<211> LENGTH: 18
<212> TYPE: PRT
<213> ORGANISM: Artificial
<220> FEATURE:
<223> OTHER INFORMATION: Synthetic peptide

<400> SEQUENCE: 544

Phe Phe Glu Lys Phe Ala Glu Ala Phe Lys Asp Tyr Val Ala Lys Trp
1               5                   10                  15

Lys Asp

<210> SEQ ID NO 545
<211> LENGTH: 18
<212> TYPE: PRT
<213> ORGANISM: Artificial
<220> FEATURE:
<223> OTHER INFORMATION: Synthetic peptide

<400> SEQUENCE: 545

Phe Phe Glu Lys Phe Ala Glu Ala Phe Lys Glu Tyr Val Ala Lys Trp
1               5                   10                  15

Lys Glu

<210> SEQ ID NO 546
<211> LENGTH: 18
<212> TYPE: PRT
<213> ORGANISM: Artificial
<220> FEATURE:
<223> OTHER INFORMATION: Synthetic peptide

<400> SEQUENCE: 546

Phe Phe Asp Lys Phe Ala Asp Ala Phe Lys Asp Tyr Val Ala Lys Trp
1               5                   10                  15

Lys Asp

<210> SEQ ID NO 547
<211> LENGTH: 18
<212> TYPE: PRT
<213> ORGANISM: Artificial
<220> FEATURE:
<223> OTHER INFORMATION: Synthetic peptide

<400> SEQUENCE: 547

Phe Phe Glu Arg Phe Ala Glu Ala Phe Lys Asp Tyr Val Ala Lys Trp
1               5                   10                  15

Lys Asp
```

<210> SEQ ID NO 548
<211> LENGTH: 18
<212> TYPE: PRT
<213> ORGANISM: Artificial
<220> FEATURE:
<223> OTHER INFORMATION: Synthetic peptide

<400> SEQUENCE: 548

Phe Phe Glu Arg Phe Ala Glu Ala Phe Arg Asp Tyr Val Ala Lys Trp
1               5                   10                  15

Lys Asp

<210> SEQ ID NO 549
<211> LENGTH: 18
<212> TYPE: PRT
<213> ORGANISM: Artificial
<220> FEATURE:
<223> OTHER INFORMATION: Synthetic peptide

<400> SEQUENCE: 549

Phe Phe Glu Lys Phe Ala Glu Ala Phe Lys Asp Tyr Val Ala Arg Trp
1               5                   10                  15

Lys Asp

<210> SEQ ID NO 550
<211> LENGTH: 18
<212> TYPE: PRT
<213> ORGANISM: Artificial
<220> FEATURE:
<223> OTHER INFORMATION: Synthetic peptide

<400> SEQUENCE: 550

Phe Phe Glu Arg Phe Ala Glu Ala Phe Lys Asp Tyr Val Ala Lys Trp
1               5                   10                  15

Arg Asp

<210> SEQ ID NO 551
<211> LENGTH: 18
<212> TYPE: PRT
<213> ORGANISM: Artificial
<220> FEATURE:
<223> OTHER INFORMATION: Synthetic peptide

<400> SEQUENCE: 551

Phe Phe Asp Lys Phe Ala Glu Ala Phe Lys Asp Tyr Val Ala Lys Trp
1               5                   10                  15

Lys Asp

<210> SEQ ID NO 552
<211> LENGTH: 18
<212> TYPE: PRT
<213> ORGANISM: Artificial
<220> FEATURE:
<223> OTHER INFORMATION: Synthetic peptide

<400> SEQUENCE: 552

Phe Phe Glu Lys Phe Ala Asp Ala Phe Lys Asp Tyr Val Ala Lys Trp
1               5                   10                  15

Lys Asp

<210> SEQ ID NO 553
<211> LENGTH: 18
<212> TYPE: PRT

```
<213> ORGANISM: Artificial
<220> FEATURE:
<223> OTHER INFORMATION: Synthetic peptide

<400> SEQUENCE: 553

Phe Phe Glu Arg Phe Ala Glu Ala Phe Lys Glu Tyr Val Ala Lys Trp
1               5                   10                  15

Lys Asp

<210> SEQ ID NO 554
<211> LENGTH: 18
<212> TYPE: PRT
<213> ORGANISM: Artificial
<220> FEATURE:
<223> OTHER INFORMATION: Synthetic peptide

<400> SEQUENCE: 554

Phe Phe Glu Arg Phe Ala Glu Ala Phe Lys Asp Tyr Val Ala Lys Trp
1               5                   10                  15

Lys Glu

<210> SEQ ID NO 555
<211> LENGTH: 18
<212> TYPE: PRT
<213> ORGANISM: Artificial
<220> FEATURE:
<223> OTHER INFORMATION: Synthetic peptide

<400> SEQUENCE: 555

Phe Phe Glu Lys Phe Lys Glu Phe Phe Lys Asp Tyr Phe Ala Lys Phe
1               5                   10                  15

Trp Asp

<210> SEQ ID NO 556
<211> LENGTH: 18
<212> TYPE: PRT
<213> ORGANISM: Artificial
<220> FEATURE:
<223> OTHER INFORMATION: Synthetic peptide

<400> SEQUENCE: 556

Phe Phe Asp Lys Phe Lys Asp Phe Phe Lys Asp Tyr Phe Ala Lys Phe
1               5                   10                  15

Trp Asp

<210> SEQ ID NO 557
<211> LENGTH: 18
<212> TYPE: PRT
<213> ORGANISM: Artificial
<220> FEATURE:
<223> OTHER INFORMATION: Synthetic peptide

<400> SEQUENCE: 557

Phe Phe Glu Lys Phe Lys Glu Phe Phe Lys Glu Tyr Phe Ala Lys Phe
1               5                   10                  15

Trp Glu

<210> SEQ ID NO 558
<211> LENGTH: 18
<212> TYPE: PRT
<213> ORGANISM: Artificial
<220> FEATURE:
<223> OTHER INFORMATION: Synthetic peptide
```

<400> SEQUENCE: 558

Phe Phe Glu Arg Phe Lys Glu Phe Phe Lys Asp Tyr Phe Ala Lys Phe
1               5                   10                  15

Trp Asp

<210> SEQ ID NO 559
<211> LENGTH: 18
<212> TYPE: PRT
<213> ORGANISM: Artificial
<220> FEATURE:
<223> OTHER INFORMATION: Synthetic peptide

<400> SEQUENCE: 559

Phe Phe Glu Lys Phe Arg Glu Phe Phe Lys Asp Tyr Phe Ala Lys Phe
1               5                   10                  15

Trp Asp

<210> SEQ ID NO 560
<211> LENGTH: 18
<212> TYPE: PRT
<213> ORGANISM: Artificial
<220> FEATURE:
<223> OTHER INFORMATION: Synthetic peptide

<400> SEQUENCE: 560

Phe Phe Glu Lys Phe Lys Glu Phe Phe Arg Asp Tyr Phe Ala Lys Phe
1               5                   10                  15

Trp Asp

<210> SEQ ID NO 561
<211> LENGTH: 18
<212> TYPE: PRT
<213> ORGANISM: Artificial
<220> FEATURE:
<223> OTHER INFORMATION: Synthetic peptide

<400> SEQUENCE: 561

Phe Phe Glu Lys Phe Lys Glu Phe Phe Lys Asp Tyr Phe Ala Arg Phe
1               5                   10                  15

Trp Asp

<210> SEQ ID NO 562
<211> LENGTH: 18
<212> TYPE: PRT
<213> ORGANISM: Artificial
<220> FEATURE:
<223> OTHER INFORMATION: Synthetic peptide

<400> SEQUENCE: 562

Phe Phe Asp Lys Phe Lys Glu Phe Phe Lys Asp Tyr Phe Ala Lys Phe
1               5                   10                  15

Trp Asp

<210> SEQ ID NO 563
<211> LENGTH: 18
<212> TYPE: PRT
<213> ORGANISM: Artificial
<220> FEATURE:
<223> OTHER INFORMATION: Synthetic peptide

<400> SEQUENCE: 563

Phe Phe Glu Lys Phe Lys Asp Phe Phe Lys Asp Tyr Phe Ala Lys Phe
1               5                   10                  15

Trp Asp

<210> SEQ ID NO 564
<211> LENGTH: 18
<212> TYPE: PRT
<213> ORGANISM: Artificial
<220> FEATURE:
<223> OTHER INFORMATION: Synthetic peptide

<400> SEQUENCE: 564

Phe Phe Glu Lys Phe Lys Glu Phe Phe Lys Glu Tyr Phe Ala Lys Phe
1               5                   10                  15

Trp Asp

<210> SEQ ID NO 565
<211> LENGTH: 18
<212> TYPE: PRT
<213> ORGANISM: Artificial
<220> FEATURE:
<223> OTHER INFORMATION: Synthetic peptide

<400> SEQUENCE: 565

Phe Phe Glu Lys Phe Lys Glu Phe Phe Lys Asp Tyr Phe Ala Lys Phe
1               5                   10                  15

Trp Glu

<210> SEQ ID NO 566
<211> LENGTH: 33
<212> TYPE: PRT
<213> ORGANISM: Artificial
<220> FEATURE:
<223> OTHER INFORMATION: Synthetic peptide

<400> SEQUENCE: 566

Glu Val Arg Ala Lys Leu Glu Glu Gln Ala Gln Gln Ile Arg Leu Gln
1               5                   10                  15

Ala Glu Ala Phe Gln Ala Arg Leu Lys Ser Trp Phe Glu Pro Leu Val
                20                  25                  30

Glu

<210> SEQ ID NO 567
<211> LENGTH: 29
<212> TYPE: PRT
<213> ORGANISM: Artificial
<220> FEATURE:
<223> OTHER INFORMATION: Synthetic peptide

<400> SEQUENCE: 567

Glu Val Arg Ala Lys Leu Glu Glu Gln Ala Gln Gln Ile Arg Leu Gln
1               5                   10                  15

Ala Glu Ala Phe Gln Ala Arg Leu Lys Ser Trp Phe Glu
                20                  25

<210> SEQ ID NO 568
<211> LENGTH: 26
<212> TYPE: PRT
<213> ORGANISM: Artificial
<220> FEATURE:
<223> OTHER INFORMATION: Synthetic peptide

<400> SEQUENCE: 568

Glu Val Arg Ser Lys Leu Glu Glu Trp Phe Ala Ala Phe Arg Glu Phe
1               5                   10                  15

Ala Glu Glu Phe Leu Ala Arg Leu Lys Ser
            20                  25

<210> SEQ ID NO 569
<211> LENGTH: 22
<212> TYPE: PRT
<213> ORGANISM: Artificial
<220> FEATURE:
<223> OTHER INFORMATION: Synthetic peptide

<400> SEQUENCE: 569

Pro Val Leu Asp Leu Phe Arg Glu Leu Leu Asn Glu Leu Leu Glu Ala
1               5                   10                  15

Leu Lys Gln Lys Leu Lys
            20

<210> SEQ ID NO 570
<211> LENGTH: 37
<212> TYPE: PRT
<213> ORGANISM: Artificial
<220> FEATURE:
<223> OTHER INFORMATION: Synthetic peptide

<400> SEQUENCE: 570

Asp Trp Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
            35

<210> SEQ ID NO 571
<211> LENGTH: 37
<212> TYPE: PRT
<213> ORGANISM: Artificial
<220> FEATURE:
<223> OTHER INFORMATION: Synthetic peptide

<400> SEQUENCE: 571

Glu Glu Leu Lys Glu Lys Leu Glu Glu Leu Lys Glu Lys Leu Glu Glu
1               5                   10                  15

Lys Leu Pro Glu Glu Leu Lys Glu Lys Leu Glu Glu Leu Lys Glu Lys
            20                  25                  30

Leu Glu Glu Lys Leu
            35

<210> SEQ ID NO 572
<211> LENGTH: 37
<212> TYPE: PRT
<213> ORGANISM: Artificial
<220> FEATURE:
<223> OTHER INFORMATION: Synthetic peptide

<400> SEQUENCE: 572

Glu Glu Leu Lys Ala Lys Leu Glu Glu Leu Lys Ala Lys Leu Glu Glu
1               5                   10                  15

Lys Leu Pro Glu Glu Leu Lys Ala Lys Leu Glu Glu Leu Lys Ala Lys
            20                  25                  30

Leu Glu Glu Lys Leu
            35

<210> SEQ ID NO 573

```
<211> LENGTH: 37
<212> TYPE: PRT
<213> ORGANISM: Artificial
<220> FEATURE:
<223> OTHER INFORMATION: Synthetic peptide

<400> SEQUENCE: 573

Glu Lys Leu Lys Ala Leu Leu Glu Lys Leu Leu Ala Lys Leu Lys Glu
1               5                   10                  15

Leu Leu Pro Glu Lys Leu Lys Ala Leu Leu Glu Lys Leu Leu Ala Lys
            20                  25                  30

Leu Lys Glu Leu Leu
        35

<210> SEQ ID NO 574
<211> LENGTH: 37
<212> TYPE: PRT
<213> ORGANISM: Artificial
<220> FEATURE:
<223> OTHER INFORMATION: Synthetic peptide

<400> SEQUENCE: 574

Glu Trp Leu Lys Glu Leu Leu Glu Lys Leu Leu Glu Lys Leu Lys Glu
1               5                   10                  15

Leu Leu Pro Glu Trp Leu Lys Glu Leu Leu Glu Lys Leu Leu Glu Lys
            20                  25                  30

Leu Lys Glu Leu Leu
        35

<210> SEQ ID NO 575
<211> LENGTH: 37
<212> TYPE: PRT
<213> ORGANISM: Artificial
<220> FEATURE:
<223> OTHER INFORMATION: Synthetic peptide

<400> SEQUENCE: 575

Glu Lys Phe Lys Glu Leu Leu Glu Lys Phe Leu Glu Lys Phe Lys Glu
1               5                   10                  15

Leu Leu Pro Glu Lys Phe Lys Glu Leu Leu Glu Lys Phe Leu Glu Lys
            20                  25                  30

Phe Lys Glu Leu Leu
        35

<210> SEQ ID NO 576
<211> LENGTH: 37
<212> TYPE: PRT
<213> ORGANISM: Artificial
<220> FEATURE:
<223> OTHER INFORMATION: Synthetic peptide

<400> SEQUENCE: 576

Glu Lys Leu Lys Glu Leu Leu Glu Lys Leu Leu Glu Leu Leu Lys Lys
1               5                   10                  15

Leu Leu Pro Glu Lys Leu Lys Glu Leu Leu Glu Lys Leu Leu Glu Leu
            20                  25                  30

Leu Lys Lys Leu Leu
        35

<210> SEQ ID NO 577
<211> LENGTH: 37
<212> TYPE: PRT
<213> ORGANISM: Artificial
```

<220> FEATURE:
<223> OTHER INFORMATION: Synthetic peptide

<400> SEQUENCE: 577

Glu Lys Leu Lys Glu Leu Leu Glu Lys Leu Lys Ala Lys Leu Glu Glu
1               5                   10                  15

Leu Leu Pro Glu Lys Leu Lys Glu Leu Glu Lys Leu Lys Ala Lys
            20                  25                  30

Leu Glu Glu Leu Leu
        35

<210> SEQ ID NO 578
<211> LENGTH: 37
<212> TYPE: PRT
<213> ORGANISM: Artificial
<220> FEATURE:
<223> OTHER INFORMATION: Synthetic peptide

<400> SEQUENCE: 578

Glu Lys Leu Lys Glu Leu Leu Glu Lys Leu Leu Ala Lys Leu Lys Glu
1               5                   10                  15

Leu Leu Pro Glu Lys Leu Lys Glu Leu Leu Glu Lys Leu Leu Ala Lys
            20                  25                  30

Leu Lys Glu Leu Leu
        35

<210> SEQ ID NO 579
<211> LENGTH: 37
<212> TYPE: PRT
<213> ORGANISM: Artificial
<220> FEATURE:
<223> OTHER INFORMATION: Synthetic peptide

<400> SEQUENCE: 579

Glu Lys Phe Lys Glu Leu Leu Glu Lys Leu Leu Glu Lys Leu Lys Glu
1               5                   10                  15

Leu Leu Pro Glu Lys Phe Lys Glu Leu Leu Glu Lys Leu Leu Glu Lys
            20                  25                  30

Leu Lys Glu Leu Leu
        35

<210> SEQ ID NO 580
<211> LENGTH: 37
<212> TYPE: PRT
<213> ORGANISM: Artificial
<220> FEATURE:
<223> OTHER INFORMATION: Synthetic peptide

<400> SEQUENCE: 580

Glu Lys Leu Lys Ala Lys Leu Glu Glu Leu Lys Ala Lys Leu Glu Glu
1               5                   10                  15

Leu Leu Pro Glu Lys Leu Lys Ala Lys Leu Glu Glu Leu Lys Ala Lys
            20                  25                  30

Leu Glu Glu Leu Leu
        35

<210> SEQ ID NO 581
<211> LENGTH: 36
<212> TYPE: PRT
<213> ORGANISM: Artificial
<220> FEATURE:
<223> OTHER INFORMATION: Synthetic peptide -continued

<400> SEQUENCE: 581

Glu Glu Leu Lys Glu Leu Leu Lys Glu Leu Leu Lys Lys Leu Glu Lys
1               5                   10                  15

Leu Leu Pro Glu Leu Lys Glu Leu Leu Lys Glu Leu Leu Lys Lys Leu
            20                  25                  30

Glu Lys Leu Leu
        35

<210> SEQ ID NO 582
<211> LENGTH: 37
<212> TYPE: PRT
<213> ORGANISM: Artificial
<220> FEATURE:
<223> OTHER INFORMATION: Synthetic peptide

<400> SEQUENCE: 582

Glu Glu Leu Lys Lys Leu Leu Glu Glu Leu Leu Lys Lys Leu Lys Glu
1               5                   10                  15

Leu Leu Pro Glu Glu Leu Lys Lys Leu Leu Glu Glu Leu Leu Lys Lys
            20                  25                  30

Leu Lys Glu Leu Leu
        35

<210> SEQ ID NO 583
<211> LENGTH: 37
<212> TYPE: PRT
<213> ORGANISM: Artificial
<220> FEATURE:
<223> OTHER INFORMATION: Synthetic peptide

<400> SEQUENCE: 583

Glu Lys Leu Lys Glu Leu Leu Glu Lys Leu Leu Glu Lys Leu Lys Glu
1               5                   10                  15

Leu Leu Ala Glu Lys Leu Lys Glu Leu Leu Glu Lys Leu Leu Glu Lys
            20                  25                  30

Leu Lys Glu Leu Leu
        35

<210> SEQ ID NO 584
<211> LENGTH: 38
<212> TYPE: PRT
<213> ORGANISM: Artificial
<220> FEATURE:
<223> OTHER INFORMATION: Synthetic peptide

<400> SEQUENCE: 584

Glu Lys Leu Lys Glu Leu Leu Glu Lys Leu Leu Glu Lys Leu Lys Glu
1               5                   10                  15

Leu Leu Ala Ala Glu Lys Leu Lys Glu Leu Leu Glu Lys Leu Leu Glu
            20                  25                  30

Lys Leu Lys Glu Leu Leu
        35

<210> SEQ ID NO 585
<211> LENGTH: 37
<212> TYPE: PRT
<213> ORGANISM: Artificial
<220> FEATURE:
<223> OTHER INFORMATION: Synthetic peptide

<400> SEQUENCE: 585

Glu Lys Leu Lys Ala Lys Leu Glu Glu Leu Lys Ala Lys Leu Glu Glu

```
1               5                   10                  15
Leu Leu Pro Glu Lys Ala Lys Ala Ala Leu Glu Glu Ala Lys Ala Lys
            20                  25                  30

Ala Glu Glu Leu Ala
            35

<210> SEQ ID NO 586
<211> LENGTH: 37
<212> TYPE: PRT
<213> ORGANISM: Artificial
<220> FEATURE:
<223> OTHER INFORMATION: Synthetic peptide

<400> SEQUENCE: 586

Glu Lys Leu Lys Ala Lys Leu Glu Glu Leu Lys Ala Lys Leu Glu Glu
1               5                   10                  15

Leu Leu Pro Glu His Ala Lys Ala Ala Leu Glu Glu Ala Lys Cys Lys
            20                  25                  30

Ala Glu Glu Leu Ala
            35

<210> SEQ ID NO 587
<211> LENGTH: 37
<212> TYPE: PRT
<213> ORGANISM: Artificial
<220> FEATURE:
<223> OTHER INFORMATION: Synthetic peptide

<400> SEQUENCE: 587

Asp His Leu Lys Ala Phe Tyr Asp Lys Val Ala Cys Lys Leu Lys Glu
1               5                   10                  15

Ala Phe Pro Asp Trp Ala Lys Ala Ala Tyr Asp Lys Ala Ala Glu Lys
            20                  25                  30

Ala Lys Glu Ala Ala
            35

<210> SEQ ID NO 588
<211> LENGTH: 37
<212> TYPE: PRT
<213> ORGANISM: Artificial
<220> FEATURE:
<223> OTHER INFORMATION: Synthetic peptide

<400> SEQUENCE: 588

Asp Trp Leu Lys Ala Phe Tyr Asp Lys Val Ala Glu Lys Leu Lys Glu
1               5                   10                  15

Ala Phe Pro Asp His Ala Lys Ala Ala Tyr Asp Lys Ala Ala Cys Lys
            20                  25                  30

Ala Lys Glu Ala Ala
            35

<210> SEQ ID NO 589
<211> LENGTH: 37
<212> TYPE: PRT
<213> ORGANISM: Artificial
<220> FEATURE:
<223> OTHER INFORMATION: Synthetic peptide

<400> SEQUENCE: 589

Asp Trp Leu Lys Ala Phe Tyr Asp Lys Val Ala Cys Lys Leu Lys Glu
1               5                   10                  15

Ala Phe Pro Asp Trp Ala Lys Ala Ala Tyr Asn Lys Ala Ala Glu Lys
```

```
                    20                  25                  30

Ala Lys Glu Ala Ala
        35

<210> SEQ ID NO 590
<211> LENGTH: 37
<212> TYPE: PRT
<213> ORGANISM: Artificial
<220> FEATURE:
<223> OTHER INFORMATION: Synthetic peptide

<400> SEQUENCE: 590

Asp His Leu Lys Ala Phe Tyr Asp Lys Val Ala Glu Lys Leu Lys Glu
1               5                   10                  15

Ala Phe Pro Asp Trp Ala Lys Ala Ala Tyr Asp Lys Ala Ala Glu Lys
                20                  25                  30

Ala Lys Glu Ala Ala
        35

<210> SEQ ID NO 591
<211> LENGTH: 23
<212> TYPE: PRT
<213> ORGANISM: Artificial
<220> FEATURE:
<223> OTHER INFORMATION: Synthetic peptide

<400> SEQUENCE: 591

Val Leu Glu Ser Phe Lys Val Ser Phe Leu Ser Ala Leu Glu Glu Tyr
1               5                   10                  15

Thr Lys Lys Leu Asn Thr Gln
            20

<210> SEQ ID NO 592
<211> LENGTH: 18
<212> TYPE: PRT
<213> ORGANISM: Artificial
<220> FEATURE:
<223> OTHER INFORMATION: Synthetic peptide

<400> SEQUENCE: 592

Asp Lys Trp Lys Ala Val Tyr Asp Lys Phe Ala Glu Ala Phe Lys Glu
1               5                   10                  15

Phe Leu

<210> SEQ ID NO 593
<211> LENGTH: 18
<212> TYPE: PRT
<213> ORGANISM: Artificial
<220> FEATURE:
<223> OTHER INFORMATION: Synthetic peptide

<400> SEQUENCE: 593

Asp Lys Leu Lys Ala Phe Tyr Asp Lys Val Phe Glu Trp Ala Lys Glu
1               5                   10                  15

Ala Phe

<210> SEQ ID NO 594
<211> LENGTH: 11
<212> TYPE: PRT
<213> ORGANISM: Artificial
<220> FEATURE:
<223> OTHER INFORMATION: Synthetic peptide

<400> SEQUENCE: 594
```

```
Ala Val Thr Thr Val Arg Leu Tyr Tyr Gln Asp
1               5                   10

<210> SEQ ID NO 595
<211> LENGTH: 11
<212> TYPE: PRT
<213> ORGANISM: Artificial
<220> FEATURE:
<223> OTHER INFORMATION: Synthetic peptide

<400> SEQUENCE: 595

Asp Gln Tyr Tyr Leu Arg Val Thr Thr Val Ala
1               5                   10

<210> SEQ ID NO 596
<211> LENGTH: 19
<212> TYPE: PRT
<213> ORGANISM: Artificial
<220> FEATURE:
<223> OTHER INFORMATION: Synthetic peptide

<400> SEQUENCE: 596

Glu Cys Lys Pro Cys Leu Lys Gln Thr Cys Met Lys Phe Tyr Ala Arg
1               5                   10                  15

Val Cys Arg

<210> SEQ ID NO 597
<211> LENGTH: 14
<212> TYPE: PRT
<213> ORGANISM: Artificial
<220> FEATURE:
<223> OTHER INFORMATION: Synthetic peptide

<400> SEQUENCE: 597

Phe Ser Arg Ala Ser Ser Ile Ile Asp Glu Leu Phe Gln Asp
1               5                   10

<210> SEQ ID NO 598
<211> LENGTH: 21
<212> TYPE: PRT
<213> ORGANISM: Artificial
<220> FEATURE:
<223> OTHER INFORMATION: Synthetic peptide

<400> SEQUENCE: 598

Ile Gln Asn Ala Val Asn Gly Val Lys Gln Ile Lys Thr Leu Ile Glu
1               5                   10                  15

Lys Thr Asn Glu Glu
            20

<210> SEQ ID NO 599
<211> LENGTH: 18
<212> TYPE: PRT
<213> ORGANISM: Artificial
<220> FEATURE:
<223> OTHER INFORMATION: Synthetic peptide

<400> SEQUENCE: 599

Leu Leu Glu Gln Leu Asn Glu Gln Phe Asn Trp Val Ser Arg Leu Ala
1               5                   10                  15

Asn Leu

<210> SEQ ID NO 600
<211> LENGTH: 22
```

```
<212> TYPE: PRT
<213> ORGANISM: Artificial
<220> FEATURE:
<223> OTHER INFORMATION: Synthetic peptide

<400> SEQUENCE: 600

Leu Leu Glu Gln Leu Asn Glu Gln Phe Asn Trp Val Ser Arg Leu Ala
1               5                   10                  15

Asn Leu Thr Glu Gly Glu
            20

<210> SEQ ID NO 601
<211> LENGTH: 22
<212> TYPE: PRT
<213> ORGANISM: Artificial
<220> FEATURE:
<223> OTHER INFORMATION: Synthetic peptide

<400> SEQUENCE: 601

Leu Leu Glu Gln Leu Asn Glu Gln Phe Asn Trp Val Ser Arg Leu Ala
1               5                   10                  15

Asn Leu Thr Gln Gly Glu
            20

<210> SEQ ID NO 602
<211> LENGTH: 10
<212> TYPE: PRT
<213> ORGANISM: Artificial
<220> FEATURE:
<223> OTHER INFORMATION: Synthetic peptide

<400> SEQUENCE: 602

Leu Val Gly Arg Gln Leu Glu Glu Phe Leu
1               5                   10

<210> SEQ ID NO 603
<211> LENGTH: 12
<212> TYPE: PRT
<213> ORGANISM: Artificial
<220> FEATURE:
<223> OTHER INFORMATION: Synthetic peptide

<400> SEQUENCE: 603

Met Asn Gly Asp Arg Ile Asp Ser Leu Leu Glu Asn
1               5                   10

<210> SEQ ID NO 604
<211> LENGTH: 25
<212> TYPE: PRT
<213> ORGANISM: Artificial
<220> FEATURE:
<223> OTHER INFORMATION: Synthetic peptide

<400> SEQUENCE: 604

Asn Glu Leu Gln Glu Met Ser Asn Gln Gly Ser Lys Tyr Val Asn Lys
1               5                   10                  15

Glu Ile Gln Asn Ala Val Asn Gly Val
            20                  25

<210> SEQ ID NO 605
<211> LENGTH: 16
<212> TYPE: PRT
<213> ORGANISM: Artificial
<220> FEATURE:
<223> OTHER INFORMATION: Synthetic peptide
```

```
<400> SEQUENCE: 605

Pro Cys Leu Lys Gln Thr Cys Met Lys Phe Tyr Ala Arg Val Cys Arg
1               5                   10                  15

<210> SEQ ID NO 606
<211> LENGTH: 15
<212> TYPE: PRT
<213> ORGANISM: Artificial
<220> FEATURE:
<223> OTHER INFORMATION: Synthetic peptide

<400> SEQUENCE: 606

Pro Phe Leu Glu Met Ile His Glu Ala Gln Gln Ala Met Asp Ile
1               5                   10                  15

<210> SEQ ID NO 607
<211> LENGTH: 16
<212> TYPE: PRT
<213> ORGANISM: Artificial
<220> FEATURE:
<223> OTHER INFORMATION: Synthetic peptide

<400> SEQUENCE: 607

Pro Gly Val Cys Asn Glu Thr Met Met Ala Leu Trp Glu Glu Cys Lys
1               5                   10                  15

<210> SEQ ID NO 608
<211> LENGTH: 21
<212> TYPE: PRT
<213> ORGANISM: Artificial
<220> FEATURE:
<223> OTHER INFORMATION: Synthetic peptide

<400> SEQUENCE: 608

Pro Lys Phe Met Glu Thr Val Ala Glu Lys Ala Leu Gln Glu Tyr Arg
1               5                   10                  15

Lys Lys His Arg Glu
            20

<210> SEQ ID NO 609
<211> LENGTH: 14
<212> TYPE: PRT
<213> ORGANISM: Artificial
<220> FEATURE:
<223> OTHER INFORMATION: Synthetic peptide

<400> SEQUENCE: 609

Pro Ser Gly Val Thr Glu Val Val Val Lys Leu Phe Asp Ser
1               5                   10

<210> SEQ ID NO 610
<211> LENGTH: 32
<212> TYPE: PRT
<213> ORGANISM: Artificial
<220> FEATURE:
<223> OTHER INFORMATION: Synthetic peptide

<400> SEQUENCE: 610

Pro Ser Gln Ala Lys Leu Arg Arg Glu Leu Asp Glu Ser Leu Gln Val
1               5                   10                  15

Ala Glu Arg Leu Thr Arg Lys Tyr Asn Glu Leu Leu Lys Ser Tyr Gln
                20                  25                  30

<210> SEQ ID NO 611
<211> LENGTH: 11
```

```
<212> TYPE: PRT
<213> ORGANISM: Artificial
<220> FEATURE:
<223> OTHER INFORMATION: Synthetic peptide

<400> SEQUENCE: 611

Pro Thr Glu Phe Ile Arg Glu Gly Asp Asp
1               5                   10

<210> SEQ ID NO 612
<211> LENGTH: 11
<212> TYPE: PRT
<213> ORGANISM: Artificial
<220> FEATURE:
<223> OTHER INFORMATION: Synthetic peptide

<400> SEQUENCE: 612

Gln Gln Thr His Met Leu Asp Val Met Gln Asp
1               5                   10

<210> SEQ ID NO 613
<211> LENGTH: 32
<212> TYPE: PRT
<213> ORGANISM: Artificial
<220> FEATURE:
<223> OTHER INFORMATION: Synthetic peptide

<400> SEQUENCE: 613

Arg Lys Thr Leu Leu Ser Asn Leu Glu Glu Ala Lys Lys Lys Glu
1               5                   10                  15

Asp Ala Leu Asn Glu Thr Arg Glu Ser Glu Thr Lys Lys Glu Leu
            20                  25                  30

<210> SEQ ID NO 614
<211> LENGTH: 15
<212> TYPE: PRT
<213> ORGANISM: Artificial
<220> FEATURE:
<223> OTHER INFORMATION: Synthetic peptide

<400> SEQUENCE: 614

Arg Met Lys Asp Gln Cys Asp Lys Cys Arg Glu Ile Leu Ser Val
1               5                   10                  15

<210> SEQ ID NO 615
<211> LENGTH: 18
<212> TYPE: PRT
<213> ORGANISM: Artificial
<220> FEATURE:
<223> OTHER INFORMATION: Synthetic peptide

<400> SEQUENCE: 615

Gly Val Phe Ala Lys Ile Phe Lys Trp Ile Ser Gly Leu Phe Lys Lys
1               5                   10                  15

Ile Gly

<210> SEQ ID NO 616
<211> LENGTH: 18
<212> TYPE: PRT
<213> ORGANISM: Artificial
<220> FEATURE:
<223> OTHER INFORMATION: Synthetic peptide

<400> SEQUENCE: 616

Gly Ile Lys Lys Phe Leu Gly Ser Ile Trp Lys Phe Ile Lys Ala Phe
1               5                   10                  15
```

Val Gly

<210> SEQ ID NO 617
<211> LENGTH: 18
<212> TYPE: PRT
<213> ORGANISM: Artificial
<220> FEATURE:
<223> OTHER INFORMATION: Synthetic peptide

<400> SEQUENCE: 617

Gly Phe Lys Lys Phe Leu Gly Ser Trp Ala Lys Ile Tyr Lys Ala Phe
1               5                   10                  15

Val Gly

<210> SEQ ID NO 618
<211> LENGTH: 18
<212> TYPE: PRT
<213> ORGANISM: Artificial
<220> FEATURE:
<223> OTHER INFORMATION: Synthetic peptide

<400> SEQUENCE: 618

Gly Phe Arg Arg Phe Leu Gly Ser Trp Ala Arg Ile Tyr Arg Ala Phe
1               5                   10                  15

Val Gly

<210> SEQ ID NO 619
<211> LENGTH: 20
<212> TYPE: PRT
<213> ORGANISM: Artificial
<220> FEATURE:
<223> OTHER INFORMATION: Synthetic peptide

<400> SEQUENCE: 619

Thr Glu Glu Leu Arg Val Arg Leu Ala Ser His Leu Arg Lys Leu Arg
1               5                   10                  15

Lys Arg Leu Leu
            20

<210> SEQ ID NO 620
<211> LENGTH: 17
<212> TYPE: PRT
<213> ORGANISM: Artificial
<220> FEATURE:
<223> OTHER INFORMATION: Synthetic peptide

<400> SEQUENCE: 620

Thr Glu Glu Leu Arg Val Arg Leu Ala Ser His Leu Arg Lys Leu Arg
1               5                   10                  15

Lys

<210> SEQ ID NO 621
<211> LENGTH: 17
<212> TYPE: PRT
<213> ORGANISM: Artificial
<220> FEATURE:
<223> OTHER INFORMATION: Synthetic peptide

<400> SEQUENCE: 621

Leu Arg Val Arg Leu Ala Ser His Leu Arg Lys Leu Arg Lys Arg Leu
1               5                   10                  15

Leu

```
<210> SEQ ID NO 622
<211> LENGTH: 14
<212> TYPE: PRT
<213> ORGANISM: Artificial
<220> FEATURE:
<223> OTHER INFORMATION: Synthetic peptide

<400> SEQUENCE: 622

Arg Leu Ala Ser His Leu Arg Lys Leu Arg Lys Arg Leu Leu
1               5                   10

<210> SEQ ID NO 623
<211> LENGTH: 11
<212> TYPE: PRT
<213> ORGANISM: Artificial
<220> FEATURE:
<223> OTHER INFORMATION: Synthetic peptide

<400> SEQUENCE: 623

Ser His Leu Arg Lys Leu Arg Lys Arg Leu Leu
1               5                   10

<210> SEQ ID NO 624
<211> LENGTH: 9
<212> TYPE: PRT
<213> ORGANISM: Artificial
<220> FEATURE:
<223> OTHER INFORMATION: Synthetic peptide

<400> SEQUENCE: 624

Leu Arg Lys Leu Arg Lys Arg Leu Leu
1               5

<210> SEQ ID NO 625
<211> LENGTH: 18
<212> TYPE: PRT
<213> ORGANISM: Artificial
<220> FEATURE:
<223> OTHER INFORMATION: Synthetic peptide

<400> SEQUENCE: 625

Leu Arg Lys Leu Arg Lys Arg Leu Leu Leu Arg Lys Leu Arg Lys Arg
1               5                   10                  15

Leu Leu

<210> SEQ ID NO 626
<211> LENGTH: 27
<212> TYPE: PRT
<213> ORGANISM: Artificial
<220> FEATURE:
<223> OTHER INFORMATION: Synthetic peptide

<400> SEQUENCE: 626

Leu Arg Lys Leu Arg Lys Arg Leu Leu Leu Arg Lys Leu Arg Lys Arg
1               5                   10                  15

Leu Leu Leu Arg Lys Leu Arg Lys Arg Leu Leu
            20                  25

<210> SEQ ID NO 627
<211> LENGTH: 34
<212> TYPE: PRT
<213> ORGANISM: Artificial
<220> FEATURE:
<223> OTHER INFORMATION: Synthetic peptide

<400> SEQUENCE: 627
```

Arg Gln Ile Lys Ile Trp Phe Gln Asn Arg Arg Met Lys Trp Lys Lys
1               5                   10                  15

Cys Leu Arg Val Arg Leu Ala Ser His Leu Arg Lys Leu Arg Lys Arg
                20                  25                  30

Leu Leu

<210> SEQ ID NO 628
<211> LENGTH: 17
<212> TYPE: PRT
<213> ORGANISM: Artificial
<220> FEATURE:
<223> OTHER INFORMATION: Synthetic peptide

<400> SEQUENCE: 628

Leu Arg Val Arg Leu Ala Ser His Leu Arg Lys Leu Arg Lys Arg Leu
1               5                   10                  15

Leu

<210> SEQ ID NO 629
<211> LENGTH: 61
<212> TYPE: PRT
<213> ORGANISM: Artificial
<220> FEATURE:
<223> OTHER INFORMATION: Synthetic peptide

<400> SEQUENCE: 629

Glu Glu Leu Arg Val Arg Leu Ala Ser His Leu Arg Lys Leu Arg Lys
1               5                   10                  15

Arg Leu Leu Arg Asp Ala Asp Asp Leu Gln Lys Arg Leu Ala Val Tyr
                20                  25                  30

Glu Glu Gln Ala Gln Gln Ile Arg Leu Gln Ala Glu Ala Phe Gln Ala
            35                  40                  45

Arg Leu Lys Ser Trp Phe Glu Pro Leu Val Glu Asp Met
        50                  55                  60

<210> SEQ ID NO 630
<211> LENGTH: 33
<212> TYPE: PRT
<213> ORGANISM: Artificial
<220> FEATURE:
<223> OTHER INFORMATION: Synthetic peptide

<400> SEQUENCE: 630

Cys Glu Glu Leu Arg Val Arg Leu Ala Ser His Leu Arg Lys Leu Arg
1               5                   10                  15

Lys Arg Leu Leu Arg Asp Ala Asp Asp Leu Gln Lys Arg Leu Ala Val
                20                  25                  30

Tyr

<210> SEQ ID NO 631
<211> LENGTH: 30
<212> TYPE: PRT
<213> ORGANISM: Artificial
<220> FEATURE:
<223> OTHER INFORMATION: Synthetic peptide

<400> SEQUENCE: 631

Leu Arg Lys Leu Arg Lys Arg Leu Leu Arg Asp Ala Asp Asp Leu Leu
1               5                   10                  15

Arg Lys Leu Arg Lys Arg Leu Leu Arg Asp Ala Asp Asp Leu
                20                  25                  30

```
<210> SEQ ID NO 632
<211> LENGTH: 20
<212> TYPE: PRT
<213> ORGANISM: Artificial
<220> FEATURE:
<223> OTHER INFORMATION: Synthetic peptide

<400> SEQUENCE: 632

Thr Glu Glu Leu Arg Val Arg Leu Ala Ser His Leu Arg Lys Leu Arg
1               5                   10                  15

Lys Arg Leu Leu
            20

<210> SEQ ID NO 633
<211> LENGTH: 20
<212> TYPE: PRT
<213> ORGANISM: Artificial
<220> FEATURE:
<223> OTHER INFORMATION: Synthetic peptide

<400> SEQUENCE: 633

Thr Glu Glu Leu Arg Val Arg Leu Ala Ser His Leu Glu Lys Leu Arg
1               5                   10                  15

Lys Arg Leu Leu
            20

<210> SEQ ID NO 634
<211> LENGTH: 20
<212> TYPE: PRT
<213> ORGANISM: Artificial
<220> FEATURE:
<223> OTHER INFORMATION: Synthetic peptide

<400> SEQUENCE: 634

Thr Glu Glu Leu Arg Val Arg Leu Ala Ser His Leu Arg Glu Leu Arg
1               5                   10                  15

Lys Arg Leu Leu
            20

<210> SEQ ID NO 635
<211> LENGTH: 20
<212> TYPE: PRT
<213> ORGANISM: Artificial
<220> FEATURE:
<223> OTHER INFORMATION: Synthetic peptide

<400> SEQUENCE: 635

Leu Arg Glu Lys Lys Leu Arg Val Ser Ala Leu Arg Thr His Arg Leu
1               5                   10                  15

Glu Leu Arg Leu
            20

<210> SEQ ID NO 636
<211> LENGTH: 28
<212> TYPE: PRT
<213> ORGANISM: Artificial
<220> FEATURE:
<223> OTHER INFORMATION: Synthetic peptide

<400> SEQUENCE: 636

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
```

```
                    20                  25

<210> SEQ ID NO 637
<211> LENGTH: 28
<212> TYPE: PRT
<213> ORGANISM: Artificial
<220> FEATURE:
<223> OTHER INFORMATION: Synthetic peptide

<400> SEQUENCE: 637

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 638
<211> LENGTH: 28
<212> TYPE: PRT
<213> ORGANISM: Artificial
<220> FEATURE:
<223> OTHER INFORMATION: Synthetic peptide

<400> SEQUENCE: 638

Arg Arg Arg Arg Arg Arg Arg Arg Arg Arg Asp Trp Leu Lys Ala Phe
1               5                   10                  15

Tyr Asp Lys Val Ala Glu Lys Leu Lys Glu Ala Phe
            20                  25

<210> SEQ ID NO 639
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is 3,3'-diphenyl alanine

<400> SEQUENCE: 639

Arg Glu Xaa Thr Gly Leu Ala Trp Glu Trp Trp Arg Thr Val
1               5                   10
```